United States Patent
Dasseux

(10) Patent No.: US 7,709,515 B2
(45) Date of Patent: May 4, 2010

(54) COMPOSITIONS COMPRISING ETHER COMPOUNDS AND PHARMACEUTICAL USES THEREFOR

(75) Inventor: Jean-Louis Henri Dasseux, Brighton, MI (US)

(73) Assignee: Esperion Therapeutics, Inc., Plymouth, MI (US)

( * ) Notice: Subject to any disclaimer, the term of this patent is extended or adjusted under 35 U.S.C. 154(b) by 1473 days.

(21) Appl. No.: 10/990,304

(22) Filed: Nov. 16, 2004

(65) Prior Publication Data

US 2005/0119333 A1 Jun. 2, 2005

Related U.S. Application Data

(62) Division of application No. 10/305,440, filed on Nov. 26, 2002, now Pat. No. 6,831,105, which is a division of application No. 09/540,739, filed on Mar. 31, 2000, now Pat. No. 6,506,799.

(60) Provisional application No. 60/127,321, filed on Apr. 1, 1999.

(51) Int. Cl.
| | |
|---|---|
| A61K 31/415 | (2006.01) |
| A61K 31/66 | (2006.01) |
| A61K 31/44 | (2006.01) |
| A61K 31/335 | (2006.01) |
| A61K 31/35 | (2006.01) |
| A61K 31/34 | (2006.01) |
| A61K 31/08 | (2006.01) |
| A61K 9/00 | (2006.01) |

(52) U.S. Cl. .................. 514/389; 514/106; 514/79; 514/301; 514/449; 514/460; 514/473; 514/722; 514/866; 424/400

(58) Field of Classification Search ................. 514/999, 514/301, 449, 460, 473, 722, 389, 106, 79, 514/866; 424/400
See application file for complete search history.

(56) References Cited

U.S. PATENT DOCUMENTS 3,152,148 A 10/1964 Easterly et al.

(Continued)

FOREIGN PATENT DOCUMENTS

EP 88300709.8 1/1988

(Continued)

OTHER PUBLICATIONS

Zinman "Glucose control in type I diabetes: From conventional to intensive therapy," Diabetes, 1995, vol. 1, No. 3, pp. 29-38.*

(Continued)

*Primary Examiner*—Shengjun Wang
(74) *Attorney, Agent, or Firm*—Brinks Hofer Gilson & Lione

(57) ABSTRACT

The present invention relates to novel ether compounds, compositions comprising ether compounds, and methods useful for treating and preventing cardiovascular diseases, dyslipidemias, dysproteinemias, and glucose metabolism disorders comprising administering a composition comprising an ether compound. The compounds, compositions, and methods of the invention are also useful for treating and preventing Alzheimer's Disease, Syndrome X, peroxisome proliferator activated receptor-related disorders, septicemia, thrombotic disorders, obesity, pancreatitis, hypertension, renal disease, cancer, inflammation, and impotence. In certain embodiments, the compounds, compositions, and methods of the invention are useful in combination therapy with other therapeutics, such as hypocholesterolemic and hypoglycemic agents.

19 Claims, 21 Drawing Sheets

U.S. PATENT DOCUMENTS

| | | | |
|---|---|---|---|
| 3,773,946 | A | 11/1973 | Creger |
| 3,930,024 | A | 12/1975 | Creger |
| 4,287,200 | A | 9/1981 | Kawamatsu et al. |
| 4,584,321 | A | 4/1986 | Manghisi et al. |
| 4,613,593 | A | 9/1986 | Yamatsu et al. |
| 4,634,719 | A | 1/1987 | Takaishi et al. |
| 4,689,344 | A | 8/1987 | Bar-Tana |
| 4,711,896 | A | 12/1987 | Bar-Tana et al. |
| 4,714,762 | A | 12/1987 | Hoefle et al. |
| 5,166,174 | A | 11/1992 | Ueno et al. |
| 5,225,439 | A | 7/1993 | Ueno et al. |
| 5,284,858 | A | 2/1994 | Ueno et al. |
| 5,380,709 | A | 1/1995 | Ueno et al. |
| 5,428,062 | A | 6/1995 | Ueno et al. |
| 5,468,755 | A * | 11/1995 | Cincotta et al. ............ 514/288 |
| 5,648,387 | A | 7/1997 | Bisgaier et al. |
| 5,750,569 | A | 5/1998 | Bisgaier et al. |
| 5,756,344 | A | 5/1998 | Onda et al. |
| 5,756,544 | A | 5/1998 | Bisgaier et al. |
| 5,783,600 | A | 7/1998 | Bisgaier et al. |
| 5,834,596 | A | 11/1998 | Ageland et al. |
| 5,886,034 | A | 3/1999 | Ueno et al. |
| 6,004,925 | A | 12/1999 | Dasseux et al. |
| 6,037,323 | A | 3/2000 | Dasseux |
| 2005/0004082 | A1 | 1/2005 | Dasseux et al. |

FOREIGN PATENT DOCUMENTS

| | | |
|---|---|---|
| EP | 0 749 751 A2 * | 6/1996 |
| FR | 2013926 | 4/1970 |
| GB | 1269658 | 3/1972 |
| WO | WO 96/30328 | 10/1996 |
| WO | WO 98/30530 | 7/1998 |
| WO | WO 99/00116 | 1/1999 |

OTHER PUBLICATIONS

Ackerly et al., 1995, "A novel approach to dual-acting thromboxane receptor antagonist/synthase inhibitors based on the link of 1,3-dioxane-thrombaxane receptor antagonists and -thromboxane synthase inhibitors", J. Med. Chem. 38: 1608-1628.

Acton et al., 1996, "Identification of scavenger receptor SR-BI as a high density lipoprotein receptor", Science. 271(5248):518-20.

Ahrens et al., 1967, "A direct method for preparing pyridoxal and 4-pyridoxic acid (1)", J. Heterocycl. Chem. 4:625-26.

Alexander, K et al., 1948, "4,4'-Dichlorodibutyl ether and its derivatives from tetrahydrofuran", J. Am. Chem. Soc. 70:1839-42.

Badimon et al., 1992, "Role of high density lipoproteins in the regression of atherosclerosis", Circulation 86(6 Suppl):11186-94.

Bailey, et al., 1990, "Convenient general method for the preparation of primary alkeyllithiums by lithium-iodine exchange", J. Org. Chem. 55:5404-06.

Barrans et al., 1996, "Pre-beta HDL; structure and metabolism", Biochim. Biophys. Acta. 1300(2):73-85.

Becker et al., 1982, "Intramolecular photoaddition of terminal allenes to conjugated cyclohexenones", J. Org. Chem. 47: 3297-3310.

Bernady et al., 1979, "Prostaglandins and congeners. 20.1,2 Synthesis of prostaglandins via conjugate addition of lithium trans-1-alkenyltrialkylalanate reagents. A novel reagent for conjugate 1,4-additions", J. Org. Chem. 44:1438-47.

Bhanot et al., 1977, "Synthetic Studies on Terpenoids.5.Syntheses of γ- and δ-Lactones from β-(2,7-Dimethyl-1,2-dihydroxycycloheptyl)propionic Acid", J. Org. Chem. 42:1623-1627.

Bisgaier et al., 1998, "A novel compound that elevates high density lipoprotein and activates the peroxisome proliferator activated receptor", J Lipid Res. 39(1):17-30.

Bisgaier et al., 1997, "Attenuation of plasma low density lipoprotein cholesterol by select 3-hydroxy-3-methylglutaryl coenzyme A reductase inhibitors in mice devoid of low density lipoprotein receptors", J Lipid Res 38(12):2502-2515.

Bongini et al., 1979, "A simple and practical method for tetrahydropyranylation of alcohols and phenols", Synthesis 618-620.

Brown et al., 1965, "Selective reductions. VII. Reaction of lithium trimethoxyluminohydride with selected organic compounds containing representative functional groups", J. Am. Chem. Soc. 87:5614-20.

Brown et al., 1980, "Selective reductions. 26 Lithium triethylborohydride as an exceptionally powerful and selective reducing agent in organic synthesis. Exploration of the reactions with selected organic compounds containing representative functional groups, 1,2", J. Org. Chem 45:1-12.

Bruce et al., 1998, "Plasma lipid transfer proteins, high-density lipoproteins, and reverse cholesterol transport", Annu Rev Nutr. 1998;18:297-330.

Campagna et al., 1994, "Cyclic Amidine Analogues of Taurine and Homotaurine: Synthesis and Effects on Rat Skeletal Muscle", Farmaco, Ed. Sci 49:653-658.

Carothers, 1924, "Platinum oxide as a catalyst in the reduction of organic compounds. V. The preparation of primary alcohols by the catalytic hydrogenation of aldehydes1", J. Am. Chem. Soc. 46:1675-83.

Cerny et al., 1969, "Properties of Sodium Bis-(2-Methoxyethoxy__Aluminum Hydride", Collect Czech Chem Commn. 34:1025-33.

Chadwick et al., 1979, "Reaction between N-Alkylpyrroles and Alkyl-lithium Reagents"J. Chem Soc., Perkin Trans. I 2845.

Chaikin et al., 1949, "Lithium Borohydride as a Reducing Agent", J. Am. Chem. Soc. 71:3245-46.

Chen et al., 1998, "Asymmetric total synthesis of phosphatidylinositol 3-phosphate and 4-phosphate derivatives", J. Org. Chem. 63:6511-22.

Comins et al., 1981, "A one pot synthesis of unsymmetrical secondary alcohols from two grignard reagents", Tetrahedron Lett. 22:1085-88.

Corbridge, 1985, "Phosphorus: An Outline of Its Chemistry, Biochemistry and Technology", Studies in Inorganic Chemistry, 3RD ed, pp. 357-395.

Corey et al., 1978, "Total Synthesis of (S)-12—Hydroxy-5,8,14-cis,-10-trans-eicosatetraenoic Acid (Samuelssons's HETE)", J. Am. Chem Soc. 100:1942-1943.

Corey et al., 1979, "Useful procedures for the oxidation of alcohols involving pyridinum dichromate in aprotic media", Tetrahedron Lett. 5: 399-402.

Corey et al., 1967, "A useful method for the conversion of alcohols into iodides", J. Org. Chem. 32: 4160-4161.

Danheiser et al., 1991, "A Practical and Efficient Method for Synthesis of β-Lactones", J. Org. Chem. 56:1176-1185.

Dansky HM, Fisher EA, 1999, "High-density lipoprotein and plaque regression: the good cholesterol gets even better", Circulation 100(17):1762-3.

Decossin et al., 1997, "Subclasses of LpA-I in coronary artery disease: distribution and cholesterol efflux ability", Eur J Clin Invest. 27(4):299-307.

DeSarlo et al., 1971, "Isoxazolin-5-one", J. Chem Soc.86-89.

Eaton et al., 1972, "Hydroxypropylation", J. Org. Chem. 37:1947-50.

Ehlinger, et al., 1980, "Silicon in Synthesis. 10. The (trimethylsilyl)allyl Anion: A β-Acyl anion equivalent for the conversion of aldehydes and ketones into λ-lactones", J. Am. Chem. Soc. 102:5004-11.

Eisch et al., 1978, "Synthesis of lactones via the titanium-catalyzed hydromagnesiation of alkenols", J. Organo. Met. Chem. 160:C8-C12.

Fielding & Fielding, 1995, "Molecular physiology of reverse cholesterol transport", J Lipid Res. 36(2):211-28.

Fraser et al., 1985, "Acidity measurements in the THF. V.1 Heteroaromatic compounds containing 5-membered rings", Can. J. Chem 63:3505-09.

Garegg et al., 1980, "Novel Reagent System for converting a Hydroxy-group into an Iodo-group in carbohydrates with Inversion of Configuration", J.C.S. Perkin I 2866-2868.

Gearing et al., 1993, "Interaction of the peroxisome-proliferator-activated receptor and retinoid X receptor", Proc. Natl. Acad. Sci. USA 90(4):1440-1444.

Gigg et al., 1967, "The Preparation of Unsymmetrical Diglycerides", J. Chem. Soc., C, 431-434.

Green and Kehinde, 1975, "An established preadipose cell line and its differentiation in culture. II. Factors affecting the adipose conversion", Cell. 5(1):19-27.

Greene, T.W., 1999, "Protection for the Hydroxyl Group, Including 1,2- and 1,3-Diols", Protective Groups in Organic Synthesis, 3rd Edition 17-245.

Harris and Kletzien, 1994, "Localization of a pioglitazone response element in the adipocyte fatty acid-binding protein gene", Mol Pharmacol. 45(3):439-45.

Hayden and Ma, 1992, "Molecular genetics of human lipoprotein lipase deficiency", Mol Cell Biochem. 113(2)171-6.

Heyman, et al., 1992, "9-cis retinoic acid is a high affinity ligand for the retinoid X receptor", Cell 68(2):397-406.

Hidaka and Fidge, 1992, "Affinity purification of the hepatic high-density lipoprotein receptor identifies two acidic glycoproteins and enables further characterization of their binding properties", Biochem. J. 15(Pt1):161-7.

Hirano et al., 1997, "Genetic cholesteryl ester transfer protein deficiency is extremely frequent in the Omagari area of Japan. Marked hyeralphalipoproteinemia caused by CETP gene mutation is not associated with longevity", Arterioscler. Thromb. Vasc. Biol. 17(6):1053-1059.

Hoyer et al., 1986, "Catalysis by acidic clay of the protective tetrahydropyranylation of alcohols and phenols", Synthesis 655-57.

Hudlicky, M., 1996, "Reduction of esters and lactones of coraboxylic acids", Reductions in Organic Chemistry, 2nd Ed., pp. 212-217.

Hudlicky, M, 1996, "Reduction of aldehydes and their derivatives", Reductions in Organic Chemistry, 2nd ed. pp. 137-139.

Ishibashi, et al., 1994, "Massive xanthomatosis and atherosclerosis in cholesterol-fed low density lipoprotein receptor-negative mice", J Clin Invest. 93(5):1885-93.

Ishibashi et al., 1993, "Hypercholesterolemia in low density lipoprotein receptor knockout mice and its reversal by adenovirus-mediated gene delivery", J Clin Invest. 92(2):883-93.

Isseman and Green, 1990, "Activation of a member of the steroid hormone receptor superfamily by peroxisome proliferators", Nature 347(6294):645-650.

Iwai et al., 1966, "Studies on acetylenic compounds. XLIV. 1 Synthesis of 3-aminoisoxazoles and 3-hydroxyisoxazoles (3-isoxazolones)", Chem. Pharm. Bull. 14:1277-86.

Johnston et al., 1988, "A new, mild heterogeneous catalyst for the tetrahydropyranylation of alcohols andphelos", Synthesis 393-4.

Joule et al., 1995, "Reactivity of Aromatic Heterocycles: Organometallic Derivatives", Heterocyclic Chemistry, 3rd ed., pp. 30-42.

Katritzky et al., 1993, "Generation and Reactions of sp2-Carbanionic Centers in the Vicinity of Heterocyclic Nitrogen Atoms", Adv. Het. Chem. 56:155-303.

Keller and Wahli, 1993, "Peroxisome proliferator-activated receptors—A link between endocrinology and Nutrition?", TEM, 4:291-296.

Keller et al., 1993, "Fatty acids and retinoids control lipid metabolism through activation of peroxisome proliferator-activated receptor-retinoid X receptor heterodimers", Proc. Natl. Acad. Sci. USA 90(6):2160-2164.

Kessar et al., 1997, "Lewis acid complexion of tertiary animes and related compounds: A strategy for a $\alpha$-deprotonation and stereocontrol", Chem. Rev. 97:721-37.

Kliewer et al., 1992, "Convergence of 9-cis retinoic acid and peroxisome proliferator signalling pathways through heterodimer formation of their receptors", Nature. 27;358(6389):771-4.

Kletzein et al., 1991, "Enhancement of adipocyte differentiation by an insulin-sensitizing agent", Mol Pharmacol 41(2):393-398.

Kurata et al., 1998, "A candidate high density lipoprotein (HDL) receptor, HB2, with possible multiple functions shows sequence homology with adhesion molecules", J. Atherosclerosis and Thrombosis 4(3):112-7.

Kurz et al., 1985, "Anomalous selectivities in methyl transfers to water: An explanation using free energy surfaces which model the effects of non-equilibrium solvation", Isr. J. Chem. 26:339-48.

Kurz et al., 1986, "Evidence for a rate-determining solvation change in methyl transfer to water. Solvent dependence of H2O/D2O kinetic isotope effects", J. Am. Chem 108:2960-68.

Lagrost et al., 1996, "Opposite effects of cholesteryl ester transfer protein and phospholipid transfer protein on the size distribution of plasma high density lipoproteins. Physiological relevance in alcoholic patients", J Biol Chem. 271(32):19058-65.

Landshulz et al., 1996, "Regulation of scavenger receptor, class B, type I, a high density lipoprotein receptor, in liver and steroidogenic tissues of the rat", J. Clin. Invest. 98(4):984-995.

Larock, 1989, Comprehensive Organic Transformations; Ch. 6, VCH: New York, pp. 446-448.

Lazarow and Fujiki, 1985, "Biogenesis of peroxisomes", Annu Rev Cell Biol. 1:489-530.

Levin et al., 1992, "9-cis retinoic acid stereoisomer binds and activates the nuclear receptor RXR alpha", Nature 355(6358):359-61.

Ludwig et al., 1989, "Rapid and efficient synthesis of nucleoside 5'-O-(1-thiotriphosphates), 5'-Triphosphates and 2',3'—Cyclophosphorothioates using 2-Chloro-4H-1,3,2-benzodioxaphosphorin-4-one", J. Org. Chem. 54:631-35.

Maddaford et al., 1993, "A general asymmetric synthesis of (-)-$\alpha$-Dimethylretrodendrin and its diastereomers", J. Org. Chem 58:4132-38.

March, J, 1992, Advanced Organic Chemistry; reactions Mechanisms, and Structure, 4th ed., pp. 248-272, 1196-1198, 437-438, 920-929.

Masamune et al., 1976, "Tylonolide hemiacetal, the aglycone of tylosin, and its partial synthesis [letter]", J Am Chem Soc. 98(24):7874-5.

Masayuma et al., 2000, "Regio- and diastereocontrol in carbonyl allylation by 1-halobut-2-enes with Tin(II) halides", J. Org Chem. 65(2):494-8.

Menger et al., 1981, "Synthetically useful oxidations at solid sodium permanganate surfaces", Tetrahedron Lett. 22:1655-56.

Miyashita et al., 1977, "Pyridinium p-Toluenesulfonate. A mild and efficient catalyst for the tetrahydropyranylation of alcohols", J. Org. Chem 42:3772-74.

Moffet et al., 1963, "2-(1-Pyrrolidyl)Propanol", Org. Synth. Collect 4:834-5.

Mulzer, 1995 Comprehensive Organic Functional Group Transformations Oxford 5 pp. 161.

Myers et al., 1992, "Studies on the thermal generation and reactivity of a class of ($\sigma$, $\pi$)- 1,4-biradicals", J. Am. Chem. Soc. 114:9369-86.

Nemali et al., 1988, "Comparison of constitutive and inducible levels of expression of peroxisomal beta-oxidation and catalase genes in liver and extrahepatic tissues of rat", Cancer Res. 48(18):5316-24.

Nystrom et al., 1947, "Reduction of Organic Compounds by Lithium Aluminum Hydride", J. Am. Chem Soc. 69:1197-1199.

Nystrom et al., 1949, "Lithium borohydride as a reducing agent", J. Am. Chem. 71:3245-47.

Ogata et al., 1969, "Kinetics of the baeyer—Villiger reaction of benzaldehydes with perbenzoic acid in aquoorganic solvents", J. Org. Chem 34: 3985-91.

Olah et al., 1984, "N-Formylmorpholine: A New and Effective Formylating Agent for the Preparation of Aldehydes and Dialkyl (1-Formylalkyl)phosphonates from Grignard or Organolithium Reagents", J, Org. Chem 49:3856-3857.

Okamoto et al., 1985, "Synthesis of Alkyl Dihydrogenphosphate by the Reaction of Alcohols and Silyl Polyphosphate", Bull Chem. Soc. Jpn. 58:3393-3394.

Olah et al., 1987, "Formylating Agents", Chem Rec. 87:4, 671-686.

Olah et al., 1979, "Transformations with Chlorotrimethylsilane/Sodium Iodide, a Convenient in Situ Iodotrimethylsilane Reagent", J . Org. Chem 44:8, 1247-1251.

Oster et al., 1983, "Generation and Reactions of the Dianion of 3-Hydroxy-5-methylisoxazole, a convenient $\beta$-Keto Amide Synthon", J. Org. Chem 48:4307-4311.

Parra et al., 1992, "A case-control study of lipoprotein particles in two populations at contrasting risk for coronary heart disease. The ECTIM Study", Arterioscler Thromb. 12:701-707.

Plourde,. G., 1983, "Impact of obesity on glucose and lipid profiles in adolescents at different age groups in relation to adulthood", BMC Family Practice, 3(18): 1-14.

Pop et al., 1997, "Allylic and Phenolic Phosphate Esters of Dexanabinol", Org. Prep. And Proc. Int. 29:341-347.

Ramirez et al., 1978, "Phosphorylation by means of cyclic enediol phosphates1", Acc. Chem. Res. 11:239.

Raunio et al., 1957, "Addition of Propargyl Acetal to Cyclohexanone in the Presence of Sodamide", J. Org. Chem 22:570.

Reaven, 1993, "Role of insulin resistance in human disease (syndrome X): an expanded definition", Annu Rev Med. 44:121-31.

Reddy and Lalwani, 1983, "Carcinogenesis by hepatic peroxisome proliferators: evaluation of the risk of hypolipidemic drugs and industrial plasticizers to humans", Crit Rev Toxicol. 12(1)1-58.

Reppe, W et al., 1955, Am. Chem, 595: 169-178.

Rigotti et al., 1996, "Regulation by adrenocorticotropic hormone of the in vivo expression of scavenger receptor class B type I (SR-BI), a high density lipoprotein receptor, in steroidogenic cells of the murine adrenal gland", J. Biol Chem 271(52):33545-9.

Robins and Fasulo, 1997, "High density lipoproteins, but not other lipoproteins, provide a vehicle for sterol transport to bile", J Clin Invest. 99(3):380-4.

Sam et al., 1972, "Crown Polyether Chemistry. Potassium Permanganate Oxidations in Benzene", J. Am. Chem. Soc. 94:4024.

Saulnier et al., 1982, "Generation and Reactions of 3-Lithio-1-(phenylsulfonyl) indole", J. Org. Chem 47:757.

Shirley et al., 1995, "Metalation of pyrrole, 1-methylpyrrole, and 1-phenylpyrrole with n-Butyllithium", J. Org. Chem 20:225-31.

Sianesi et al., 1971, "2.4-dihydro-1H-2.1-, 3.4-Dihydro-2H-1.2- und 3.4-Dihydro- 1H-2.3-benzothiazin-S.S-dioxid", Chem. Ber. 104:1880-91.

Skinner et al., 1995, "Benzoylcyanamide from ethyl benzoyltioncarbomate", J. Am. Chem. Soc. 77:5440-42.

Smith et al., 1957, "Nitrogen Compounds of thePhosphoric and Phosphonic Acids, III, Preparation andand Properties of Amides of Phenylphosphonic and Phenylphosphonothioic Acids", J. Org. Chem. 22:265-267.

Song et al., 1999, "Prapctical asymmetric synthesis of an endothelin receptor antagonist", J. Org. Chem. 64:9658-67.

Staels and Auwerx, 1998, "Regulation of apo A-1 gene expression by fibrates", Atherosclerosis 137 Suppl:S19-23.

Stevens et al., 1982, "Further studies on the utility of sodium hypochlorite in organic synthesis. Selective oxidation of diols and direct conversion of aldehydes to esters", Tetrahedron Lett. 23:4647-4650.

Stowell et al., 1995, "A new method for the phosphorylation of alcohols and phenols", Tetrahedron Lett. 36(11):1825-26.

Sundararaman et al., 1978, "One step conversion of aldehydes to esters", Tetrahedron Lett. 19: 1627-1628.

Sweeney, 1995, "Comprehensive Organic Functional Groups Transformations", Oxford, vol. 2, pp. 104-109.

Taravel et al., 1988, "Interglycosidic 13C-1 H Coupling Constants", Tetrahedeon Lett. 29:199-202.

Tomioka et al., 1995, "Catalytic Asymmetric Conjugate Addition of Grignard Reagents Mediated by Copper(I)-Chiral Bedentate Phosphine Complex", Tetrahedron Lett. 36:4275-4278.

Tontonoz et al., 1994, "Adipocyte-specific transcription factor ARF6 is a heterodimeric complex of two nuclear hormone receptors, PPAR gamma and RXR alpha", Nucleic Acids Res. 22(25):5628-34.

Uhlmann et al., 1986, "Chemical 5'-phosphorylation of oligonucleotides valuable in automated dna synthesis", Tetrahedron Lett. 27:102326.

Ulrich, et al., 1995, "Cultured hepatocytes as investigational models for hepatic toxicity: practical applications in drug discovery and development", Toxicol Lett 82/83:107-15.

Urata et al., 1991, "Transition metal complex catalyzed carbonylation od organic halides in the presence of molecular sieves instead of base", Tetrahedron Lett. 32:36, 4733-36.

Vamecq and Draye, 1989, "Pathophysiology of peroxisomal beta-oxidation", Essays Biochem 24:115-225.

Vogtle et al., 1987, "Doubly Clamped Cope Systems", J. Org. Chem. 52:5560-5564.

Blatt ed., 1943, "Gilbert Sulfonation and Related Reactions" pp. 135-142, 160-165; Org. Synth. Coll. vol. II, Wiley, NY and Org. Synth. Coll. vol. IV, 1963, Wiley NY 529-531.

Williams et al., 1988, "Bromine as an oxidant for direct conversion of aldehydes to esters", Tetrahedron Lett. 29:5087-90.

Wilson et al., 1982, "A novel, nonoxidative method for the conversion of aldehydes to esters", J. Org. Chem. 47:1360-6.

Wroblewski and LaDue, 1995, "Lactic dehydrogenase activity in blood", Proc. Soc. Exp. Biol. Med. 90:210-213.

Yanagisawa et al., 1994 "Allylbarium Reagents: unprecedented regio- and stereoselectiv eallylation reactions of carbonyl compounds", J. Am. Chem. Soc. 116:6130-6141.

Yoshikawa et al., 1986, "Ruthenium Complex Catalyzed Regioselective Dehydrogenation of Unsymmetrical α ω-Diols", J. Org. Chem. 51:2034.

Yoshikawa et al., 1983, "Catalytic Regioselective Dehydrogenationof Unsymmetrical $\alpha,\omega$-Diols Using Ruthenium Complexes", Tetrahedron Lett. 26:2677-2680.

Yu et al., 1988,"A novel reagent for the synthesis of myo-inositol phosphates: n, n-diisopropyl dibenzyl phosphoramidite", Tetrahedron Lett. 29:979-82.

Yunker et al., 1978, "Alpha-oxygenated fatty acids occurring as amides of 2-methylene-β-alanine in a marine sponge", Tetrahedron Lett. 47:4651-52.

Xu et al., 1989, "The retinoblastoma susceptibility gene product: a characteristic pattern in normal cells and abnormal expression in malignant cells" Oncogene 4:807-812.

K F. Bernardy et al, "Prostaglandins and congeners: synthesis of 2-(w-carbalkoxyalkyl)cyclopent-2-en-1-ones intermediates for prostaglandin syntheses", Journal of Organic Chemistry, vol. 45, 1980, pp. 4702-4715.

P Friedman et al., "the gem-dimethyl effect in thiacyclodecanes" Journal of Organic Chemistry, vol. 27, 1962, pp. 1095-1096.

F Nagatsugi et al., "18F-Labeled octanoates as potential agents for cerebral fatty acid studies", Chem Pharm Bull, vol. 43, No. 4, 1995, pp. 607-615.

Y Okamoto et al, "Reaction of allykbenzene with nBuLi in tetrahydrofuran" Bull chem Soc. JPN, vol. 41, 1968, pp. 677-683.

Bisgaier CL et al., preparation of terminal carboxy or tetrazole group-containing dialkyl ethers as anticholestermics and antideabetics Retrieved from STN Database accession No. 1968:689457 & WO 9630328 A Oct. 3, 1996.

Beilstein Nr 7125912.

M Shin-Ichi et al, J Med Chem, 31(6), 1205-1209(1988).

N Ackerley et al, J Med Chem, 38(10), 1608-1628 (1995).

* cited by examiner

COMPOSITIONS COMPRISING ETHER COMPOUNDS AND PHARMACEUTICAL USES THEREFOR

This application is a division of U.S. application Ser. No. 10/305,440 filed Nov. 26, 2002, now U.S. Pat. No. 6,831,105, which is a division of U.S. application Ser. No. 09/540,739, filed Mar. 31, 2000, now U.S. Pat. No. 6,506,799, which claims the benefit of U.S. Provisional Application No. 60/127,321,filed Apr. 1, 1999, the entire contents of each of which are incorporated herein by reference.

1. FIELD OF THE INVENTION

The present invention relates to ether compounds and pharmaceutically acceptable salts thereof; methods for synthesizing the ether compounds; compositions comprising an ether compound or a pharmaceutically acceptable salt thereof; and methods for treating or preventing a disease or disorder selected from the group consisting of a cardiovascular disease, dyslipidemia, dyslipoproteinemia, a disorder of glucose metabolism, Alzheimer's Disease, Syndrome X, a peroxisome proliferator activated receptor-associated disorder, septicemia, a thrombotic disorder, obesity, pancreatitis, hypertension, renal disease, cancer, inflammation, and impotence, comprising administering a therapeutically effective amount of a composition comprising an ether compound or a pharmaceutically acceptable salt thereof. The ether compounds and compositions of the invention may also be used to reduce the fat content of meat in livestock and reduce the cholesterol content of eggs.

2. BACKGROUND OF THE INVENTION

Obesity, hyperlipidemia, and diabetes have been shown to play a casual role in atherosclerotic cardiovascular diseases, which currently account for a considerable proportion of morbidity in Western society. Further, one human disease, termed "Syndrome X" or "Metabolic Syndrome", is manifested by defective glucose metabolism (insulin resistance), elevated blood pressure (hypertension), and a blood lipid imbalance (dyslipidemia). See e.g. Reaven, 1993, *Annu. Rev. Med.* 44:121-131.

The evidence linking elevated serum cholesterol to coronary heart disease is overwhelming. Circulating cholesterol is carried by plasma lipoproteins, which are particles of complex lipid and protein composition that transport lipids in the blood. Low density lipoprotein (LDL) and high density lipoprotein (HDL) are the major cholesterol-carrier proteins. LDL are believed to be responsible for the delivery of cholesterol from the liver, where it is synthesized or obtained from dietary sources, to extrahepatic tissues in the body. The term "reverse cholesterol transport" describes the transport of cholesterol from extrahepatic tissues to the liver, where it is catabolized and eliminated. It is believed that plasma HDL particles play a major role in the reverse transport process, acting as scavengers of tissue cholesterol. HDL is also responsible for the removal non-cholesterol lipid, oxidized cholesterol and other oxidized products from the bloodstream.

Atherosclerosis, for example, is a slowly progressive disease characterized by the accumulation of cholesterol within the arterial wall. Compelling evidence supports the belief that lipids deposited in atherosclerotic lesions are derived primarily from plasma apolipoprotein B (apo B)-containing lipoproteins, which include chylomicrons, CLDL, IDL and LDL. The apo B-containing lipoprotein, and in particular LDL, has popularly become known as the "bad" cholesterol. In contrast, HDL serum levels correlate inversely with coronary heart disease. Indeed, high serum levels of HDL is regarded as a negative risk factor. It is hypothesized that high levels of plasma HDL is not only protective against coronary artery disease, but may actually induce regression of atherosclerotic plaque (e.g., see Badimon et al., 1992, *Circulation* 86:(Suppl. III)86-94; Dansky and Fisher, 1999, *Circulation* 100: 1762-3.). Thus, HDL has popularly become known as the "good" cholesterol.

2.1. Cholesterol Transport

The fat-transport system can be divided into two pathways: an exogenous one for cholesterol and triglycerides absorbed from the intestine and an endogenous one for cholesterol and triglycerides entering the bloodstream from the liver and other non-hepatic tissue.

In the exogenous pathway, dietary fats are packaged into lipoprotein particles called chylomicrons, which enter the bloodstream and deliver their triglycerides to adipose tissue for storage and to muscle for oxidation to supply energy. The remnant of the chylomicron, which contains cholesteryl esters, is removed from the circulation by a specific receptor found only on liver cells. This cholesterol then becomes available again for cellular metabolism or for recycling to extrahepatic tissues as plasma lipoproteins.

In the endogenous pathway, the liver secretes a large, very-low-density lipoprotein particle (VLDL) into the bloodstream. The core of VLDL consists mostly of triglycerides synthesized in the liver, with a smaller amount of cholesteryl esters either synthesized in the liver or recycled from chylomicrons. Two predominant proteins are displayed on the surface of VLDL, apolipoprotein B-100 (apo B-100) and apolipoprotein E (apo E), although other apolipoproteins are present, such as apolipoprotein CIII (apo CIII) and apolipoprotein CII (apo CII). When a VLDL reaches the capillaries of adipose tissue or of muscle, its triglyceride is extracted. This results in the formation of a new kind of particle called intermediate-density lipoprotein (IDL) or VLDL remnant, decreased in size and enriched in cholesteryl esters relative to a VLDL, but retaining its two apoproteins.

In human beings, about half of the IDL particles are removed from the circulation quickly, generally within two to six hours of their formation. This is because IDL particles bind tightly to liver cells, which extract IDL cholesterol to make new VLDL and bile acids. The IDL not taken up by the liver is catabolized by the hepatic lipase, an enzyme bound to the proteoglycan on liver cells. Apo E dissociates from IDL as it is transformed to LDL. Apo B-100 is the sole protein of LDL.

Primarily, the liver takes up and degrades circulating cholesterol to bile acids, which are the end products of cholesterol metabolism. The uptake of cholesterol-containing particles is mediated by LDL receptors, which are present in high concentrations on hepatocytes. The LDL receptor binds both apo E and apo B-100 and is responsible for binding and removing both IDL and LDL from the circulation. IN addition, remnant receptors are responsible for clearing chylomicrons and VLDL remnants i.e., IDL). However, the affinity of apo E for the LDL receptor is greater than that of apo B-100. As a result, the LDL particles have a much longer circulating life span than IDL particles; LDL circulates for an average of two and a half days before binding to the LDL receptors in the liver and other tissues. High serum levels of LDL, the "bad" cholesterol, are positively associated with coronary heart disease. For example, in atherosclerosis, cholesterol derived from circulating LDL accumulates in the walls of arteries. This accumulation forms bulky plaques that inhibit the flow of blood until a clot eventually forms, obstructing an artery and causing a heart attack or stroke.

Ultimately, the amount of intracellular cholesterol liberated from the LDL controls cellular cholesterol metabolism. The accumulation of cellular cholesterol derived from VLDL and LDL controls three processes. First, it reduces the cell's ability to make its own cholesterol by turning off the synthesis of HMGCoA reductase, a key enzyme in the cholesterol biosynthetic pathway. Second, the incoming LDL-derived cholesterol promotes storage of cholesterol by the action of ACAT, the cellular enzyme that converts cholesterol into cholesteryl esters that are deposited in storage droplets. Third, the accumulation of cholesterol within the cell drives a feedback mechanism that inhibits cellular synthesis of new LDL receptors. Cells, therefore, adjust their complement of LDL receptors so that enough cholesterol is brought in to meet their metabolic needs, without overloading (for a review, see Brown & Goldstein, In, The Pharmacological Basis Of Therapeutics, 8th Ed., Goodman & Gilman, Pergaman Press, NY, 1990, Ch. 36, pp. 874-896).

High levels of apo B-containing lipoproteins can be trapped in the subendothelial space of an artery and undergo oxidation. The oxidized lipoprotein is recognized by scavenger receptors on macrophages. Binding of oxidized lipoprotein to the scavenger receptors can enrich the macrophages with cholesterol and cholesteryl esters independently of the LDL receptor. Macrophages can also produce cholesteryl esters by the action of ACAT. LDL can also be complexed to a high molecular weight glycoprotein called apolipoprotein (a), also known as apo(a), through a disulfide bridge. The LDL-apo(a) complex is known as Lipoprotein(a) or Lp(a). Elevated levels of Lp(a) are detrimental, having been associated with atherosclerosis, coronary heart disease, myocardial infarction, stroke, cerebral infarction, and restenosis following angioplasty.

2.2. Reverse Cholesterol Transport

Peripheral (non-hepatic) cells predominantly obtain their cholesterol from a combination of local synthesis and uptake of preformed sterol from VLDL and LDL. Cells expressing scavenger receptors, such as macrophages and smooth muscle cells, can also obtain cholesterol from oxidized apo B-containing lipoproteins. In contrast, reverse cholesterol transport (RCT) is the pathway by which peripheral cell cholesterol can be returned to the liver for recycling to extrahepatic tissues, hepatic storage, or excretion into the intestine in bile. The RCT pathway represents the only means of eliminating cholesterol from most extrahepatic tissues and is crucial to maintenance of the structure and function of most cells in the body.

The enzyme in blood involved in the RCT pathway, lecithin:cholesterol acyltransferase (LCAT), converts cell-derived cholesterol to cholesteryl esters, which are sequestered in HDL destined for removal. LCAT is produced mainly in the liver and circulates in plasma associated with the HDL fraction. Cholesterol ester transfer protein (CETP) and another lipid transfer protein, phospholipid transfer protein (PLTP), contribute to further remodeling the circulating HDL population (see for example Bruce et al., 1998, *Annu. Rev. Nutr.* 18:297-330). PLTP supplies lecithin to HDL, and CETP can move cholesteryl ester made by LCAT to other lipoproteins, particularly apoB-containing lipoproteins, such as VLDL. HDL triglyceride can be catabolized by the extracellular hepatic triglyceride lipase, and lipoprotein cholesterol is removed by the liver via several mechanisms.

Each HDL particle contains at least one molecule, and usually two to four molecules, of apolipoprotein (apo A-I). Apo A-I is synthesized by the liver and small intestine as preproapolipoprotein which is secreted as a proprotein that is rapidly cleaved to generate a mature polypeptide having 243 amino acid residues. Apo A-I consists mainly of a 22 amino acid repeating segment, spaced with helix-breaking proline residues. Apo A-I forms three types of stable structures with lipids: small, lipid-poor complexes referred to as pre-beta-1 HDL; flattened discoidal particles, referred to as pre-beta-2 HDL, which contain only polar lipids (e.g., phospholipid and cholesterol); and spherical particles containing both polar and nonpolar lipids, referred to as spherical or mature HDL ($HDL_3$ and $HDL_2$). Most HDL in the circulating population contains both apo A-I and apo A-II, a second major HDL protein. This apo A-I- and apo A-II-containing fraction is referred to herein as the AI/AII-HDL fraction of HDL. But the fraction of HDL containing only apo A-I, referred to herein as the AI-HDL fraction, appears to be more effective in RCT. Certain epidemiologic studies support the hypothesis that the AI-HDL fraction is antiartherogenic (Parra et al., 1992, *Arterioscier. Thromb.* 12:701-707; Decossin et al., 1997, *Eur. J. Clin. Invest.* 27:299-307).

Although the mechanism for cholesterol transfer from the cell surface is unknown, it is believed that the lipid-poor complex, pre-beta-1 HDL, is the preferred acceptor for cholesterol transferred from peripheral tissue involved in RCT. Cholesterol newly transferred to pre-beta-1 HDL from the cell surface rapidly appears in the discoidal pre-beta-2 HDL. PLTP may increase the rate of disc formation (Lagrost et al., 1996, *J. Biol. Chem.* 271:19058-19065), but data indicating a role for PLTP in RCT is lacking. LCAT reacts preferentially with discoidal and spherical HDL, transferring the 2-acyl group of lecithin or phosphatidylethanolamine to the free hydroxyl residue of fatty alcohols, particularly cholesterol, to generate cholesteryl esters (retained in the HDL) and lysolecithin. The LCAT reaction requires an apoliprotein such apo A-I or apo A-IV as an activator. ApoA-I is one of the natural cofactors for LCAT. The conversion of cholesterol to its HDL-sequestered ester prevents re-entry of cholesterol into the cell, resulting in the ultimate removal of cellular cholesterol. Cholesteryl esters in the mature HDL particles of the AI-HDL fraction are removed by the liver and processed into bile more effectively than those derived from the AI/AII-HDL fraction. This may be due, in part, to the more effective binding of AI-HDL to the hepatocyte membrane. Several HDL receptor receptors have been identified, the most well characterized of which is the scavenger receptor class B, type I (SR-BI) (Acton et al., 1996, *Science* 271:518-520). The SR-BI is expressed most abundantly in steroidogenic tissues (e.g., the adrenals), and in the liver (Landshulz et al., 1996, *J. Clin. Invest.* 98:984-995; Rigotti et al., 1996, *J. Biol. Chem.* 271:33545-33549). Other proposed HDL receptors include HB1 and HB2 (Hidaka and Fidge, 1992, *Biochem J.* 15:161-7; Kurata et al., 1998, *J. Atherosclerosis and Thrombosis* 4:112-7).

While there is a consensus that CETP is involved in the metabolism of VLDL- and LDL-derived lipids, its role in RCT remains controversial. However, changes in CETP activity or its acceptors, VLDL and LDL, play a role in "remodeling" the HDL population. For example, in the absence of CETP, the HDL becomes enlarged particles that are poorly removed from the circulation (for reviews on RCT and HDLs, see Fielding & Fielding, 1995, *J. Lipid Res.*

36:211-228; Barrans et al., 1996, *Biochem. Biophys. Acta.* 1300:73-85; Hirano et al., 1997, *Arterioscler. Thromb. Vasc. Biol.* 17:1053-1059).

2.2.1. Reverse Transport of Other Lipids

HDL is not only involved in the reverse transport of cholesterol, but also plays a role in the reverse transport of other lipids, i.e., the transport of lipids from cells, organs, and tissues to the liver for catabolism and excretion. Such lipids include sphingomyelin, oxidized lipids, and lysophophatidylcholine. For example, Robins and Fasulo (1997, *J. Clin. Invest.* 99:380-384) have shown that HDL stimulates the transport of plant sterol by the liver into bile secretions.

2.3. Peroxisome Proliferator Activated Receptor Pathway

Peroxisome proliferators are a structurally diverse group of compounds that, when administered to rodents, elicit dramatic increases in the size and number of hepatic and renal peroxisomes, as well as concomitant increases in the capacity of peroxisomes to metabolize fatty acids via increased expression of the enzymes required for the β-oxidation cycle (Lazarow and Fujiki, 1985, *Ann. Rev. Cell Biol.* 1:489-530; Vamecq and Draye, 1989, *Essays Biochem.* 24:1115-225; and Nelali et al., 1988, *Cancer Res.* 48:5316-5324). Chemicals included in this group are the fibrate class of hypolipidermic drugs, herbicides, and phthalate plasticizers (Reddy and Lalwani, 1983, *Crit. Rev. Toxicol.* 12:1-58). Peroxisome proliferation can also be elicited by dietary or physiological factors, such as a high-fat diet and cold acclimatization.

Insight into the mechanism whereby peroxisome proliferators exert their pleiotropic effects was provided by the identification of a member of the nuclear hormone receptor superfamily activated by these chemicals (Isseman and Green, 1990, *Nature* 347:645-650). This receptor, termed peroxisome proliferator activated receptor α ($PPAR_\alpha$), was subsequently shown to be activated by a variety of medium and long-chain fatty acids. $PPAR_\alpha$ activates transcription by binding to DNA sequence elements, termed peroxisome proliferator response elements (PPRE), in the form of a heterodimer with the retinoid X receptor (RXR). RXR is activated by 9-cis retinoic acid (see Kliewer et al., 1992, *Nature* 358:771-774; Gearing et al., 1993, *Proc. Natl. Acad. Sci. USA* 90:1440-1444, Keller et al., 1993, *Proc. Natl. Acad. Sci. USA* 90:2160-2164; Heyman et al., 1992, *Cell* 68:397-406, and Levin et al., 1992, *Nature* 355:359-361). Since the discovery of $PPAR_\alpha$, additional isoforms of PPAR have been identified, e.g., $PPAR_\beta$, $PPAR_\gamma$ and $PPAR_\delta$, which are have similar functions and are similarly regulated.

PPREs have been identified in the enhancers of a number of genes encoding proteins that regulate lipid metabolism. These proteins include the three enzymes required for peroxisomal β-oxidation of fatty acids; apolipoprotein A-I; medium-chain acyl-CoA dehydrogenase, a key enzyme in mitochondrial β-oxidation; and aP2, a lipid binding protein expressed exclusively in adipocytes (reviewed in Keller and Whali, 1993, *TEM,* 4:291-296; see also Staels and Auwerx, 1998, *Atherosclerosis* 137 Suppl:S19-23). The nature of the PPAR target genes coupled with the activation of PPARs by fatty acids and hypolipidemic drugs suggests a physiological role for the PPARs in lipid homeostasis.

Pioglitazone, an antidiabetic compound of the thiazolidinedione class, was reported to stimulate expression of a chimeric gene containing the enhancer/promoter of the lipid-binding protein aP2 upstream of the chloroamphenicol acetyl transferase reporter gene (Harris and Kletzien, 1994, *Mol. Pharmacol.* 45:439-445). Deletion analysis led to the identification of an approximately 30 bp region responsible for pioglitazone responsiveness. In an independent study, this 30 bp fragment was shown to contain a PPRE (Tontonoz et al., 1994, *Nucleic Acids Res.* 22:5628-5634). Taken together, these studies suggested the possibility that the thiazolidinediones modulate gene expression at the transcriptional level through interactions with a PPAR and reinforce the concept of the interrelatedness of glucose and lipid metabolism.

2.4. Current Cholesterol Management Therapies

In the past two decades or so, the segregation of cholesterolemic compounds into HDL and LDL regulators and recognition of the desirability of decreasing blood levels of the latter has led to the development of a number of drugs. However, many of these drugs have undesirable side effects and/or are contraindicated in certain patients, particularly when administered in combination with other drugs.

Bile-acid-binding resins are a class of drugs that interrupt the recycling of bile acids from the intestine to the liver. Examples of bile-acid-binding resins are cholestyramine (QUESTRAN LIGHT, Bristol-Myers Squibb), and colestipol hydrochloride (COLESTID, Pharmacia & Upjohn Company). When taken orally, these positively charged resins bind to negatively charged bile acids in the intestine. Because the resins cannot be absorbed from the intestine, they are excreted, carrying the bile acids with them. The use of such resins, however, at best only lowers serum cholesterol levels by about 20%. Moreover, their use is associated with gastrointestinal side-effects, including constipation and certain vitamin deficiencies. Moreover, since the resins bind to drugs, other oral medications must be taken at least one hour before or four to six hours subsequent to ingestion of the resin, complicating heart patients' drug regimens.

The statins are inhibitors of cholesterol synthesis. Sometimes, the statins are used in combination therapy with bile-acid-binding resins. Lovastatin (MEVACOR, Merck & Co., Inc.), a natural product derived from a strain of *Aspergillus*; pravastatin (PRAVACHOL, Bristol-Myers Squibb Co.); and atorvastatin (LIPITOR, Warner Lambert) block cholesterol synthesis by inhibiting HMGCoA, the key enzyme involved in the cholesterol biosynthetic pathway. Lovastatin significantly reduces serum cholesterol and LDL-serum levels. It also slows progression of coronary atherosclerosis. However, serum HDL levels are only slightly increased following lovastatin administration. The mechanism of the LDL-lowering effect may involve both reduction of VLDL concentration and induction of cellular expression of LDL-receptor, leading to reduced production and/or increased catabolism of LDL. Side effects, including liver and kidney dysfunction are associated with the use of these drugs.

Niacin, also known as nicotinic acid, is a water-soluble vitamin B-complex used as a dietary supplement and antihyperlipidemic agent. Niacin diminishes production of VLDL and is effective at lowering LDL. It is used in combination with bile-acid-binding resins. Niacin can increase HDL when administered at therapeutically effective doses; however, its usefulness is limited by serious side effects.

Fibrates are a class of lipid-lowering drugs used to treat various forms of hyperlipidemia, elevated serum triglycerides, which may also be associated with hypercholesterolemia. Fibrates appear to reduce the VLDL fraction and modestly increase HDL; however, the effects of these drugs on serum cholesterol is variable. In the United States, fibrates have been approved for use as antilipidemic drugs, but have not received approval as hypercholesterolemia agents. For example, clofibrate (ATROMID-S, Wyeth-Ayerst Laboratories) is an antilipidemic agent that acts to lower serum triglycerides by reducing the VLDL fraction. Although ATROMID-S may reduce serum cholesterol levels in certain patient subpopulations, the biochemical response to the drug is variable, and is not always possible to predict which patients will obtain favorable results. ATROMID-S has not been shown to be effective for prevention of coronary heart disease. The chemically and pharmacologically related drug, gemfibrozil (LOPID, Parke-Davis), is a lipid regulating agent which moderately decreases serum triglycerides and VLDL cholesterol. LOPID also increases HDL cholesterol, particularly the $HDL_2$ and $HDL_3$ subfractions, as well as both the AI/AII-HDL fraction. However, the lipid response to LOPID is heterogeneous, especially among different patient populations. Moreover, while prevention of coronary heart disease was observed in male patients between the ages of 40 and 55 without history or symptoms of existing coronary heart disease, it is not clear to what extent these findings can be extrapolated to other patient populations (e.g., women, older and younger males). Indeed, no efficacy was observed in patients with established coronary heart disease. Serious side-effects are associated with the use of fibrates, including toxicity; malignancy, particularly malignancy of gastrointestinal cancer; gallbladder disease; and an increased incidence in non-coronary mortality. These drugs are not indicated for the treatment of patients with high LDL or low HDL as their only lipid abnormality.

Oral estrogen replacement therapy may be considered for moderate hypercholesterolemia in post-menopausal women. However, increases in HDL may be accompanied with an increase in triglycerides. Estrogen treatment is, of course, limited to a specific patient population, postmenopausal women, and is associated with serious side effects, including induction of malignant neoplasms; gall bladder disease; thromboembolic disease; hepatic adenoma; elevated blood pressure; glucose intolerance; and hypercalcemia.

Long chain carboxylic acids, particularly long chain α,ω-dicarboxylic acids with distinctive substitution patterns, and their simple derivatives and salts, have been disclosed for treating atherosclerosis, obesity, and diabetes (See, e.g., Bisgaier et al., 1998, *J. Lipid Res.* 39:17-30, and references cited therein; International Patent Publication WO 98/30530; U.S. Pat. No. 4,689,344; International Patent Publication WO 99/00116; and U.S. Pat. No. 5,756,344). However, some of these compounds, for example the α,ω-dicarboxylic acids substituted at their α,α'-carbons (U.S. Pat. No. 3,773,946), while having serum triglyceride and serum cholesterol-lowering activities, have no value for treatment of obesity and hypercholesterolemia (U.S. Pat. No. 4,689,344).

U.S. Pat. No. 4,689,344 discloses β,β,β',β'-tetrasubstituted-α,ω-alkanedioic acids that are optionally substituted at their α,α,α',α' positions, and alleges that they are useful for treating obesity, hyperlipidemia, and diabetes. According to this reference, both triglycerides and cholesterol are lowered significantly by compounds such as 3,3,14,14-tetramethyl-hexadecane-1,16-dioic acid. U.S. Pat. No. 4,689,344 further discloses that the β,β,β',β'-tetramethyl-alkanediols of U.S. Pat. No. 3,930,024 also are not useful for treating hypercholesterolemia or obesity.

Other compounds are disclosed in U.S. Pat. No. 4,711,896. In U.S. Pat. No. 5,756,544, α,ω-dicarboxylic acid-terminated dialkane ethers are disclosed to have activity in lowering certain plasma lipids, including Lp(a), triglycerides, VLDL-cholesterol, and LDL-cholesterol, in animals, and elevating others, such as HDL-cholesterol. The compounds are also stated to increase insulin sensitivity. In U.S. Pat. No. 4,613,593, phosphates of dolichol, a polyprenol isolated from swine liver, are stated to be useful in regenerating liver tissue, and in treating hyperuricuria, hyperlipemia, diabetes, and hepatic diseases in general.

U.S. Pat. No. 4,287,200 discloses azolidinedione derivatives with anti-diabetic, hypolipidemic, and anti-hypertensive properties. However, these administration of these compounds to patients can produce side effects such as bone marrow depression, and both liver and cardiac cytotoxicity. Further, the compounds disclosed by U.S. Pat. No. 4,287,200 stimulate weight gain in obese patients.

It is clear that none of the commercially available cholesterol management drugs has a general utility in regulating lipid, lipoprotein, insulin and glucose levels in the blood. Thus, compounds that have one or more of these utilities are clearly needed. Further, there is a clear need to develop safer drugs that are efficacious at lowering serum cholesterol, increasing HDL serum levels, preventing coronary heart disease, and/or treating existing disease such as atherosclerosis, obesity, diabetes, and other diseases that are affected by lipid metabolism and/or lipid levels. There is also is a clear need to develop drugs that may be used with other lipid-altering treatment regimens in a synergistic manner. There is still a further need to provide useful therapeutic agents whose solubility and Hydrophile/Lipophile Balance (HLB) can be readily varied.

Citation or identification of any reference in Section 2 of this application is not an admission that such reference is available as prior art to the present invention.

3. SUMMARY OF THE INVENTION

In one embodiment, the invention provides novel compounds having the general formula I:

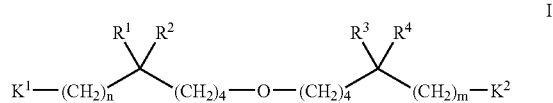

and pharmaceutically acceptable salts thereof, wherein:

$R^1$, $R^2$, $R^3$, and $R^4$ are independently selected from the group consisting of ($C_1$-$C_6$)alkyl, ($C_2$-$C_6$)alkenyl, ($C_2$-$C_6$)alkynyl, phenyl, and benzyl; or $R^1$, $R^2$, and the carbon to which they are attached are taken together to form a ($C_3$-$C_7$)cycloalkyl group; or $R^3$, $R^4$, and the carbon to which they are attached are taken together to form a ($C_3$-$C_7$)cycloalkyl group; or $R^1$, $R^2$, and the carbon to which they are attached are taken together to form a ($C_3$-$C_7$)cycloalkyl group and $R^3$, $R^4$, and the carbon to which they are attached are taken together to form a ($C_3$-$C_7$)cycloalkyl group, with the proviso that none of $R^1$, $R^2$, $R^3$, or $R^4$ is —$(CH_2)_{0-4}$C≡CH;

n and m are independent integers ranging from 0 to 4;

$K^1$ and $K^2$ are independently selected from the group consisting of —$CH_2OH$, —C(O)OH, —CHO, —C(O)$OR^5$, —OC(O)$R^5$, —$SO_3H$,

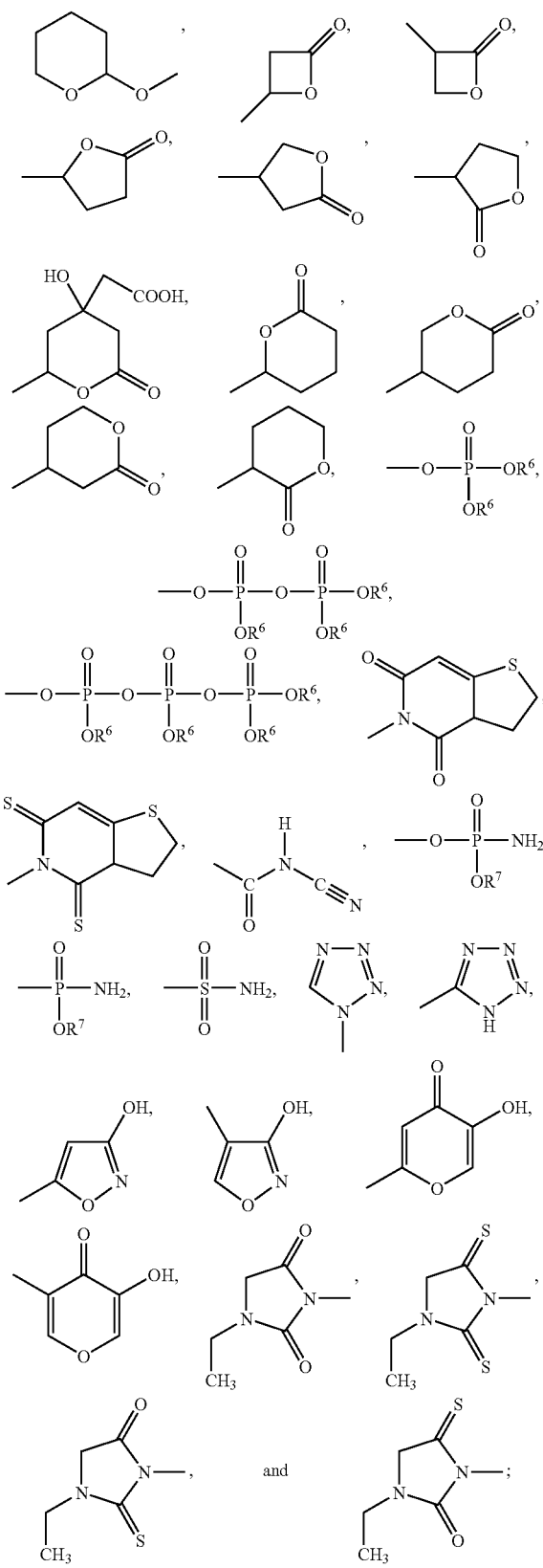

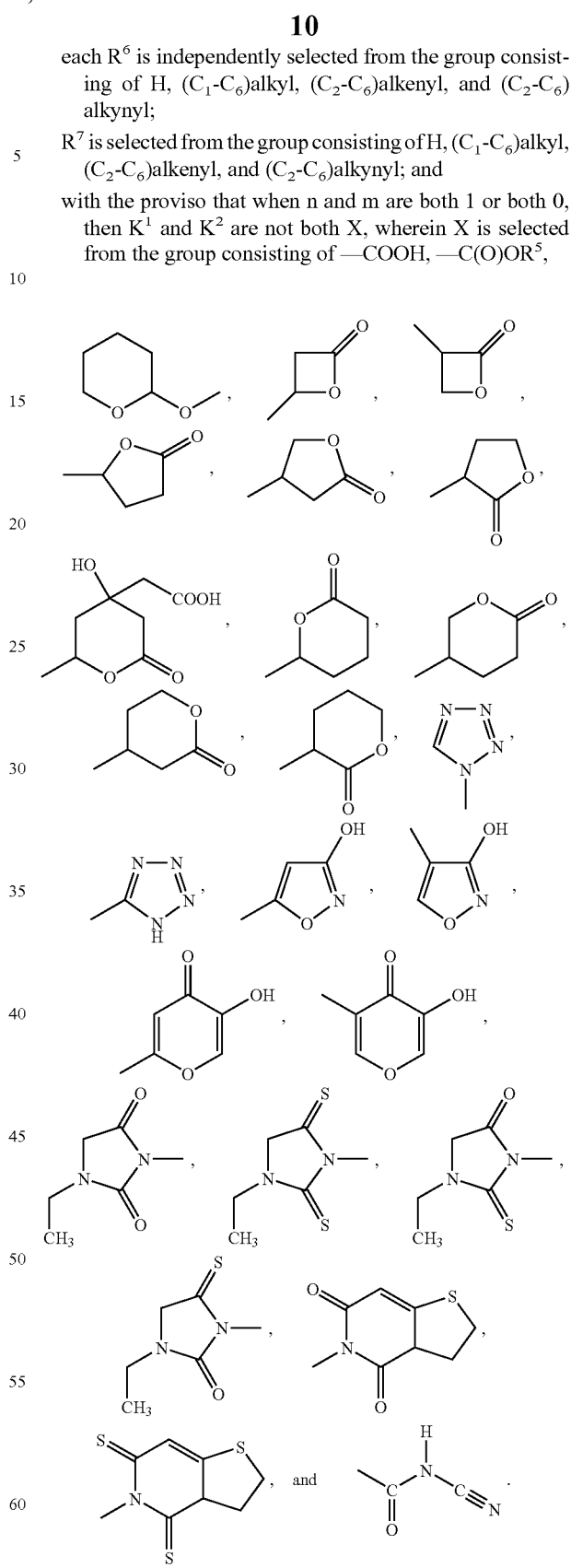

$R^5$ is selected from the group consisting of $(C_1-C_6)$alkyl, $(C_2-C_6)$alkenyl, $(C_2-C_6)$alkynyl, phenyl, and benzyl;

each $R^6$ is independently selected from the group consisting of H, $(C_1-C_6)$alkyl, $(C_2-C_6)$alkenyl, and $(C_2-C_6)$alkynyl;

$R^7$ is selected from the group consisting of H, $(C_1-C_6)$alkyl, $(C_2-C_6)$alkenyl, and $(C_2-C_6)$alkynyl; and with the proviso that when n and m are both 1 or both 0, then $K^1$ and $K^2$ are not both X, wherein X is selected from the group consisting of —COOH, —C(O)OR$^5$, In another embodiment, the invention provides novel compounds having the general formula I, and pharmaceutically acceptable salts thereof, wherein:

$R^1$, $R^2$, $R^3$, and $R^4$ are independently selected from the group consisting of $(C_1$-$C_6)$alkyl, $(C_2$-$C_6)$alkenyl, $(C_2$-$C_6)$alkynyl, phenyl, and benzyl; or $R^1$, $R^2$, and the carbon to which they are attached are taken together to form a $(C_3$-$C_7)$cycloalkyl group; or $R^3$, $R^4$, and the carbon to which they are attached are taken together to form a $(C_3$-$C_7)$cycloalkyl group; or $R^1$, $R^2$, and the carbon to which they are attached are taken together to form a $(C_3$-$C_7)$cycloalkyl group and $R^3$, $R^4$, and the carbon to which they are attached are taken together to form a $(C_3$-$C_7)$cycloalkyl group, with the proviso that none of $R^1$, $R^2$, $R^3$, or $R^4$ is $-(CH_2)_{0-4}C\equiv CH$;

n and m are independent integers ranging from 0 to 4;

$K^1$ and $K^2$ are independently selected from the group consisting of $-CH_2OH$, $-C(O)OH$, $-CHO$, $-C(O)OR^5$, $-OC(O)R^5$, $-SO_3H$,

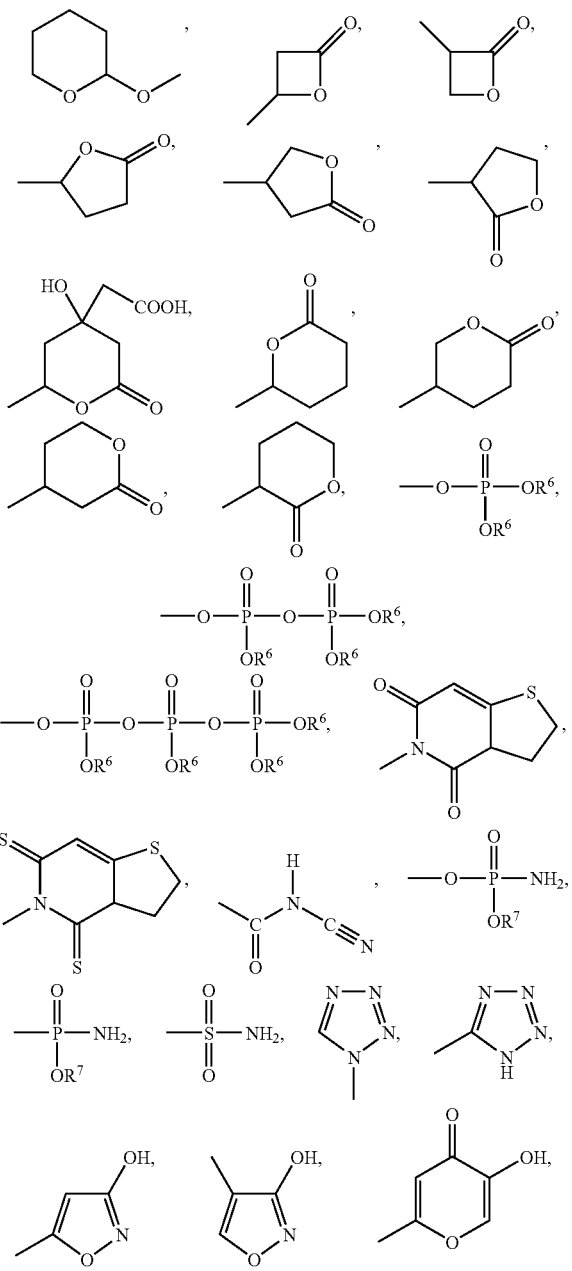

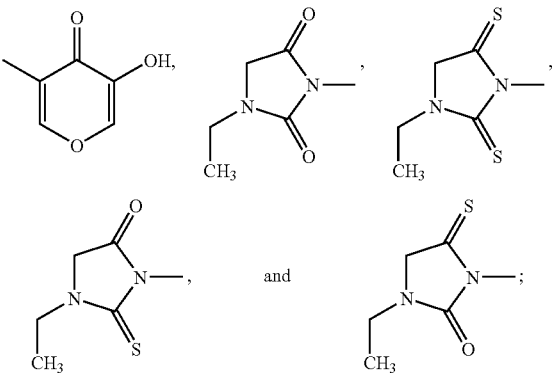

$R^5$ is selected from the group consisting of $(C_1$-$C_6)$alkyl, $(C_2$-$C_6)$alkenyl, $(C_2$-$C_6)$alkynyl, phenyl, and benzyl;

each $R^6$ is independently selected from the group consisting of H, $(C_1$-$C_6)$alkyl, $(C_2$-$C_6)$alkenyl, and $(C_2$-$C_6)$alkynyl;

$R^7$ is selected from the group consisting of H, $(C_1$-$C_6)$alkyl, $(C_2$-$C_6)$alkenyl, and $(C_2$-$C_6)$alkynyl; and with the proviso that when n and m are both 1 or both 0, then $K^1$ and $K^2$ are not both X, wherein X is selected from the group consisting of $-COOH$, $-C(O)OR^5$,

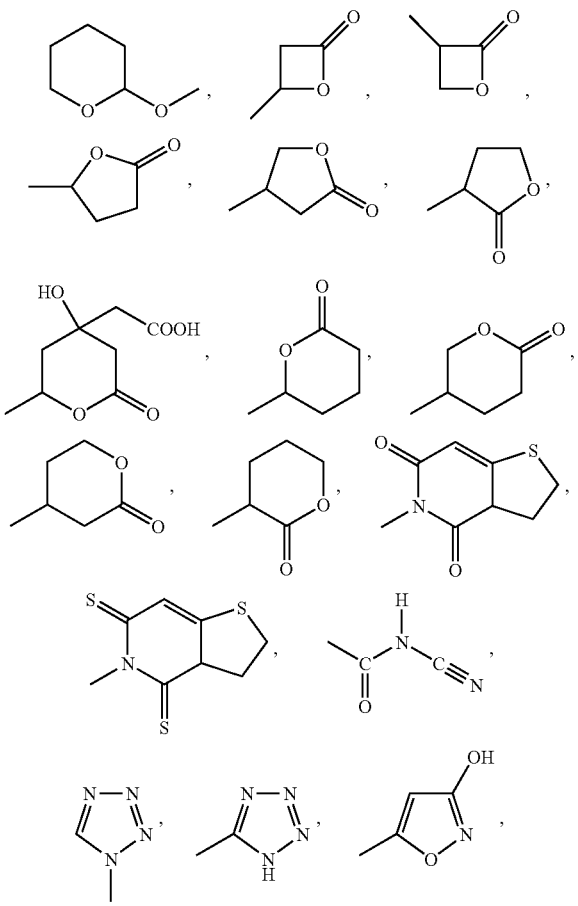

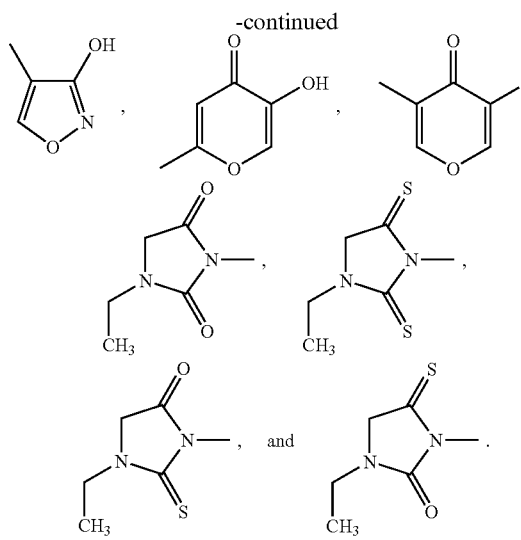

In yet another embodiment, the invention provides novel compounds having the general formula I, and pharmaceutically acceptable salts thereof, wherein:

$R^1$, $R^2$, $R^3$, and $R^4$ are independently selected from the group consisting of ($C_1$-$C_6$)alkyl, ($C_2$-$C_6$)alkenyl, ($C_2$-$C_6$)alkynyl, phenyl, and benzyl; or $R^1$, $R^2$, and the carbon to which they are attached are taken together to form a ($C_3$-$C_7$)cycloalkyl group; or $R^3$, $R^4$, and the carbon to which they are attached are taken together to form a ($C_3$-$C_7$)cycloalkyl group; or $R^1$, $R^2$, and the carbon to which they are attached are taken together to form a ($C_3$-$C_7$)cycloalkyl group and $R^3$, $R^4$, and the carbon to which they are attached are taken together to form a ($C_3$-$C_7$)cycloalkyl group, with the proviso that none of $R^1$, $R^2$, $R^3$, or $R^4$ is —$(CH_2)_{0-4}$C≡CH;

n and m are independent integers ranging from 0 to 4;

$K^1$ is selected from the group consisting of —$CH_2OH$, —OC(O)$R^5$, —CHO, —$SO_3H$,

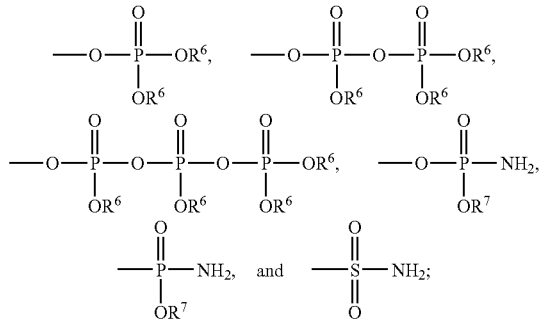

$K^2$ is selected from the group consisting of —$CH_2OH$, —C(O)OH, —CHO, —C(O)$OR^5$, —OC(O)$R^5$, —$SO_3H$,

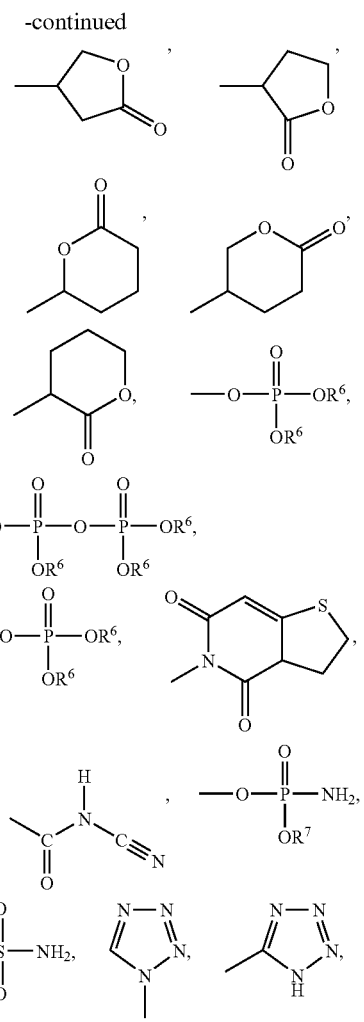

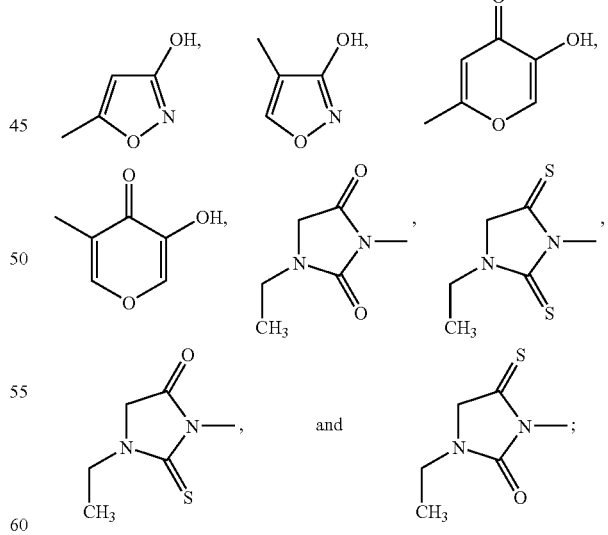

$R^5$ is selected from the group consisting of ($C_1$-$C_6$)alkyl, ($C_2$-$C_6$)alkenyl, ($C_2$-$C_6$)alkynyl, phenyl, and benzyl;

each $R^6$ is independently selected from the group consisting of H, ($C_1$-$C_6$)alkyl, ($C_2$-$C_6$)alkenyl, and ($C_2$-$C_6$)alkynyl;

$R^7$ is selected from the group consisting of H, $(C_1\text{-}C_6)$alkyl, $(C_2\text{-}C_6)$alkenyl, and $(C_2\text{-}C_6)$alkynyl; and with the proviso that when n and m are both 1 or both 0, then $K^1$ and $K^2$ are not both X, wherein X is selected from the group consisting of —COOH, —C(O)OR$^5$,

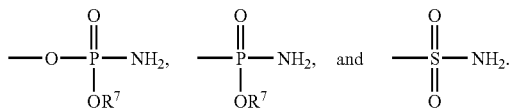

In yet another embodiment, the invention provides novel compounds having the general formula I and pharmaceutically acceptable salts thereof, wherein:

$R^1$, $R^2$, $R^3$, and $R^4$ are independently selected from the group consisting of $(C_1\text{-}C_6)$alkyl, $(C_2\text{-}C_6)$alkenyl, $(C_2\text{-}C_6)$alkynyl, phenyl, and benzyl; or $R^1$, $R^2$, and the carbon to which they are attached are taken together to form a $(C_3\text{-}C_7)$cycloalkyl group; or $R^3$, $R^4$, and the carbon to which they are attached are taken together to form a $(C_3\text{-}C_7)$cycloalkyl group; or $R^1$, $R^2$, and the carbon to which they are attached are taken together to form a $(C_3\text{-}C_7)$cycloalkyl group and $R^3$, $R^4$, and the carbon to which they are attached are taken together to form a $(C_3\text{-}C_7)$cycloalkyl group, with the proviso that none of $R^1$, $R^2$, $R^3$, or $R^4$ is —$(CH_2)_{0-4}C\equiv CH$;

n and m are independent integers ranging from 0 to 4;

$K^1$ and $K^2$ are independently selected from the group consisting of —CH$_2$OH, —OC(O)R$^5$, —CHO, —SO$_3$H,

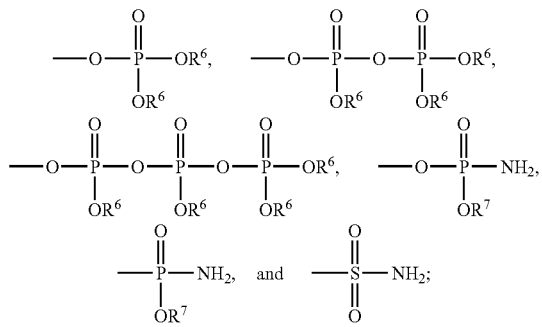

$R^5$ is selected from the group consisting of $(C_1\text{-}C_6)$alkyl, $(C_2\text{-}C_6)$alkenyl, $(C_2\text{-}C_6)$alkynyl, phenyl, and benzyl;

each $R^6$ is independently selected from the group consisting of H, $(C_1\text{-}C_6)$alkyl, $(C_2\text{-}C_6)$alkenyl, and $(C_2\text{-}C_6)$alkynyl;

$R^7$ is selected from the group consisting of H, $(C_1\text{-}C_6)$alkyl, $(C_2\text{-}C_6)$alkenyl, and $(C_2\text{-}C_6)$alkynyl; and with the proviso that when n and m are both 1 or both 0, then $K^1$ and $K^2$ are not both X, wherein X is selected from the group consisting of —COOH, —C(O)OR$^5$,

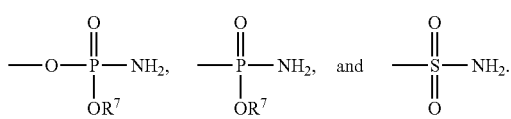

In still another embodiment, the invention provides novel compounds having the general formula I, and pharmaceutically acceptable salts thereof, wherein:

$R^1$, $R^2$, $R^3$, and $R^4$ are independently selected from the group consisting of $(C_1\text{-}C_6)$alkyl, $(C_2\text{-}C_6)$alkenyl, $(C_2\text{-}C_6)$alkynyl, phenyl, and benzyl; or $R^1$, $R^2$, and the carbon to which they are attached are taken together to form a $(C_3\text{-}C_7)$cycloalkyl group; or $R^3$, $R^4$, and the carbon to which they are attached are taken together to form a $(C_3\text{-}C_7)$cycloalkyl group; or $R^1$, $R^2$, and the carbon to which they are attached are taken together to form a $(C_3\text{-}C_7)$cycloalkyl group and $R^3$, $R^4$, and the carbon to which they are attached are taken together to form a $(C_3\text{-}C_7)$cycloalkyl group, with the proviso that none of $R^1$, $R^2$, $R^3$, or $R^4$ is —$(CH_2)_{0-4}C\equiv CH$;

n and m are independent integers ranging from 0 to 4;

$K^1$ and $K^2$ are independently —CH$_2$OH or —OC(O)R$^5$; and $R^5$ is selected from the group consisting of $(C_1\text{-}C_6)$alkyl, $(C_2\text{-}C_6)$alkenyl, $(C_2\text{-}C_6)$alkynyl, phenyl, and benzyl.

The compounds of formula I and pharmaceutically acceptable salts thereof are useful for treating or preventing cardiovascular diseases, dyslipidemias, dyslipoproteinemias, disorders of glucose metabolism, Alzheimer's Disease, Syndrome X, PPAR-associated disorders, septicemia, thrombotic disorders, obesity, pancreatitis, hypertension, renal diseases, cancer, inflammation, or impotence.

In another embodiment, the invention comprises a compound of the formula IV:

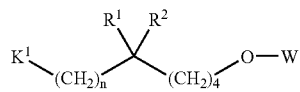

wherein:

n is an integer ranging from 1 to 4;

$K^1$ selected from the group consisting of —CH$_2$OH, —C(O)OH, —CHO, —C(O)OR$^5$, —OC(O)R$^5$, —SO$_3$H,

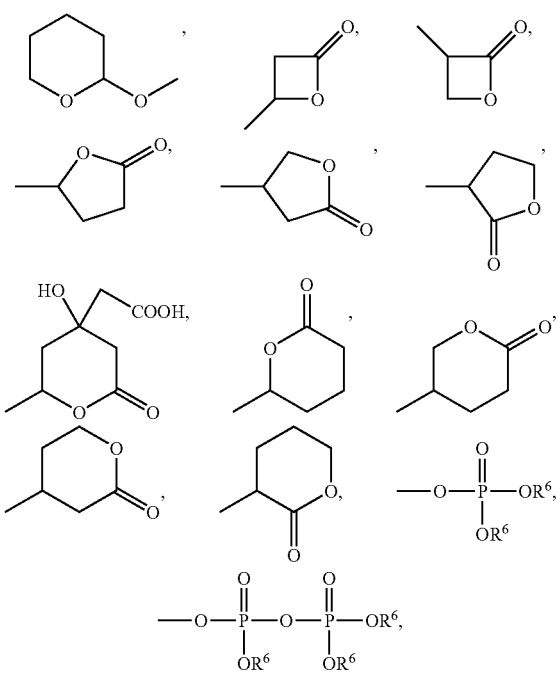

R¹, and R² are independently selected from the group consisting of (C₁-C₆)alkyl, (C₂-C₆)alkenyl, (C₂-C₆)alkynyl, phenyl, and benzyl; or R¹, R², and the carbon to which they are attached are taken together to form a (C₃-C₇) cycloalkyl group; or R³, R⁴, and the carbon to which they are attached are taken together to form a (C₃-C₇) cycloalkyl group; or R¹, R², and the carbon to which they are attached are taken together to form a (C₃-C₇) cycloalkyl group and R³, R⁴, and the carbon to which they are attached are taken together to form a (C₃-C₇) cycloalkyl group, with the proviso that none of R¹, R², R³, or R⁴ is —(CH$_2$)$_{0-4}$C≡CH;

R⁵ is selected from the group consisting of (C₁-C₆)alkyl, (C₂-C₆)alkenyl, (C₂-C₆)alkynyl, phenyl, and benzyl;

each R⁶ is independently selected from the group consisting of H, (C₁-C₆)alkyl, (C₂-C₆)alkenyl, and (C₂-C₆)alkynyl;

R⁷ is selected from the group consisting of H, (C₁-C₆)alkyl, (C₂-C₆)alkenyl, and (C₂-C₆)alkynyl; and W is selected from the group consisting of H, (C₁-C₆)alkyl, and a hydroxy protecting group.

In another embodiment, the invention provides a compound of the formula V:

wherein:

n is an integer ranging from 1 to 4;

K¹ selected from the group consisting of —CH$_2$OH, —C(O)OH, —CHO, —C(O)OR⁵, —OC(O)R⁵, —SO$_3$H, -continued

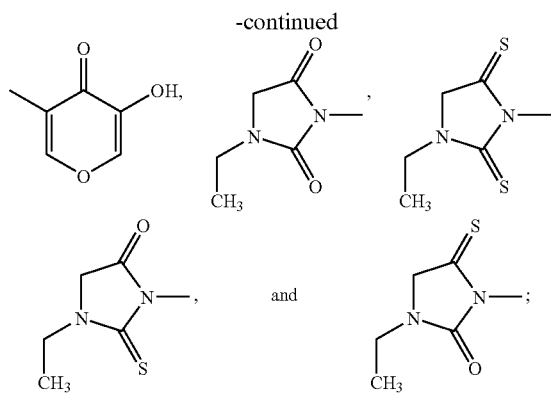

$R^3$, and $R^4$ are independently selected from the group consisting of $(C_1-C_6)$alkyl, $(C_2-C_6)$alkenyl, $(C_2-C_6)$alkynyl, phenyl, and benzyl; or $R^1$, $R^2$, and the carbon to which they are attached are taken together to form a $(C_3-C_7)$ cycloalkyl group; or $R^3$, $R^4$, and the carbon to which they are attached are taken together to form a $(C_3-C_7)$ cycloalkyl group; or $R^1$, $R^2$, and the carbon to which they are attached are taken together to form a $(C_3-C_7)$ cycloalkyl group and $R^3$, $R^4$, and the carbon to which they are attached are taken together to form a $(C_3-C_7)$ cycloalkyl group, with the proviso that none of $R^1$, $R^2$, $R^3$, or $R^4$ is $-(CH_2)_{0-4}C\equiv CH$;

$R^5$ is selected from the group consisting of $(C_1-C_6)$alkyl, $(C_2-C_6)$alkenyl, $(C_2-C_6)$alkynyl, phenyl, and benzyl;

each $R^6$ is independently selected from the group consisting of H, $(C_1-C_6)$alkyl, $(C_2-C_6)$alkenyl, and $(C_2-C_6)$alkynyl;

$R^7$ is selected from the group consisting of H, $(C_1-C_6)$alkyl, $(C_2-C_6)$alkenyl, and $(C_2-C_6)$alkynyl; and Hal is selected from the group consisting of chloro, bromo, and iodo.

The compounds of formulas IV and V are useful as intermediates for synthesizing the compounds of formula I.

In still another embodiment, the invention provides a method for the synthesis of a compound of a formula II:

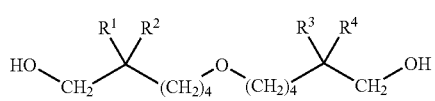

comprising (a) contacting in the presence of a base a compound of a formula XXIV:

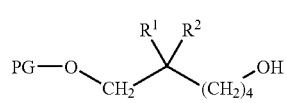

with a compound of a formula XXVIII:

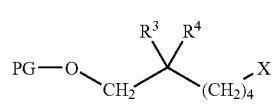

to provide a compound of a formula XXIX:

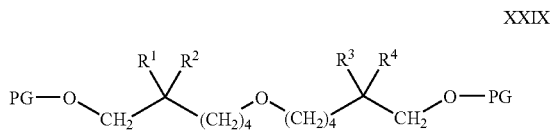

and (b) deprotecting the compound of the formula XXIX to provide the compound of the formula II, wherein:

$R^1$, $R^2$, $R^3$, and $R^4$ are independently selected from the group consisting of $(C_1-C_6)$alkyl, $(C_2-C_6)$alkenyl, $(C_2-C_6)$alkynyl, phenyl, and benzyl; or $R^1$, $R^2$, and the carbon to which they are attached are taken together to form a $(C_3-C_7)$cycloalkyl group; or $R^3$, $R^4$, and the carbon to which they are attached are taken together to form a $(C_3-C_7)$cycloalkyl group; or $R^1$, $R^2$, and the carbon to which they are attached are taken together to form a $(C_3-C_7)$cycloalkyl group and $R^3$, $R^4$, and the carbon to which they are attached are taken together to form a $(C_3-C_7)$cycloalkyl group, with the proviso that none of $R^1$, $R^2$, $R^3$, or $R^4$ is $-(CH_2)_{0-4}C\equiv CH$; and PG is a hydroxy protecting group.

In still another embodiment, the invention provides a method for the synthesis of a compound of formula III:

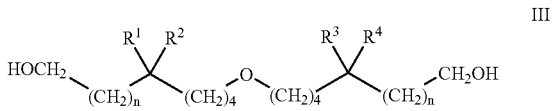

comprising contacting a compound of a formula of formula VI:

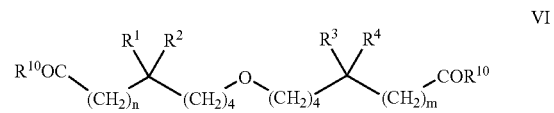

with a reducing agent, wherein:

$R^1$, $R^2$, $R^3$, and $R^4$ are independently selected from the group consisting of $(C_1-C_6)$alkyl, $(C_2-C_6)$alkenyl, $(C_2-C_6)$alkynyl, phenyl, and benzyl; or $R^1$, $R^2$, and the carbon to which they are attached are taken together to form a $(C_3-C_7)$cycloalkyl group; or $R^3$, $R^4$, and the carbon to which they are attached are taken together to form a $(C_3-C_7)$cycloalkyl group; or $R^1$, $R^2$, and the carbon to which they are attached are taken together to form a $(C_3-C_7)$cycloalkyl group and $R^3$, $R^4$, and the carbon to which they are attached are taken together to form a $(C_3-C_7)$cycloalkyl group, with the proviso that none of $R^1$, $R^2$, $R^3$, or $R^4$ is $-(CH_2)^{0-4}C\equiv CH$;

each $R^{10}$ is independently selected from the group consisting of —H, —OH, $(C_1-C_8)$alkoxy, $(C_6)$aryloxy, $-O(C_2-C_6)$alkenyl, $-O-C_2-C_6)$alkynyl, halo; and n and m are independent integers ranging from 0 to 4.

The present invention further provides compositions comprising a compound of the formula I or a pharmaceutically acceptable salt thereof; and a pharmaceutically acceptable vehicle. These compositions are useful for treating or preventing a disease or disorder selected from the group consisting of a cardiovascular disease, dyslipidemia, dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, and impotence. These composition are also useful for reducing the fat content of meat in livestock and reducing the cholesterol content of eggs.

The present invention provides a method for treating or preventing a cardiovascular disease, dyslipidemia, dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, and impotence, comprising administering to a patient in need of such treatment or prevention a therapeutically effective amount of a composition comprising a compound of formula I, or a pharmaceutically acceptable salt thereof; and a pharmaceutically acceptable vehicle.

The present invention further provides a method for reducing the fat content of meat in livestock comprising administering to livestock in need of such fat-content reduction a therapeutically effective amount of a composition comprising a compound of formula I or a pharmaceutically acceptable salt thereof; and a pharmaceutically acceptable vehicle.

The present invention provides a method for reducing the cholesterol content of a fowl egg comprising administering to a fowl species a therapeutically effective amount of a compound of formula I or a pharmaceutically acceptable salt thereof; and a pharmaceutically acceptable vehicle.

The present invention may be understood more fully by reference to the figures, detailed description, and examples, which are intended to exemplify non-limiting embodiments of the invention.

4. BRIEF DESCRIPTION OF THE DRAWINGS

5. DETAILED DESCRIPTION OF THE INVENTION

Figure 1:
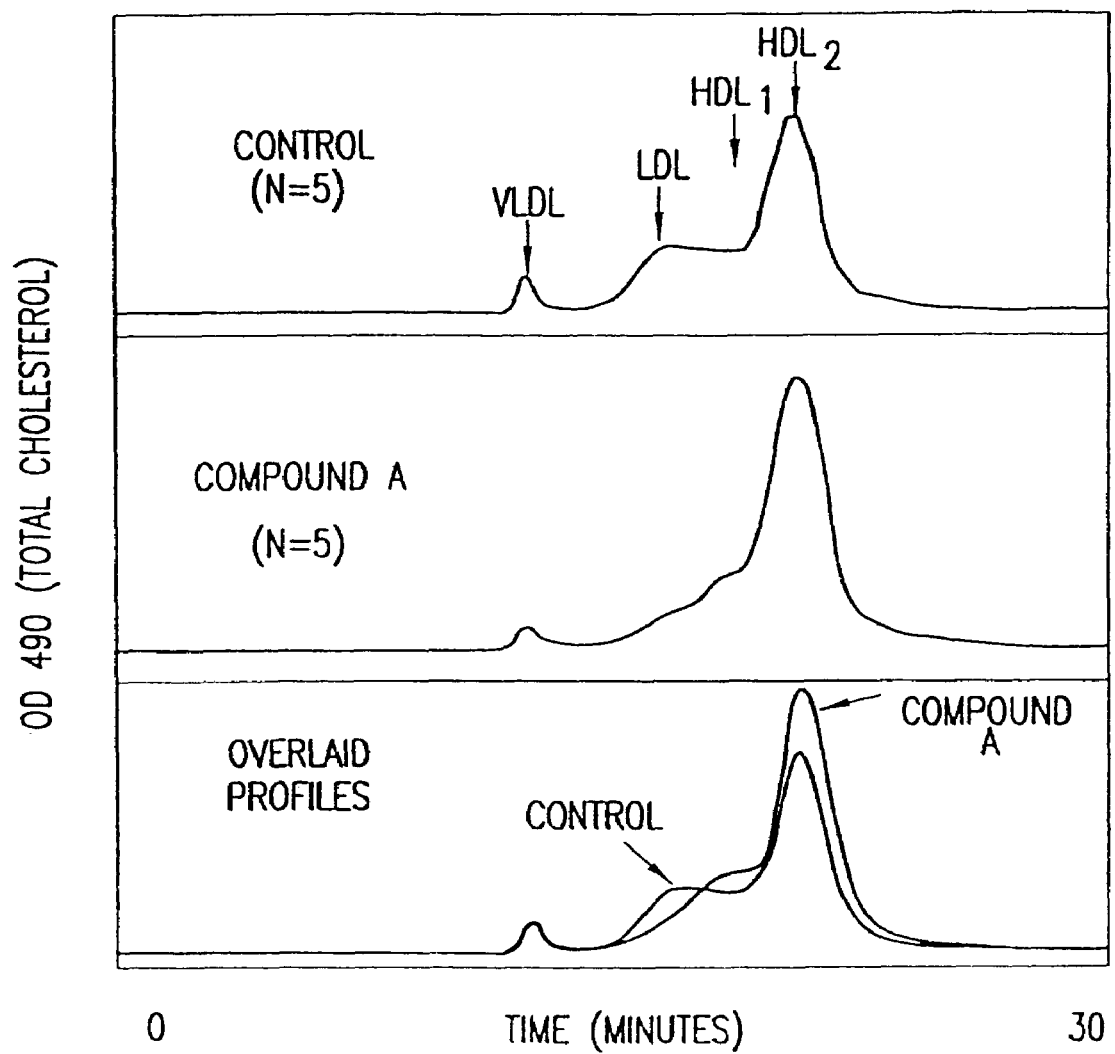
FIG. 1 shows the serum cholesterol profiles of Male Sprague-Dawley rats following one week of treatment with Compound A.

The present invention provides novel compounds having the general formula

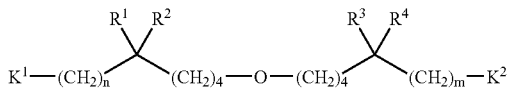

or a pharmaceutically acceptable salt thereof, wherein:

$R^1$, $R^2$, $R^3$, and $R^4$ are independently selected from the group consisting of ($C_1$-$C_6$)alkyl, ($C_2$-$C_6$)alkenyl, ($C_2$-$C_6$)alkynyl, phenyl, and benzyl; or $R^1$, $R^2$, and the carbon to which they are attached are taken together to form a ($C_3$-$C_7$)cycloalkyl group; or $R^3$, $R^4$, and the carbon to which they are attached are taken together to form a ($C_3$-$C_7$)cycloalkyl group; or $R^1$, $R^2$, and the carbon to which they are attached are taken together to form a ($C_3$-$C_7$)cycloalkyl group and $R^3$, $R^4$, and the carbon to which they are attached are taken together to form a ($C_3$-$C_7$)cycloalkyl group, with the proviso that none of $R^1$, $R^2$, $R^3$, or $R^4$ is —$(CH_2)_{0-4}C\equiv CH$;

n and m are independent integers ranging from 0 to 4;

$K^1$ and $K^2$ are independently selected from the group consisting of —$CH_2OH$, —$C(O)OH$, —$CHO$, —$C(O)OR^5$, —$OC(O)R^5$, —$SO_3H$,

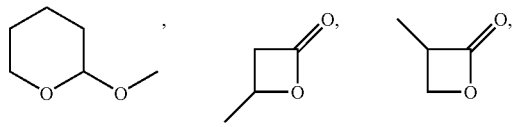

-continued

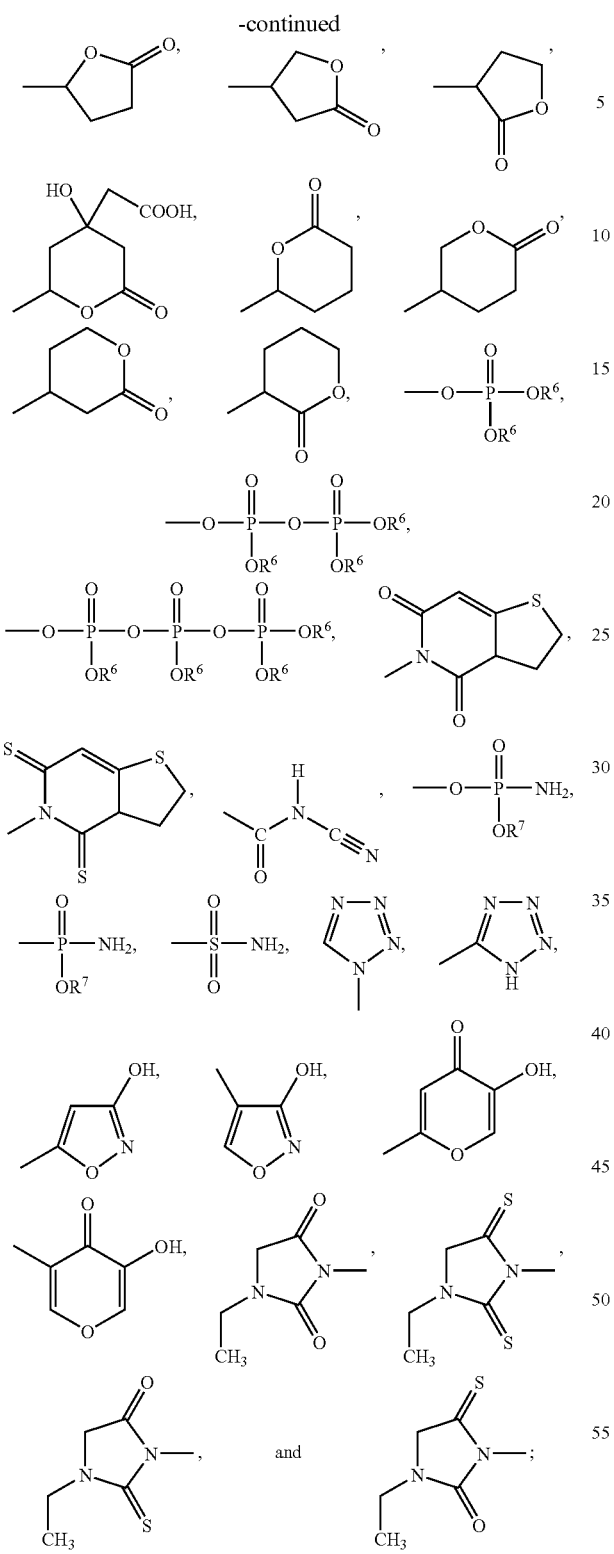

$R^5$ is selected from the group consisting of $(C_1$-$C_6)$alkyl, $(C_2$-$C_6)$alkenyl, $(C_2$-$C_6)$alkynyl, phenyl, and benzyl;

each $R^6$ is independently selected from the group consisting of H, $(C_1$-$C_6)$alkyl, $(C_2$-$C_6)$alkenyl, and $(C_2$-$C_6)$alkynyl;

$R^7$ is selected from the group consisting of H, $(C_1$-$C_6)$alkyl, $(C_2$-$C_6)$alkenyl, and $(C_2$-$C_6)$alkynyl; and with the proviso that when n and m are both 1 or both 0, then $K^1$ and $K^2$ are not both X, wherein X is selected from the group consisting of COOH, —C(O)OR$^5$,

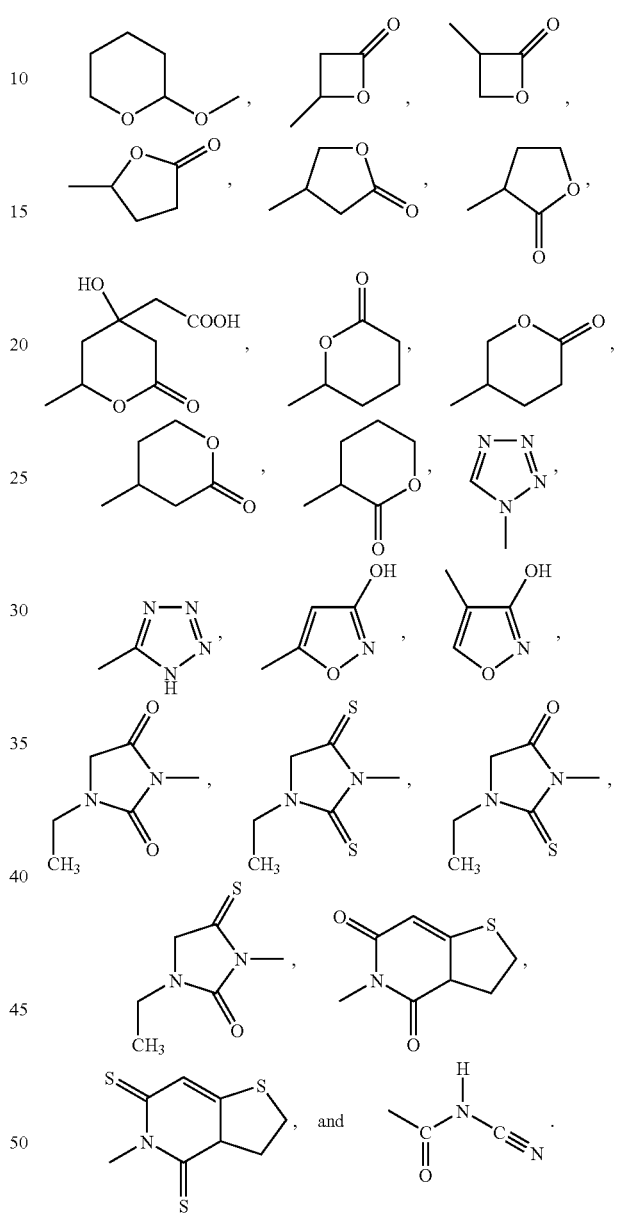

The compounds of formula I and pharmaceutically acceptable salts thereof are useful for treating or preventing cardiovascular diseases, dyslipidemias, dyslipoproteinemias, disorders of glucose metabolism, Alzheimer's Disease, Syndrome X, PPAR-associated disorders, septicemia, thrombotic disorders, obesity, pancreatitis, hypertension, renal diseases, cancer, inflammation, or impotence. In this regard, the compounds of formula I are particularly useful when incorporated in a composition. A composition of the invention need not contain an ingredient, including an excipient, other than a compound of the invention. Accordingly, in one embodiment, the compositions of the invention can omit a pharmaceutically acceptable vehicle. Accordingly, the present invention provides methods for treating or preventing cardiovascular diseases, dyslipidemias, dyslipoproteinemias, disorders of glucose metabolism, Alzheimer's Disease, Syndrome X, PPAR-associated disorders, septicemia, thrombotic disorders, obesity, pancreatitis, hypertension, renal diseases, cancer, inflammation, or impotence, comprising administering to a patient in need thereof a therapeutically effective amount of a composition comprising a compound of formula I or a pharmaceutically acceptable salt thereof, and a pharmaceutically acceptable vehicle.

In certain embodiments of the invention, a compound of formula I or a pharmaceutically acceptable salt thereof is administered in combination with another therapeutic agent. The other therapeutic agent provides additive or synergistic value relative to the administration of a compound of formula I alone. The therapeutic agent can be a statin; a PPAR agonist, e.g., a thiazolidinedione or fibrate; a bile-acid-binding-resin; a niacin; a RXR agonist; an anti-obesity drug; a hormone; a tyrophostine; a sulfonylurea-based drug; a biguanide; an α-glucosidase inhibitor; an apolipoprotein A-I agonist; apolipoprotein E; a cardiovascular drug; an HDL-raising drug; an HDL enhancer; or a regulator of the apolipoprotein A-I, apolipoprotein A-IV and/or apolipoprotein genes.

The present invention further encompasses compositions comprising a pharmaceutically acceptable vehicle; and a compound of formula I or a pharmaceutically acceptable salt thereof.

Preferably, the compounds of formula I and pharmaceutically acceptable salts thereof, are those wherein:

$R^1$, $R^2$, $R^3$, and $R^4$ are independently selected from the group consisting of $(C_1-C_6)$alkyl, $(C_2-C_6)$alkenyl, $(C_2-C_6)$alkynyl, phenyl, and benzyl; or $R^1$, $R^2$, and the carbon to which they are attached are taken together to form a $(C_3-C_7)$cycloalkyl group; or $R^3$, $R^4$, and the carbon to which they are attached are taken together to form a $(C_3-C_7)$cycloalkyl group; or $R^1$, $R^2$, and the carbon to which they are attached are taken together to form a $(C_3-C_7)$cycloalkyl group and $R^3$, $R^4$, and the carbon to which they are attached are taken together to form a $(C_3-C_7)$cycloalkyl group, with the proviso that none of $R^1$, $R^2$, $R^3$, or $R^4$ is $-(CH_2)_{0-4}C\equiv CH$;

n and m are independent integers ranging from 0 to 4;

$K^1$ and $K^2$ are independently selected from the group consisting of $-CH_2OH$, $-C(O)OH$, $-CHO$, $-C(O)OR^5$, $-OC(O)R^5$, $-SO_3H$,

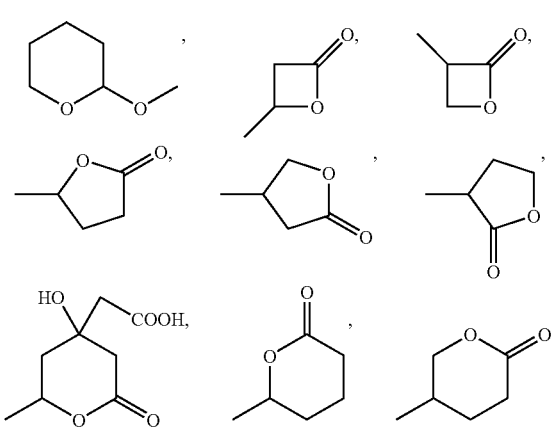

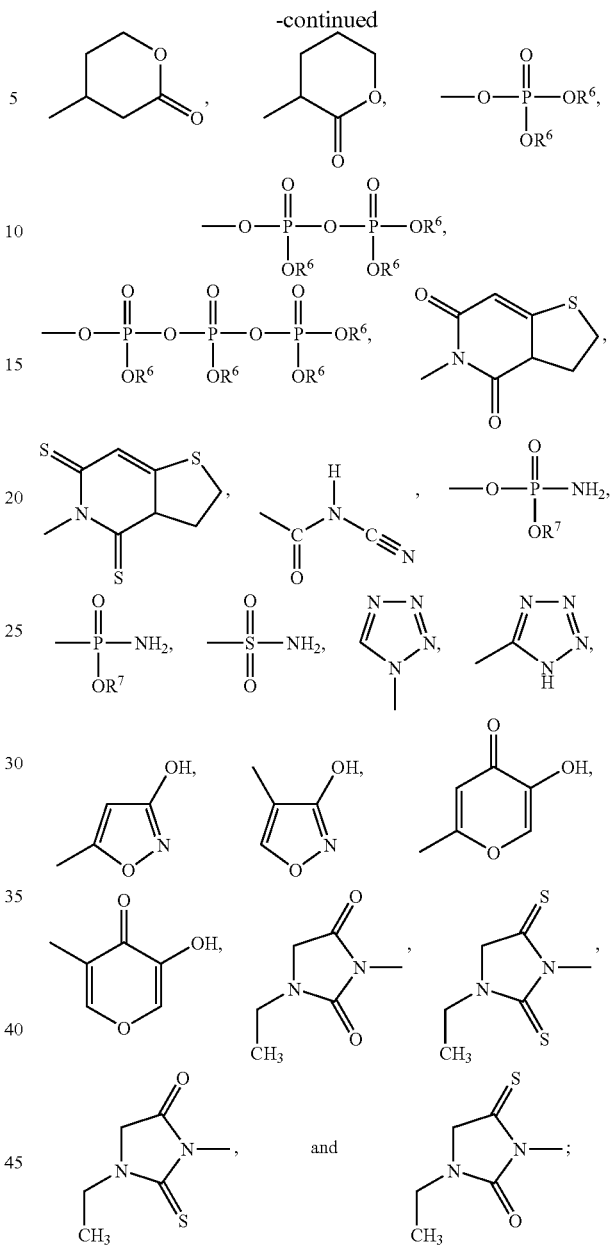

$R^5$ is selected from the group consisting of $(C_1-C_6)$alkyl, $(C_2-C_6)$alkenyl, $(C_2-C_6)$alkynyl, phenyl, and benzyl;

each $R^6$ is independently selected from the group consisting of H, $(C_1-C_6)$alkyl, $(C_2-C_6)$alkenyl, and $(C_2-C_6)$alkynyl;

$R^7$ is selected from the group consisting of H, $(C_1-C_6)$alkyl, $(C_2-C_6)$alkenyl, and $(C_2-C_6)$alkynyl; and with the proviso that when n and m are both 1 or both 0, then $K^1$ and $K^2$ are not both X, wherein X is selected from the group consisting of $-COOH$, $-C(O)OR^5$,

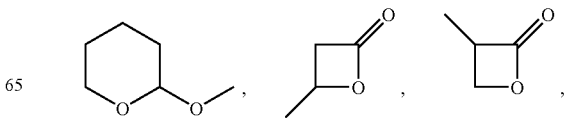

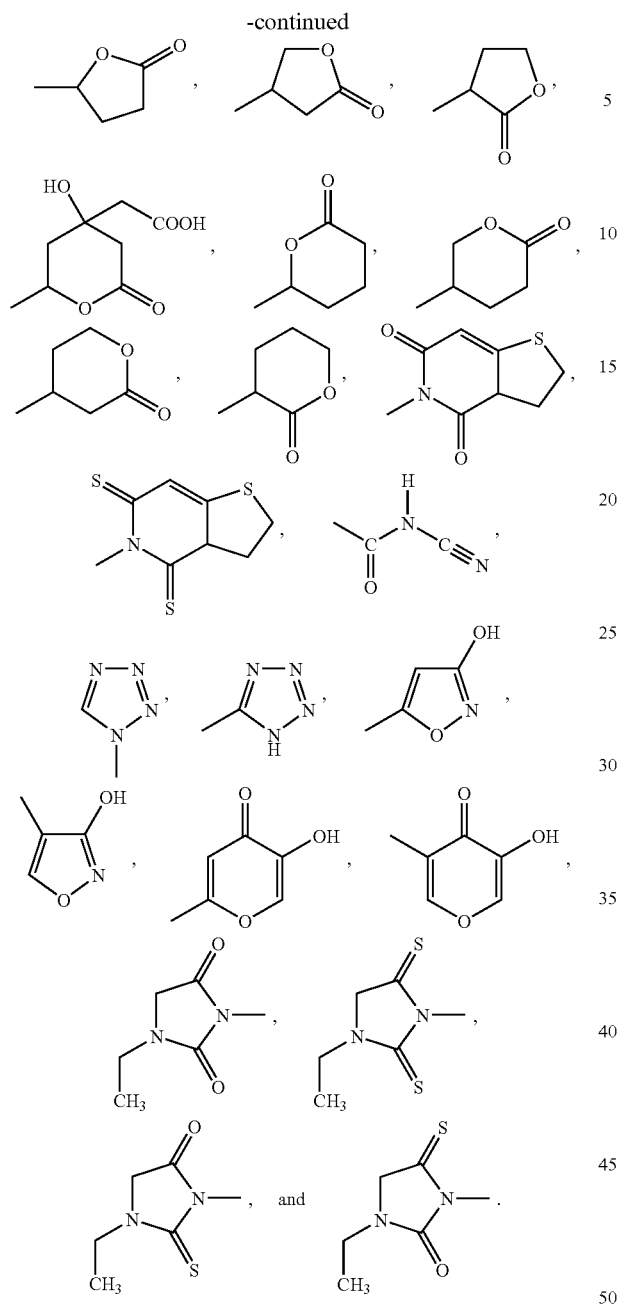

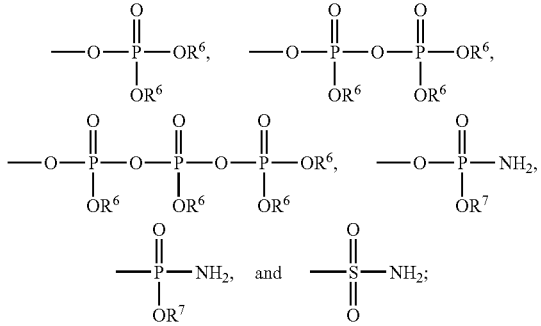

More preferably, the compounds of formula I and pharmaceutically acceptable salts thereof, are those wherein:

R$^1$, R$^2$, R$^3$, and R$^4$ are independently selected from the group consisting of (C$_1$-C$_6$)alkyl, (C$_2$-C$_6$)alkenyl, (C$_2$-C$_6$)alkynyl, phenyl, and benzyl; or R$^1$, R$^2$, and the carbon to which they are attached are taken together to form a (C$_3$-C$_7$)cycloalkyl group; or R$^3$, R$^4$, and the carbon to which they are attached are taken together to form a (C$_3$-C$_7$)cycloalkyl group; or R$^1$, R$^2$, and the carbon to which they are attached are taken together to form a (C$_3$-C$_7$)cycloalkyl group and R$^3$, R$^4$, and the carbon to which they are attached are taken together to form a (C$_3$-C$_7$)cycloalkyl group, with the proviso that none of R$^1$, R$^2$, R$^3$, or R$^4$ is —(CH$_2$)$_{0-4}$C≡CH;

n and m are independent integers ranging from 0 to 4;

K$^1$ is selected from the group consisting of —CH$_2$OH, —OC(O)R$^5$, —CHO, —SO$_3$H,

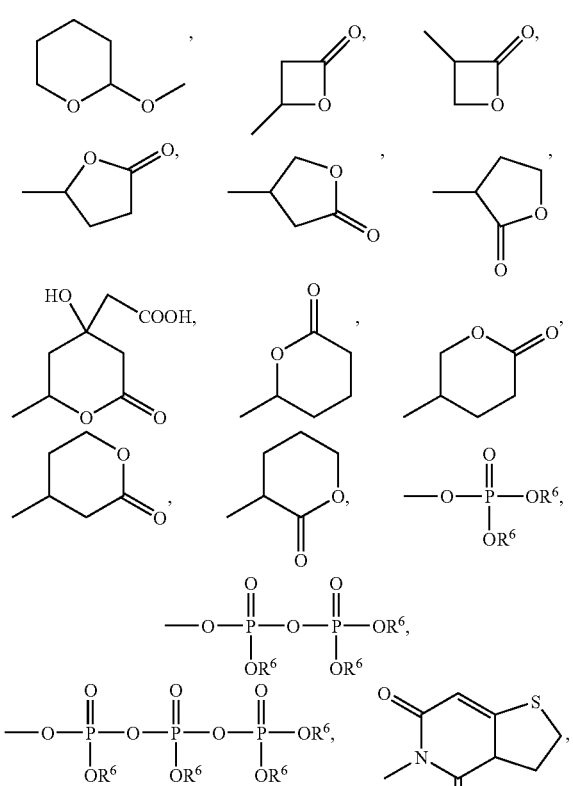

K$^2$ is selected from the group consisting of —CH$_2$OH, —C(O)OH, —CHO, —C(O)OR$^5$, —OC(O)R$^5$, —SO$_3$H,

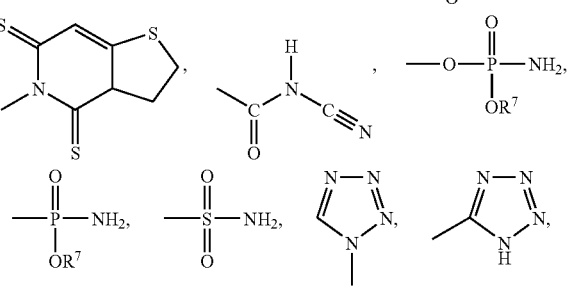

-continued

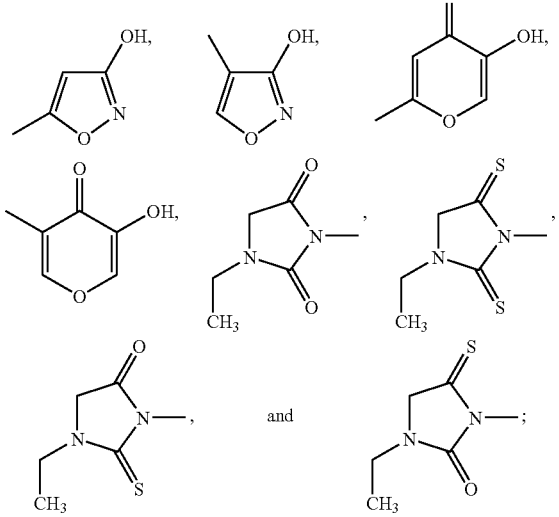

R[5] is selected from the group consisting of $(C_1-C_6)$alkyl, $(C_2-C_6)$alkenyl, $(C_2-C_6)$alkynyl, phenyl, and benzyl;

each R[6] is independently selected from the group consisting of H, $(C_1-C_6)$alkyl, $(C_2-C_6)$alkenyl, and $(C_2-C_6)$alkynyl;

R[7] is selected from the group consisting of H, $(C_1-C_6)$alkyl, $(C_2-C_6)$alkenyl, and $(C_2-C_6)$alkynyl; and with the proviso that when n and m are both 1 or both 0, then K[1] and K[2] are not both X, wherein X is selected from the group consisting of —COOH, —C(O)OR[5],

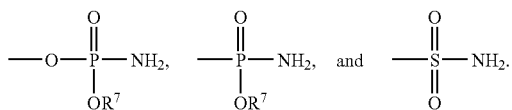

Still more preferably, the compounds of formula I and pharmaceutically acceptable salts thereof, are those wherein:

R[1], R[2], R[3], and R[4] are independently selected from the group consisting of $(C_1-C_6)$alkyl, $(C_2-C_6)$alkenyl, $(C_2-C_6)$alkynyl, phenyl, and benzyl; or R[1], R[2], and the carbon to which they are attached are taken together to form a $(C_3-C_7)$cycloalkyl group; or R[3], R[4], and the carbon to which they are attached are taken together to form a $(C_3-C_7)$cycloalkyl group; or R[1], R[2], and the carbon to which they are attached are taken together to form a $(C_3-C_7)$cycloalkyl group and R[3], R[4], and the carbon to which they are attached are taken together to form a $(C_3-C_7)$cycloalkyl group, with the proviso that none of R[1], R[2], R[3], or R[4] is —(CH$_2$)$_{0-4}$C≡CH;

n and m are independent integers ranging from 0 to 4;

K[1] and K[2] are independently selected from the group consisting of —CH$_2$OH, —OC(O)R[5], —CHO, —SO$_3$H,

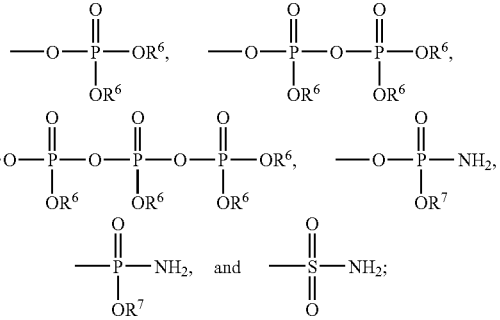

R[5] is selected from the group consisting of $(C_1-C_6)$alkyl, $(C_2-C_6)$alkenyl, $(C_2-C_6)$alkynyl, phenyl, and benzyl;

each R[6] is independently selected from the group consisting of H, $(C_1-C_6)$alkyl, $(C_2-C_6)$alkenyl, and $(C_2-C_6)$alkynyl;

R[7] is selected from the group consisting of H, $(C_1-C_6)$alkyl, $(C_2-C_6)$alkenyl, and $(C_2-C_6)$alkynyl; and with the proviso that when n and m are both 1 or both 0, then K[1] and K[2] are not both X, wherein X is selected from the group consisting of —COOH, —C(O)OR[5],

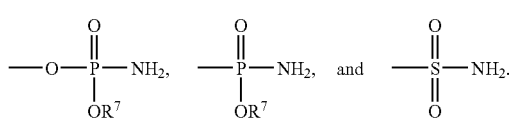

Still more preferably, the compounds of formula I and pharmaceutically acceptable salts thereof, are those wherein:

R[1], R[2], R[3], and R[4] are independently selected from the group consisting of $(C_1-C_6)$alkyl, $(C_2-C_6)$alkenyl, $(C_2-C_6)$alkynyl, phenyl, and benzyl; or R[1], R[2], and the carbon to which they are attached are taken together to form a $(C_3-C_7)$cycloalkyl group; or R[3], R[4], and the carbon to which they are attached are taken together to form a $(C_3-C_7)$cycloalkyl group; or R[1], R[2], and the carbon to which they are attached are taken together to form a $(C_3-C_7)$cycloalkyl group and R[3], R[4], and the carbon to which they are attached are taken together to form a $(C_3-C_7)$cycloalkyl group, with the proviso that none of R[1], R[2], R[3], or R[4] is —(CH$_2$)$_{0-4}$C≡CH;

n and m are independent integers ranging from 0 to 4;

K[1] and K[2] are independently —CH$_2$OH or —OC(O)R[5]; and

R[5] is selected from the group consisting of $(C_1-C_6)$alkyl, $(C_2-C_6)$alkenyl, $(C_2-C_6)$alkynyl, phenyl, and benzyl.

Preferred compounds of formula I are selected from the group consisting of:

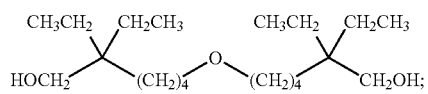

2,2-diethyl-6-(5-ethyl-5-hydroxymethyl-heptyloxy)-hexan-1-ol

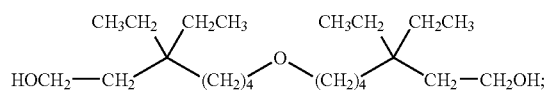

7-(5,5-diethyl-7-hydroxy-heptyloxy)-3,3-diethyl-heptan-1-ol

-continued

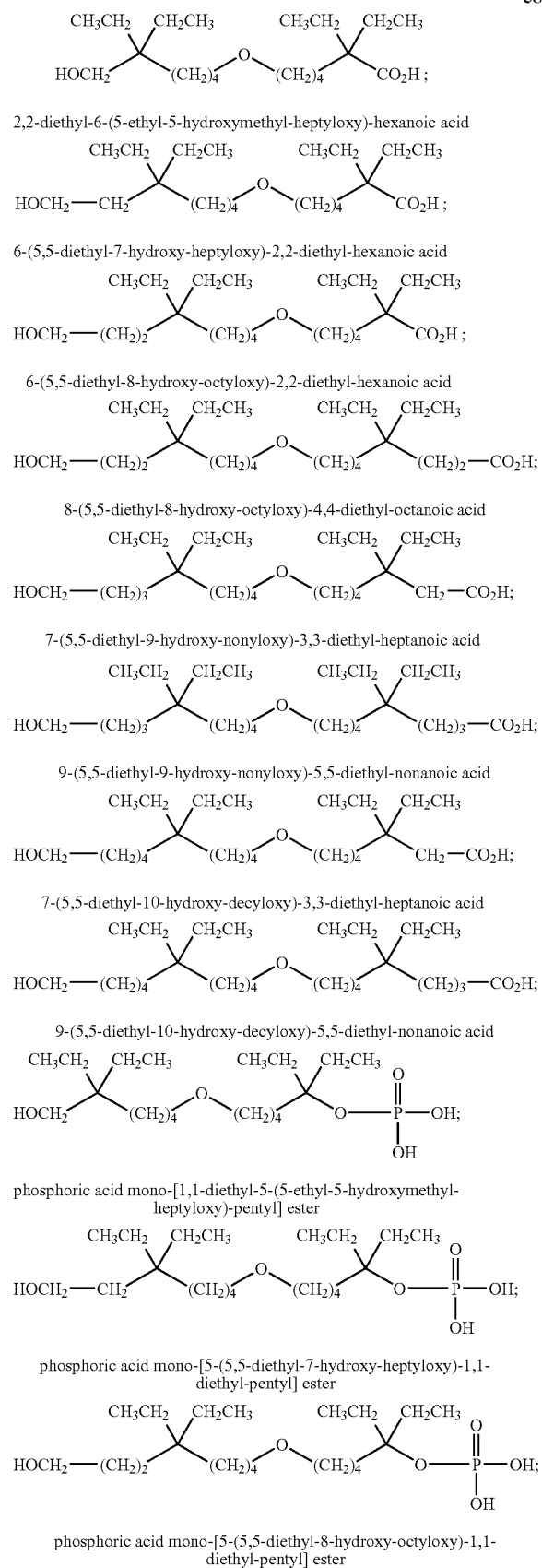

2,2-diethyl-6-(5-ethyl-5-hydroxymethyl-heptyloxy)-hexanoic acid 6-(5,5-diethyl-7-hydroxy-heptyloxy)-2,2-diethyl-hexanoic acid 6-(5,5-diethyl-8-hydroxy-octyloxy)-2,2-diethyl-hexanoic acid 8-(5,5-diethyl-8-hydroxy-octyloxy)-4,4-diethyl-octanoic acid 7-(5,5-diethyl-9-hydroxy-nonyloxy)-3,3-diethyl-heptanoic acid 9-(5,5-diethyl-9-hydroxy-nonyloxy)-5,5-diethyl-nonanoic acid 7-(5,5-diethyl-10-hydroxy-decyloxy)-3,3-diethyl-heptanoic acid 9-(5,5-diethyl-10-hydroxy-decyloxy)-5,5-diethyl-nonanoic acid phosphoric acid mono-[1,1-diethyl-5-(5-ethyl-5-hydroxymethyl-heptyloxy)-pentyl] ester phosphoric acid mono-[5-(5,5-diethyl-7-hydroxy-heptyloxy)-1,1-diethyl-pentyl] ester phosphoric acid mono-[5-(5,5-diethyl-8-hydroxy-octyloxy)-1,1-diethyl-pentyl] ester

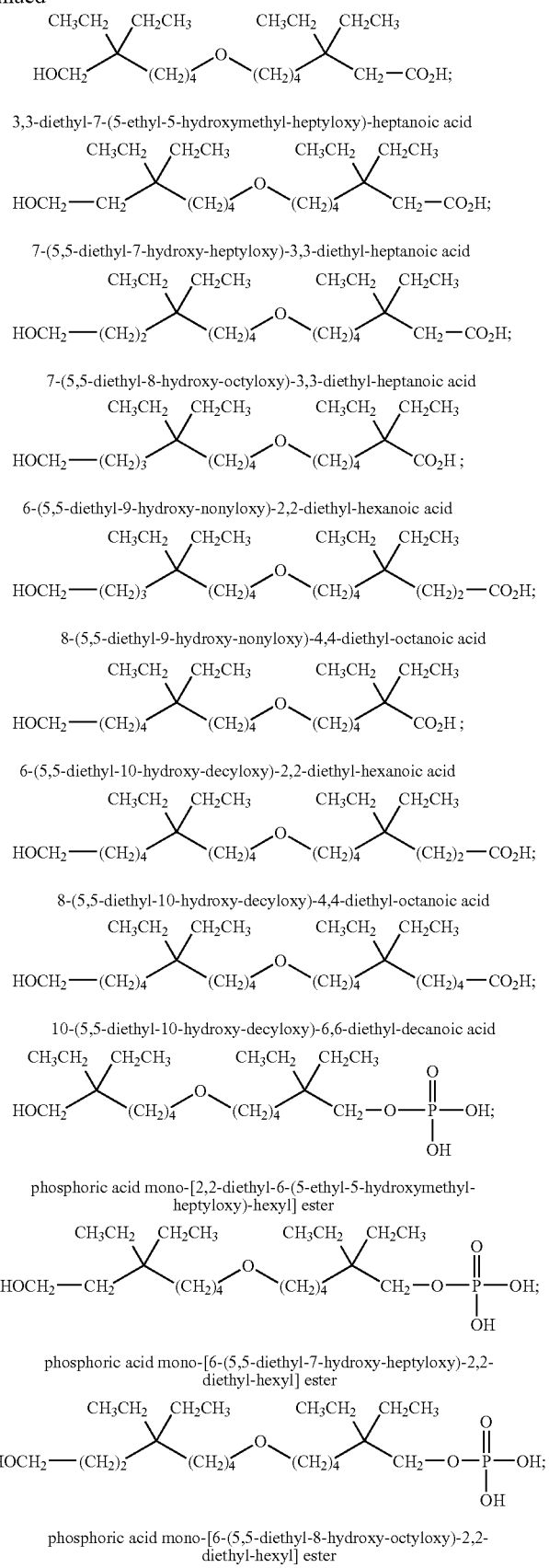

3,3-diethyl-7-(5-ethyl-5-hydroxymethyl-heptyloxy)-heptanoic acid 7-(5,5-diethyl-7-hydroxy-heptyloxy)-3,3-diethyl-heptanoic acid 7-(5,5-diethyl-8-hydroxy-octyloxy)-3,3-diethyl-heptanoic acid 6-(5,5-diethyl-9-hydroxy-nonyloxy)-2,2-diethyl-hexanoic acid 8-(5,5-diethyl-9-hydroxy-nonyloxy)-4,4-diethyl-octanoic acid 6-(5,5-diethyl-10-hydroxy-decyloxy)-2,2-diethyl-hexanoic acid 8-(5,5-diethyl-10-hydroxy-decyloxy)-4,4-diethyl-octanoic acid 10-(5,5-diethyl-10-hydroxy-decyloxy)-6,6-diethyl-decanoic acid phosphoric acid mono-[2,2-diethyl-6-(5-ethyl-5-hydroxymethyl-heptyloxy)-hexyl] ester phosphoric acid mono-[6-(5,5-diethyl-7-hydroxy-heptyloxy)-2,2-diethyl-hexyl] ester phosphoric acid mono-[6-(5,5-diethyl-8-hydroxy-octyloxy)-2,2-diethyl-hexyl] ester -continued

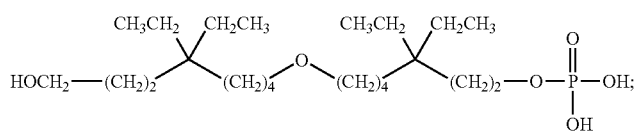

phosphoric acid mono-[7-(5,5-diethyl-8-hydroxy-octyloxy)-3,3-diethyl-heptyl] ester

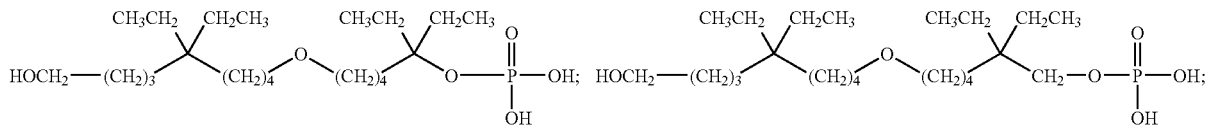

phosphoric acid mono-[5-(5,5-diethyl-9-hydroxy-nonloxy)-1,1-diethyl-pentyl] ester phosphoric acid mono-[6-(5,5-diethyl-9-hydroxy-nonloxy)-2,2-diethyl-hexyl] ester

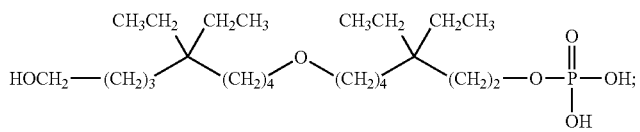

phosphoric acid mono-[7-(5,5-diethyl-9-hydroxy-nonloxy)-3,3-diethyl-heptyl] ester

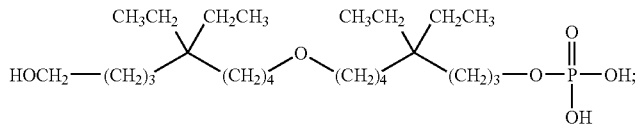

phosphoric acid mono-[8-(5,5-diethyl-9-hydroxy-nonloxy)-4,4-diethyl-octyl] ester

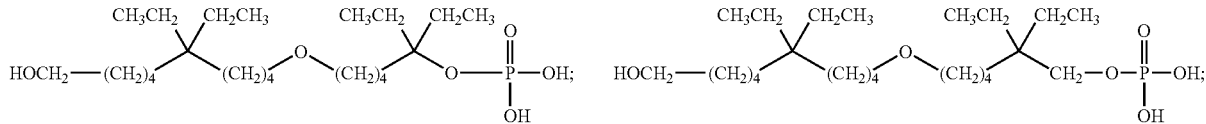

phosphoric acid mono-[5-(5,5-diethyl-10-hydroxy-decyloxy)-1,1-diethyl-pentyl] ester phosphoric acid mono-[6-(5,5-diethyl-10-hydroxy-decyloxy)-2,2-diethyl-heptyl] ester

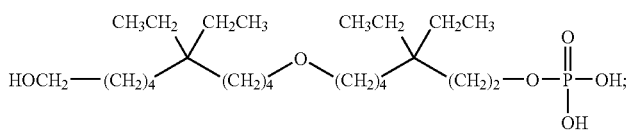

phosphoric acid mono-[7-(5,5-diethyl-10-hydroxy-decyloxy)-3,3-diethyl-heptyl] ester

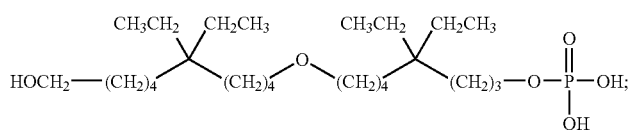

phosphoric acid mono-[8-(5,5-diethyl-10-hydroxy-decyloxy)-4,4-diethyl-octyl] ester

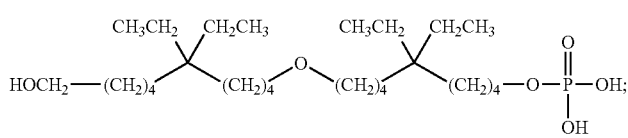

phosphoric acid mono-[9-(5,5-diethyl-10-hydroxy-decyloxy)-5,5-diethyl-nonyl] ester

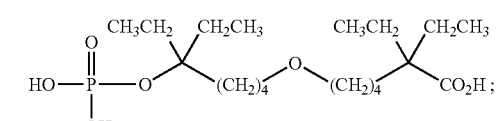

2,2-diethyl-6-(5-ethyl-5-phosphonooxy-heptyloxy)-hexanoic acid

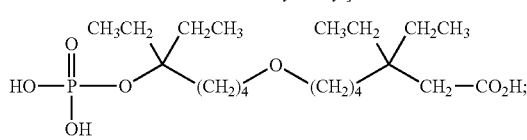

3,3-diethyl-7-(5-ethyl-5-phosphonooxy-heptyloxy)-heptanoic acid

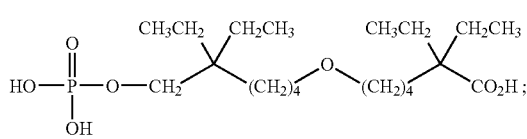

2,2-diethyl-6-(5-ethyl-5-phosphonooxymethyl-heptyloxy)-hexanoic acid

-continued

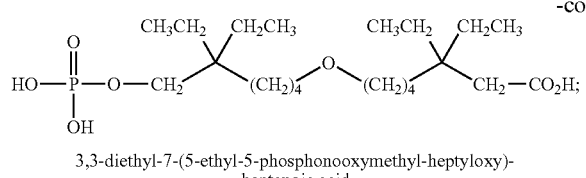

3,3-diethyl-7-(5-ethyl-5-phosphonooxymethyl-heptyloxy)-heptanoic acid

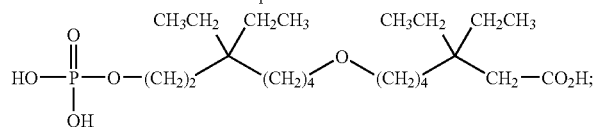

7-(5,5-diethyl-7-phosphonooxy-heptyloxy)-3,3-diethyl-heptanoic acid

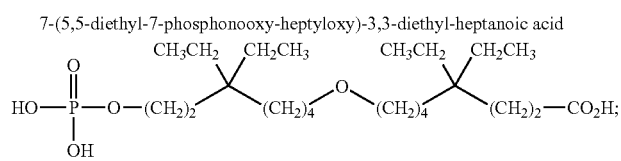

8-(5,5-diethyl-7-phosphonooxy-heptyloxy)-4,4-diethyl-octanoic acid

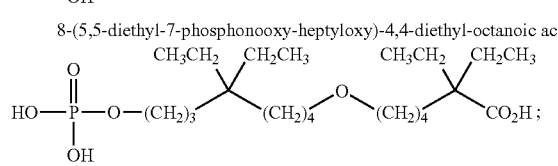

6-(5,5-diethyl-8-phosphonooxy-octyloxy)-2,2-diethyl-hexanoic acid

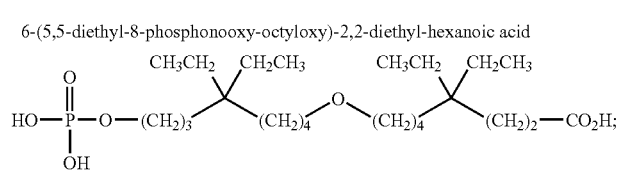

8-(5,5-diethyl-8-phosphonooxy-octyloxy)-4,4-diethyl-octanoic acid

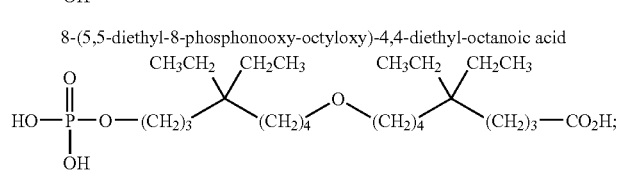

9-(5,5-diethyl-8-phosphonooxy-octyloxy)-5,5-diethyl-nonanoic acid

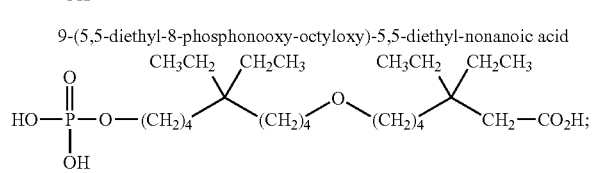

7-(5,5-diethyl-9-phosphonooxy-nonyloxy)-3,3-diethyl-heptanoic acid

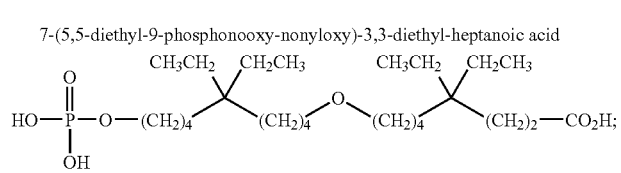

8-(5,5-diethyl-9-phosphonooxy-nonyloxy)-4,4-diethyl-octanoic acid

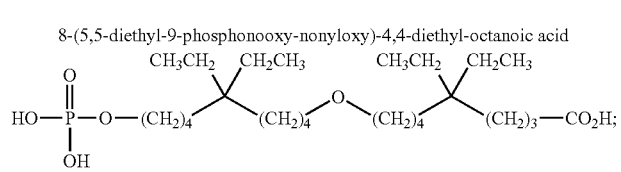

9-(5,5-diethyl-9-phosphonooxy-nonyloxy)-5,5-diethyl-nonanoic acid

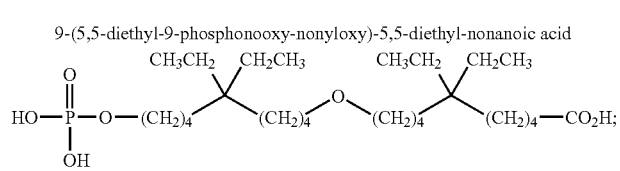

10-(5,5-diethyl-9-phosphonooxy-nonyloxy)-6,6-diethyl-decanoic acid

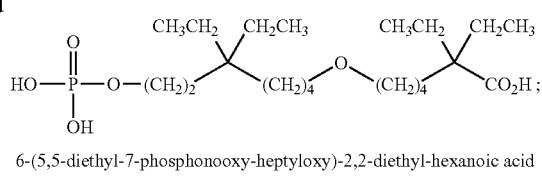

6-(5,5-diethyl-7-phosphonooxy-heptyloxy)-2,2-diethyl-hexanoic acid

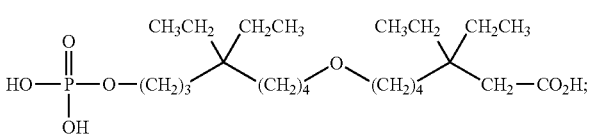

7-(5,5-diethyl-8-phosphonooxy-octyloxy)-3,3-diethyl-heptanoic acid

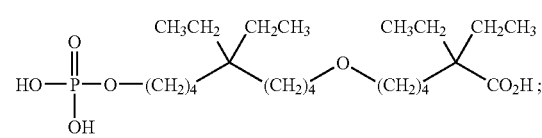

6-(5,5-diethyl-9-phosphonooxy-nonyloxy)-2,2-diethyl-hexanoic acid

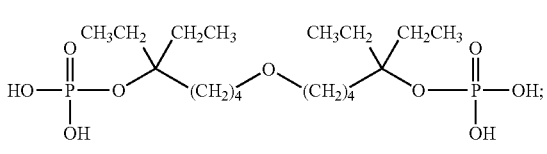

phosphoric acid mono-[1,1-diethyl-5-(5-ethyl-5-phosphonooxy-heptyloxy)-pentyl] ester

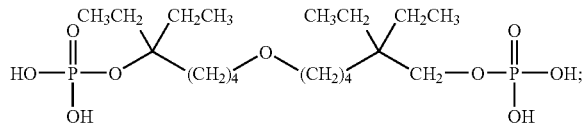

phosphoric acid mono-[1,1-diethyl-5-(5-ethyl-5-phosphonooxymethyl-heptyloxy)-pentyl] ester

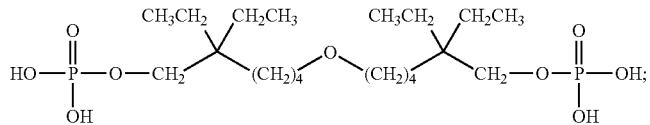

phosphoric acid mono-[2,2-diethyl-6-(5-ethyl-5-phosphonooxymethyl-heptyloxy)-hexyl] ester

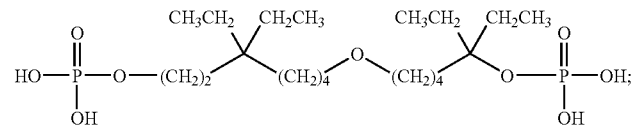

phosphoric acid mono-[3,3-diethyl-7-(5-ethyl-5-phosphonooxy-heptyloxy)-heptyl] ester

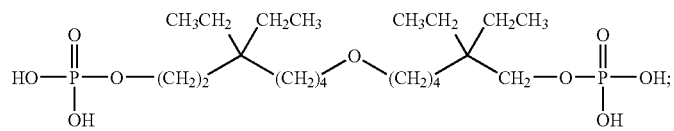

phosphoric acid mono-[3,3-diethyl-7-(5-ethyl-5-phosphonooxymethyl-heptyloxy)-heptyl] ester

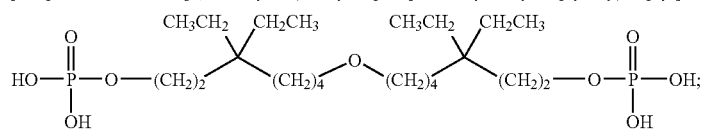

phosphoric acid mono-[7-(5,5-diethyl-7-phosphonooxy-heptyloxy)-3,3-diethyl-heptyl] ester

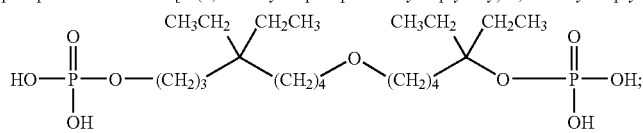

phosphoric acid mono-[4,4-diethyl-8-(5-ethyl-5-phosphonooxy-heptyloxy)-octyl] ester

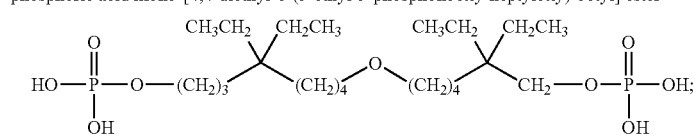

phosphoric acid mono-[4,4-diethyl-8-(5-ethyl-5-phosphonooxymethyl-heptyloxy)-octyl] ester

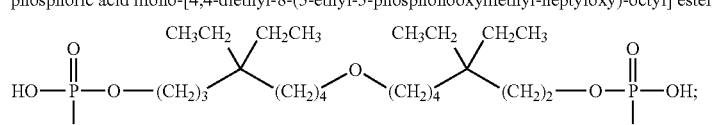

phosphoric acid mono-[8-(5,5-diethyl-7-phosphonooxy-heptyloxy)-4,4-diethyl-octyl] ester

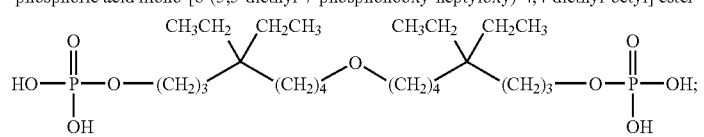

phosphoric acid mono-[8-(5,5-diethyl-8-phosphonooxy-octyloxy)-4,4-diethyl-octyl] ester

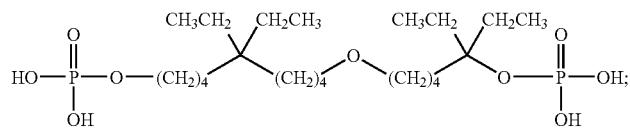

phosphoric acid mono-[5,5-diethyl-9-(5-ethyl-5-phosphonooxy-heptyloxy)-nonyl] ester -continued

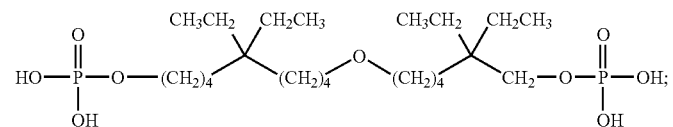

phosphoric acid mono-[5,5-diethyl-9-(5-ethyl-5-phosphonooxymethyl-heptyloxy)-nonyl] ester

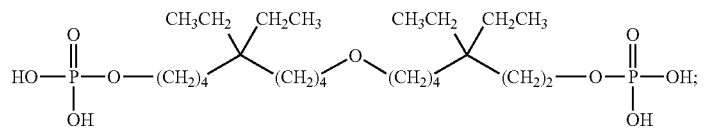

phosphoric acid mono-[9-(5,5-diethyl-7-phosphonooxy-heptyloxy)-5,5-diethyl-nonyl] ester

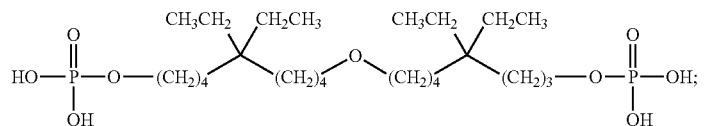

phosphoric acid mono-[9-(5,5-diethyl-8-phosphonooxy-octyloxy)-5,5-diethyl-nonyl] ester

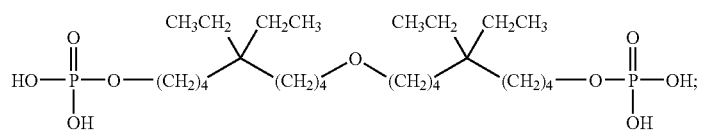

phosphoric acid mono-[9-(5,5-diethyl-9-phosphonooxy-nonyloxy)-5,5-diethyl-nonyl] ester

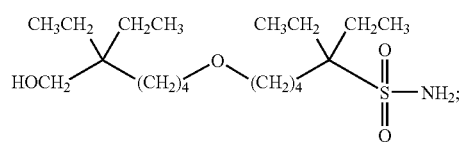

6-(6-hydroxy-5,5-diethyl-hexyloxy)-3-ethyl-heptane-2-sulfonic acid amide

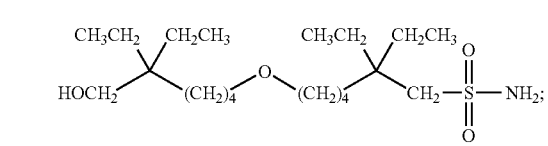

6-(6-hydroxy-5,5-diethyl-hexyloxy)-2,2-diethyl-hexane-1-sulfonic acid amide

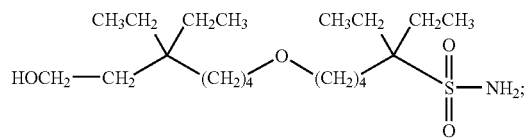

6-(7-hydroxy-5,5-diethyl-heptyloxy)-3-ethyl-heptane-2-sulfonic acid amide

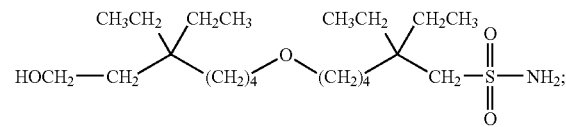

6-(7-hydroxy-5,5-diethyl-heptyloxy)-2,2-diethyl-hexane-1-sulfonic acid amide

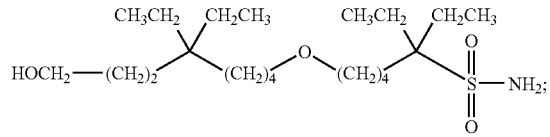

7-(5,5-diethyl-8-hydroxy-octyloxy)-3-ethyl-heptane-3-sulfonic acid amide

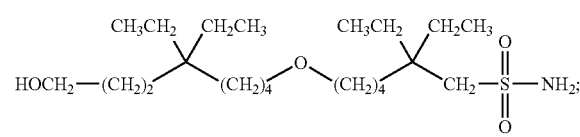

6-(5,5-diethyl-8-hydroxy-octyloxy)-2,2-diethyl-hexane-1-sulfonic acid amide

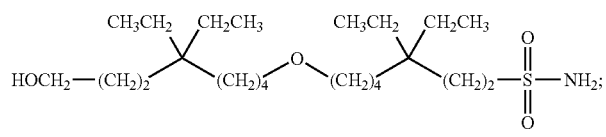

7-(5,5-diethyl-8-hydroxy-octyloxy)-3,3-diethyl-heptane-1-sulfonic acid amide

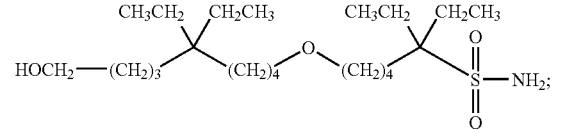

7-(5,5-diethyl-9-hydroxy-nonyloxy)-3-ethyl-heptane-3-sulfonic acid amide

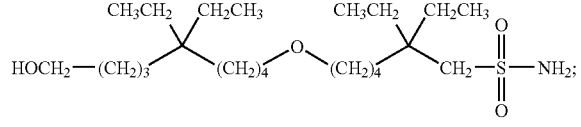

6-(5,5-diethyl-9-hydroxy-nonyloxy)-2,2-diethyl-hexane-1-sulfonic acid amide

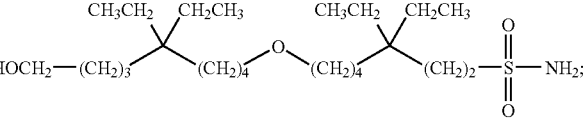

7-(5,5-diethyl-9-hydroxy-nonyloxy)-3,3-diethyl-heptane-1-sulfonic acid amide

-continued

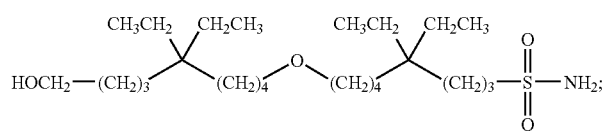

8-(5,5-diethyl-9-hydroxy-nonyloxy)-4,4-diethyl-octane-1-sulfonic acid amide

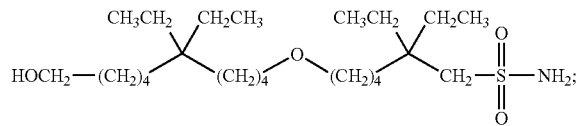

6-(5,5-diethyl-10-hydroxy-decyloxy)-2,2-diethyl-hexane-1-sulfonic acid amide

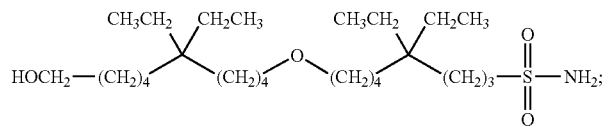

8-(5,5-diethyl-10-hydroxy-decyloxy)-4,4-diethyl-octane-1-sulfonic acid amide

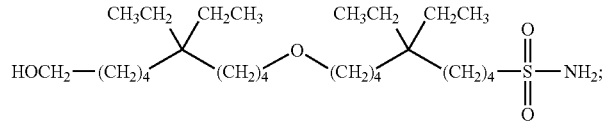

9-(5,5-diethyl-10-hydroxy-decyloxy)-5,5-diethyl-nonane-1-sulfonic acid amide

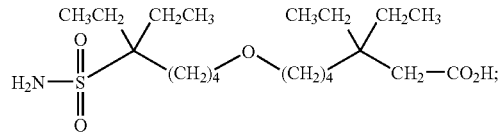

3,3-diethyl-7-(5-ethyl-5-sulfamoyl-heptyloxy)-heptanoic acid

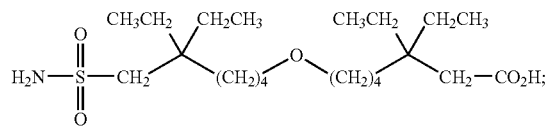

3,3-diethyl-7-(5-ethyl-5-sulfamoylmethyl-heptyloxy)-heptanoic acid

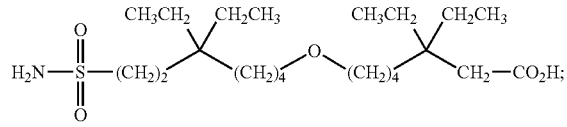

7-(5,5-diethyl-7-sulfamoyl-heptyloxy)-3,3-diethyl-heptanoic acid

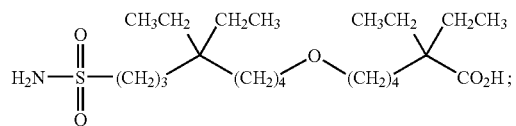

6-(5,5-diethyl-8-sulfamoyl-octyloxy)-2,2-diethyl-octanoic acid

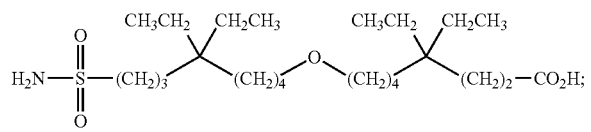

8-(5,5-diethyl-8-sulfamoyl-octyloxy)-4,4-diethyl-octanoic acid

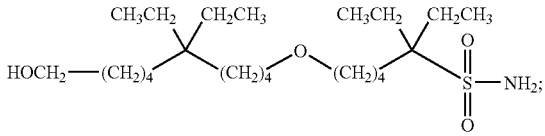

7-(5,5-diethyl-10-hydroxy-decyloxy)-3-ethyl-heptane-3-sulfonic acid amide

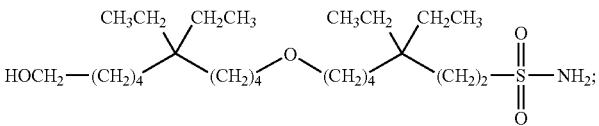

7-(5,5-diethyl-10-hydroxy-decyloxy)-3,3-diethyl-heptane-1-sulfonic acid amide

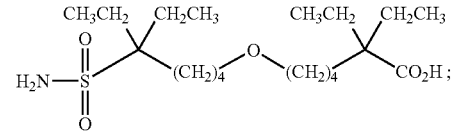

2,2-diethyl-6-(5-ethyl-5-sulfamoyl-heptyloxy)-hexanoic acid

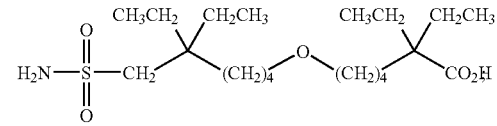

2,2-diethyl-6-(5-ethyl-5-sulfamoylmethyl-heptyloxy)-hexanoic acid

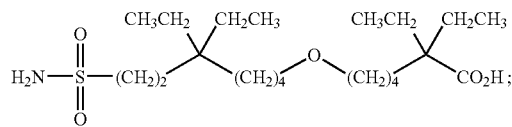

6-(5,5-diethyl-7-sulfamoyl-heptyloxy)-2,2-diethyl-hexanoic acid

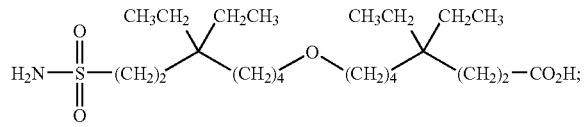

8-(5,5-diethyl-7-sulfamoyl-heptyloxy)-4,4-diethyl-octanoic acid

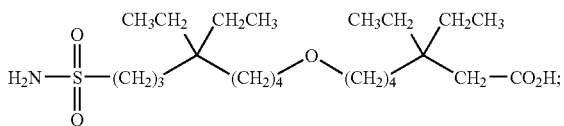

7-(5,5-diethyl-8-sulfamoyl-octyloxy)-3,3-diethyl-heptanoic acid

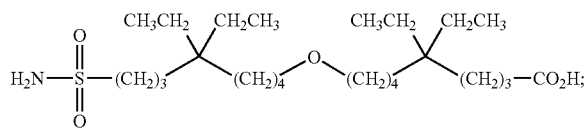

9-(5,5-diethyl-8-sulfamoyl-octyloxy)-5,5-diethyl-nonanoic acid

-continued 6-(5,5-diethyl-9-sulfamoyl-nonyloxy)-2,2-diethyl-hexanoic acid 7-(5,5-diethyl-9-sulfamoyl-nonyloxy)-3,3-diethyl-heptanoic acid 8-(5,5-diethyl-9-sulfamoyl-nonyloxy)-4,4-diethyl-octanoic acid 9-(5,5-diethyl-9-sulfamoyl-nonyloxy)-5,5-diethyl-nonanoic acid 10-(5,5-diethyl-9-sulfamoyl-nonyloxy)-6,6-diethyl-decanoic acid 3-ethyl-7-(5-ethyl-5-sulfamoyl-heptyloxy)-heptane-3-sulfonic acid amide 3-ethyl-7-(5-ethyl-5-sulfamoylmethyl-heptyloxy)-heptane-3-sulfonic acid amide 2,2-diethyl-6-(5-ethyl-5-sulfamoylmethyl-heptyloxy)-hexane-1-sulfonic acid amide 3,3-diethyl-7-(5-ethyl-5-sulfamoyl-heptyloxy)-heptane-1-sulfonic acid amide 3,3-diethyl-7-(5-ethyl-5-sulfamoylmethyl-heptyloxy)-heptane-1-sulfonic acid amide 7-(5,5-diethyl-7-sulfamoyl-heptyloxy)-3,3-diethyl-heptane-1-sulfonic acid amide 4,4-diethyl-8-(5-ethyl-5-sulfamoyl-heptyloxy)-octane-1-sulfonic acid amide 4,4-diethyl-8-(5-ethyl-5-sulfamoylmethyl-heptyloxy)-octane-1-sulfonic acid amide 8-(5,5-diethyl-7-sulfamoyl-heptyloxy)-4,4-diethyl-octane-1-sulfonic acid amide 8-(5,5-diethyl-8-sulfamoyl-octyloxy)-4,4-diethyl-octane-1-sulfonic acid amide 5,5-diethyl-9-(5-ethyl-5-sulfamoyl-heptyloxy)-nonane-1-sulfonic acid amide -continued

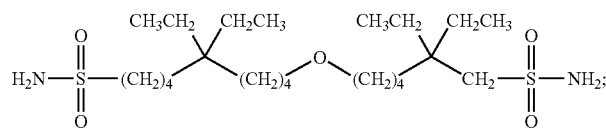

5,5-diethyl-9-(5-ethyl-5-sulfamoylmethyl-heptyloxy)-nonane-1-sulfonic acid amide

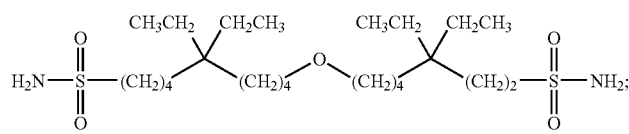

9-(5,5-diethyl-7-sulfamoyl-heptyloxy)-5,5-diethyl-nonane-1-sulfonic acid amide

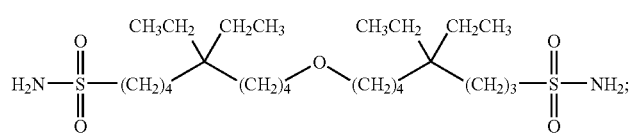

9-(5,5-diethyl-8-sulfamoyl-octyloxy)-5,5-diethyl-nonane-1-sulfonic acid amide

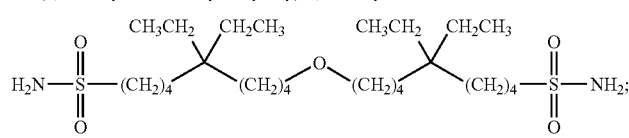

9-(5,5-diethyl-9-sulfamoyl-nonyloxy)-5,5-diethyl-nonane-1-sulfonic acid amide

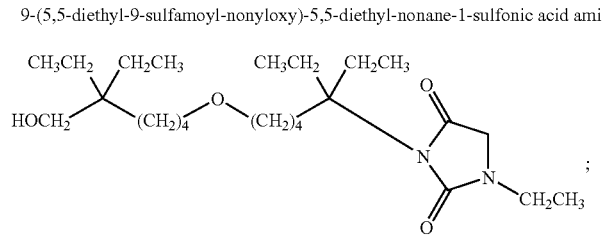

3-[1,1-diethyl-5-(5-ethyl-5-hydroxymethyl-heptyloxy)-pentyl]-1-ethyl-imidazolidine-2,4-dione

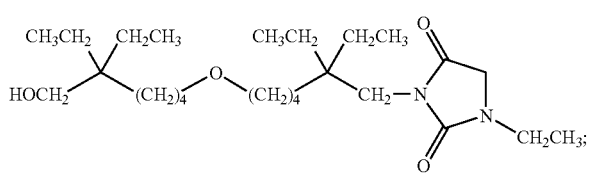

3-[2,2-diethyl-6-(5-ethyl-5-hydroxymethyl-heptyloxy)-hexyl]-1-ethyl-imidazolidine-2,4-dione

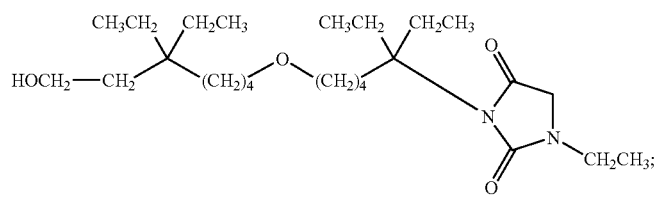

3-[5-(5,5-diethyl-7-hydroxy-heptyloxy)-1,1-diethyl-pentyl]-1-ethyl-imidazolidine-2,4-dione

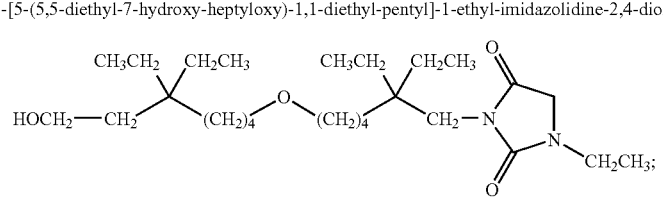

3-[6-(5,5-diethyl-7-hydroxy-heptyloxy)-2,2-diethyl-hexyl]-1-ethyl-imidazolidine-2,4-dione

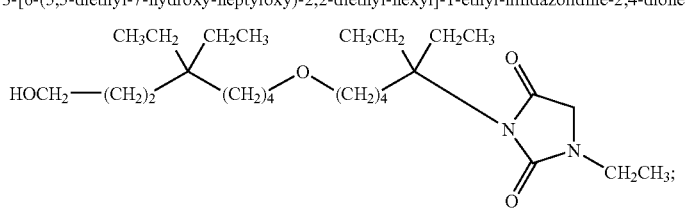

3-[5-(5,5-diethyl-8-hydroxy-octyloxy)-1,1-diethyl-pentyl]-1-ethyl-imidazolidine-2,4-dione -continued

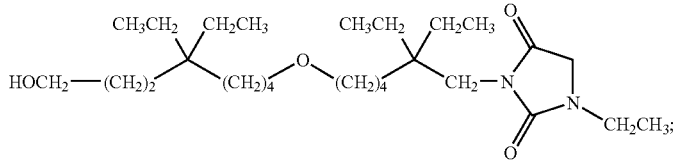

3-[6-(5,5-diethyl-8-hydroxy-octyloxy)-2,2-diethyl-hexyl]-1-ethyl-imidazolidine-2,4-dione

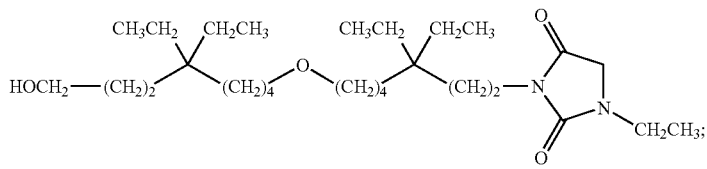

3-[7-(5,5-diethyl-8-hydroxy-octyloxy)-3,3-diethyl-heptyl]-1-ethyl-imidazolidine-2,4-dione

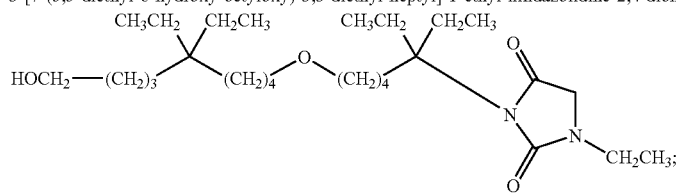

3-[5-(5,5-diethyl-9-hydroxy-nonyloxy)-1,1-diethyl-pentyl]-1-ethyl-imidazolidine-2,4-dione

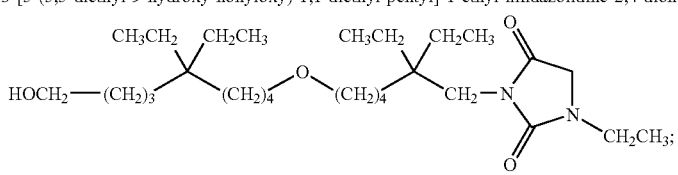

3-[6-(5,5-diethyl-9-hydroxy-nonyloxy)-2,2-diethyl-hexyl]-1-ethyl-imidazolidine-2,4-dione

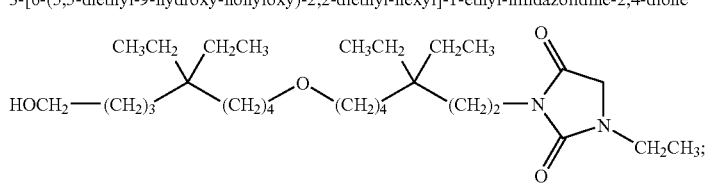

3-[7-(5,5-diethyl-9-hydroxy-nonyloxy)-3,3-diethyl-heptyl]-1-ethyl-imidazolidine-2,4-dione

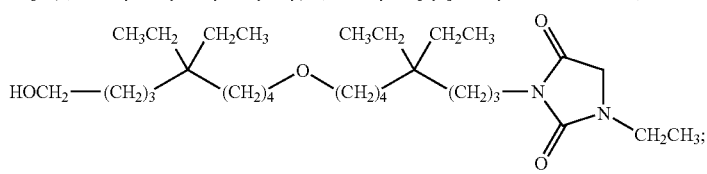

3-[8-(5,5-diethyl-9-hydroxy-nonyloxy)-4,4-diethyl-octyl]-1-ethyl-imidazolidine-2,4-dione

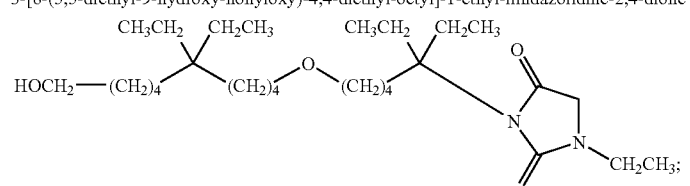

3-[5-(5,5-diethyl-10-hydroxy-decyloxy)-1,1-diethyl-pentyl]-1-ethyl-imidazolidine-2,4-dione

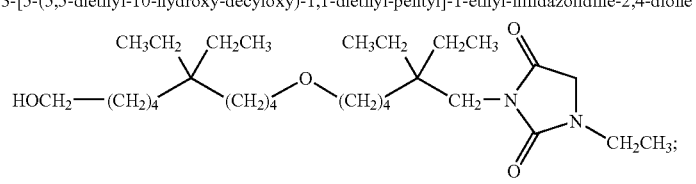

3-[6-(5,5-diethyl-10-hydroxy-decyloxy)-2,2-diethyl-hexyl]-1-ethyl-imidazolidine-2,4-dione -continued

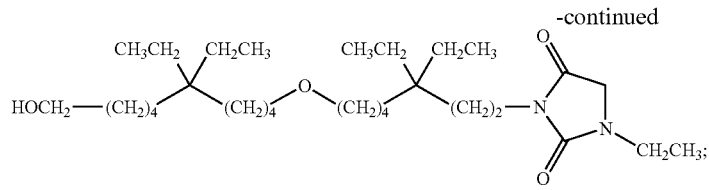

3-[7-(5,5-diethyl-10-hydroxy-decyloxy)-3,3-diethyl-heptyl]-1-ethyl-imidazolidine-2,4-dione

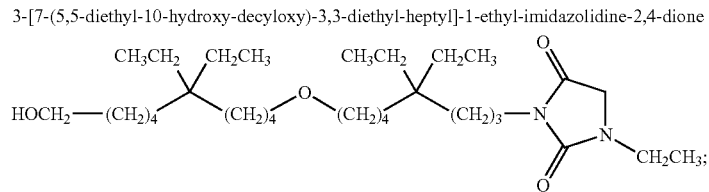

3-[8-(5,5-diethyl-10-hydroxy-decyloxy)-4,4-diethyl-octyl]-1-ethyl-imidazolidine-2,4-dione

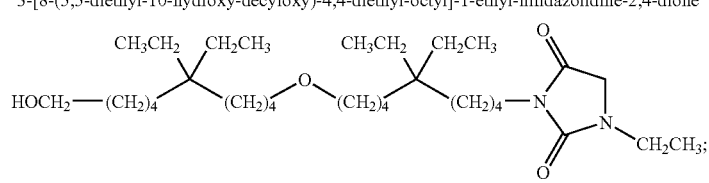

3-[9-(5,5-diethyl-10-hydroxy-decyloxy)-5,5-diethyl-nonyl]-1-ethyl-imidazolidine-2,4-dione

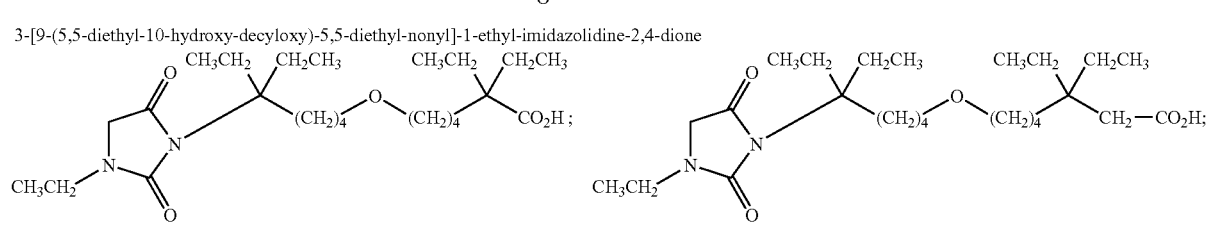

2,2-diethyl-6-[5-ethyl-5-(3-ethyl-2,5-dioxo-imidazolidin-1-yl)-heptyloxy]-hexanoic acid 3,3-diethyl-7-[5-ethyl-5-(3-ethyl-2,5-dioxo-imidazolidin-1-yl)-heptyloxy]-hexanoic acid

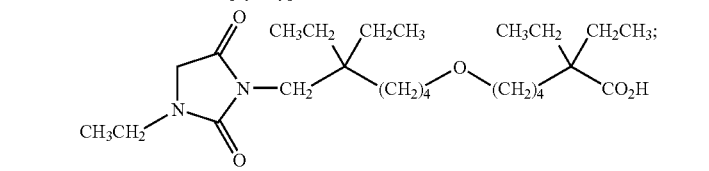

2,2-diethyl-6-[5-ethyl-5-(3-ethyl-2,5-dioxo-imidazolidin-1-ylmethyl)-heptyloxy]-hexanoic acid

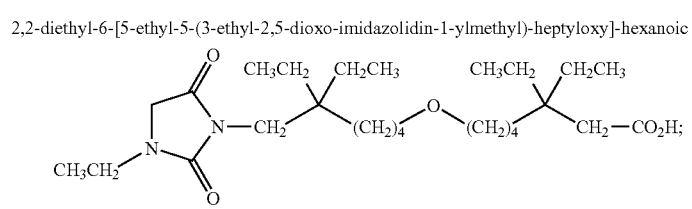

3,3-diethyl-7-[5-ethyl-5-(3-ethyl-2,5-dioxo-imidazolidin-1-ylmethyl)-heptyloxy]-hexanoic acid

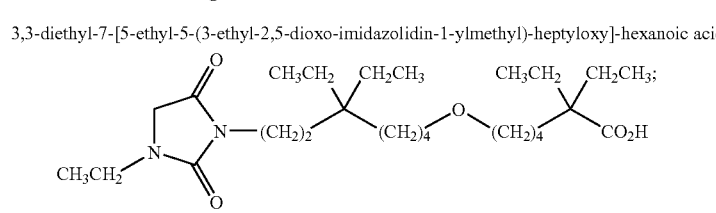

6-[5,5-diethyl-7-(3-ethyl-2,5-dioxo-imidazolidin-1-yl)-heptyloxy]-2,2-diethyl-hexanoic acid

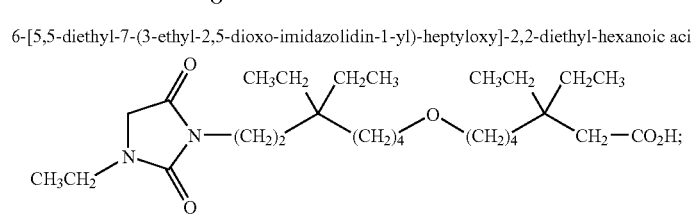

7-[5,5-diethyl-7-(3-ethyl-2,5-dioxo-imidazolidin-1-yl)-heptyloxy]-3,3-diethyl-hexanoic acid -continued

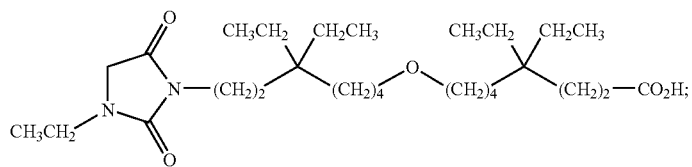

8-[5,5-diethyl-7-(3-ethyl-2,5-dioxo-imidazolidin-1-yl)-heptyloxy]-4,4-diethyl-hexanoic acid

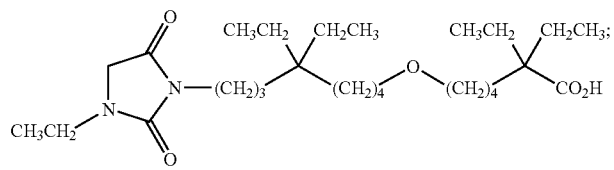

6-[5,5-diethyl-8-(3-ethyl-2,5-dioxo-imidazolidin-1-yl)-octyloxy]-2,2-diethyl-hexanoic acid

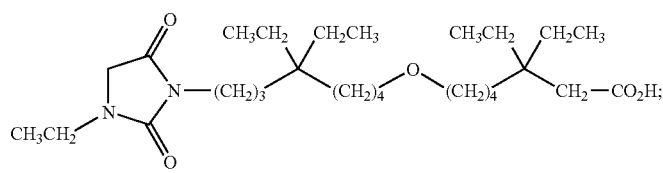

7-[5,5-diethyl-8-(3-ethyl-2,5-dioxo-imidazolidin-1-yl)-octyloxy]-3,3-diethyl-heptanoic acid

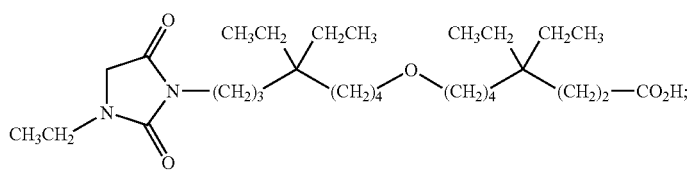

8-[5,5-diethyl-8-(3-ethyl-2,5-dioxo-imidazolidin-1-yl)-octyloxy]-4,4-diethyl-octanoic acid

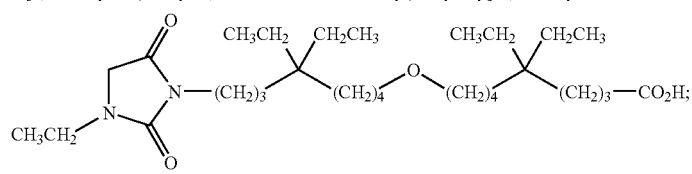

9-[5,5-diethyl-8-(3-ethyl-2,5-dioxo-imidazolidin-1-yl)-octyloxy]-5,5-diethyl-nonanoic acid

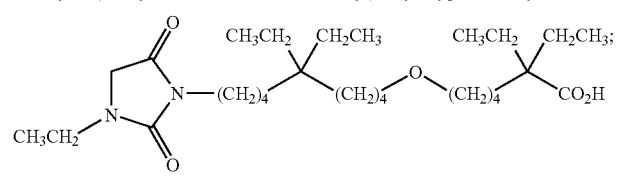

6-[5,5-diethyl-9-(3-ethyl-2,5-dioxo-imidazolidin-1-yl)-nonyloxy]-2,2-diethyl-hexanoic acid

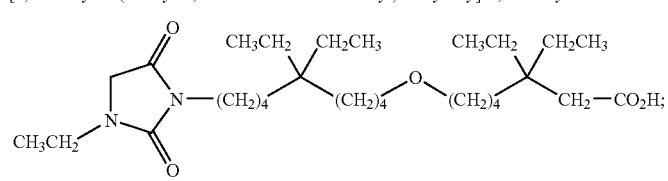

7-[5,5-diethyl-9-(3-ethyl-2,5-dioxo-imidazolidin-1-yl)-nonyloxy]-3,3-diethyl-heptanoic acid

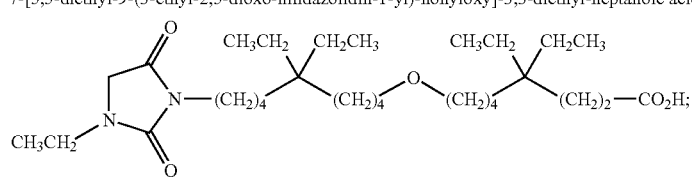

8-[5,5-diethyl-9-(3-ethyl-2,5-dioxo-imidazolidin-1-yl)-nonyloxy]-4,4-diethyl-octanoic acid -continued

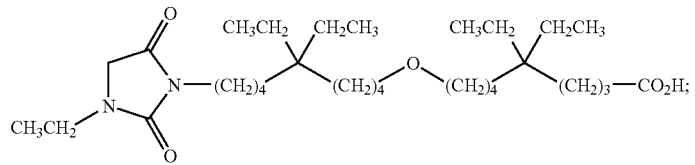

9-[5,5-diethyl-9-(3-ethyl-2,5-dioxo-imidazolidin-1-yl)-nonyloxy]-5,5-diethyl-nonanoic acid

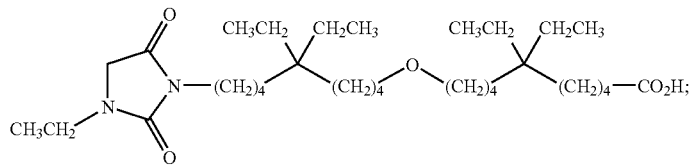

10-[5,5-diethyl-9-(3-ethyl-2,5-dioxo-imidazolidin-1-yl)-nonyloxy]-6,6-diethyl-decanoic acid

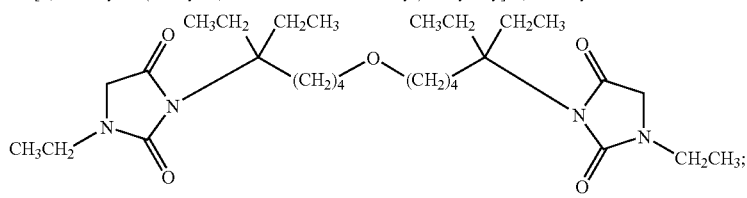

3-[5-(5-ethyl-2,5-dioxo-imidazolidin-1-yl)-5-ethyl-heptyloxy)-1,1-diethyl-pentyl]-1-ethyl-imidazolidine-2,4-dione

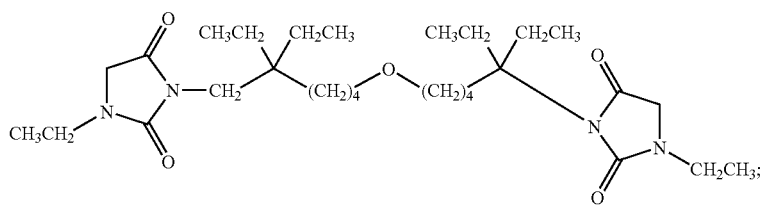

3-[5-(5-ethyl-2,5-dioxo-imidazolidin-1-yl)-methyl-5-ethyl-heptyloxy)-1,1-diethyl-pentyl]-1-ethyl-imidazolidine-2,4-dione

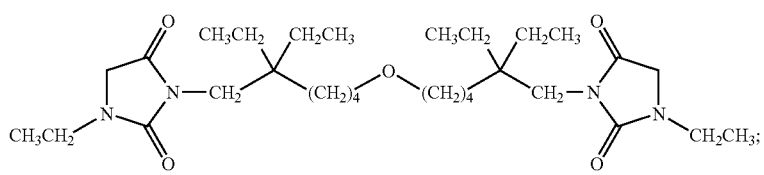

3-[6-(5-ethyl-2,5-dioxo-imidazolidin-1-yl)-methyl-5-ethyl-heptyloxy)-2,2-diethyl-hexyl]-1-ethyl-imidazolidine-2,4-dione

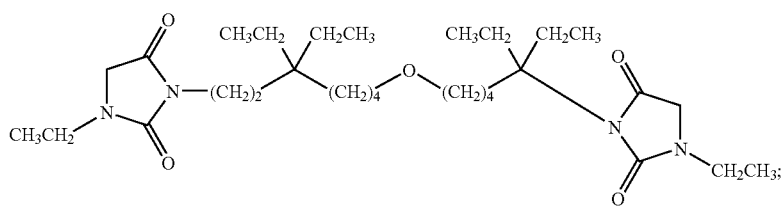

3-[5-(7-(3-ethyl-2,5-dioxo-imidazolidin-1-yl)-5,5-diethyl-heptyloxy)-1,1-diethyl-pentyl]-1-ethyl-imidazolidine-2,4-dione

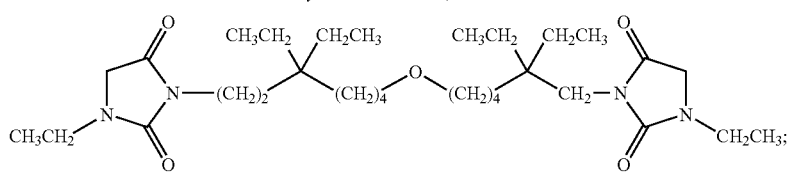

3-[6-(7-(3-ethyl-2,5-dioxo-imidazolidin-1-yl)-5,5-diethyl-heptyloxy)-2,2-diethyl-hexyl]-1-ethyl-imidazolidine-2,4-dione

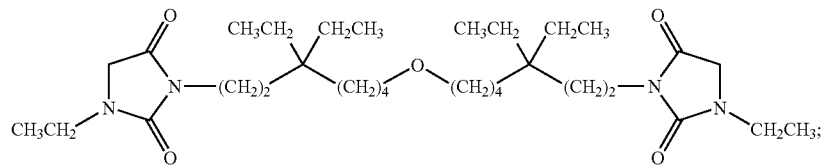

3-[7-(7-(3-ethyl-2,5-dioxo-imidazolidin-1-yl)-5,5-diethyl-heptyloxy)-3,3-diethyl-heptyl]-1-ethyl-imidazolidine-2,4-dione

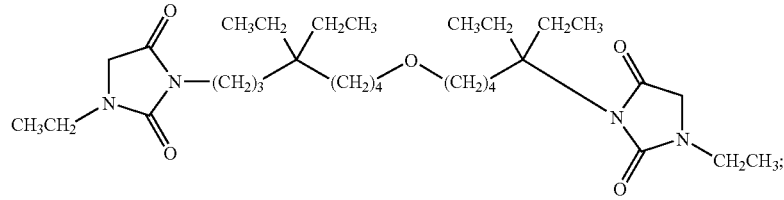

3-[5-(8-(3-ethyl-2,5-dioxo-imidazolidin-1-yl)-5,5-diethyl-octyloxy)-1,1-diethyl-pentyl]-1-ethyl-imidazolidine-2,4-dione

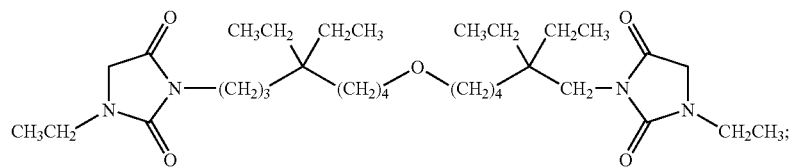

3-[6-(8-(3-ethyl-2,5-dioxo-imidazolidin-1-yl)-5,5-diethyl-octyloxy)-2,2-diethyl-hexyl]-1-ethyl-imidazolidine-2,4-dione

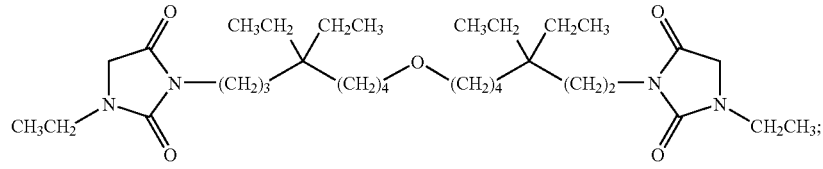

3-[7-(8-(3-ethyl-2,5-dioxo-imidazolidin-1-yl)-5,5-diethyl-octyloxy)-3,3-diethyl-heptyl]-1-ethyl-imidazolidine-2,4-dione

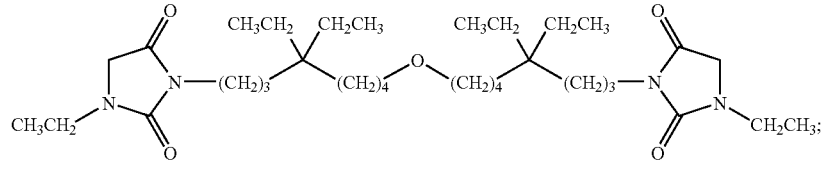

3-[8-(8-(3-ethyl-2,5-dioxo-imidazolidin-1-yl)-5,5-diethyl-octyloxy)-4,4-diethyl-octyl]-1-ethyl-imidazolidine-2,4-dione

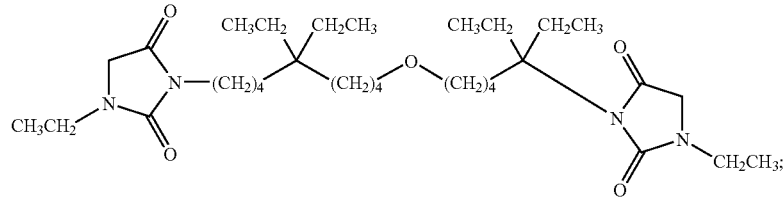

3-[5-(9-(3-ethyl-2,5-dioxo-imidazolidin-1-yl)-5,5-diethyl-nonyloxy)-1,1-diethyl-pentyl]-1-ethyl-imidazolidine-2,4-dione

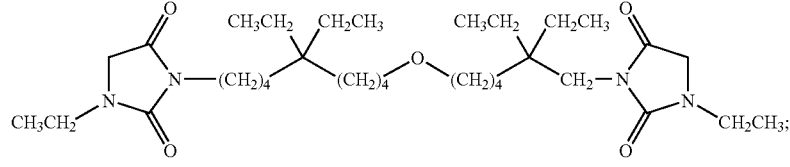

3-[6-(9-(3-ethyl-2,5-dioxo-imidazolidin-1-yl)-5,5-diethyl-nonyloxy)-2,2-diethyl-hexyl]-1-ethyl-imidazolidine-2,4-dione -continued

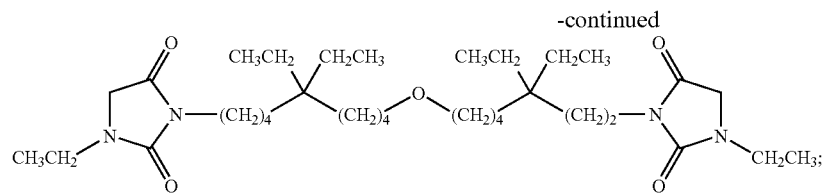

3-[7-(9-(3-ethyl-2,5-dioxo-imidazolidin-1-yl)-5,5-diethyl-nonyloxy)-3,3-diethyl-heptyl]-1-ethyl-imidazolidine-2,4-dione

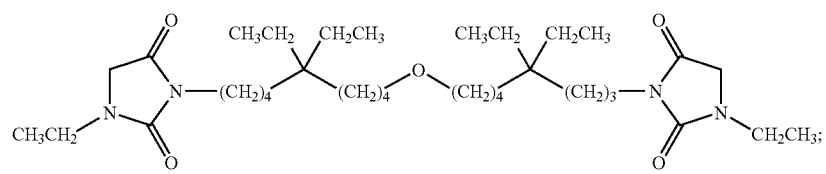

3-[8-(9-(3-ethyl-2,5-dioxo-imidazolidin-1-yl)-5,5-diethyl-nonyloxy)-4,4-diethyl-octyl]-1-ethyl-imidazolidine-2,4-dione

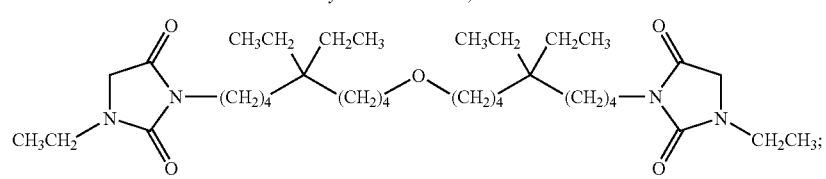

3-[9-(9-(3-ethyl-2,5-dioxo-imidazolidin-1-yl)-5,5-diethyl-nonyloxy)-4,4-diethyl-nonyl]-1-ethyl-imidazolidine-2,4-dione

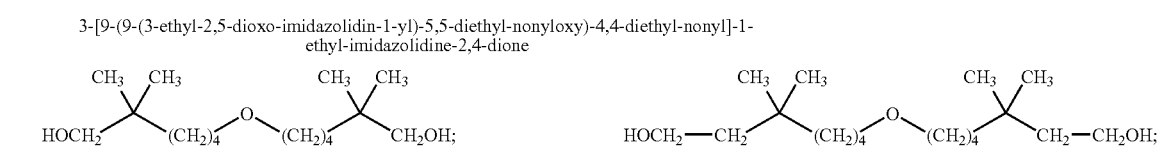

6-(6-hydroxy-5,5-dimethyl-hexyloxy)-2,2-dimethyl-hexan-1-ol 7-(7-hydroxy-5,5-dimethyl-heptyloxy)-3,3-dimethyl-heptan-1-ol 6-(6-hydroxy-5,5-dimethyl-hexyloxy)-2,2-dimethyl-hexanoic acid 7-(6-hydroxy-5,5-dimethyl-hexyloxy)-3,3-dimethyl-heptanoic acid 6-(7-hydroxy-5,5-dimethyl-heptyloxy)-2,2-dimethyl-hexanoic acid 7-(7-hydroxy-5,5-dimethyl-heptyloxy)-3,3-dimethyl-heptanoic acid 6-(8-hydroxy-5,5-dimethyl-octyloxy)-2,2-dimethyl-hexanoic acid 7-(8-hydroxy-5,5-dimethyl-octyloxy)-3,3-dimethyl-heptanoic acid 8-(8-hydroxy-5,5-dimethyl-octyloxy)-4,4-dimethyl-octanoic acid 6-(9-hydroxy-5,5-dimethyl-nonyloxy)-2,2-dimethyl-hexanoic acid 7-(9-hydroxy-5,5-dimethyl-nonyloxy)-3,3-dimethyl-heptanoic acid 8-(9-hydroxy-5,5-dimethyl-nonyloxy)-4,4-dimethyl-octanoic acid 9-(9-hydroxy-5,5-dimethyl-nonyloxy)-5,5-dimethyl-nonanoic acid 6-(10-hydroxy-5,5-dimethyl-decyloxy)-2,2-dimethyl-hexanoic acid

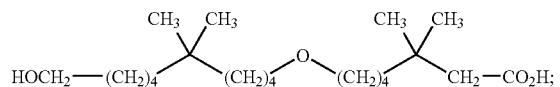

7-(10-hydroxy-5,5-dimethyl-decyloxy)-3,3-dimethyl-heptanoic acid

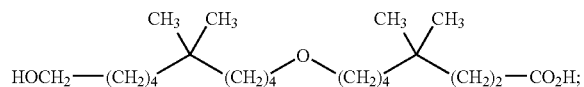

8-(10-hydroxy-5,5-dimethyl-decyloxy)-4,4-dimethyl-octanoic acid

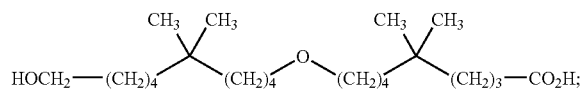

9-(10-hydroxy-5,5-dimethyl-decyloxy)-5,5-dimethyl-nonanoic acid

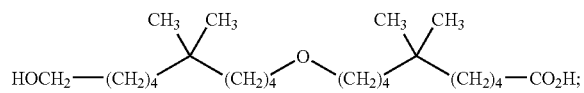

10-(10-hydroxy-5,5-dimethyl-decyloxy)-6,6-dimethyl-decanoic acid

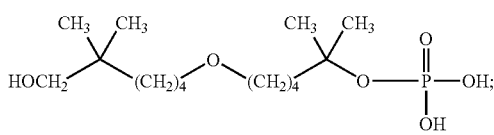

phosphoric acid mono-[5-(6-hydroxy-5,5-dimethyl-hexyloxy)-1,1-dimethyl-pentyl] ester

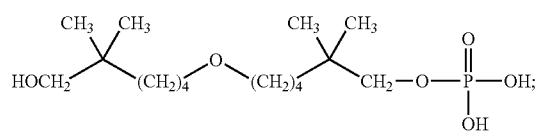

phosphoric acid mono-[6-(6-hydroxy-5,5-dimethyl-hexyloxy)-2,2-dimethyl-hexyl] ester

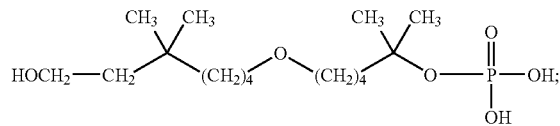

phosphoric acid mono-[5-(7-hydroxy-5,5-dimethyl-heptyloxy)-1,1-dimethyl-pentyl] ester

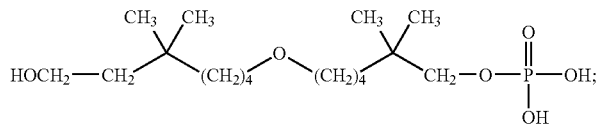

phosphoric acid mono-[6-(7-hydroxy-5,5-dimethyl-heptyloxy)-2,2-dimethyl-hexyl] ester

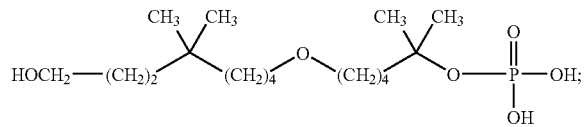

phosphoric acid mono-[5-(8-hydroxy-5,5-dimethyl-octyloxy)-1,1-dimethyl-pentyl] ester

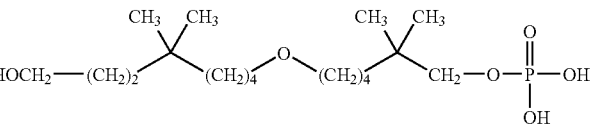

phosphoric acid mono-[6-(8-hydroxy-5,5-dimethyl-octyloxy)-2,2-dimethyl-hexyl] ester

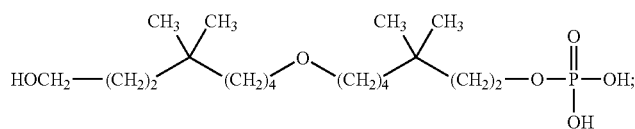

phosphoric acid mono-[7-(8-hydroxy-5,5-dimethyl-octyloxy)-3,3-dimethyl-heptyl] ester

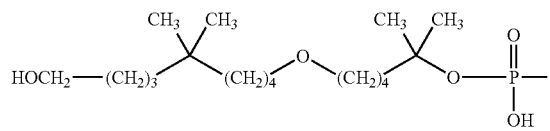

phosphoric acid mono-[5-(9-hydroxy-5,5-dimethyl-nonyloxy)-1,1-dimethyl-pentyl] ester

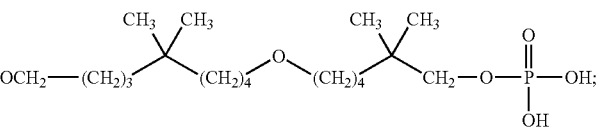

phosphoric acid mono-[6-(9-hydroxy-5,5-dimethyl-nonyloxy)-2,2-dimethyl-hexyl] ester

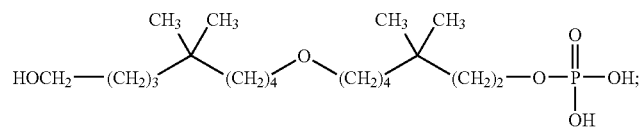

phosphoric acid mono-[7-(9-hydroxy-5,5-dimethyl-nonyloxy)-3,3-dimethyl-heptyl] ester

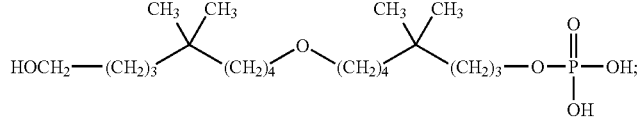

phosphoric acid mono-[8-(9-hydroxy-5,5-dimethyl-nonyloxy)-4,4-dimethyl-octyl] ester

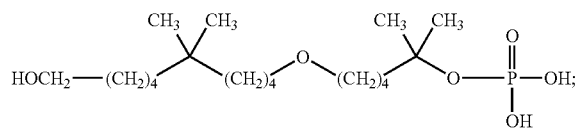

phosphoric acid mono-[5-(10-hydroxy-5,5-dimethyl-decyloxy)-1,1-dimethyl-pentyl] ester

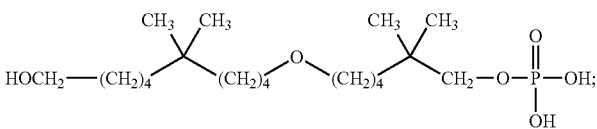

phosphoric acid mono-[6-(10-hydroxy-5,5-dimethyl-decyloxy)-2,2-dimethyl-hexyl] ester

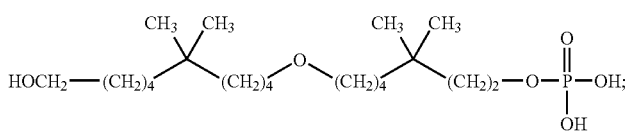

phosphoric acid mono-[7-(10-hydroxy-5,5-dimethyl-decyloxy)-3,3-dimethyl-heptyl] ester

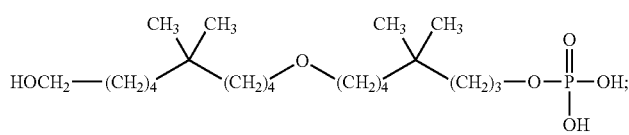

phosphoric acid mono-[8-(10-hydroxy-5,5-dimethyl-decyloxy)-4,4-dimethyl-octyl] ester

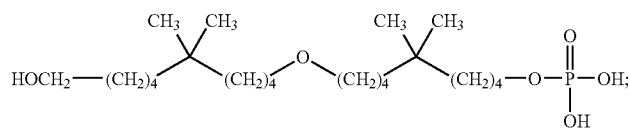

phosphoric acid mono-[9-(10-hydroxy-5,5-dimethyl-decyloxy)-5,5-dimethyl-nonyl] ester

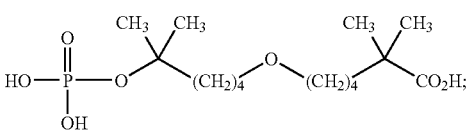

2,2-dimethyl-6-(5-methyl-5-phosphonooxy-hexyloxy)-hexanoic acid

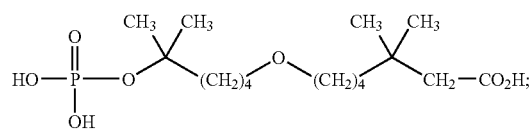

3,3-dimethyl-7-(5-methyl-5-phosphonooxy-hexyloxy)-heptanoic acid

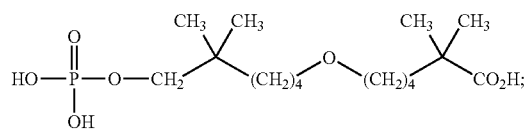

6-(5,5-dimethyl-6-phosphonooxy-hexyloxy)-2,2-dimethyl-hexanoic acid

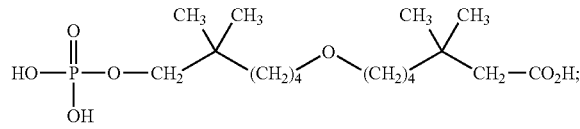

7-(5,5-dimethyl-6-phosphonooxy-hexyloxy)-3,3-dimethyl-heptanoic acid

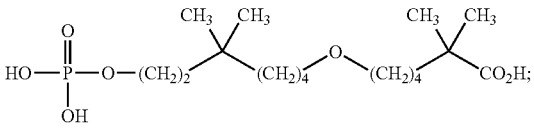

6-(5,5-dimethyl-7-phosphonooxy-heptyloxy)-2,2-dimethyl-hexanoic acid

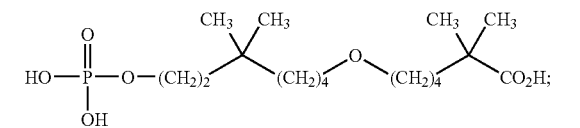

7-(5,5-dimethyl-7-phosphonooxy-heptyloxy)-3,3-dimethyl-heptanoic acid

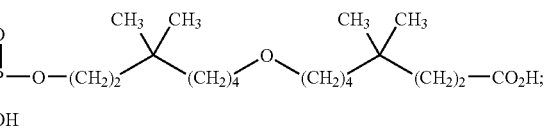

8-(5,5-dimethyl-7-phosphonooxy-heptyloxy)-4,4-dimethyl-octanoic acid

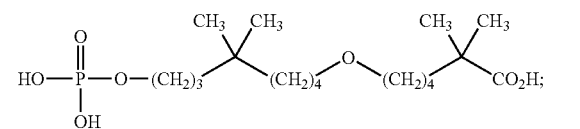

6-(5,5-dimethyl-8-phosphonooxy-octyloxy)-2,2-dimethyl-hexanoic acid

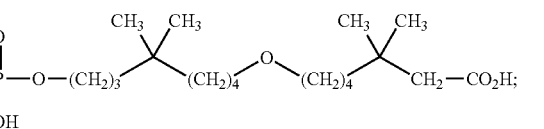

7-(5,5-dimethyl-8-phosphonooxy-octyloxy)-3,3-dimethyl-heptanoic acid

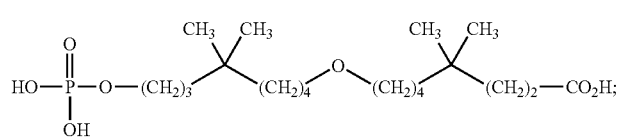

8-(5,5-dimethyl-8-phosphonooxy-octyloxy)-4,4-dimethyl-octanoic acid

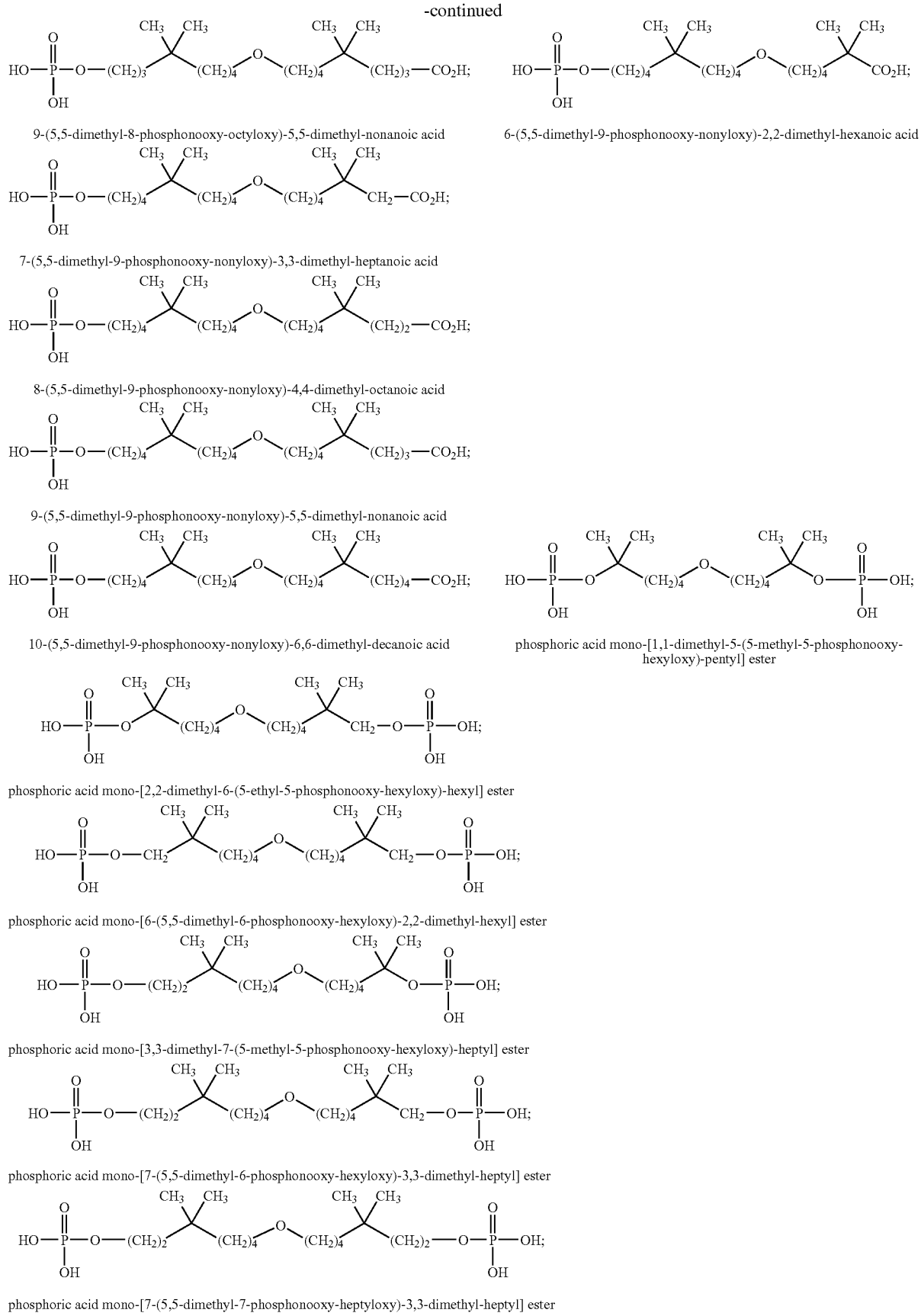

-continued

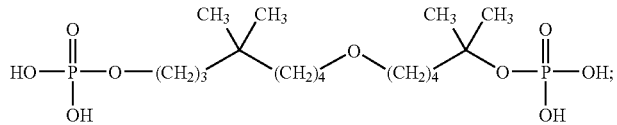

phosphoric acid mono-[4,4-dimethyl-8-(5-methyl-5-phosphonooxy-hexyloxy)-octyl] ester

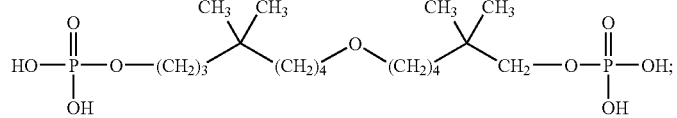

phosphoric acid mono-[8-(5,5-dimethyl-6-phosphonooxy-hexyloxy)-4,4-dimethyl-octyl] ester

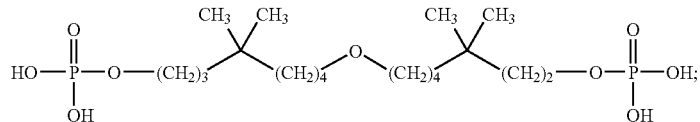

phosphoric acid mono-[8-(5,5-dimethyl-7-phosphonooxy-heptyloxy)-4,4-dimethyl-octyl] ester

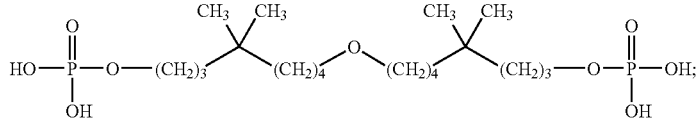

phosphoric acid mono-[8-(5,5-dimethyl-8-phosphonooxy-octyloxy)-4,4-dimethyl-octyl] ester

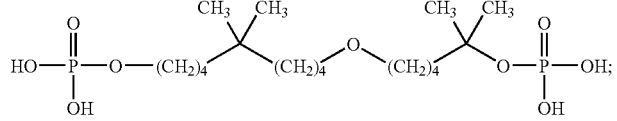

phosphoric acid mono-[5,5-dimethyl-9-(5-methyl-5-phosphonooxy-hexyloxy-nonyl] ester

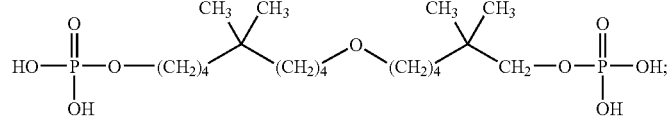

phosphoric acid mono-[9-(5,5-dimethyl-6-phosphonooxy-hexyloxy)-5,5-dimethyl-nonyl] ester

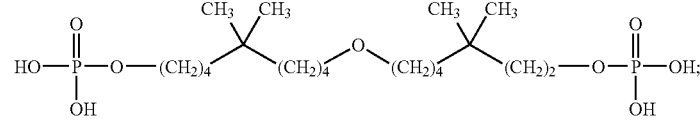

phosphoric acid mono-[9-(5,5-dimethyl-7-phosphonooxy-heptyloxy)-5,5-dimethyl-nonyl] ester

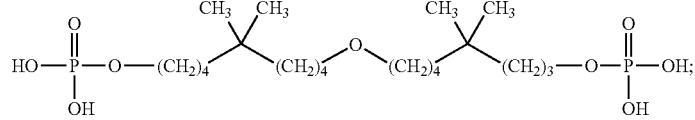

phosphoric acid mono-[9-(5,5-dimethyl-8-phosphonooxy-octyloxy)-5,5-dimethyl-nonyl] ester

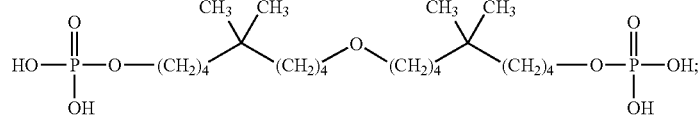

phosphoric acid mono-[9-(5,5-dimethyl-9-phosphonooxy-nonyloxy)-5,5-dimethyl-nonyl] ester

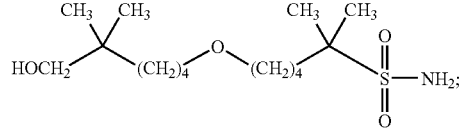

6-(6-hydroxy-5,5-dimethyl-hexyloxy)-2-methyl-hexane-2-sulfonic acid amide

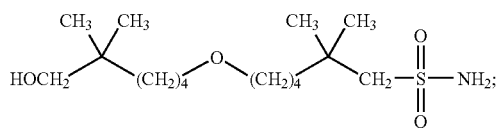

6-(6-hydroxy-5,5-dimethyl-hexyloxy)-2,2-dimethyl-hexane-1-sulfonic acid amide

-continued

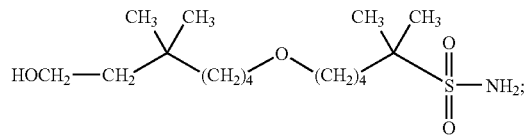

6-(7-hydroxy-5,5-dimethyl-heptyloxy)-2-methyl-hexane-2-sulfonic acid amide

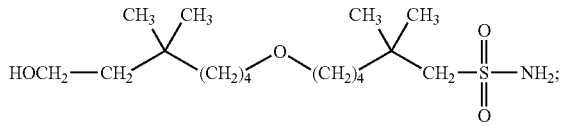

6-(7-hydroxy-5,5-dimethyl-heptyloxy)-2,2-dimethyl-hexane-1-sulfonic acid amide

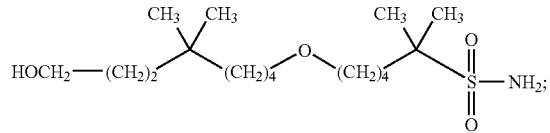

6-(8-hydroxy-5,5-dimethyl-octyloxy)-3-methyl-hexane-2-sulfonic acid amide

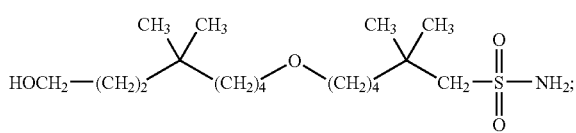

6-(8-hydroxy-5,5-dimethyl-octyloxy)-2,2-dimethyl-hexane-1-sulfonic acid amide

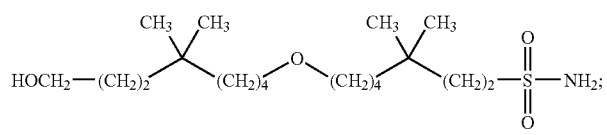

7-(8-hydroxy-5,5-dimethyl-octyloxy)-3,3-dimethyl-heptane-1-sulfonic acid amide

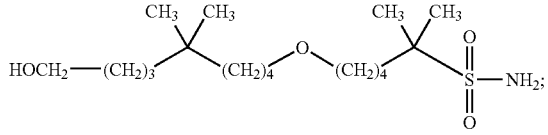

6-(9-hydroxy-5,5-dimethyl-nonyloxy)-2-methyl-hexane-2-sulfonic acid amide

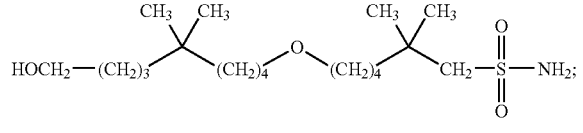

6-(9-hydroxy-5,5-dimethyl-nonyloxy)-2,2-dimethyl-hexane-1-sulfonic acid amide

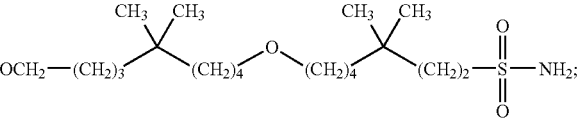

7-(9-hydroxy-5,5-dimethyl-nonyloxy)-3,3-dimethyl-heptane-1-sulfonic acid amide

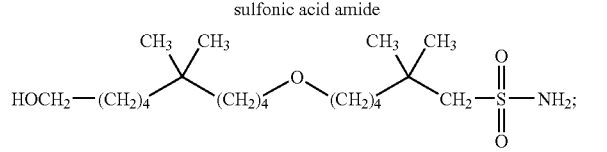

8-(9-hydroxy-5,5-dimethyl-nonyloxy)-4,4-dimethyl-octane-1-sulfonic acid amide

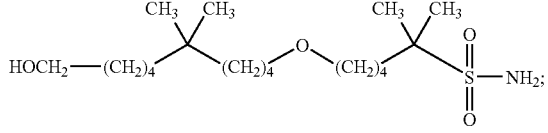

6-(10-hydroxy-5,5-dimethyl-decyloxy)-2-methyl-hexane-2-sulfonic acid amide

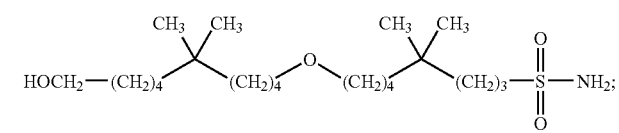

6-(10-hydroxy-5,5-dimethyl-decyloxy)-2,2-dimethyl-hexane-1-sulfonic acid amide

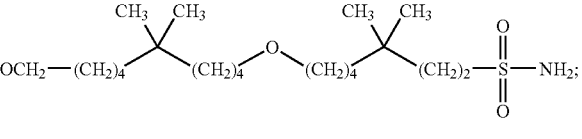

7-(10-hydroxy-5,5-dimethyl-decyloxy)-3,3-dimethyl-heptane-1-sulfonic acid amide

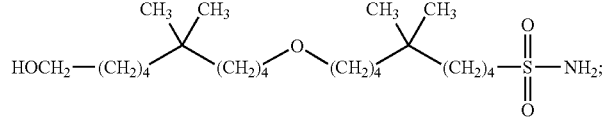

8-(10-hydroxy-5,5-dimethyl-decyloxy)-4,4-dimethyl-octane-1-sulfonic acid amide

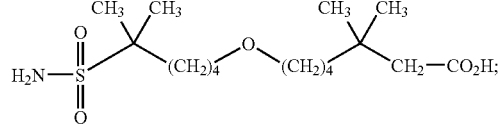

9-(10-hydroxy-5,5-dimethyl-decyloxy)-5,5-dimethyl-nonane-1-sulfonic acid amide

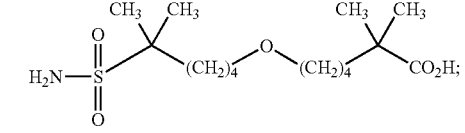

2,2-dimethyl-6-(5-methyl-5-sulfamoyl-hexyloxy)-hexanoic acid

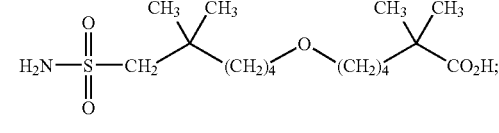

3,3-dimethyl-7-(5-methyl-5-sulfamoyl-hexyloxy)-heptanoic acid 6-(5,5-dimethyl-6-sulfamoyl-hexyloxy)-2,2-dimethyl-hexanoic acid -continued

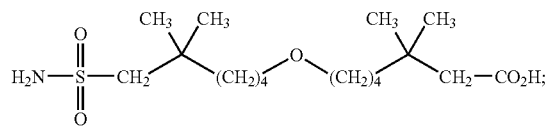

7-(5,5-dimethyl-6-sulfamoyl-hexyloxy)-3,3-dimethyl-heptanoic acid

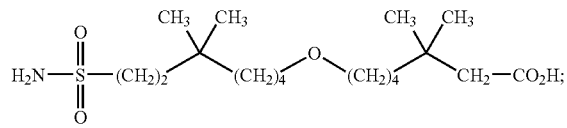

7-(5,5-dimethyl-7-sulfamoyl-heptyloxy)-3,3-dimethyl-heptanoic acid

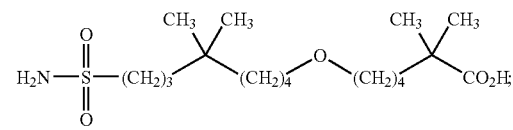

6-(5,5-dimethyl-8-sulfamoyl-octyloxy)-2,2-dimethyl-hexanoic acid

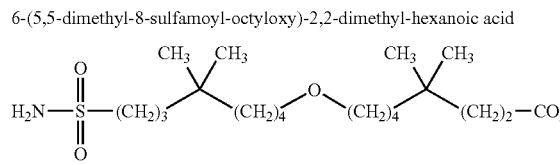

8-(5,5-dimethyl-8-sulfamoyl-octyloxy)-4,4-dimethyl-octanoic acid

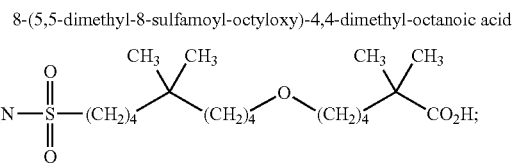

6-(5,5-dimethyl-9-sulfamoyl-nonyloxy)-2,2-dimethyl-hexanoic acid

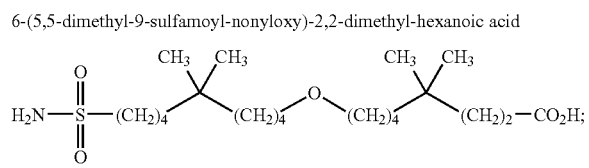

8-(5,5-dimethyl-9-sulfamoyl-nonyloxy)-4,4-dimethyl-octanoic acid

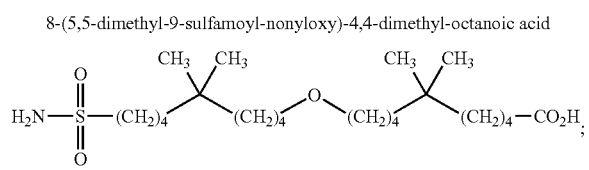

10-(5,5-dimethyl-9-sulfamoyl-nonyloxy)-6,6-dimethyl-decanoic acid

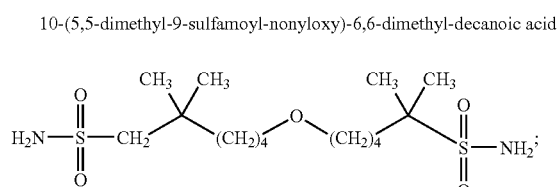

2,2-dimethyl-6-(5-methyl-5-sulfamoyl-hexyloxy)-hexane-1-sulfonic acid amide

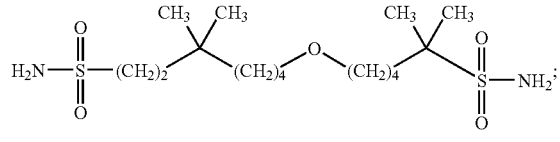

3,3-dimethyl-7-(5-methyl-5-sulfamoyl-hexyloxy)-heptane-1-sulfonic acid amide

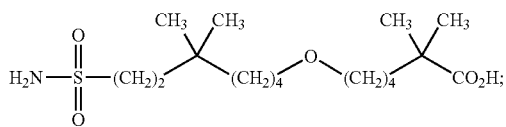

6-(5,5-dimethyl-7-sulfamoyl-heptyloxy)-2,2-dimethyl-hexanoic acid

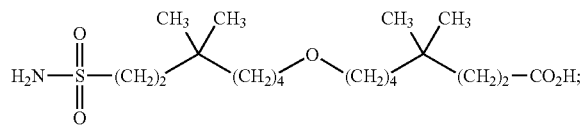

8-(5,5-dimethyl-7-sulfamoyl-heptyloxy)-4,4-dimethyl-octanoic acid

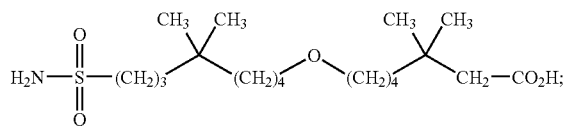

7-(5,5-dimethyl-8-sulfamoyl-octyloxy)-3,3-dimethyl-heptanoic acid

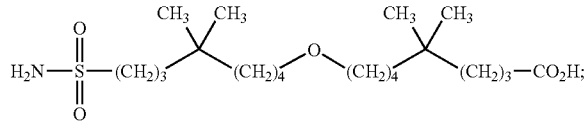

9-(5,5-dimethyl-8-sulfamoyl-octyloxy)-5,5-dimethyl-nonanoic acid

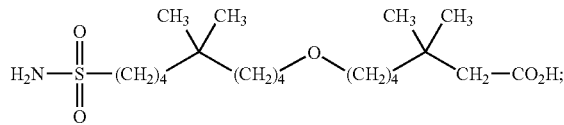

7-(5,5-dimethyl-9-sulfamoyl-nonyloxy)-3,3-dimethyl-heptanoic acid

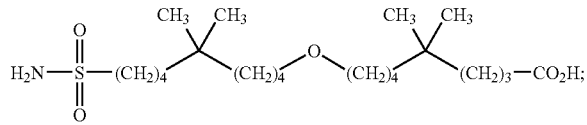

9-(5,5-dimethyl-9-sulfamoyl-nonyloxy)-5,5-dimethyl-nonanoic acid

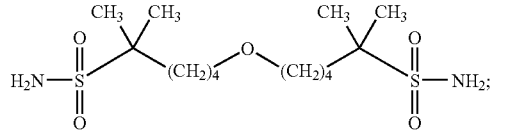

2-methyl-6-(5-methyl-5-sulfamoyl-hexyloxy)-hexane-2-sulfonic acid amide

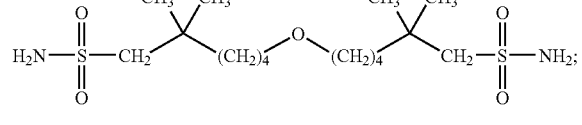

6-(5,5-dimethyl-6-sulfamoyl-hexyloxy)-hexane-1-sulfonic acid amide

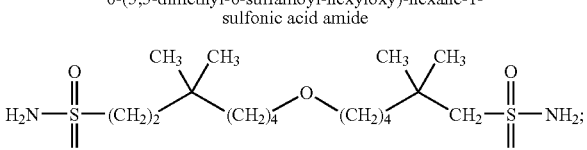

7-(5,5-dimethyl-6-sulfamoyl-hexyloxy)-3,3-dimethyl-heptane-1-sulfonic acid amide -continued

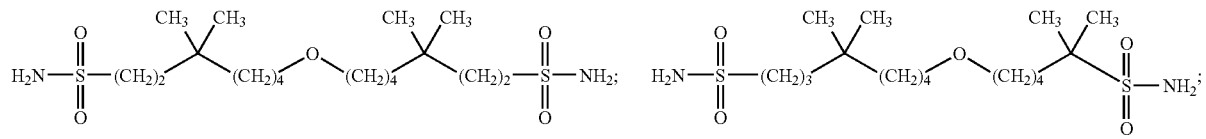

7-(5,5-dimethyl-7-sulfamoyl-heptyloxy)-3,3-dimethyl-heptane-1-sulfonic acid amide 4,4-dimethyl-8-(5-methyl-5-sulfamoyl-hexyloxy)-octane-1-sulfonic acid amide

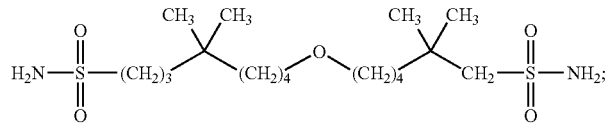

8-(5,5-dimethyl-6-sulfamoyl-hexyloxy)-4,4-dimethyl-octane-1-sulfonic acid amide

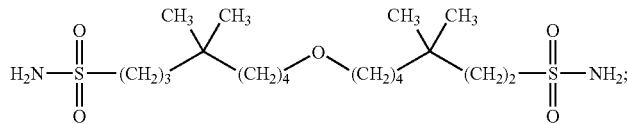

8-(5,5-dimethyl-7-sulfamoyl-heptyloxy)-4,4-dimethyl-octane-1-sulfonic acid amide

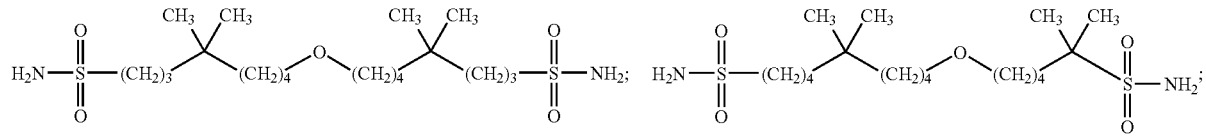

8-(5,5-dimethyl-8-sulfamoyl-octyloxy)-4,4-dimethyl-octane-1-sulfonic acid amide 5,5-dimethyl-9-(5-methyl-5-sulfamoyl-hexyloxy)-nonane-1-sulfonic acid amide

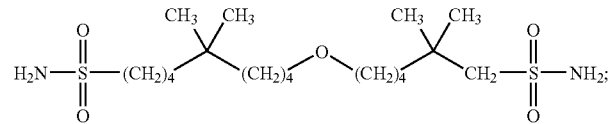

9-(5,5-dimethyl-6-sulfamoyl-hexyloxy)-5,5-dimethyl-nonane-1-sulfonic acid amide

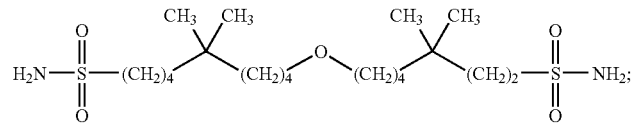

9-(5,5-dimethyl-7-sulfamoyl-heptyloxy)-5,5-dimethyl-nonane-1-sulfonic acid amide

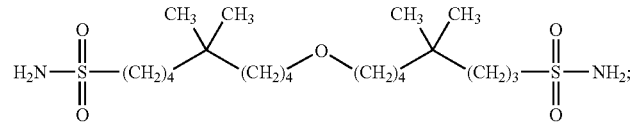

9-(5,5-dimethyl-8-sulfamoyl-octyloxy)-5,5-dimethyl-nonane-1-sulfonic acid amide

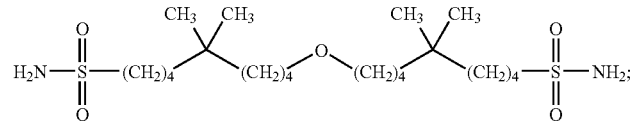

9-(5,5-dimethyl-9-sulfamoyl-octyloxy)-5,5-dimethyl-nonane-1-sulfonic acid amide

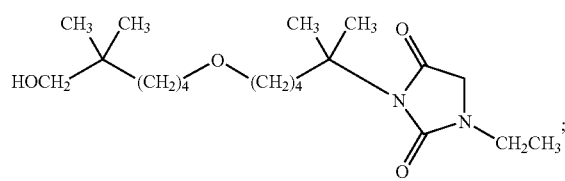

1-ethyl-3-[5-(6-hydroxy-5,5-dimethyl-hexyloxy)-1,1-dimethyl-pentyl]imidazolidine-2,4-dione

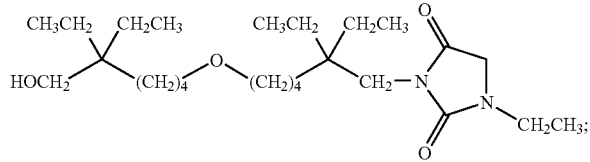

1-ethyl-3-[6-(6-hydroxy-5,5-dimethyl-hexyloxy)-2,2-dimethyl-hexyl]imidazolidine-2,4-dione -continued

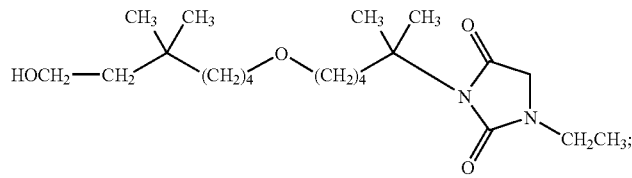

1-ethyl-3-[5-(7-hydroxy-5,5-dimethyl-heptyloxy)-1,1-dimethyl-pentyl]-imidazolidine-2,4-dione

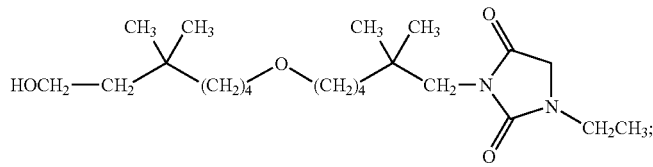

1-ethyl-3-[6-(7-hydroxy-5,5dimethyl-heptyloxy)-2,2-dimethyl-hexyl]-imidazolidine-2,4-dione

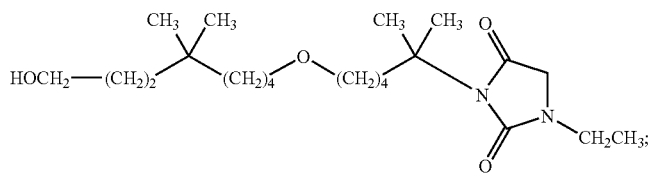

1-ethyl-3-[5-(8-hydroxy-5,5-dimethyl-octyloxy)-1,1-dimethyl-pentyl]-imidazolidine-2,4-dione

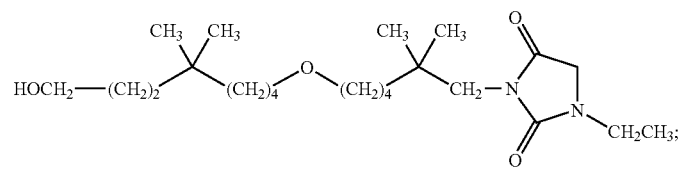

1-ethyl-3-[6-(8-hydroxy-5,5-dimethyl-octyloxy)-2,2-dimethyl-hexyl]-imidazolidine-2,4-dione

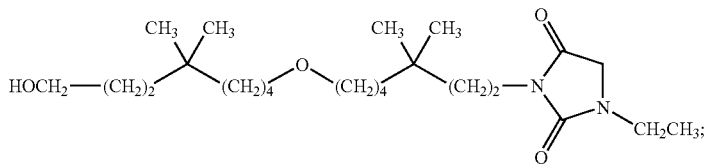

1-ethyl-3-[7-(8-hydroxy-5,5-dimethyl-octyloxy)-3,3-dimethyl-heptyl]-imidazolidine-2,4-dione

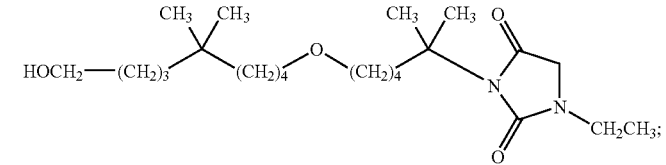

1-ethyl-3-[5-(9-hydroxy-5,5-dimethyl-nonyloxy)-1,1-dimethyl-pentyl]-imidazolidine-2,4-dione

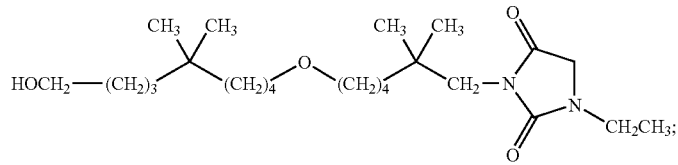

1-ethyl-3-[6-(9-hydroxy-5,5-dimethyl-nonyloxy)-2,2-dimethyl-hexyl]-imidazolidine-2,4-dione

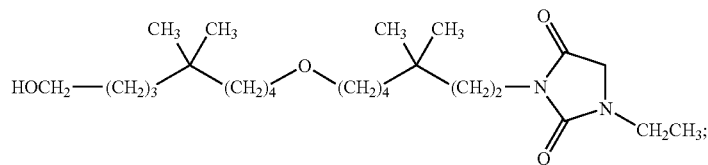

1-ethyl-3-[7-(9-hydroxy-5,5-dimethyl-nonyloxy)-3,3-dimethyl-heptyl]-imidazolidine-2,4-dione -continued

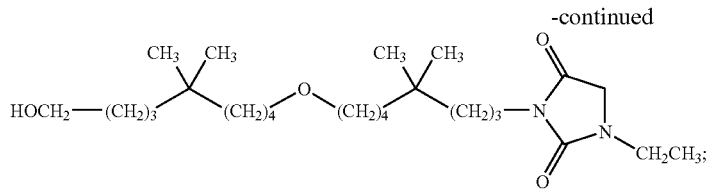

1-ethyl-3-[8-(9-hydroxy-5,5-dimethyl-nonyloxy)-4,4-dimethyl-octyl]-imidazolidine-2,4-dione

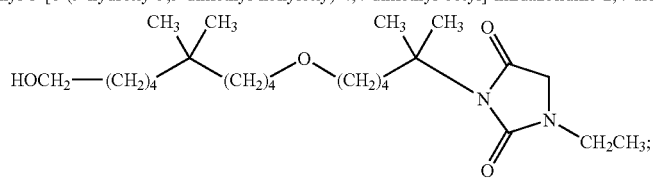

1-ethyl-3-[5-(10-hydroxy-5,5-dimethyl-decyloxy)-1,1-dimethyl-pentyl]-imidazolidine-2,4-dione

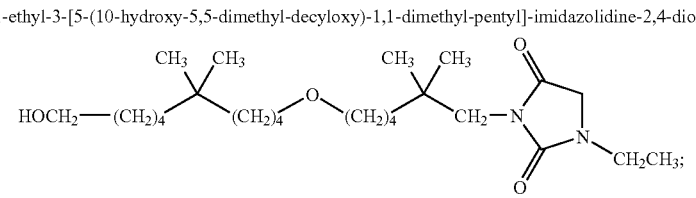

1-ethyl-3-[6-(10-hydroxy-5,5-dimethyl-decyloxy)-2,2-dimethyl-hexyl]-imidazolidine-2,4-dione

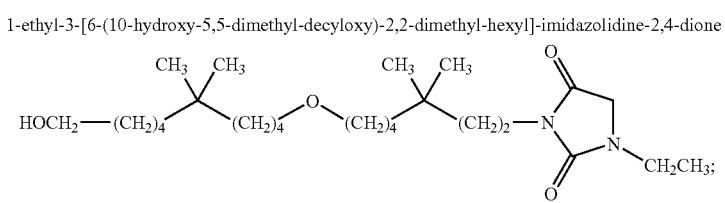

1-ethyl-3-[7-(10-hydroxy-5,5-dimethyl-decyloxy)-3,3-dimethyl-heptyl]-imidazolidine-2,4-dione

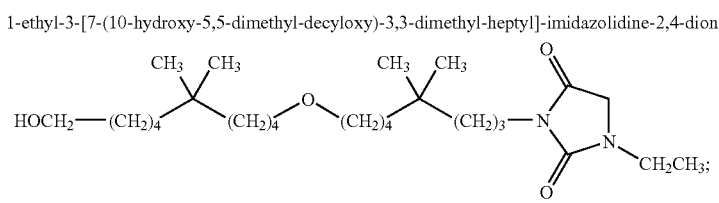

1-ethyl-3-[8-(10-hydroxy-5,5-dimethyl-decyloxy)-4,4-dimethyl-octyl]-imidazolidine-2,4-dione

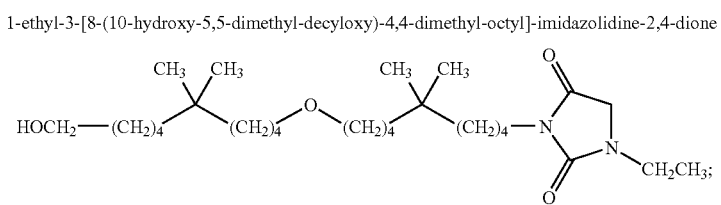

1-ethyl-3-[9-(10-hydroxy-5,5-dimethyl-decyloxy)-5,5-dimethyl-nonyl]-imidazolidine-2,4-dione

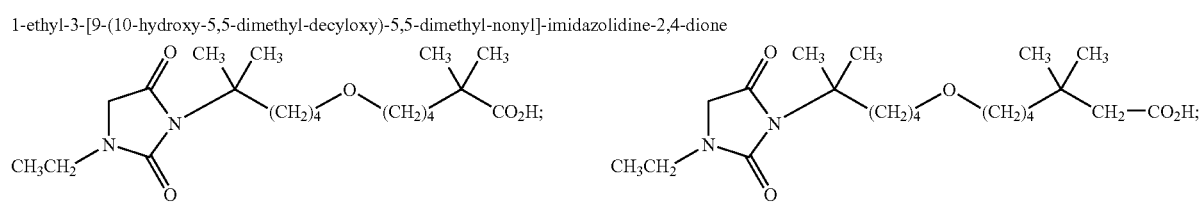

6-[5-(3-ethyl-2,5-dioxo-imidazolidin-1-yl)-5-methyl-hexyloxy]-2,2-dimethyl-hexanoic acid  
7-[5-(3-ethyl-2,5-dioxo-imidazolidin-1-yl)-5-methyl-hexyloxy]-3,3-dimethyl-heptanoic acid

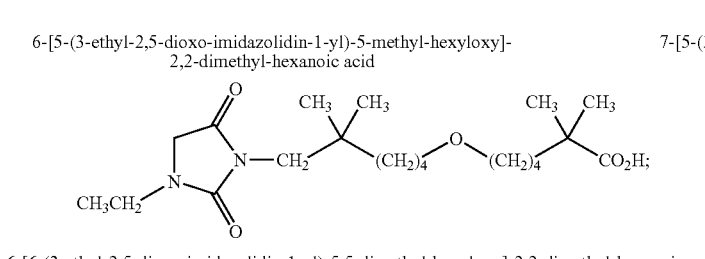

6-[6-(3-ethyl-2,5-dioxo-imidazolidin-1-yl)-5,5-dimethyl-hexyloxy]-2,2-dimethyl-hexanoic acid -continued

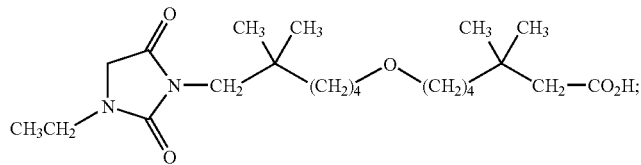

7-[6-(3-ethyl-2,5-dioxo-imidazolidin-1-yl)-5,5-dimethyl-hexyloxy]-3,3-dimethyl-heptanoic acid

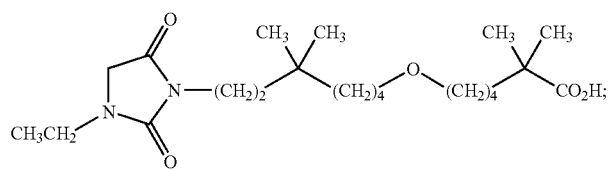

6-[7-(3-ethyl-2,5-dioxo-imidazolidin-1-yl)-5,5-dimethyl-heptyloxy]-2,2-dimethyl-hexanoic acid

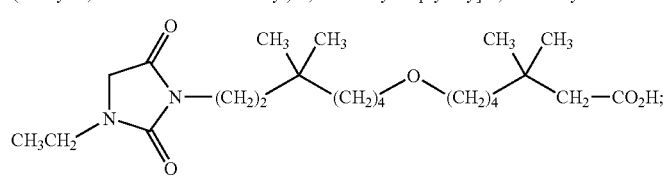

7-[7-(3-ethyl-2,5-dioxo-imidazolidin-1-yl)-5,5-dimethyl-heptyloxy]-3,3-dimethyl-heptanoic acid

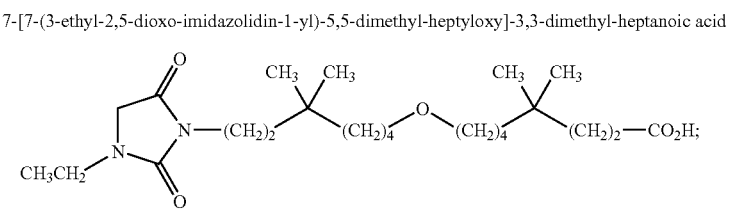

8-[7-(3-ethyl-2,5-dioxo-imidazolidin-1-yl)-5,5-dimethyl-heptyloxy]-4,4-dimethyl-octanoic acid

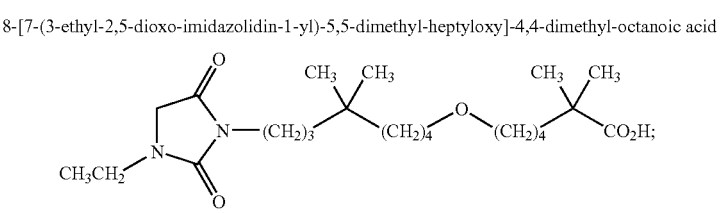

6-[8-(3-ethyl-2,5-dioxo-imidazolidin-1-yl)-5,5-dimethyl-octyloxy]-2,2-dimethyl-hexanoic acid

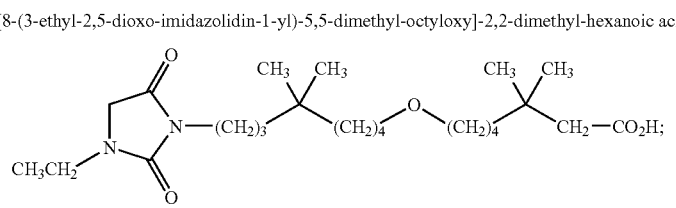

7-[8-(3-ethyl-2,5-dioxo-imidazolidin-1-yl)-5,5-dimethyl-octyloxy]-3,3-dimethyl-heptanoic acid

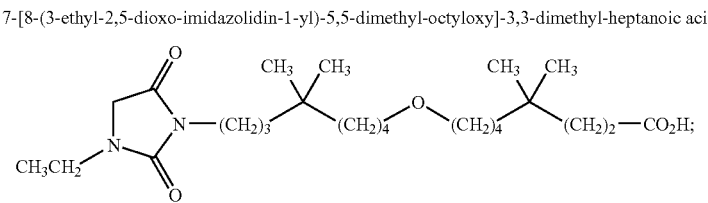

8-[8-(3-ethyl-2,5-dioxo-imidazolidin-1-yl)-5,5-dimethyl-octyloxy]-4,4-dimethyl-octanoic acid

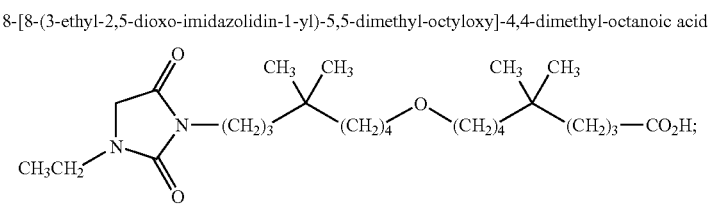

9-[8-(3-ethyl-2,5-dioxo-imidazolidin-1-yl)-5,5-dimethyl-octyloxy]-5,5-dimethyl-nonanoic acid -continued

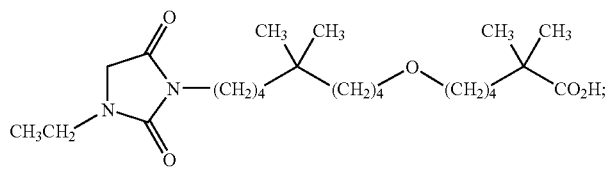

6-[9-(3-ethyl-2,5-dioxo-imidazolidin-1-yl)-5,5-dimethyl-nonyloxy]-2,2-dimethyl-hexanoic acid

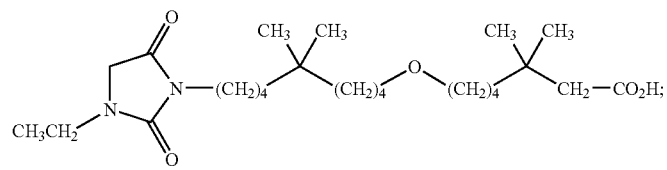

7-[9-(3-ethyl-2,5-dioxo-imidazolidin-1-yl)-5,5-dimethyl-nonyloxy]-3,3-dimethyl-heptanoic acid

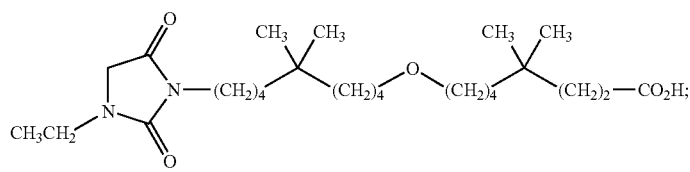

8-[9-(3-ethyl-2,5-dioxo-imidazolidin-1-yl)-5,5-dimethyl-nonyloxy]-4,4-dimethyl-octanoic acid

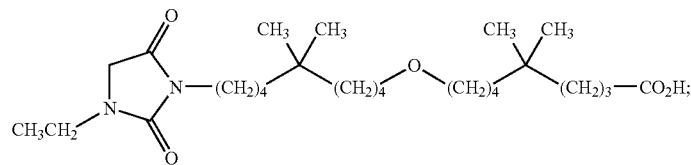

9-[9-(3-ethyl-2,5-dioxo-imidazolidin-1-yl)-5,5-dimethyl-nonyloxy]-5,5-dimethyl-nonanoic acid

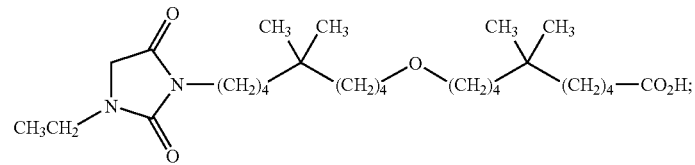

10-[9-(3-ethyl-2,5-dioxo-imidazolidin-1-yl)-5,5-dimethyl-nonyloxy]-6,6-dimethyl-decanoic acid

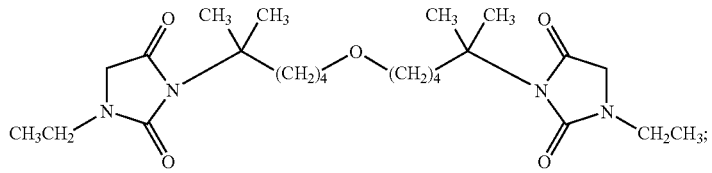

3-[5-(5-(3-ethyl-2,5-dioxo-imidazolidin-1-yl)-5-methyl-hexyloxy)-1,1-dimethyl-pentyl]-1-ethyl-imidazolidine-2,4-dione

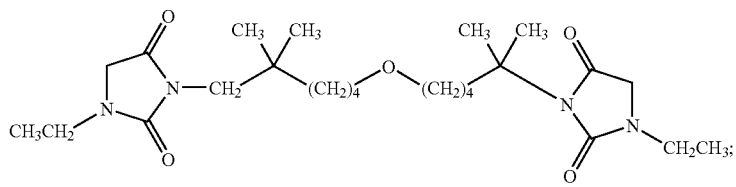

3-[5-(6-(3-ethyl-2,5-dioxo-imidazolidin-1-yl)-5,5-dimethyl-hexyloxy)-1,1-dimethyl-pentyl]-1-ethyl-imidazolidine-2,4-dione -continued

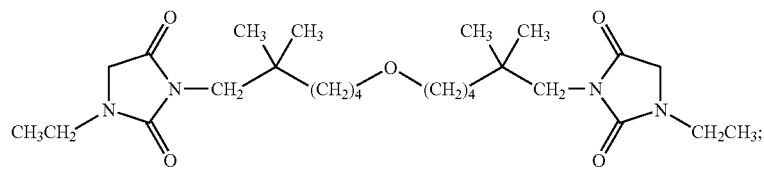
3-[6-(6-(3-ethyl-2,5-dioxo-imidazolidin-1-yl)-5,5-dimethyl-hexyloxy)-2,2-dimethyl-hexyl]-1-ethyl-imidazolidine-2,4-dione

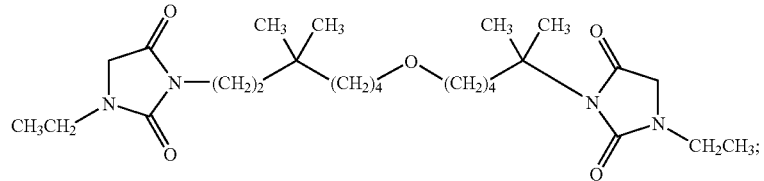
3-[5-(7-cyclopentyl-5,5-dimethyl-heptyloxy)-1,1-dimethyl-pentyl]-1-ethyl-imadazolidine-2,4-dione

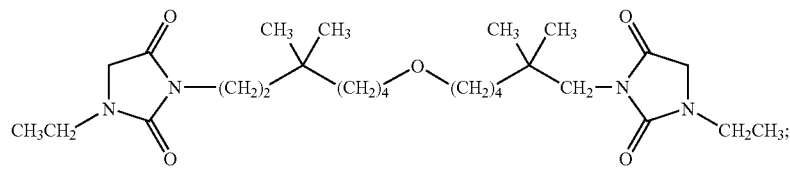
3-[6-(7-(3-ethyl-2,5-dioxo-imidazolidin-1-yl)-5,5-dimethyl-heptyloxy)-2,2-dimethyl-hexyl]-1-ethyl-imidazolidine-2,4-dione

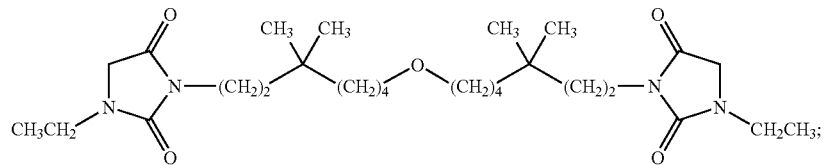
3-[7-(7-(3-ethyl-2,5-dioxo-imidazolidin-1-yl)-5,5-dimethyl-heptyloxy)-3,3-dimethyl-heptyl]-1-ethyl-imidazolidine-2,4-dione

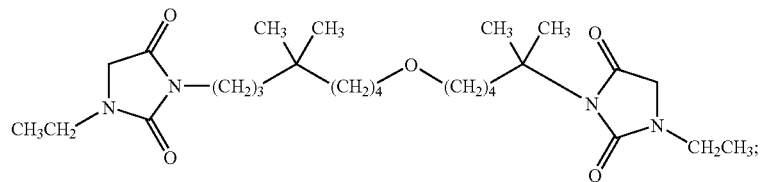
3-[5-(8-(3-ethyl-2,5-dioxo-imidazolidin-1-yl)-5,5-dimethyl-octyloxy)-1,1-dimethyl-pentyl]-1-ethyl-imidazolidine-2,4-dione

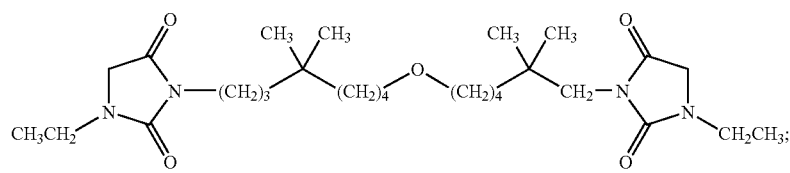
3-[6-(8-(3-ethyl-2,5-dioxo-imidazolidin-1-yl)-5,5-dimethyl-octyloxy)-2,2-dimethyl-hexyl]-1-ethyl-imidazolidine-2,4-dione

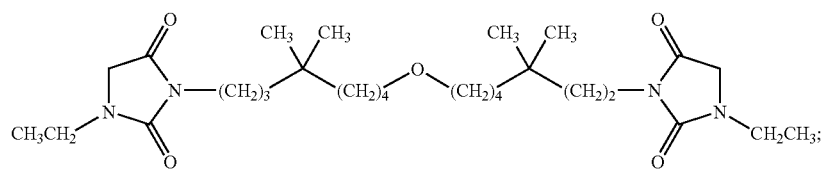
3-[7-(8-(3-ethyl-2,5-dioxo-imidazolidin-1-yl)-5,5-dimethyl-octyloxy)-3,3-dimethyl-heptyl]-1-ethyl-imidazolidine-2,4-dione

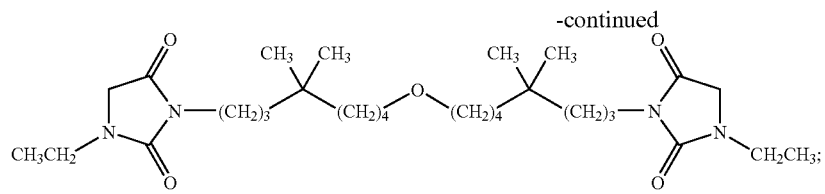

3-[8-(8-(3-ethyl-2,5-dioxo-imidazolidin-1-yl)-5,5-dimethyl-octyloxy)-4,4-dimethyl-octyl]-1-ethyl-imidazolidine-2,4-dione

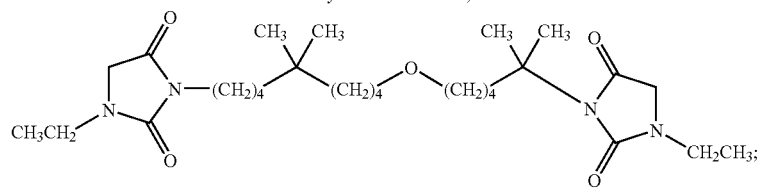

3-[5-(9-cyclopentyl-5,5-dimethyl-nonyloxy)-1,1-dimethyl-pentyl]-1-ethyl-imidazolidine-2,4-dione

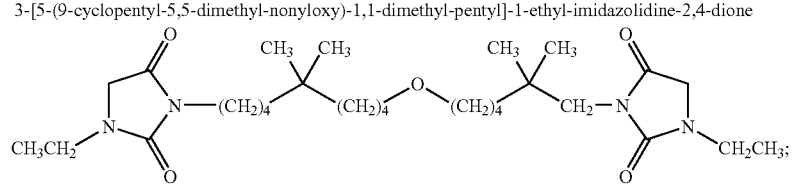

3-[6-(9-(3-ethyl-2,5-dioxo-imidazolidin-1-yl)-5,5-dimethyl-nonyloxy)-2,2-dimethyl-hexyl]-1-ethyl-imidazolidine-2,4-dione

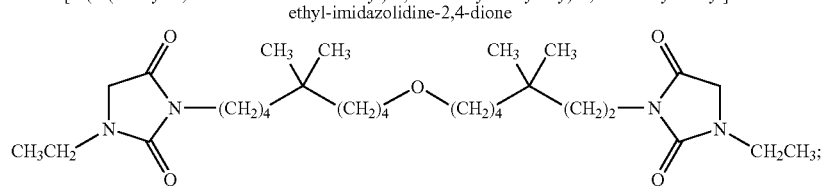

3-[7-(9-(3-ethyl-2,5-dioxo-imidazolidin-1-yl)-5,5-dimethyl-nonyloxy)-3,3-dimethyl-heptyl]-1-ethyl-imidazolidine-2,4-dione

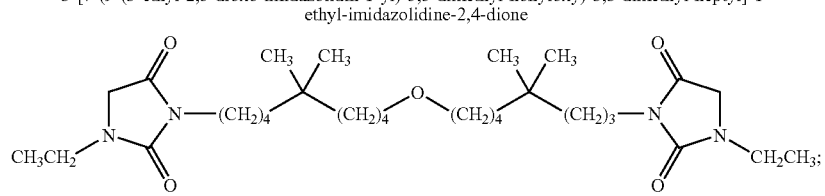

3-[8-(9-(3-ethyl-2,5-dioxo-imidazolidin-1-yl)-5,5-dimethyl-nonyloxy)-4,4-dimethyl-octyl]-1-ethyl-imidazolidine-2,4-dione

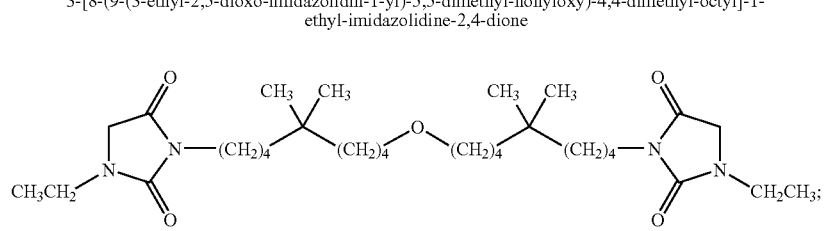

3-[9-(9-(3-ethyl-2,5-dioxo-imidazolidin-1-yl)-5,5-dimethyl-nonyloxy)-5,5-dimethyl-nonyl]-1-ethyl-imidazolidine-2,4-dione and pharmaceutically acceptable salts thereof.

In a preferred embodiment, the compound of the invention is 6-(6-Hydroxy-5,5-dimethyl-hexyloxy)-2,2-dimethyl-hexan-1-ol;

phosphoric acid mono-(1,1-dimethyl-5-(5-methyl-5-phosphonooxy-hexyloxy)-pentyl) ester sodium salt;

phosphoric acid dibenzyl ester 5-(5-(bis-benzyloxy-phosphoryloxy)-5-methyl-hexyloxy)-1,1-dimethyl-pentyl ester;

phosphoric acid mono-(1,1-dimethyl-4-(4-methyl-4-phosphonooxy-pentyloxy)-butyl) ester sodium salt;

phosphoric acid dibenzyl ester 4-(4-(bis-benzyloxy-phosphoryloxy)-4-methyl-pentyloxy)-1,1-dimethyl-butyl ester; or 6-(5-hydroxy-5-methyl-hexyloxy)-2-methyl-hexan-2-ol.

5.1. Definitions and Abbreviations

Apo(a): apolipoprotein(a)
Apo A-I: apolipoprotein A-I
Apo B: apolipoprotein B
Apo E: apolipoprotein E
Compound A: 6-(6-hydroxy-5,5-dimethylhexyloxy)-2,2-dimethyl-hexan-1-ol
Compound B: phosphoric acid mono-(1,1-dimethyl-5-(5-methyl-5-phosphonooxy-hexyloxy)-pentyl)ester sodium salt
Compound C: phosphoric acid dibenzyl ester 5-(5-(bis-benzyloxy-phosphoryloxy)-5-methyl-hexyloxy)-1,1-dimethyl-pentyl ester
Compound D: phosphoric acid mono-(1,1-dimethyl-4-(4-methyl-4-phosphonooxy-pentyloxy)-butyl)ester sodium salt
Compound E: phosphoric acid dibenzyl ester 4-(4-(bis-benzyloxy-phosphoryloxy)-4-methyl-pentyloxy)-1,1-dimethyl-butyl ester
Compound F: 6-(5-hydroxy-5-methyl-hexyloxy)-2-methyl-hexan-2-ol
FH: Familial hypercholesterolemia
FCH: Familial combined hyperlipidemia
GDM: Gestational diabetes mellitus
HDL: High density lipoprotein
IDL: Intermediate density lipoprotein
IDDM: Insulin dependent diabetes mellitus
LDH: Lactate dehdyrogenase
LDL: Low density lipoprotein
Lp(a): Lipoprotein (a)
MODY: Maturity onset diabetes of the young
NIDDM: Non-insulin dependent diabetes mellitus
PPAR: Peroxisome proliferator activated receptor
RXR: Retinoid X receptor
VLDL: Very low density lipoprotein.

5.2. Compounds of the Invention

As used herein, the term "compounds of the invention" means, collectively, the compounds of formulas I, XL, XLI, and XLII and pharmaceutically acceptable salts thereof. The compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

When administered to a patient, e.g., to an animal for veterinary use or for improvement of livestock, or to a human for clinical use, the compounds of the invention are administered in isolated form. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single ether compound of the invention by weight of the isolate.

The phrase "pharmaceutically acceptable salt(s)," as used herein includes but are not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds, included in the present compositions, that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

"Altering lipid metabolism" indicates an observable (measurable) change in at least one aspect of lipid metabolism, including but not limited to total blood lipid content, blood HDL cholesterol, blood LDL cholesterol, blood VLDL cholesterol, blood triglyceride, blood Lp(a), blood apo A-I, blood apo E and blood non-esterified fatty acids.

"Altering glucose metabolism" indicates an observable (measurable) change in at least one aspect of glucose metabolism, including but not limited to total blood glucose content, blood insulin, the blood insulin to blood glucose ratio, insulin sensitivity, and oxygen consumption.

A "therapeutically effective amount" of a composition of the invention is measured by the therapeutic effectiveness of a compound of the invention.

As used herein, the term "alkyl group" means a saturated, monovalent unbranched or branched hydrocarbon chain. Examples of alkyl groups include, but are not limited to, $(C_1-C_6)$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

An "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to ($C_2$-$C_6$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

An "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$)alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

An "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "($C_6$) aryl".

A "heteroaryl group" means a monocyclic- or polycyclic aromatic ring comprising carbon atoms, hydrogen atoms, and one or more heteroatoms, preferably 1 to 3 heteroatoms, independently selected from nitrogen, oxygen, and sulfur. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, furyl, phienyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "($C_2$-$C_5$) heteroaryl".

A "cycloalkyl group" means a monocyclic or polycyclic saturated ring comprising carbon and hydrogen atoms and having no carbon-carbon multiple bonds. Examples of cycloalkyl groups include, but are not limited to, ($C_3$-$C_7$) cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. Preferably, the cycloalkyl group is a monocyclic ring or bicyclic ring.

A "heterocycloalkyl group" means a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and form 1 to 3 heteroatoms, referred to herein as ($C_1$-$C_6$)heterocycloalkyl.

As used herein a "heterocyclic radical" or "heterocyclic ring" means a heterocycloalkyl group or a heteroaryl group.

The term "alkoxy group" means an —O-alkyl group, wherein alkyl is as defined above. An alkoxy group can be unsubstituted or substituted with one or two suitable substituents. Preferably, the alkyl chain of an alkyloxy group is from 1 to 6 carbon atoms in length, referred to herein as "($C_1$-$C_6$) alkoxy".

The term "aryloxy group" means an aryl group, wherein aryl is as defined above. An aryloxy group can be unsubstituted or substituted with one or two suitable substituents. Preferably, the aryl ring of an aryloxy group is a monocyclic ring, wherein the ring comprises 6 carbon atoms, referred to herein as "($C_6$)aryloxy".

The term "benzyl" means —$CH_2$-phenyl.

The term "phenyl" means —$C_6H_5$. A phenyl group can be unsubstituted or substituted with one or two suitable substituents.

A "hydrocarbyl" group means a monovalent group selected from ($C_1$-$C_8$)alkyl, ($C_2$-$C_8$)alkenyl, and ($C_2$-$C_8$) alkynyl, optionally substituted with one or two suitable substituents. Preferably, the hydrocarbon chain of a hydrocarbyl group is from 1 to 6 carbon atoms in length, referred to herein as "($C_1$-$C_6$)hydrocarbyl".

A "carbonyl" group is a divalent group of the formula —C(O)—.

An "alkoxycarbonyl" group means a monovalent group of the formula —C(O)-alkoxy. Preferably, the hydrocarbon chain of an alkoxycarbonyl group is from 1 to 8 carbon atoms in length, referred to herein as a "lower alkoxycarbonyl" group.

A "carbamoyl" group means the radical —C(O)N(R')$_2$, wherein R' is chosen from the group consisting of hydrogen, alkyl, and aryl.

As used herein, "halogen" means fluorine, chlorine, bromine, or iodine. Correspondingly, the meaning of the terms "halo" and "Hal" encompass fluoro, chloro, bromo, and iodo.

As used herein, a "suitable substituent" means a group that does not nullify the synthetic or pharmaceutical utility of the compounds of the invention or the intermediates useful for preparing them. Examples of suitable substituents include, but are not limited to: ($C_1$-$C_8$)alkyl; ($C_1$-$C_8$)alkenyl; ($C_1$-$C_8$) alkynyl; ($C_6$)aryl; ($C_2$-$C_5$)heteroaryl; ($C_3$-$C_7$)cycloalkyl; ($C_1$-$C_8$)alkoxy; ($C_6$)aryloxy; —CN; —OH; oxo; halo, —$CO_2H$; —$NH_2$; —NH(($C_1$-$C_8$)alkyl); —N(($C_1$-$C_8$)alkyl)$_2$; —NH(($C_6$)aryl); —N(($C_6$)aryl)$_2$; —CHO; —CO(($C_1$-$C_8$) alkyl); —CO(($C_6$)aryl); —$CO_2$(($C_1$-$C_8$)alkyl); and —$CO_2$ (($C_6$)aryl). One of skill in art can readily choose a suitable substituent based on the stability and pharmacological and synthetic activity of the compound of the invention.

5.3. Synthesis of the Compounds of the Invention

The compounds of the invention can be obtained via the synthetic methodology illustrated in Schemes 1-9. Starting materials useful for preparing the compounds of the invention and intermediates therefor, are commercially available or can be prepared by well known synthetic methods.

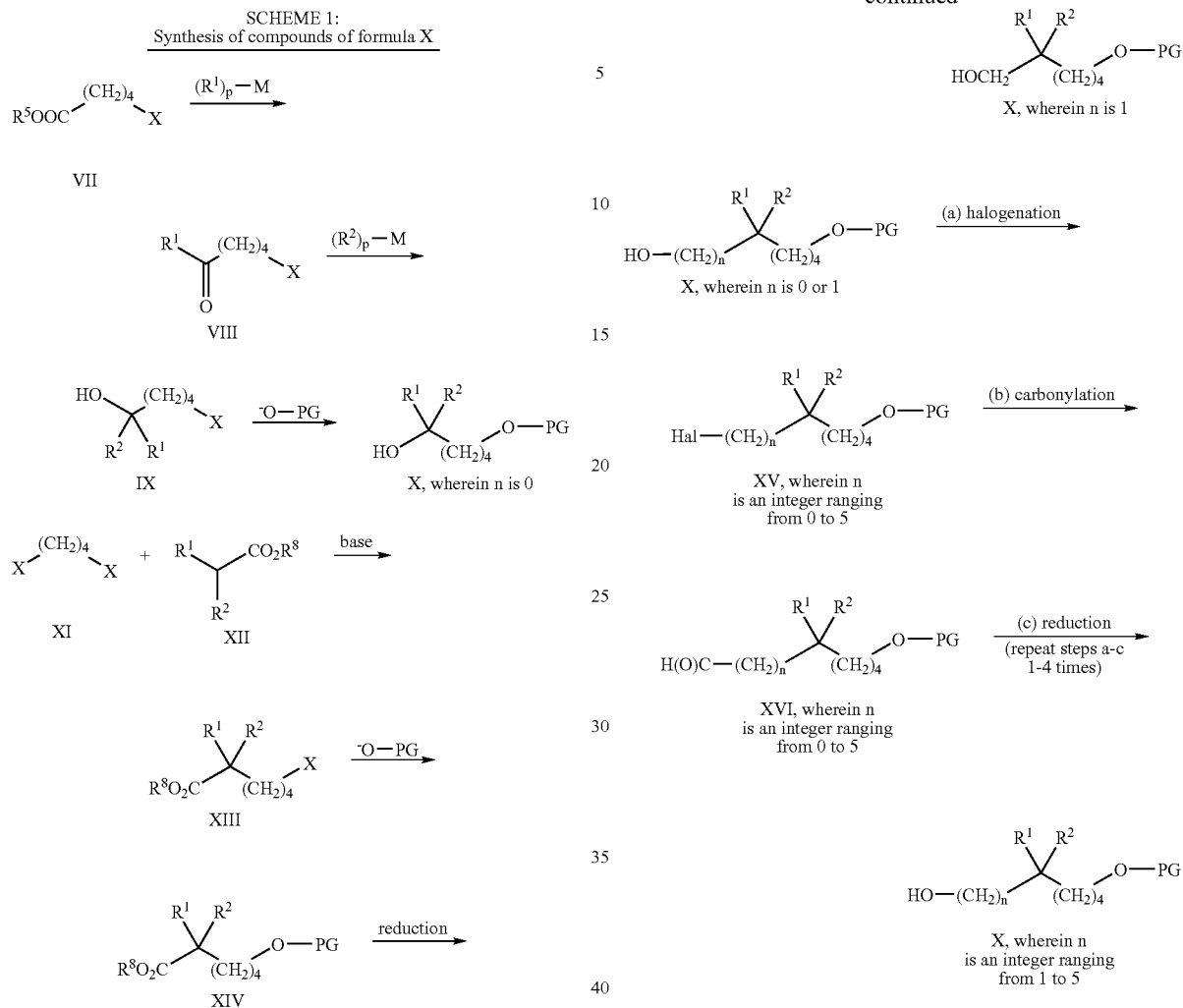
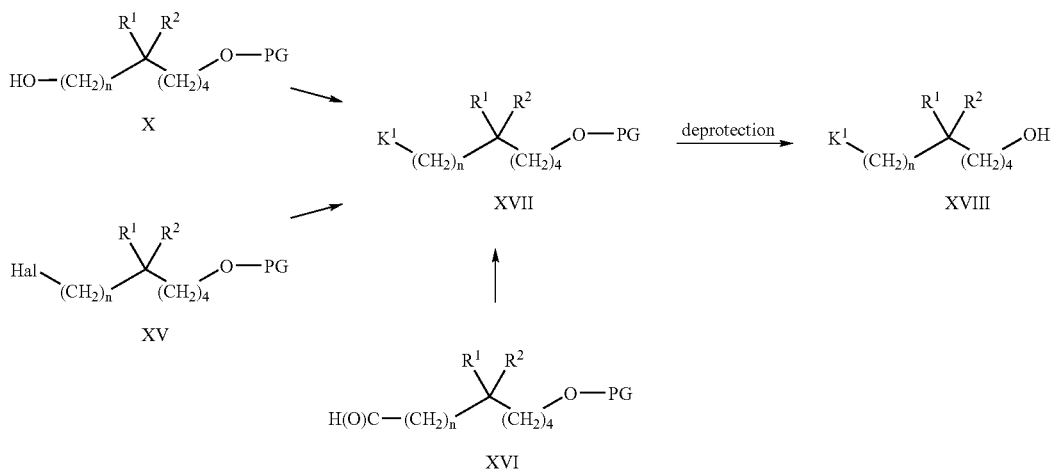

SCHEME 3:
Synthesis of compounds of formula XXI
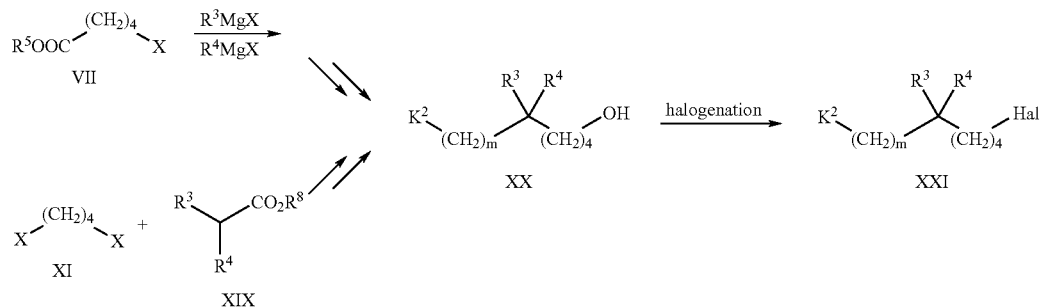
SCHEME 4:
Synthesis of compounds of formula I
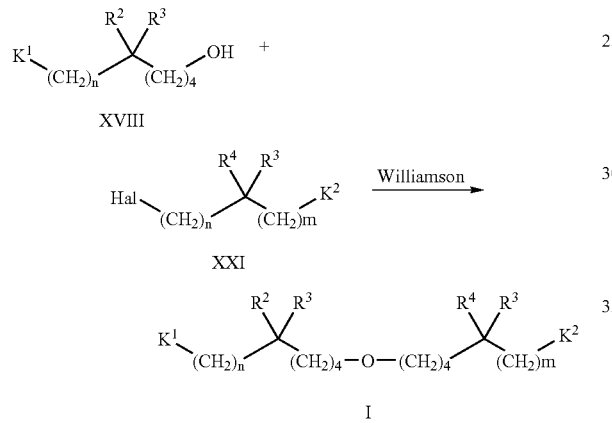
SCHEME 5:
Synthesis of compounds of formula XXIV
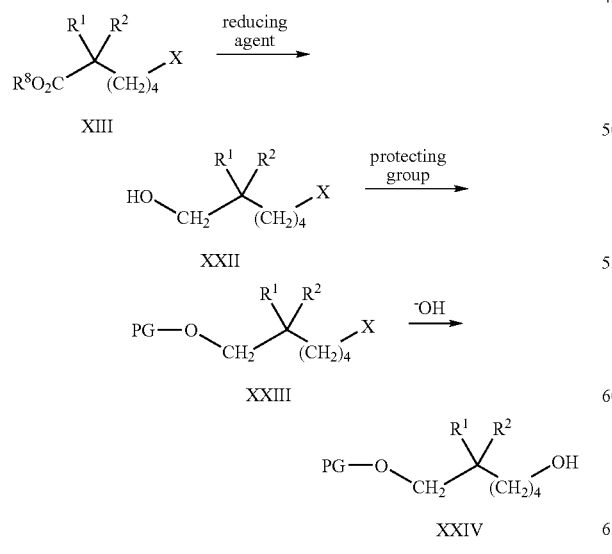
SCHEME 6:
Synthesis of compound of formula XXVIII
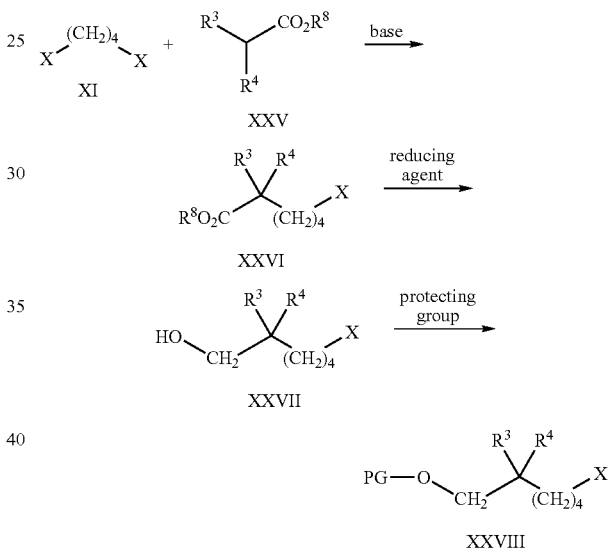
SCHEME 7:
Synthesis of compounds of formula I wherein n and m are both 0 and $K^1$ and $K^2$ are both —CH$_2$OH
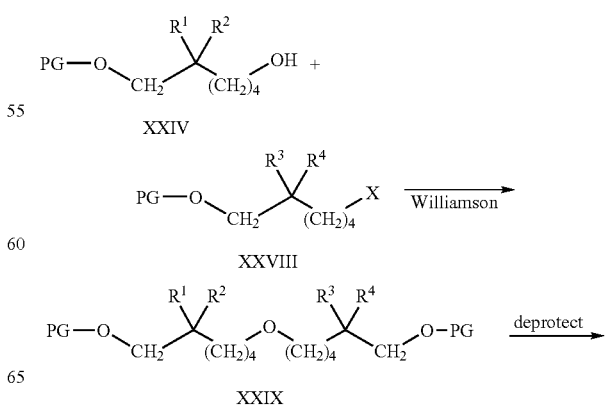

-continued

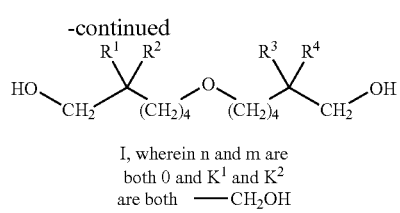

I, wherein n and m are
both 0 and K$^1$ and K$^2$
are both ——CH$_2$OH

SCHEME 8:
Synthesis of compounds of formula I, wherein n and m are identical
integers ranging from 1 to 4 and K$^1$ and K$^2$ are both
——CH$_2$OH

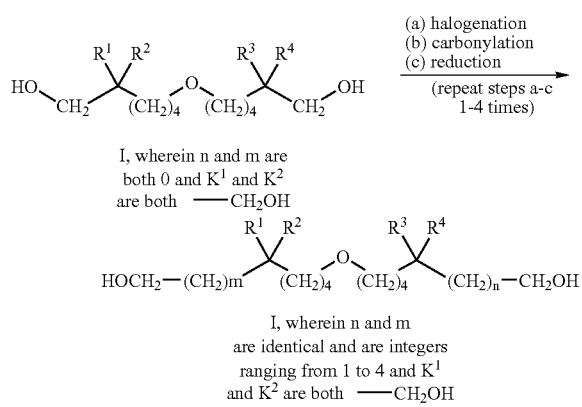

I, wherein n and m
are identical and are integers
ranging from 1 to 4 and K$^1$
and K$^2$ are both ——CH$_2$OH SCHEME 9:
Synthesis of compounds of formula I, wherein K$^1$ and
K$^2$ are both ——CH$_2$OH

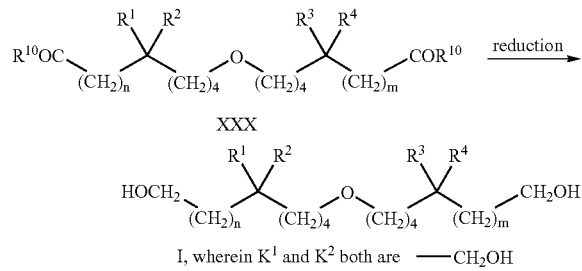

I, wherein K$^1$ and K$^2$ both are ——CH$_2$OH

Scheme 1 illustrates the synthesis of mono-protected diols of the formula X, wherein n is an integer ranging from 0 to 5 and R$^1$ and R$^2$ are as defined above. Scheme 1 first outlines the synthesis of mono-protected diols X, wherein n is 0, where esters of formula VII are successively reacted with a first ((R$^1$)$_p$-M) then a second ((R$^2$)$_p$-M) organometallic reagent providing ketones of formula VIII and alcohols of formula IX, respectively. M is a metal group and p is the metal's valency value (e.g., the valency of Li is 1 and that of Zn is 2). Suitable metals include, but are not limited to, Zn, Na, Li, and —Mg-Hal, wherein Hal is a halide selected from iodo, bromo, or chloro. Preferably, M is —Mg-Hal, in which case the organometallic reagents, (R$^1$)$_p$—Mg-Hal and (R$^2$)$_p$—Mg-Hal, are known in the art as a Grignard reagents. Esters of formula VII are available commercially (e.g., Aldrich Chemical Co., Milwaukee, Wis.) or can be prepared by well-known synthetic methods, for example, via esterification of the appropriate 5-halovaleric acid (commercially available, e.g., Aldrich Chemical Co., Milwaukee, Wis.). Both (R$^1$)$_p$-M and (R$^2$)$_p$-M are available commercially (e.g., Aldrich Chemical Co., Milwaukee, Wis.) or can be prepared by well-known methods (see e.g., Kharasch et al., *Grignard Reactions of Non-Metallic Substances*; Prentice-Hall, Englewood Cliffs, N.J., pp. 138-528 (1954) and Hartley; Patai, *The Chemistry of the Metal-Carbon Bond*, Vol. 4, Wiley: New York, pp. 159-306 and pp. 162-175 (1989), both citations are incorporated by reference herein). The reaction of a first ((R$^1$)$_p$-M) then a second ((R$^2$)$_p$-M) organometallic reagent with esters VII can be performed using the general procedures referenced in March, J. *Advanced Organic Chemistry; Reactions Mechanisms, and Structure*, 4th ed., 1992, pp. 920-929 and Eicher, Patai, *The Chemistry of the Carbonyl Group*, pt. 1, pp. 621-693; Wiley: New York, (1966), incorporated by reference herein. For example, the synthetic procedure described in Comins et al., 1981, *Tetrahedron Lett.* 22:1085, incorporated by reference herein, can be used. As one example, the reaction can be performed by adding an organic solution of (R$^1$)$_p$-M (about 0.5 to about 1 equivalents) to a stirred, cooled (about 0° C. to about −80° C.) solution comprising esters VII, under an inert atmosphere (e.g., nitrogen) to give a reaction mixture comprising ketones VIII. Preferably, (R$^1$)$_p$-M is added at a rate such that the reaction-mixture temperature remains within about one to two degrees of the initial reaction-mixture temperature. The progress of the reaction can be followed by using an appropriate analytical method, such as thin-layer chromatography or high-performance-liquid chromatography. Next, an organic solution of (R$^2$)$_p$-M (about 0.5 to about 1 equivalent) is added to the reaction mixture comprising ketones VIII in the same manner used to add (R$^1$)$_p$-M. After the reaction providing alcohols IX is substantially complete, the reaction mixture can be quenched and the product can be isolated by workup. Suitable solvents for obtaining alcohols IX include, but are not limited to, dichloromethane, diethyl ether, tetrahydrofuran, benzene, toluene, xylene, hydrocarbon solvents (e.g., pentane, hexane, and heptane), and mixtures thereof. Preferably, the organic solvent is diethyl ether or tetrahydrofuran. Next, alcohols IX are converted to mono-protected diols X, wherein n is 0, using the well-known Williamson ether synthesis. This involves reacting alcohols IX with ⁻O—PG, wherein —PG is a hydroxy-protecting group. For a general discussion of the Williamson ether synthesis, see March, J. *Advanced Organic Chemistry; Reactions Mechanisms, and Structure*, 4th ed., 1992, pp. 386-387, and for a list of procedures and reagents useful in the Williamson ether synthesis see Larock *Comprehensive Organic Transformations*; VCH: New York, 1989, pp. 446-448, both of which references are incorporated herein by reference. As used herein, a "hydroxy-protecting group" means a group that is reversibly attached to a hydroxy moiety that renders the hydroxy moiety unreactive during a subsequent reaction(s) and that can be selectively cleaved to regenerate the hydroxy moiety once its protecting purpose has been served. Examples of hydroxy-protecting groups are found in Greene, T. W., *Protective Groups in Organic Synthesis*, 3rd edition 17-237 (1999), incorporated herein by reference. Preferably, the hydroxy-protecting group is stable in a basic reaction medium, but can be cleaved by acid. Examples of suitable base-stable acid-labile hydroxy-protecting groups suitable for use with the invention include, but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahyrofuranyl, tetrahydrothiofuranyl, 1-ethoxyethyl, 1-methyl-1-methoxyethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, and triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably—PG is methoxymethyl ($CH_3OCH_2$—). Reaction of alcohols IX with $^-$O—PG under the conditions of the Williamson ether synthesis involves adding a base to a stirred organic solution comprising HO—PG (e.g., methoxymethanol), maintained at a constant temperature within the range of about 0° C. to about 80° C., preferably at about room temperature. Preferably, the base is added at a rate such that the reaction-mixture temperature remains within about one to two degrees of the initial reaction-mixture temperature. The base can be added as an organic solution or in undiluted form. Preferably, the base will have a base strength sufficient to deprotonate a proton, wherein the proton has a $pK_a$ of greater than about 15, preferably greater than about 20. As is well known in the art, the $pK_a$ is a measure of the acidity of an acid H-A, according to the equation $pK_a = -\log K_a$, wherein $K_a$ is the equilibrium constant for the proton transfer. The acidity of an acid H-A is proportional to the stability of its conjugate base A. For tables listing $pK_a$ values for various organic acids and a discussion on $pK_a$ measurement, see March, J. *Advanced Organic Chemistry; Reactions Mechanisms, and Structure*, 4th ed., 1992, pp. 248-272, incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. The preferred base is lithium diisopropylamide. Solvents suitable for reacting alcohols IX with —OPG include, but are not limited to, dimethyl sulfoxide, dichloromethane, ethers, and mixtures thereof, preferably tetrahydrofuran. After addition of the base, the reaction mixture can be adjusted to within a temperature range of about 0° C. to about room temperature and alcohols IX can be added, preferably at a rate such that the reaction-mixture temperature remains within about one to two degrees of the initial reaction-mixture temperature. Alcohols of formula IX can be diluted in an organic solvent or added in their undiluted form. The resulting reaction mixture is stirred until the reaction is substantially complete as determined by using an appropriate analytical method, preferably by gas chromatography, then the mono-protected diols X can be isolated by workup and purification.

Next, Scheme 1 outlines a method useful for synthesizing mono-protected diols X, wherein n is 1. First, compounds of formula XI, wherein X is a suitable leaving group, are reacted with compounds of formula XII, wherein $R^1$ and $R^2$ are as defined above and $R^8$ is H, $(C_1-C_6)$alkyl or $(C_6)$aryl, providing compounds of formula XIII. Compounds of formula XI are available commercially (e.g., Aldrich Chemical Co., Milwaukee, Wis.) or can be prepared by well-known methods such as halogenation or sulfonation of butanediol. Compounds of formula XII are also available commercially (e.g., Aldrich Chemical Co., Milwaukee, Wis.) or by well-known methods, such as those listed in Larock *Comprehensive Organic Transformations*; Wiley-VCH: New York, 1999, pp. 1754-1755 and 1765. A review on alkylation of esters of type XII is given in J. Mulzer in Comprehensive Organic Functional Transformations, Pergamon, Oxford 1995, pp. 148-151 and exemplary synthetic procedures for reacting compounds of formula XI with compounds of formula XII are described in U.S. Pat. No. 5,648,387, column 6 and Ackerly, et al., 1995, *J. Med. Chem.* 1608, all of which citations are incorporated by reference herein. The reaction requires the presence of a suitable base. Preferably, a suitable base will have a $pK_a$ of greater than about 25, more preferably greater than about 30. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; hydride bases such as sodium hydride and potassium hydride. Metal amide bases, such as lithium diisopropylamide are preferred. Preferably, to react compounds of formula XI with compounds of formula XII, a solution of about 1 to about 2 equivalents of a suitable base is added to a stirred solution comprising esters of formula XII and a suitable organic solvent, under an inert atmosphere, the solution maintained at a constant temperature within the range of about −95° C. to about room temperature, preferably at about −78° C. to about −20° C. Preferably, the base is diluted in a suitable organic solvent before addition. Preferably, the base is added at a rate of about 1.5 moles per hour. Organic solvents suitable for the reaction of compounds of formula XI with the compounds of formula XII include, but are not limited to, dichloromethane, diethyl ether, tetrahydrofuran, dimethylformamide, dimethyl sulfoxide, benzene, toluene, xylene, hydrocarbon solvents (e.g., pentane, hexane, and heptane), and mixtures thereof. After addition of the base, the reaction mixture is allowed to stir for about 1 to about 2 hours, and a compound of formula XI, preferably dissolved in a suitable organic solvent, is added, preferably at a rate such that the reaction-mixture temperature remains within about one to two degrees of the initial reaction-mixture temperature. After addition of compounds of formula XI, the reaction-mixture temperature can be adjusted to within a temperature range of about −20° C. to about room temperature, preferably to about room temperature, and the reaction mixture is allowed to stir until the reaction is substantially complete as determined by using an appropriated analytical method, preferably thin-layer chromatography or high-performance liquid chromatography. Then the reaction mixture is quenched and compounds XIII, wherein n is 1 can be isolated by workup. Compounds XIV are then synthesized by reacting compounds XIII with $^-$O—PG according to the protocol described above for reacting alcohols IX with $^-$O—PG. Next, compounds XIV can be converted to mono-protected diols X, wherein n is 1, by reduction of the ester group of compounds XIV to an alcohol group with a suitable reducing agent. A wide variety of reagents are available for reduction of such esters to alcohols, e.g., see M. Hudlicky, *Reductions in Organic Chemistry*, 2nd ed., 1996 pp. 212-217, incorporated by reference herein. Preferably, the reduction is effected with a hydride type reducing agent, for example, lithium aluminum hydride, lithium borohydride, lithium triethyl borohydride, diisobutylaluminum hydride, lithium trimethoxyaluminum hydride, or sodium bis(2-methoxy)aluminum hydride. For exemplary procedures for reducing esters to alcohols, see Nystrom et al., 1947, *J. Am. Chem. Soc.* 69:1197; and Moffet et al., 1963, *Org. Synth., Collect.* 834(4), lithium aluminum hydride; Brown et al., 1965, *J. Am. Chem. Soc.* 87:5614, lithium trimethoxyaluminum hydride; Cerny et al., 1969, *Collect. Czech. Chem. Commun.* 34:1025, sodium bis(2-methoxy)aluminum hydride; Nystrom et al., 1949, *J. Am. Chem.* 71:245, lithium borohydride; and Brown et al., 1980, *J. Org. Chem.* 45:1, lithium triethyl borohydride, all of which citations are incorporated herein by reference. Preferably, the reduction is conducted by adding an organic solution of compounds XIV to a stirred mixture comprising a reducing agent, preferably lithium aluminum hydride, and an organic solvent. During the addition, the reaction mixture is maintained at a constant temperature within the range of about −20° C. to about 80° C., preferably at about room temperature. Organic solvents suitable for reacting XIII with —OPG include, but are not limited to, dichloromethane, diethyl ether, tetrahydrofuran or mixtures thereof, preferably tetrahydrofuran. After the addition, the reaction mixture is stirred at a constant temperature within the range of about room temperature to about 60° C., until the reaction is substantially complete as determined by using an appropriate analytical method, preferably thin-layer chromatography or high-performance-liquid chromatography. Then the reaction mixture can be quenched and mono-protected diols X, wherein n is 1, can be isolated by workup and purification.

Scheme 1 next illustrates a three step synthetic sequence for homologating mono-protected diols X comprising: (a) halogenation (converting —$CH_2OH$ to —$CH_2$-Hal); (b) carbonylation (replacing -Hal with —CHO); and (c) reduction (converting —CHO to —$CH_2OH$), wherein a reaction sequence of (a), (b), and (c) increases the value of n by 1. In step (a) protected halo-alcohols of formula XV, wherein Hal is a halide selected from the group of chloro, bromo, or iodo, preferably iodo, can be prepared by halogenating mono-protected diols X, by using well-known methods (for a discussion of various methods for conversion of alcohols to halides see March, J. *Advanced Organic Chemistry; Reactions Mechanisms, and Structure,* 4th ed., 1992, pp. 431-433, incorporated herein by reference). For example, protected iodo-alcohols XV can be synthesized starting from mono-protected diols X by treatment with $Ph_3/I_2$/imidazole (Garegg et al., 1980, *J.C.S Perkin I* 2866); 1,2-dipheneylene phosphorochloridite/$I_2$ (Corey et al, 1967, *J. Org. Chem.* 82:4160); or preferably with $Me_3SiCl$/NaI (Olah et al., 1979, *J. Org. Chem.* 44:8, 1247), all of which citations are incorporated by reference herein. Step (b); carbonylation of alkyl halides, such as protected halo-alcohols XV, is reviewed in Olah et al., 1987, *Chem Rev.* 87:4, 671; and March, J., *Advanced Organic Chemistry; Reactions Mechanisms, and Structure,* 4th ed., 1992, pp. 483-484, both of which are incorporated by reference herein). Protected halo-alcohols XV can be carbonylated with Li($BF_3.Et_2O$)/$HCONMe_2$ using the procedure described in Maddaford et al., 1993, *J. Org. Chem.* 58:4132; Becker et al., 1982, *J. Org. Chem.* 3297; or Myers et al., 1992, *J. Am. Chem Soc.* 114:9369 or, alternatively, with an organometallic/N-formylmorpholine using the procedure described in Olah et al., 1984, *J. Org. Chem.* 49:3856 or Vogtle et al., 1987, *J. Org. Chem.* 52:5560, all of which citations are incorporated by reference herein. The method of described in Olah et al., 1984, *J. Org. Chem.* 49:3856 is preferred. Reduction step (c) useful for synthesizing mono-protected diols X from aldehydes of formula XVI, can be accomplished by well-known methods in the art for reduction of aldehydes to the corresponding alcohols (for a discussion see M. Hudlicky, *Reductions in Organic Chemistry,* 2nd ed., 1996 pp 137-139), for example, by catalytic hydrogenation (see e.g., Carothers, 1949, *J. Am. Chem. Soc.* 46:1675) or, preferably by reacting aldehydes XVI with a hydride reducing agent, such as lithium aluminum hydride, lithium borohydride, sodium borohydride (see e.g., the procedures described in Chaikin et al., 1949, *J. Am. Chem. Soc.* 71:3245; Nystrom et al., 1947, *J. Am. Chem. Soc.* 69:1197; and Nystrom et al., 1949, *J. Am. Chem.* 71:3245, all of which are incorporated by reference herein). Reduction with lithium aluminum hydride is preferred.

Scheme 2 outlines methodology for the synthesis of protected alcohols of formula XVII, wherein $K^1$, $R^1$, $R^2$, and n are defined as above, which protected alcohols can be converted to alcohols of formula XVIII by hydroxy-group deprotection. Protected alcohols XVII, wherein $K^1$ is —C(O)OH, can be synthesized by oxidizing mono-protected diols X with an agent suitable for oxidizing a primary alcohol to a carboxylic acid (for a discussion see M. Hudlicky, *Oxidations in Organic Chemistry,* ACS Monograph 186, 1990, pp. 127-130, incorporated by reference herein). Suitable oxidizing agents include, but are not limited to, pyridinium dichromate (Corey et al., 1979, *Tetrahedron Lett.* 399); manganese dioxide (Ahrens et al., 1967, *J. Heterocycl. Chem.* 4:625); sodium permanganate monohydrate (Menger et al., 1981, *Tetrahedron Lett.* 22:1655); and potassium permanganate (Sam et al., 1972, *J. Am. Chem. Soc.* 94:4024), all of which citations are incorporated by reference herein. The preferred oxidizing reagent is pyridinium dichromate. In an alternative synthetic procedure, protected alcohols XVII, wherein $K^1$ is —C(O)OH, can be synthesized by treatment of protected halo-alcohols XV, wherein X is iodo, with CO or $CO_2$, as described in Bailey et al., 1990, *J. Org. Chem.* 55:5404 and Yanagisawa et al., 1994, *J. Am. Chem. Soc.* 116:6130, the two of which citations are incorporated by reference herein. Protected alcohols XVII, wherein $K^1$ is —C(O)$OR^5$, wherein $R^5$ is as defined above, can be synthesized by oxidation of mono-protected diols X in the presence of $R^5OH$ (see generally, March, J. *Advanced Organic Chemistry; Reactions Mechanisms, and Structure,* 4th ed., 1992, p. 1196). An exemplary procedures for such an oxidation are described in Stevens et al., 1982, *Tetrahedron Lett.* 23:4647 (HOCl); Sundararaman et al., 1978, *Tetrahedron Lett.* 1627 ($O_3$/KOH); Wilson et al., 1982, *J. Org. Chem.* 47:1360 (t-BuOOH/$Et_3N$); and Williams et al., 1988, *Tetrahedron Lett.* 29:5087 ($Br_2$), the four of which citations are incorporated by reference herein. Preferably, protected alcohols XVII, wherein $K^1$ is —C(O)$OR^5$ are synthesized from the corresponding carboxylic acid (i.e., XVII, wherein $K^1$ is —C(O)OH) by esterification with $R^5OH$ (e.g., see March, J., *Advanced Organic Chemistry; Reactions Mechanisms, and Structure,* 4th ed., 1992, p. 393-394, incorporated by reference herein). In another alternative synthesis, protected alcohols XVII, wherein $K^1$ is —C(O)$OR^5$, can be prepared from protected halo-alcohols XV by carbonylation with transition metal complexes (see e.g., March, J. *Advanced Organic Chemistry; Reactions Mechanisms, and Structure,* 4th ed., 1992, p. 484-486; Urata et al., 1991, *Tetrahedron Lett.* 32:36, 4733); and Ogata et al., 1969, *J. Org. Chem.* 3985, the three of which citations are incorporated by reference herein).

Protected alcohols XVII, wherein $K^1$ is —OC(O)$R^5$, wherein $R^5$ is as defined above, can be prepared by acylation of mono-protected diols X with a carboxylate equivalent such as an acyl halide (i.e., $R^5C(O)$-Hal, wherein Hal is iodo, bromo, or chloro, see e.g., March, J. *Advanced Organic Chemistry; Reactions Mechanisms, and Structure,* 4th ed., 1992, p. 392 and *Org. Synth. Coll.* Vol. III, Wiley, NY, pp. 142, 144, 167, and 187 (1955)) or an anhydride (i.e., $R^5C(O)$—O—(O)$CR^5$, see e.g., March, J. *Advanced Organic Chemistry; Reactions Mechanisms, and Structure,* 4th ed., 1992, p. 392-393 and *Org. Synth. Coll.* Vol. III, Wiley, NY, pp. 11, 127, 141, 169, 237, 281, 428, 432, 690, and 833 (1955), all of which citations are incorporated herein by reference). Preferably, the reaction is conducted by adding a base to a solution comprising mono-protected diols X, a carboxylate equivalent, and an organic solvent, which solution is preferably maintained at a constant temperature within the range of 0° C. to about room temperature. Solvents suitable for reacting mono-protected diols X with a carboxylate equivalent include, but are not limited to, dichloromethane, toluene, and ether, preferably dichloromethane. Suitable bases include, but are not limited to, hydroxide sources, such as sodium hydroxide, potassium hydroxide, sodium carbonate, or potassium carbonate; or an amine such as triethylamine, pyridine, or dimethylaminopyridine, amines are preferred. The progress of the reaction can be followed by using an appropriate analytical technique, such as thin layer chromatography or high performance liquid chromatography and when substantially complete, the product can be isolated by workup and purified if desired.

Protected alcohols XVII, wherein $K^1$ is one of the following phosphate ester groups

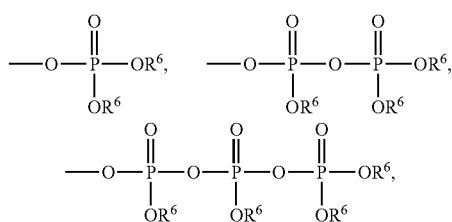

wherein $R^6$ is defined as above, can be prepared by phosphorylation of mono-protected diols X according to well-known methods (for a general reviews, see Corbridge *Phosphorus: An Outline of its Chemistry, Biochemistry, and Uses*, Studies in Inorganic Chemistry, 3rd ed., pp. 357-395 (1985); Ramirez et al., 1978, *Acc. Chem. Res.* 11:239; and Kalckare *Biological Phosphorylations*, Prentice-Hall, New York (1969); J. B. Sweeny in *Comprehensive Organic Functional Group Transformations*, A. R. Katritzky, O. Meth-Cohn and C. W. Rees, Eds. Pergamon: Oxford, 1995, vol 2, pp. 104-109, the four of which are incorporated herein by reference). Protected alcohols XVII wherein $K^1$ is a monophosphate group of the formula:

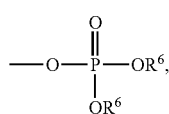

wherein $R^6$ is defined as above, can be prepared by treatment of mono-protected diol X with phosphorous oxychloride in a suitable solvent, such as xylene or toluene, at a constant temperature within the range of about 100° C. to about 150° C. for about 2 hours to about 24 hours. After the reaction is deemed substantially complete, by using an appropriate analytical method, the reaction mixture is hydrolyzed with $R^6$—OH. Suitable procedures are referenced in Houben-Weyl, Methoden der Organische Chemie, Georg Thieme Verlag Stuttgart 1964, vol. XII/2, pp. 143-210 and 872-879, incorporated by reference herein. Alternatively, when both $R^6$ are hydrogen, can be synthesized by reacting mono-protected diols X with silyl polyphosphate (Okamoto et al., 1985, *Bull Chem. Soc. Jpn.* 58:3393, incorporated herein by reference) or by hydrogenolysis of their benzyl or phenyl esters (Chen et al., 1998, *J. Org. Chem.* 63:6511, incorporated herein by reference). In another alternative procedure, when $R^6$ is ($C_1$-$C_6$)alkyl, ($C_2$-$C_6$)alkenyl, or ($C_2$-$C_6$)alkynyl, the monophosphate esters can be prepared by reacting mono-protected diols X with appropriately substituted phophoramidites followed by oxidation of the intermediate with m-chloroperbenzoic acid (Yu et al., 1988, *Tetrahedron Lett.* 29:979, incorporated herein by reference) or by reacting mono-protected diols X with dialkyl or diaryl substituted phosphorochloridates (Pop, et al, 1997, *Org. Prep. and Proc. Int.* 29:341, incorporated herein by reference). The phosphoramidites are commercially available (e.g., Aldrich Chemical Co., Milwaukee, Wis.) or readily prepared according to literature procedures (see e.g., Uhlmann et al. 1986, *Tetrahedron Lett.* 27:1023 and Tanaka et al., 1988, *Tetrahedron Lett.* 29:199, both of which are incorporated herein by reference). The phosphorochloridates are also commercially available (e.g., Aldrich Chemical Co., Milwaukee, Wis.) or prepared according to literature methods (e.g., Gajda et al, 1995, *Synthesis* 25:4099. In still another alternative synthesis, protected alcohols XVII, wherein $K^1$ is a monophosphate group and $R^6$ is alkyl or aryl, can be prepared by reacting $IP^+(OR^6)_3$ with mono-protected diols X according to the procedure described in Stowell et al., 1995, *Tetrahedron Lett.* 36:11, 1825 or by alkylation of protected halo alcohols XV with the appropriate dialkyl or diaryl phosphates (see e.g., Okamoto, 1985, *Bull Chem. Soc. Jpn.* 58:3393, incorporated herein by reference).

Protected alcohols XVII wherein $K^1$ is a diphosphate group of the formula

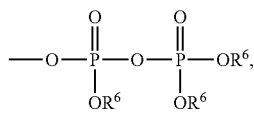

wherein $R^6$ is defined as above, can be synthesized by reacting protected alcohols XVII, of the formula:

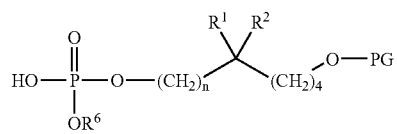

with a phosphate of the formula:

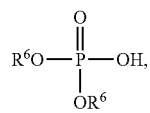

(commercially available, e.g., Aldrich Chemical Co., Milwaukee, Wis.), in the presence of carbodiimide such as dicyclohexylcarbodiimide, as described in Houben-Weyl, *Methoden der Organische Chemie*, Georg Thieme Verlag Stuttgart 1964, vol. XII/2, pp. 881-885. In the same fashion, protected alcohols XVII, wherein $K^1$ is a triphosphate group of the formula:

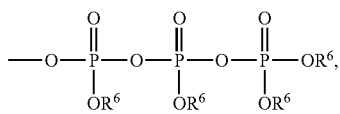

can be synthesized by reacting diphosphate protected alcohols XVII, of the formula:

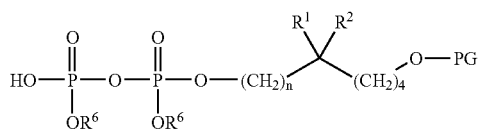

with the compound of the formula:

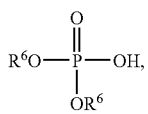

as described above. Alternatively, when $R^6$ is H, protected alcohols XVII wherein $K^1$ is the triphosphate group, can be prepared by reacting mono-protected diols X with salicyl phosphorochloridite and then pyrophosphate and subsequent cleavage of the adduct thus obtained with iodine in pyridine as described in Ludwig et al., 1989, *J. Org. Chem.* 54:631, incorporated herein by reference.

Protected alcohols XVII, wherein $K^1$ is —SO$_3$H or a heterocyclic group selected from the group consisting of:

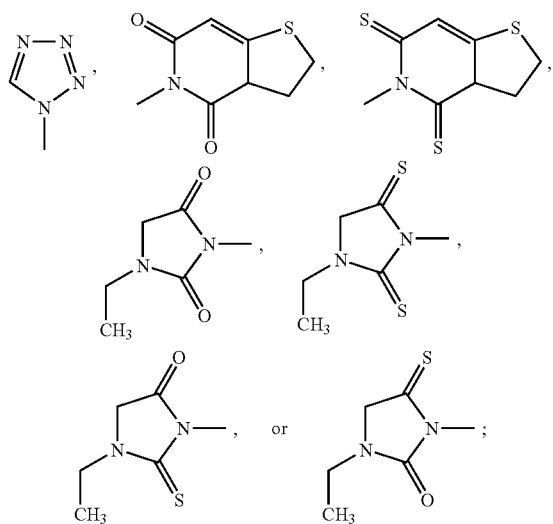

can be prepared by halide displacement from protected halo-alcohols XV. Thus, when $K^1$ is —SO$_3$H, protected alcohols XVII can by synthesized by reacting protected halo-alcohols XV with sodium sulfite as described in Gilbert *Sulfonation and Related Reactions*; Wiley: New York, 1965, pp. 136-148 and pp. 161-163; *Org. Synth. Coll.* Vol. II, Wiley, NY, 558, 564 (1943); and *Org. Synth. Coll.* Vol. IV, Wiley, NY, 529 (1963), all three of which are incorporated herein by reference. When $K^1$ is one of the above-mentioned heterocycles, protected alcohols XVII can be prepared by reacting protected halo-alcohols XV with the corresponding heterocycle in the presence of a base. The heterocycles are available commercially (e.g., Aldrich Chemical Co., Milwaukee, Wis.) or prepared by well-known synthetic methods (see the procedures described in Ware, 1950, *Chem. Rev.* 46:403-470, incorporated herein by reference). Preferably, the reaction is conducted by stirring a mixture comprising XV, the heterocycle, and a solvent at a constant temperature within the range of about room temperature to about 100° C., preferably within the range of about 50° C. to about 70° C. for about 10 to about 48 hours. Suitable bases include hydroxide bases such as sodium hydroxide, potassium hydroxide, sodium carbonate, or potassium carbonate. Preferably, the solvent used in forming protected alcohols XVII is selected from dimethylformamide; formamide; dimethyl sulfoxide; alcohols, such as methanol or ethanol; and mixtures thereof. The progress of the reaction can be followed by using an appropriate analytical technique, such as thin layer chromatography or high performance liquid chromatography and when substantially complete, the product can be isolated by workup and purified if desired.

Protected alcohols XVII, wherein $K^1$ is a heteroaryl ring selected from

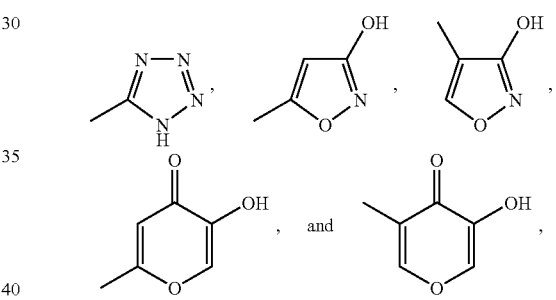

can be prepared by metallating the suitable heteroaryl ring then reacting the resulting metallated heteroaryl ring with protected halo-alcohols XV (for a review, see Katritzky *Handbook of Heterocyclic Chemistry*, Pergamon Press: Oxford 1985). The heteroaryl rings are available commercially or prepared by well-known synthetic methods (see e.g., Joule et al., *Heterocyclic Chemistry*, 3rd ed., 1995; De Sarlo et al., 1971, *J. Chem. Soc.* (C) 86; Oster et al., 1983, *J. Org. Chem.* 48:4307; Iwai et al., 1966, *Chem. Pharm. Bull.* 14:1277; and U.S. Pat. No. 3,152,148, all of which citations are incorporated herein by reference). As used herein, the term "metallating" means the forming of a carbon-metal bond, which bond may be substantially ionic in character. Metallation can be accomplished by adding about 2 equivalents of strong organometallic base, preferably with a p$K_a$ of about 25 or more, more preferably with a p$K_a$ of greater than about 35, to a mixture comprising a suitable organic solvent and the heterocycle. Two equivalents of base are required: one equivalent of the base deprotonates the —OH group or the —NH group, and the second equivalent metallates the heteroaryl ring. Alternatively, the hydroxy group of the heteroaryl ring can be protected with a base-stable, acid-labile protecting group as described in Greene, T. W., *Protective Groups in Organic Synthesis*, 3rd edition 17-237 (1999), incorporated herein by reference. Where the hydroxy group is protected, only one equivalent of base is required. Examples of suitable base-stable, acid-labile hydroxyl-protecting groups, include but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahyrofuranyl, tetrahydrothiofuranyl, 1-ethoxyethyl, 1-methyl-1-methoxyethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably, the $pK_a$ of the base is higher than the pa of the proton of the heterocycle to be deprotonated. For a listing of $pK_a$s for various heteroaryl rings, see Fraser et al., 1985, *Can. J. Chem.* 63:3505, incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. If desired, the organometallic base can be activated with a complexing agent, such as N,N,N',N'-tetramethylethylenediamine or hexamethylphosphoramide (1970, *J. Am. Chem. Soc.* 92:4664, incorporated by reference herein). Solvents suitable for synthesizing protected alcohols XVII, wherein $K^1$ is a heteroaryl ring include, but are not limited to, diethyl ether; tetrahydrofuran; and hydrocarbons, such as pentane. Generally, metallation occurs alpha to the heteroatom due to the inductive effect of the heteroatom, however, modification of conditions, such as the identity of the base and solvents, order of reagent addition, reagent addition times, and reaction and addition temperatures can be modified by one of skill in the art to achieve the desired metallation position (see e.g., Joule-et al., *Heterocyclic Chemistry*, 3rd ed., 1995, pp. 30-42, incorporated by reference herein) Alternatively, the position of metallation can be controlled by use of a halogenated heteroaryl group, wherein the halogen is located on the position of the heteroaryl ring where metallation is desired (see e.g., Joule et al., *Heterocyclic Chemistry*, 3rd ed., 1995, p. 33 and Saulnier et al., 1982, *J. Org. Chem.* 47:757, the two of which citations are incorporated by reference herein). Halogenated heteroaryl groups are available commercially (e.g., Aldrich Chemical Co., Milwaukee, Wis.) or can be prepared by well-known synthetic methods (see e.g., Joule et al., *Heterocyclic Chemistry*, 3rd ed., 1995, pp. 78, 85, 122, 193, 234, 261, 280, 308, incorporated by reference herein). After metallation, the reaction mixture comprising the metallated heteroaryl ring is adjusted to within a temperature range of about 0° C. to about room temperature and protected halo-alcohols XV (diluted with a solvent or in undiluted form) are added, preferably at a rate such that the reaction-mixture temperature remains within about one to two degrees of the initial reaction-mixture temperature. After addition of protected haloalcohols XV, the reaction mixture is stirred at a constant temperature within the range of about room temperature and about the solvent's boiling temperature and the reaction's progress can be monitored by the appropriate analytical technique, preferably thin-layer chromatography or high-performance liquid chromatography. After the reaction is substantially complete, protected alcohols XVII can be isolated by workup and purification. It is to be understood that conditions, such as the identity of protected halo-alcohol XV, the base, solvents, orders of reagent addition, times, and temperatures, can be modified by one of skill in the art to optimize the yield and selectivity. Exemplary procedures that can be used in such a transformation are described in Shirley et al., 1995, *J. Org. Chem.* 20:225; Chadwick et al., 1979, *J. Chem. Soc., Perkin Trans. I* 2845; Rewcastle, 1993, *Adv. Het. Chem.* 56:208; Katritzky et al., 1993, *Adv. Het. Chem.* 56:155; and Kessar et al., 1997, *Chem. Rev.* 97:721.

Protected alcohols XVII, wherein $K^1$ is a lactone selected from:

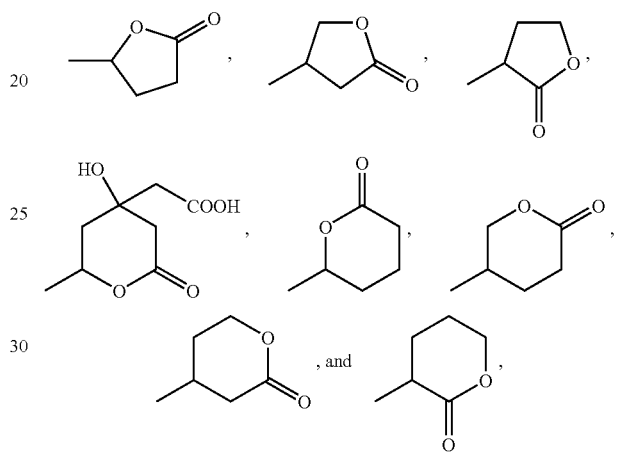

can be prepared from compounds of the formula X, XV, or XVI by using well-known condensation reactions and variations of the Michael reaction. Methods for the synthesis of lactones are disclosed in Multzer in *Comprehensive Organic Functional Group Transformations*, A. R. Katritzky, O. Meth-Cohn and C. W. Rees, Eds. Pergamon: Oxford, 1995, vol 5, pp. 161-173, incorporated herein by reference. When $K^1$ is a beta-lactone of the formula:

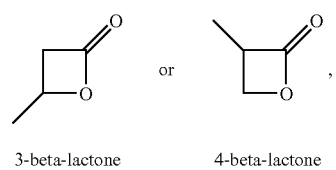

3-beta-lactone    4-beta-lactone protected alcohols XVII can be prepared from aldehydes XVI and protected halo-alcohols XV, respectively, by a one-pot-addition-lactonization according to the procedure of Masamune et al., 1976, *J. Am. Chem. Soc.* 98:7874 and Danheiser et al., 1991, *J. Org. Chem.* 56:1176, both of which are incorporated herein by reference. This one-pot-addition-lactonization methodology has been reviewed by Multzer in *Comprehensive Organic Functional Group Transformations*, A. R. Katritzky, O. Meth-Cohn and C. W. Rees, Eds. Pergamon: Oxford, 1995, vol 5, pp. 161, incorporated herein by reference When $K^1$ is a gamma- or delta-lactone of the formula:

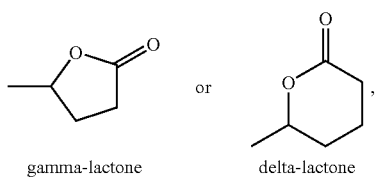

gamma-lactone    delta-lactone protected alcohols XVII can be prepared from aldehydes XVI according to well known synthetic methodology. For example, the methodology described in Masuyama et al., 2000, *J. Org. Chem.* 65:494; Eisch et al., 1978, *J. Organo. Met. Chem.* C8 160; Eaton et al., 1947, *J. Org. Chem.* 37:1947; Yunker et al., 1978, *Tetrahedron Lett.* 4651; Bhanot et al., 1977, *J. Org. Chem.* 42:1623; Ehlinger et al., 1980, *J. Am. Chem. Soc.* 102:5004; and Raunio et al., 1957, *J. Org. Chem.* 22:570, all of which citations are incorporated herein by reference. For instance, as described in Masuyama et al., 2000, *J. Org. Chem.* 65:494, aldehydes XVI can be treated with about 1 equivalent of a strong organometallic base, preferably with a $pK_a$ of about 25 or more, more preferably with a $pK_a$ of greater than about 35, in a suitable organic solvent to give a reaction mixture. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. The reaction-mixture temperature is adjusted to within the range of about 0° C. to about 100° C., preferably about room temperature to about 50° C., and a halide of the formula:

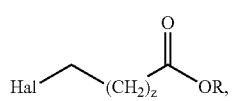

wherein z is 1 or 2 (diluted with a solvent or in undiluted form) is added. The reaction mixture is stirred for a period of about 2 hours to about 48 hours, preferably about 5 to about 10 hours, during which time the reaction's progress can be followed by using an appropriate analytical technique, such as thin layer chromatography or high performance liquid chromatography. When the reaction is deemed substantially complete, protected alcohols XVII can be isolated by workup and purified if desired. When $K^1$ is a gamma- or delta-lactone of the formula:

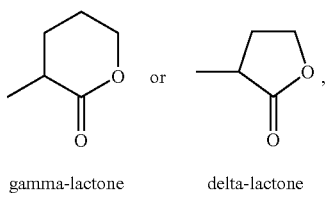

gamma-lactone    delta-lactone protected alcohols XVII can be synthesized by deprotonating the respective lactone with a strong base providing the corresponding lactone enolate and reacting the enolate with protected halo-alcohols XV (for a detailed discussion of enolate formation of active methylene compounds such as lactones, see House *Modern Synthetic Reactions*; W. A. Benjamin, Inc. Philippines 1972 pp. 492-570, and for a discussion of reaction of lactone enolates with electrophiles such as carbonyl compounds, see March, J. *Advanced Organic Chemistry; Reactions Mechanisms, and Structure*, 4th ed., 1992, pp. 944-945, both of which are incorporated herein by reference). Lactone-enolate formation can be accomplished by adding about 1 equivalent of a strong organometallic base, preferably with a $pK_a$ of about 25 or more, more preferably with a $pK_a$ of greater than about 35, to a mixture comprising a suitable organic solvent and the lactone. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Solvents suitable for lactone-enolate formation include, but are not limited to, diethyl ether and tetrahydrofuran. After enolate formation, the reaction-mixture temperature is adjusted to within the range of about −78° C. to about room temperature, preferably about −50° C. to about 0° C., and protected halo-alcohols XV (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, protected alcohols XVII can be isolated by workup and purified if desired. Protected alcohols XVII, wherein $K^1$ is a lactone of the formula:

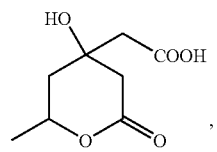

can be prepared from aldehydes XVI according to the procedure described in U.S. Pat. No. 4,622,338, incorporated by reference herein.

When $K^1$ is a gamma- or delta-lactone of the formula:

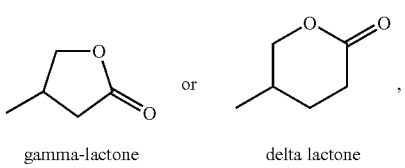

gamma-lactone    delta lactone protected alcohols XVII can be prepared according to a three step sequence. The first step comprises base-mediated reaction of protected halo-alcohols XV with succinic acid esters (i.e., RO$_2$CCH$_2$CH$_2$CO$_2$R, wherein R is alkyl) or glutaric acid esters (i.e., RO$_2$CCH$_2$CH$_2$CH$_2$CO$_2$R, wherein R is alkyl) providing a diester intermediate of the formula:

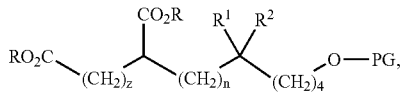

wherein z is 1 or 2 depending on the acid ester starting material. The reaction can be performed by adding about 1 equivalent of a strong organometallic base, preferably with a $pK_a$ of about 25 or more, more preferably with a $pK_a$ of greater than about 35, to a mixture comprising a suitable organic solvent and the succinic or glutaric acid ester. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. After enolate formation, the reaction-mixture temperature is adjusted to within the range of about –78° C. to about room temperature, preferably about –50° C. to about 0° C., and protected halo-alcohols XV (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, the diester intermediate be isolated by workup and purified if desired. In the second step, the intermediate diester can be reduced, with a hydride reducing agent, to yield a diol of the formula:

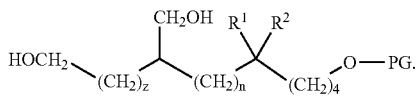

The reduction can be performed according to the procedures referenced in March, J. *Advanced Organic Chemistry; Reactions Mechanisms, and Structure*, 4th ed., 1992, p. 1214, incorporated herein by reference). Suitable reducing agents include, but are not limited to, lithium aluminum hydride, diisobutylaluminum hydride, sodium borohydride, and lithium borohydride). In the third step, the diol can be oxidatively cyclized with RuH$_2$(PPh$_3$)$_4$ to the product lactones XVII according to the procedure of Yoshikawa et al., 1986, *J. Org. Chem.* 51:2034 and Yoshikawa et al., 1983, *Tetrahedron Lett.* 26:2677, both of which citations are incorporated herein by reference. When K$^1$ is a lactone of the formula:

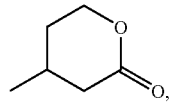

protected alcohols XVII can be synthesized by reacting the Grignard salts of protected halo-alcohols XV with 5,6-dihydro-2H-pyran-2-one, commercially available (e.g., Aldrich Chemical Co., Milwaukee, Wis.), in the presence of catalytic amounts of a 1-dimethylaminoacetyl)pyrolidine-2yl)methyl-diarylphosphine-copper (I) iodide complex as described in Tomioka et al., 1995, *Tetrahedron Lett.* 36:4275, incorporated herein by reference. When K$^1$ is

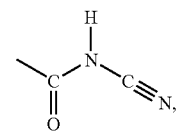

protected alcohols XVII can be prepared from their corresponding carboxylic acid derivatives (XVII, wherein K$^1$ is —CO$_2$H) as described in Belletire et al, 1988, *Synthetic Commun.* 18:2063 or from the corresponding acylchlorides (XVII, wherein K$^1$ is —CO-halo) as described in Skinner et al., 1995, *J. Am. Chem. Soc.* 77:5440, both citations are incorporated herein by reference. The acylhalides can be prepared from the carboxylic acids by well known procedures such as those described in March, J., *Advanced Organic Chemistry; Reactions Mechanisms, and Structure*, 4th ed., 1992, pp. 437-438, incorporated by reference herein. When K$^1$ is

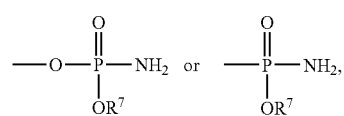

wherein R$^7$ is as defined above, protected alcohols XVII can be prepared by first reacting protected halo-alcohols XV with a trialkyl phosphite according to the procedure described in Kosolapoff, 1951, *Org. React.* 6:273 followed by reacting the derived phosphonic diester with ammonia according to the procedure described in Smith et al., 1957, *J. Org. Chem.* 22:265, incorporated herein by reference. When K$^1$ is

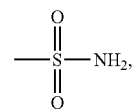

protected alcohols XVII can be prepared by reacting their sulphonic acid derivatives (i.e., XVII, wherein K$^1$ is —SO$_3$H) with ammonia as described in Sianesi et al., 1971, *Chem. Ber.* 104:1880 and Campagna et al., 1994, *Farmaco, Ed. Sci.* 49:653, both of which citations are incorporated herein by reference).

As further illustrated in Scheme 2, protected alcohols XVII can be deprotected providing alcohols XVIII. The deprotection method depends on the identity of the alcohol-protecting group, see e.g., the procedures listed in Greene, T. W., *Protective Groups in Organic Synthesis*, 3rd edition 17-237 (1999), particularly see pages 48-49, incorporated herein by reference. One of skill in the art will readily be able to choose the appropriate deprotection procedure. When the alcohol is protected as an ether function (e.g., methoxymethyl ether), the alcohol is preferably deprotected with aqueous or alcoholic acid. Suitable deprotection reagents include, but are not limited to, aqueous hydrochloric acid, p-toluenesulfonic acid in methanol, pyridinium-p-toluenesulfonate in ethanol, Amberlyst H-15 in methanol, boric acid in ethylene-glycol-monoethylether, acetic acid in a water-tetrahydrofuran mixture, aqueous hydrochloric acid is preferred. Examples of such procedures are described, respectively, in Bernady et al., 1979, *J. Org. Chem.* 44:1438; Miyashita et al., 1977, *J. Org. Chem.* 42:3772; Johnston et al., 1988, *Synthesis* 393; Bongini et al., 1979, *Synthesis* 618; and Hoyer et al., 1986, *Synthesis* 655; Gigg et al., 1967, *J. Chem. Soc. C*, 431; and Corey et al., 1978, *J. Am. Chem. Soc.* 100:1942, all of which are incorporated herein by reference.

Scheme 3 illustrates the synthesis of halides of formula XXI, wherein m, $K^2$, $R^3$ and $R^4$ are as defined above. Alcohols of formula XX can be prepared using the synthetic methods described herein for the synthesis of alcohols XVIII. As further shown in Scheme 3, halides XXI can be synthesized from alcohols XX by halogenation as described above for the synthesis of protected halo-alcohols XV.

Scheme 4 outlines the synthesis of compounds of formula I by reacting alcohols XVIII with halides XXI via the Williamson ether synthesis, as discussed above for the synthesis of mono-protected diols X. In a preferred procedure, first, a base is added to a stirred organic solution comprising alcohols XVIII, maintained at a constant temperature within the range of about 0° C. to about 80° C., preferably at about room temperature. Preferably, the base is added at a rate such that the reaction-mixture temperature remains within about one to two degrees of the initial reaction-mixture temperature. The base can be added as an organic solution or in undiluted form. Preferably, the base has a $pK_a$ of about 15 or greater. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. The preferred base is lithium diisopropylamide. Suitable solvents include, but are not limited, to dimethyl sulfoxide, dichloromethane, ethers, and mixtures thereof, preferably tetrahydrofuran. After addition of the base, the reaction mixture is adjusted to within a temperature range of about 0° C. to about room temperature and halides XXI are added, preferably at a rate such that the reaction-mixture temperature remains within about one to two degrees of the initial reaction-mixture temperature. Halides XXI can be diluted in an organic solvent or added in undiluted form. The resulting reaction mixture is heated at a constant temperature within the range of about room temperature to about the solvent's boiling temperature until the reaction is substantially complete as determined by using an appropriate analytical method, preferably by gas chromatography. The product I can be isolated by workup and purification.

As illustrated in Scheme 5, mono-protected diols of the formula XXIV can be prepared from compounds XIII, wherein X, $R^1$, $R^2$, and $R^8$ are as defined above. In the first step, compounds XIII are converted to alcohols of the formula XXII by reduction with a suitable reducing agent. A suitable reducing agent will be selective in that it will reduce the ester function of compounds XIII (i.e., $R^8O_2C$—) to hydroxymethylene (i.e., $HOCH_2$—), without displacing leaving group X. The choice of reducing agent will depend on the identities of X and $R^8$. A wide variety of synthetic procedures are available for selective reduction of such esters to alcohols (e.g., see M. Hudlicky, *Reductions in Organic Chemistry*, 2nd ed., 1996 pp 212-217). For exemplary procedures for reducing esters to alcohols with selective reducing reagents, see Brown et al. 1965, *J. Am. Chem. Soc.* 87:5614, lithium trimethoxyaluminum hydride; Cerny et al., 1969, *Collect. Czech. Chem. Commun.* 34:1025, sodium bis(2-methoxy) aluminum hydride; Nystrom et al., 1949, *J. Am. Chem.* 71:3245, lithium borohydride; and Brown et al., 1980, *J. Org. Chem.* 45:1, lithium triethyl borohydride. The reaction can be performed by stirring a mixture comprising compounds XIII, a reducing agent, and a suitable organic solvent at a constant temperature within the range of about −20° C. to about 80° C., preferably at about 0° C. to about room temperature. Solvents suitable for reducing compounds XIII include, but are not limited to, methanol, ethanol, isopropanol, dichloromethane, toluene, diethyl ether, tetrahydrofuran or mixtures thereof. The preferred reducing agent is lithium borohydride and the preferred solvent is methanol. The reaction's progress is followed by using an appropriate analytical method, preferably thin-layer chromatography or high-performance liquid chromatography, and, when complete, the reaction mixture can be quenched and the product can be isolated by workup and purification. Next in Scheme 5, the hydroxy moiety of alcohols XXII is protected with a hydroxyl-protecting group providing protected alcohols of the formula XXIII. Preferably, the protecting group is stable to base but labile under acidic conditions. Examples of suitable base-stable, acid-labile alcohol-protecting groups include, but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahyrofuranyl, tetrahydrothiofuranyl, 1-ethoxyethyl, 1-methyl-1-methoxyethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, triisopropylsilyl; and esters, such as pivaloate, adamantoate, and 2,4,6-trimethylbenzoate. Ethers are preferred, particularly cyclic ethers, such as tetrahydropyranyl. For example, when —PG is tetrahydropyranyl, protected alcohols XXIII can be prepared by contacting a stirred solution comprising alcohols XXII, an organic solvent, and an acid catalyst with dihydropyran. Preferably, the reaction mixture is stirred for about 1 to about 24 hours, more preferably about 2 to about 10 hours, at a temperature within the temperature range of about 0° C. to about 50° C., preferably at about room temperature. Suitable solvents include, but are not limited to, dichloromethane, hexane, toluene, tetrahydrofuran, acetonitrile, and mixtures thereof. Suitable acids include, but are not limited to, p-toluenesulfonic acid, pyridinium-p-toluene sulfonate, $MgBr_2$-etherate, and alumina. The reaction's progress can be followed by a suitable analytical technique (preferably thin-layer chromatography or high-performance liquid chromatography) and when the reaction is deemed substantially complete, protected alcohols XXIII can be isolated by workup and purification. Exemplary procedures for protecting a hydroxy group as the tetrahydropyranyl ether can be found in Bernady et al., 1979, *J. Org. Chem.*

44:1438; Miyashita et al., 1977, *J. Org. Chem.* 42:3772; Johnston et al., 1988, *Synthesis* 393; Bongini et al., 1979, *Synthesis* 618 and Hoyer et al., 1986, *Synthesis* 655, all of which are incorporated herein by reference. As further shown in Scheme 5, mono-protected diols XXIV can be synthesized by reacting an organic solution of protected alcohols XXIII, with about 1 to about 5 equivalents of a hydroxide source. Preferably, the reaction mixture is maintained within a temperature range of about room temperature to about 110° C., more preferably about 70° C. to about 90° C., preferably for about 1 to about 24 hours, more preferably for about 2 to about 5 hours. The reaction's progress can be followed by using an appropriate analytical technique (such as, thin-layer chromatography or high-performance liquid chromatography) and, when substantially complete, the product can be isolated by workup and purification. For a discussion of hydrolysis of alkylhalides with hydroxide see March, J. *Advanced Organic Chemistry; Reactions Mechanisms, and Structure*, 4th ed., 1992, p. 370, incorporated herein by reference. Suitable hydroxide sources include, but are not limited to, sodium carbonate, potassium carbonate, calcium carbonate, sodium hydroxide, and potassium hydroxide, preferably sodium carbonate. Suitable solvents include, but are not limited to, dimethyl sulfoxide, dimethyl formamide, hexamethylphosphoramide, and N-methyl-2-pyrrolidone, and mixtures thereof, preferably dimethyl sulfoxide. When the solvent is hexamethylphosphoramide or N-methyl-2-pyrrolidone, water can serve as the hydroxide source (see e.g., Kurz et al., 1985, *Isr. J. Chem.* 26:339 and Kurz et al., 1986, *J. Am. Chem.* 108:2960, both of which are incorporated by reference herein).

Scheme 6 shows the synthesis of protected alcohols XXVIII, which compounds are synthesized by the same synthetic methods described in Scheme 5 for protected alcohols XXIII.

Scheme 7 illustrates the synthesis of compounds of formula I, wherein n and m are both 0 and $K^1$ and $K^2$ are both —$CH_2OH$ and $R^1$, $R^2$, $R^3$, and $R^4$ are defined as above. The synthesis can be carried out by reacting mono-protected diols XXIV with protected alcohols XXVIII via the Williamson ether synthesis using the synthetic procedure of Scheme 4, providing di-protected diols of the formula XXIX. Di-protected diols XXIX can be deprotected providing compounds of formula I, wherein n and m are both 0 and $K^1$ and $K^2$ are both —$CH_2OH$, by using the synthetic deprotection methodology described above in Scheme 1 for the deprotection of protected alcohols XVII.

Scheme 8 illustrates homologation of compounds of formula I, wherein n and m are both 0 and $K^1$ and $K^2$ are both —$CH_2OH$ to provide compounds of formula I, wherein n and m are identical integers ranging from 1 to 5. Scheme 8 involves a three step homologation sequence comprising (a) halogenation (converting —$CH_2OH$ to —$CH_2$-Hal), (b) carbonylation (replacing -Hal with —CHO), and (c) reduction (converting —CHO to —$CH_2OH$) using the same synthetic procedure discussed for the homologation of mono-protected diols X in Scheme 1.

Scheme 9 outlines the synthesis of compounds of the formula I, wherein $K^1$ and $K^2$ are both —$CH_2OH$ and $R^1$, $R^2$, $R^3$, $R^4$, n, and m are defined as above, by reducing compounds XXX, wherein $R^{10}$ is independently selected from the group consisting of —H, —OH, ($C_1$-$C_6$)alkoxy, ($C_6$)aryloxy, —O—($C_2$-$C_6$)alkenyl, —O—($C_2$-$C_6$)alkynyl, and halo, with a reducing agent in a suitable organic solvent. For a discussion of procedures and references concerning reduction of compounds XXX see March, J. *Advanced Organic Chemistry; Reactions Mechanisms, and Structure*, 4th ed., 1992, p. 1212 ($R^{10}$ is —OH); p. 910 ($R^{10}$ is —H); p. 1214 ($R^{10}$ is ($C_1$-$C_6$)alkoxy, ($C_6$)aryloxy, —O—($C_2$-$C_6$)alkenyl, or —O—($C_2$-$C_6$)alkynyl); p. 446 ($R^{10}$ is -halo), incorporated herein by reference. Suitable reducing agents include, but are not limited to, hydrogen (via catalytic hydrogenation); borane; allane; and hydride reducing agents, such as lithium aluminum hydride, diisobutylaluminum hydride, and sodium borohydride. When the reducing agent is a hydride reducing agent; allane; or borane, then after reacting XXX with the reducing agent, the intermediate salt, if formed, is hydrolyzed with an aqueous proton source, such as dilute (e.g., 1 molar) hydrochloric acid. Suitable organic solvents include, but are not limited to, toluene, alcohols, dichloromethane, diethyl ether, tetrahydrofuran or mixtures thereof. Preferably, the reduction is conducted by adding an organic solution of compounds XXX to a stirred mixture comprising a hydride reducing agent, preferably lithium aluminum hydride and an organic solvent, preferably tetrahydrofuran. During the addition, the reaction mixture is maintained at a constant temperature within the range of about –20° C. to about 80° C., preferably at about room temperature. After the addition, the reaction mixture is stirred at a constant temperature within the range of about room temperature to about 60° C., until the reaction is substantially complete as determined by using an appropriate analytical method, preferably thin-layer chromatography or high-performance-liquid chromatography. Then the reaction mixture can be quenched and compounds of the formula I, wherein $K^1$ and $K^2$ are both —$CH_2OH$, can be isolated by workup and purification.

In another embodiment, compounds of formula I, wherein $K^1$ and $K^2$ are both —$CH_2OH$, can be oxidized to synthesize compounds of formula XXX wherein $R^{10}$ is —OH by using an oxidizing agent, for example, an oxidizing agent suitable for oxidizing a primary alcohol to a carboxylic acid (for a discussion see M. Hudlicky, *Oxidations in Organic Chemistry*, ACS Monograph 186, 1990, pp. 127-130). Suitable oxidizing agents include, but are not limited to, chromic acid, pyridinium dichromate (Corey et al., 1979, *Tetrahedron Lett.* 399); manganese dioxide (Ahrens et al., 1967, *J. Heterocycl. Chem.* 4:625); sodium permanganate monohydrate (Menger et al., 1981, *Tetrahedron Lett.* 22:1655); and potassium permanganate (Sam et al., 1972, *J. Am. Chem. Soc.* 94:4024). The preferred oxidizing reagent is pyridinium dichromate.

In another embodiment, the invention relates to compounds of formula XL

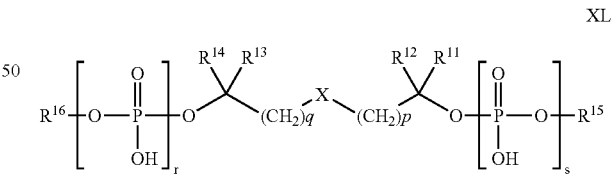

wherein:
X is a heteroatom selected from oxygen, sulfur and nitrogen, preferably oxygen;
s and r are integers ranging from 1 to 3;
p and q are integers ranging from 2 to 9, preferably 2-5, more preferably 4-5;
$R^{11}$, $R^{12}$, $R^{13}$ and $R^{14}$ are independent ($C_1$-$C_8$)hydrocarbyl groups. Preferably, ($C_1$-$C_8$)hydrocarbyl is selected from the group consisting of ($C_1$-$C_6$)alkyl, ($C_2$-$C_6$)alkenyl, ($C_2$-$C_6$)alkynyl, or $R^1$, $R^2$, and the carbon to which they are attached are taken together to form a ($C_3$-$C_6$)cycloalkyl group; or $R^3$, $R^4$, and the carbon to which they are attached are taken together to form a $(C_3$-$C_6)$cycloalkyl group; or $R^1$, $R^2$, and the carbon to which they are attached are taken together to form a $(C_3$-$C_6)$cycloalkyl group and $R^3$, $R^4$, and the carbon to which they are attached are taken together to form a $(C_3$-$C_6)$cycloalkyl group; and $R^{15}$ and $R^{16}$ are independent $(C_1$-$C_8)$hydrocarbyl groups, or both $R^{15}$ and $R^{16}$ are H. Preferably, $(C_1$-$C_8)$hydrocarbyl is selected from the group consisting of $(C_1$-$C_6)$alkyl, $(C_2$-$C_6)$alkenyl, and $(C_2$-$C_6)$alkynyl, which $(C_1$-$C_6)$alkyl, $(C_2$-$C_6)$alkenyl, $(C_2$-$C_6)$alkynyl groups may be substituted with one or two groups selected from halo, hydroxy, $(C_1$-$C_6)$alkoxy, and phenyl. Preferably, both $R^{15}$ and $R^{16}$ are H.

In yet another embodiment, the invention relates to compounds of the formula XLI

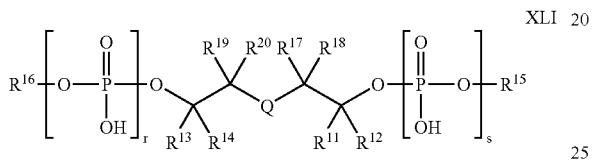

XLI or pharmaceutically acceptable salts thereof, wherein:

s and r are integers ranging from 1 to 3;

$R^{17}$, $R^{18}$, $R^{19}$ and $R^{20}$ each independently represent an unsubstituted or substituted hydrocarbyl group or a heterocyclic radical;

$R^{11}$, $R^{12}$, $R^{13}$ and $R^{14}$ are independently selected from the group consisting of hydrogen, lower alkyl, halogen, cyano, carboxy, lower alkoxycarbonyl and carbamoyl, preferably hydrogen, lower alkyl, fluoro, chloro, bromo, and cyano; and $R^{15}$ and $R^{16}$ are independent $(C_1$-$C_8)$hydrocarbyl groups, or both $R^{15}$ and $R^{16}$ are H. Preferably, $(C_1$-$C_8)$hydrocarbyl is selected from the group consisting of $(C_1$-$C_6)$alkyl, $(C_2$-$C_6)$alkenyl, and $(C_2$-$C_6)$alkynyl, which $(C_1$-$C_6)$alkyl, $(C_2$-$C_6)$alkenyl, $(C_2$-$C_6)$alkynyl groups may be substituted with one or two groups selected from halo, hydroxy, $(C_1$-$C_6)$alkoxy, and phenyl. Preferably, $R^{15}$ and $R^{16}$ are both H.

Q represents a diradical consisting of a linear chain of 8 to 14 carbon atoms, one or more of which may be replaced by heteroatoms, said chain being optionally substituted by inert substituents and one or more of said carbon or heteroatom chain members optionally forming part of a ring structure. Preferably, Q is of the formula —$(CH_2)_n$—, wherein n in an integer ranging from 8 to 14. An "inert substituent" is a suitable substituent that does not negate the pharmaceutical utility of the compound to which it is attached. If a heteroatom is present, it is preferably O, S, or N.

Preferably, compounds of formula XLI are of the formula:

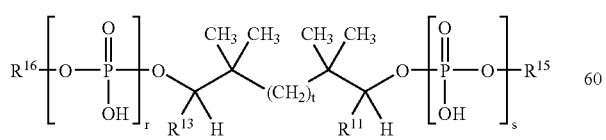

or pharmaceutically acceptable salts thereof, wherein $R^1$ and $R^3$ are independently selected from the group consisting of H, lower alkyl, fluoro, chloro, bromo, cyano, and t is an integer within the range of 8 to 14.

In still another embodiment, the invention relates to compounds of the formula XLII

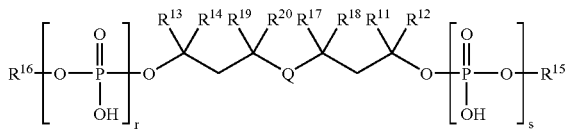

or pharmaceutically acceptable salts thereof, wherein:

s and r are integers ranging from 1 to 3;

$R^{17}$, $R^{18}$, $R^{19}$ and $R^{20}$ each independently represent an unsubstituted or substituted hydrocarbyl or heterocyclic radical;

$R^{11}$, $R^{12}$, $R^{13}$ and $R^{14}$ each independently represents H, lower alkyl, halogen, cyano, carboxy, lower alkoxycarbonyl or carbamoyl; and $R^{15}$ and $R^{16}$ are independent $(C_1$-$C_8)$hydrocarbyl groups, or both $R^{15}$ and $R^{16}$ are H. Preferably, $(C_1$-$C_8)$hydrocarbyl is selected from the group consisting of $(C_1$-$C_6)$alkyl, $(C_2$-$C_6)$alkenyl, and $(C_2$-$C_6)$alkynyl, which $(C_1$-$C_6)$alkyl, $(C_2$-$C_6)$alkenyl, $(C_2$-$C_6)$alkynyl groups may be substituted with one or two groups selected from halo, hydroxy, $(C_1$-$C_6)$alkoxy, and phenyl. Preferably, $R^{15}$ and $R^{16}$ are both H.

Q represents a diradical consisting of a linear chain of 8 to 14 carbon atoms, one or more of which may be replaced by heteroatoms, said chain being optionally substituted by inert substituents and one or more of said carbon or heteroatom chain members optionally forming part of a ring structure. If a heteroatom is present, it is preferably O, S, or N.

Preferably, compounds of the formula XLII have the structure:

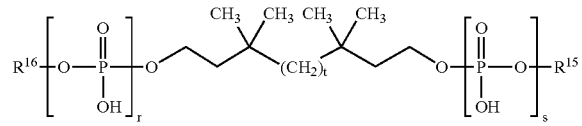

or pharmaceutically acceptable salts thereof, wherein:

t is an integer from within the range of 6 to 12, and $R^{15}$, $R^{16}$, r, and s are as defined above. The invention further contemplates pharmaceutically acceptable salts of the compounds of the formulas XL, XLI, and XLII. The compounds of the formulas XL, XLI, and XLII and pharmaceutically acceptable salts thereof, are useful in the compositions and methods disclosed herein.

Compounds of the formula XL can be prepared according to the methodology described in Schemes 1-4 above, starting from esters of the formulas XLIV and XLV

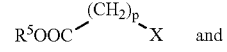

XLIV

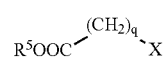

XLV where $R^5$, X, p, and q are as defined above. Esters of the formulas XLIV and XLV are available commercially (e.g., Aldrich Chemical Co., Milwaukee, Wis.) or can be prepared by well-known synthetic methods, for example, esterification of the appropriate haloalkyl carboxylic acid (commercially available, e.g., Aldrich Chemical Co., Milwaukee, Wis.).

115

Compounds of the formula XLI, can be prepared according to Scheme 10 below.

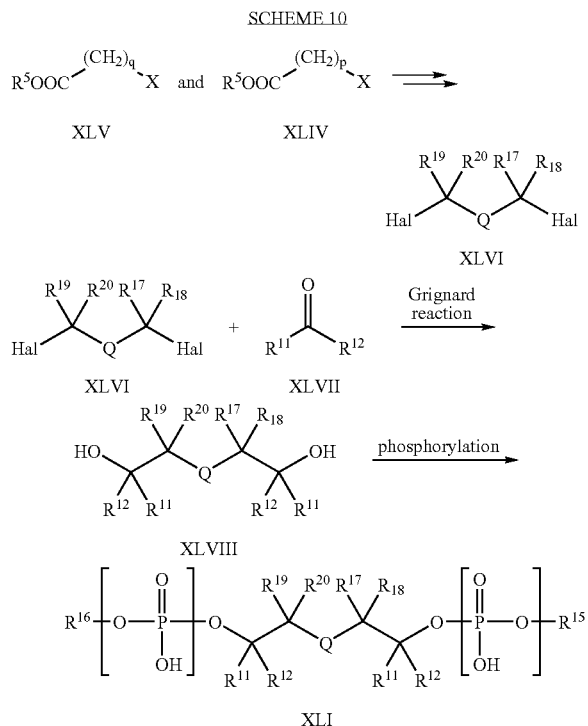

First, compounds of the formula XLVI are prepared from compounds XLIV and compounds XLV according to the methodology described in Schemes 1-4 above. It is to be understood that some modifications of the synthetic procedures outlined in Schemes 1-4 may be necessary, depending on the identity of compounds XLVI, and one of ordinary skill will readily make such modifications. As such, the identity of Q depends on the choice of compounds XLIV and compounds XLV. Next, compounds of the formula XLVIII are synthesized by Grignard reaction of compounds XLVI with compounds XLVII (commercially available, e.g., Aldrich Chemical Co., Milwaukee, Wis.) according to the synthetic procedure described in Scheme 1 for the synthesis of IX. Compounds of the formula XLVIII can then be phosphorylated to provide compounds XLI according to the methodology described above in Scheme 2 for phosphorylation of compounds of the formula X. Note, Scheme 10 above illustrates the synthesis of compounds XLI wherein $R^{13}$ is the same group as $R^{11}$, and $R^{14}$ is the same group as $R^{12}$, however, this methodology can be extended by one of ordinary skill in the art to synthesize compounds of XLI wherein $R^{11}$, $R^{12}$, $R^{13}$, and $R^{14}$ are independent groups.

Compounds of the formula XLII can be prepared according to the synthetic methodology illustrated in Scheme 11 below.

SCHEME 11

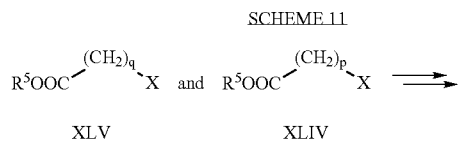

116

-continued

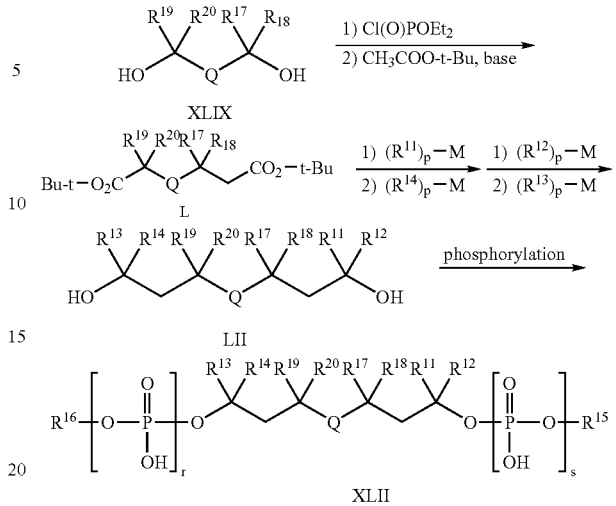

First, compounds of the formula XLIX can be prepared from compounds XLIV and compounds XLV according to the methodology described in Schemes 1-4 above. It is to be understood that some modifications of the synthetic procedures illustrated in Schemes 1-4 may be necessary, and one of ordinary skill will readily make such modifications. As such, the identity of Q depends on the choice of XLIV and XLV. Compounds XLIX can by converted to compounds L by sequential reactions with diethylchlorophosphite and t-butyl acetate in the presence of base. Suitable procedures for conversion of XLIX into L can be found in Larock *Comprehensive Organic Transformations*; Wiley-VCH: New York, 1999, pp. 102; particularly Song et al., 1999, *J. Org. Chem.* 64:9658. Compounds L can be converted to compounds LII by organometallic addition of $R^{11-14}$-M, where M is defined as in Scheme 1, to the ester function of L, using the methodology illustrated in Scheme 1 for the synthesis of compounds IX. Compounds of the formula LII can then be phosphorylated to provide compounds XLII according to the phosphorylation methodology illustrated in Scheme 2 above for phosphorylation of compounds of the formula X.

5.4. Therapeutic Uses of the Compounds of the Invention

In accordance with the invention, a composition of the invention, comprising a compound of the invention and a pharmaceutically acceptable vehicle, is administered to a patient, preferably a human, with a cardiovascular disease, a dyslipidemia, a dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, or impotence. In one embodiment, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, the compositions of the invention are administered to a patient, preferably a human, as a preventative measure against such diseases. As used herein, "prevention" or "preventing" refers to a reduction of the risk of acquiring a given disease or disorder. In a preferred mode of the embodiment, the compositions of the present invention are administered as a preventative measure to a patient, preferably a human, having a genetic predisposition to a cardiovascular disease, a dyslipidemia, a dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, or impotence. Examples of such genetic predispositions include but are not limited to the E4 allele of apolipoprotein E, which increases the likelihood of Alzheimer's Disease; a loss of function or null mutation in the lipoprotein lipase gene coding region or promoter (e.g., mutations in the coding regions resulting in the substitutions D9N and N291S; for a review of genetic mutations in the lipoprotein lipase gene that increase the risk of cardiovascular diseases, dyslipidemias and dyslipoproteinemias, see Hayden and Ma, 1992, *Mol. Cell Biochem.* 113:171-176); and familial combined hyperlipidemia and familial hypercholesterolemia.

In another preferred mode of the embodiment, the compositions of the invention are administered as a preventative measure to a patient having a non-genetic predisposition to a cardiovascular disease, a dyslipidemia, a dyslipoproteinemia, a disorder of glucose metabolism, Alzheimer's Disease, Syndrome X, a PPAR-associated disorder, septicemia, a thrombotic disorder, obesity, pancreatitis, hypertension, a renal disease, cancer, inflammation, or impotence. Examples of such non-genetic predispositions include but are not limited to cardiac bypass surgery and percutaneous transluminal coronary angioplasty, which often lead to restenosis, an accelerated form of atherosclerosis; diabetes in women, which often leads to polycystic ovarian disease; and cardiovascular disease, which often leads to impotence. Accordingly, the compositions of the invention may be used for the prevention of one disease or disorder and concurrently treating another (e.g., prevention of polycystic ovarian disease while treating diabetes; prevention of impotence while treating a cardiovascular disease).

5.4.1. Cardiovascular Diseases for Treatment or Prevention

The present invention provides methods for the treatment or prevention of a cardiovascular disease, comprising administering to a patient a therapeutically effective amount of a composition comprising a compound of the invention and a pharmaceutically acceptable vehicle. As used herein, the term "cardiovascular diseases" refers to diseases of the heart and circulatory system. These diseases are often associated with dyslipoproteinemias and/or dyslipidemias. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarcation; cerebral infarction and restenosis.

5.4.2. Dyslipidemias for Treatment or Prevention

The present invention provides methods for the treatment or prevention of a dyslipidemia comprising administering to a patient a therapeutically effective amount of a composition comprising a compound of the invention and a pharmaceutically acceptable vehicle.

As used herein, the term "dyslipidemias" refers to disorders that lead to or are manifested by aberrant levels of circulating lipids. To the extent that levels of lipids in the blood are too high, the compositions of the invention are administered to a patient to restore normal levels. Normal levels of lipids are reported in medical treatises known to those of skill in the art. For example, recommended blood levels of LDL, HDL, free triglycerides and others parameters relating to lipid metabolism can be found at the web site of the American Heart Association and that of the National Cholesterol Education Program of the National Heart, Lung and Blood Institute (http://www.americanheart.org and http://rover.nhlbi.nih.gov/chd/, respectively). At the present time, the recommended level of HDL cholesterol in the blood is above 35 mg/dL; the recommended level of LDL cholesterol in the blood is below 130 mg/dL; the recommended LDL:HDL cholesterol ratio in the blood is below 5:1, ideally 3.5:1; and the recommended level of free triglycerides in the blood is less than 200 mg/dL.

Dyslipidemias which the compositions of the present invention are useful for preventing or treating include but are not limited to hyperlipidemia and low blood levels of high density lipoprotein (HDL) cholesterol. In certain embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of ketone bodies (e.g. β-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, e.g., reducing LDL in the blood of a patient, reducing free triglycerides in the blood of a patient, increasing the ratio of HDL to LDL in the blood of a patient, and inhibiting saponified and/or non-saponified fatty acid synthesis, said methods comprising administering to the patient a composition comprising a compound of the invention in an amount effective alter lipid metabolism.

5.4.3. Dyslipoproteinemias for Treatment or Prevention

The present invention provides methods for the treatment or prevention of a dyslipoproteinemia comprising administering to a patient a therapeutically effective amount of a composition comprising a compound of the invention and a pharmaceutically acceptable vehicle.

As used herein, the term "dyslipoproteinemias" refers to disorders that lead to or are manifested by aberrant levels of circulating lipoproteins. To the extent that levels of lipoproteins in the blood are too high, the compositions of the invention are administered to a patient to restore normal levels. Conversely, to the extent that levels of lipoproteins in the blood are too low, the compositions of the invention are administered to a patient to restore normal levels. Normal levels of lipoproteins are reported in medical treatises known to those of skill in the art.

Dyslipoproteinemias which the compositions of the present invention are useful for preventing or treating include but are not limited to high blood levels of LDL; high blood levels of apolipoprotein B (apo B); high blood levels of Lp(a);

high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes; lipoprotein abnormalities associated with obesity; lipoprotein abnormalities associated with Alzheimer's Disease; and familial combined hyperlipidemia.

The present invention further provides methods for reducing apo C-II levels in the blood of a patient; reducing apo C-III levels in the blood of a patient; elevating the levels of HDL associated proteins, including but not limited to apo A-I, apo A-II, apo A-IV and apo E in the blood of a patient; elevating the levels of apo E in the blood of a patient, and promoting clearance of triglycerides from the blood of a patient, said methods comprising administering to the patient a composition comprising a compound of the invention in an amount effective to bring about said reduction, elevation or promotion, respectively.

5.4.4. Glucose Metabolism Disorders for Treatment or Prevention

The present invention provides methods for the treatment or prevention of a glucose metabolism disorder, comprising administering to a patient a therapeutically effective amount of a composition comprising a compound of the invention and a pharmaceutically acceptable vehicle. As used herein, the term "glucose metabolism disorders" refers to disorders that lead to or are manifested by aberrant glucose storage and/or utilization. To the extent that indicia of glucose metabolism (i.e., blood insulin, blood glucose) are too high, the compositions of the invention are administered to a patient to restore normal levels. Conversely, to the extent that indicia of glucose metabolism are too low, the compositions of the invention are administered to a patient to restore normal levels. Normal indicia of glucose metabolism are reported in medical treatises known to those of skill in the art.

Glucose metabolism disorders which the compositions of the present invention are useful for preventing or treating include but are not limited to impaired glucose tolerance; insulin resistance; insulin resistance related breast, colon or prostate cancer; diabetes, including but not limited to non-insulin dependent diabetes mellitus (NIDDM), insulin dependent diabetes mellitus (IDDM), gestational diabetes mellitus (GDM), and maturity onset diabetes of the young (MODY); pancreatitis; hypertension; polycystic ovarian disease; and high levels of blood insulin and/or glucose.

The present invention further provides methods for altering glucose metabolism in a patient, for example to increase insulin sensitivity and/or oxygen consumption of a patient, said methods comprising administering to the patient a composition comprising a compound of the invention in an amount effective to alter glucose metabolism.

5.4.5. PPAR Associated Disorders for Treatment or Prevention

The present invention provides methods for the treatment or prevention of a PPAR-associated disorder, comprising administering to a patient a therapeutically effective amount of a composition comprising a compound of the invention and a pharmaceutically acceptable vehicle. As used herein, "treatment or prevention of PPAR associated disorders" encompasses treatment or prevention of rheumatoid arthritis; multiple sclerosis; psoriasis; inflammatory bowel diseases; breast; colon or prostate cancer; low levels of blood HDL; low levels of blood, lymph and/or cerebrospinal fluid apo E; low blood, lymph and/or cerebrospinal fluid levels of apo A-I; high levels of blood VLDL; high levels of blood LDL; high levels of blood triglyceride; high levels of blood apo B; high levels of blood apo C-III and reduced ratio of post-heparin hepatic lipase to lipoprotein lipase activity. HDL may be elevated in lymph and/or cerebral fluid.

5.4.6. Renal Diseases for Treatment or Prevention

The present invention provides methods for the treatment or prevention of a renal disease, comprising administering to a patient a therapeutically effective amount of a composition comprising a compound of the invention and a pharmaceutically acceptable vehicle. Renal diseases that can be treated by the compounds of the present invention include glomerular diseases (including but not limited to acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (including but not limited to acute tubular necrosis and acute renal failure, polycystic renal disease medullary sponge kidney, medullary cystic disease, nephrogenic diabetes, and renal tubular acidosis), tubulointerstitial diseases (including but not limited to pyelonephritis, drug and toxin induced tubulointerstitial nephritis, hypercalcemic nephropathy, and hypokalemic nephropathy) acute and rapidly progressive renal failure, chronic renal failure, nephrolithiasis, or tumors (including but not limited to renal cell carcinoma and nephroblastoma). In a most preferred embodiment, renal diseases that are treated by the compounds of the present invention are vascular diseases, including but not limited to hypertension, nephrosclerosis, microangiopathic hemolytic anemia, atheroembolic renal disease, diffuse cortical necrosis, and renal infarcts.

5.4.7. Cancers for Treatment or Prevention

The present invention provides methods for the treatment or prevention of cancer, comprising administering to a patient a therapeutically effective amount of a composition comprising a compound of the invention and a pharmaceutically acceptable vehicle. Cancers that can be treated or prevented by administering the compounds of the invention include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon-carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In a most preferred embodiment, cancers that are treated or prevented by administering the compounds of the present invention are insulin resistance or Syndrome X related cancers, including but not limited to breast, prostate and colon cancer.

5.4.8. Other Diseases for Treatment or Prevention

The present invention provides methods for the treatment or prevention of Alzheimer's Disease, Syndrome X, septicemia, thrombotic disorders, obesity, pancreatitis, hypertension, inflammation, and impotence, comprising administering to a patient a therapeutically effective amount of a composition comprising a compound of the invention and a pharmaceutically acceptable vehicle.

As used herein, "treatment or prevention of Alzheimer's Disease" encompasses treatment or prevention of lipoprotein abnormalities associated with Alzheimer's Disease.

As used herein, "treatment or prevention of Syndrome X or Metabolic Syndrome" encompasses treatment or prevention of a symptom thereof, including but not limited to impaired glucose tolerance, hypertension and dyslipidemia/dyslipoproteinemia.

As used herein, "treatment or prevention of septicemia" encompasses treatment or prevention of septic shock.

As used herein, "treatment or prevention of thrombotic disorders" encompasses treatment or prevention of high blood levels of fibrinogen and promotion of fibrinolysis.

In addition to treating or preventing obesity, the compositions of the invention can be administered to an individual to promote weight reduction of the individual.

5.5. Surgical Uses of the Compounds of the Invention

Cardiovascular diseases such as atherosclerosis often require surgical procedures such as angioplasty. Angioplasty is often accompanied by the placement of a reinforcing a metallic tube-shaped structure known as a "stent" into a damaged coronary artery. For more serious conditions, open heart surgery such as coronary bypass surgery may be required. These surgical procedures entail using invasive surgical devices and/or implants, and are associated with a high risk of restenosis and thrombosis. Accordingly, the compounds of the invention may be used as coatings on surgical devices (e.g., catheters) and implants (e.g., stents) to reduce the risk of restenosis and thrombosis associated with invasive procedures used in the treatment of cardiovascular diseases.

5.6. Veterinary and Livestock Uses of the Compounds of the Invention

A composition of the invention can be administered to a non-human animal for a veterinary use for treating or preventing a disease or disorder disclosed herein.

In a specific embodiment, the non-human animal is a household pet. In another specific embodiment, the non-human animal is a livestock animal. In a preferred embodiment, the non-human animal is a mammal, most preferably a cow, horse, sheep, pig, cat, dog, mouse, rat, rabbit, or guinea pig. In another preferred embodiment, the non-human animal is a fowl species, most preferably a chicken, turkey, duck, goose, or quail.

In addition to veterinary uses, the compounds of the invention can be used to reduce the fat content of livestock to produce leaner meats. Alternatively, the compounds of the invention can be used to reduce the cholesterol content of eggs by administering the compounds to a chicken, quail, or duck hen. For non-human animal uses, the compounds of the invention can be administered via the animals' feed or orally as a drench composition.

5.7. Therapeutic/Prophylactic Administration and Compositions

Due to the activity of the compounds of the invention, the compounds are advantageously useful in veterinary and human medicine. As described in Section 5.3 above, the compounds of the invention are useful for the treatment or prevention of cardiovascular diseases, dyslipidemias, dyslipoproteinemias, glucose metabolism disorders, Alzheimer's Disease, Syndrome X, PPAR-associated disorders, septicemia, thrombotic disorders, obesity, pancreatitis, hypertension, renal disease, cancer, inflammation, and impotence.

The invention provides methods of treatment and prophylaxis by administration to a patient of a therapeutically effective amount of a composition comprising a compound of the invention. The patient is an animal, including, but not limited, to an animal such a cow, horse, sheep, pig, chicken, turkey, quail, cat, dog, mouse, rat, rabbit, guinea pig, etc., and is more preferably a mammal, and most preferably a human.

The present compositions, which comprise one or more compounds of the invention, are preferably administered orally. The compounds of the invention may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

In certain embodiments, for example, for the treatment of Alzheimer's Disease, it may be desirable to introduce one or more compounds of the invention into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, *Science* 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds of the invention can be delivered in a controlled release system. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled-release system can be placed in proximity of the target of the compounds of the invention, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, *Science* 249:1527-1533) may be used.

The present compositions will contain a therapeutically effective amount of a compound of the invention, optionally more than one compound of the invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin.

In a preferred embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 200 milligrams of a compound of the invention per kilogram body weight. In specific preferred embodiments of the invention, the oral dose is 0.01 milligram to 70 milligrams per kilogram body weight, more preferably 0.1 milligram to 50 milligrams per kilogram body weight, more preferably 0.5 milligram to 20 milligrams per kilogram body weight, and yet more preferably 1 milligram to 10 milligrams per kilogram body weight. In a most preferred embodiment, the oral dose is 5 milligrams of a compound of the invention per kilogram body weight. The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. In another embodiment, the kit comprises a compound of the invention and another lipid-mediating compound, including but not limited to a statin, a thiazolidinedione, or a fibrate.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for lowering fatty acid synthesis. The compounds of the invention may also be demonstrated to be effective and safe using animal model systems.

Other methods will be known to the skilled artisan and are within the scope of the invention.

5.8. Combination Therapy

In certain embodiments of the present invention, the compounds of the invention can be used in combination therapy with at least one other therapeutic agent. The compound of the invention and the therapeutic agent can act additively or, more preferably, synergistically. In a preferred embodiment, a composition comprising a compound of the invention is administered concurrently with the administration of another therapeutic agent, which can be part of the same composition as the compound of the invention or a different composition. In another embodiment, a composition comprising a compound of the invention is administered prior or subsequent to administration of another therapeutic agent. As many of the disorders for which the compounds of the invention are useful in treating are chronic disorders, in one embodiment combination therapy involves alternating between administering a composition comprising a compound of the invention and a composition comprising another therapeutic agent, e.g., to minimize the toxicity associated with a particular drug. The duration of administration of each drug or therapeutic agent can be, e.g., one month, three months, six months, or a year. In certain embodiments, when a composition of the invention is administered concurrently with another therapeutic agent that potentially produces adverse side effects including but not limited to toxicity, the therapeutic agent can advantageously be administered at a dose that falls below the threshold at which the adverse side is elicited.

The present compositions can be administered together with a statin. Statins for use in combination with the compounds of the invention include but are not limited to atorvastatin, pravastatin, fluvastatin, lovastatin, simvastatin, and cerivastatin.

The present compositions can also be administered together with a PPAR agonist, for example a thiazolidinedione or a fibrate. Thiazolidinediones for use in combination with the compounds of the invention include but are not limited to 5-((4-(2-(methyl-2-pyridinylamino)ethoxy)phenyl)methyl)-2,4-thiazolidinedione, troglitazone, pioglitazone, ciglitazone, WAY-120,744, englitazone, AD 5075, darglitazone, and rosiglitazone. Fibrates for use in combination with the compounds of the invention include but are not limited to gemfibrozil, fenofibrate, clofibrate, or ciprofibrate. As mentioned previously, a therapeutically effective amount of a fibrate or thiazolidinedione often has toxic side effects. Accordingly, in a preferred embodiment of the present invention, when a composition of the invention is administered in combination with a PPAR agonist, the dosage of the PPAR agonist is below that which is accompanied by toxic side effects.

The present compositions can also be administered together with a bile-acid-binding resin. Bile-acid-binding resins for use in combination with the compounds of the invention include but are not limited to cholestyramine and colestipol hydrochloride.

The present compositions can also be administered together with niacin or nicotinic acid.

The present compositions can also be administered together with a RXR agonist. RXR agonists for use in combination with the compounds of the invention include but are not limited to LG 100268, LGD 1069, 9-cis retinoic acid, 2-(1-(3,5,5,8,8-pentamethyl-5,6,7,8-tetrahydro-2-naphthyl)-cyclopropyl)-pyridine-5-carboxylic acid, or 4-((3,5,5,8,8-pentamethyl-5,6,7,8-tetrahydro-2-naphthyl)$_2$-carbonyl)-benzoic acid.

The present compositions can also be administered together with an anti-obesity drug. Anti-obesity drugs for use in combination with the compounds of the invention include but are not limited to β-adrenergic receptor agonists, preferably β-3 receptor agonists, fenfluramine, dexfenfluramine, sibutramine, bupropion, fluoxetine, and phentermine.

The present compositions can also be administered together with a hormone. Hormones for use in combination with the compounds of the invention include but are not limited to thyroid hormone, estrogen and insulin. Preferred insulins include but are not limited to injectable insulin, transdermal insulin, inhaled insulin, or any combination thereof. As an alternative to insulin, an insulin derivative, secretagogue, sensitizer or mimetic may be used. Insulin secretagogues for use in combination with the compounds of the invention include but are not limited to forskolin, dibutryl cAMP or isobutylmethylxanthine (IBMX).

The present compositions can also be administered together with a tyrophostine or an analog thereof. Tyrophostines for use in combination with the compounds of the invention include but are not limited to tryophostine 51.

The present compositions can also be administered together with sulfonylurea-based drugs. Sulfonylurea-based drugs for use in combination with the compounds of the invention include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide.

The present compositions can also be administered together with a biguanide. Biguanides for use in combination with the compounds of the invention include but are not limited to metformin, phenformin and buformin.

The present compositions can also be administered together with an α-glucosidase inhibitor. α-glucosidase inhibitors for use in combination with the compounds of the invention include but are not limited to acarbose and miglitol.

The present-compositions can also be administered together with an apo A-I agonist. In one embodiment, the apo A-I agonist is the Milano form of apo A-I (apo A-IM). In a preferred mode of the embodiment, the apo A-IM for administration in conjunction with the compounds of the invention is produced by the method of U.S. Pat. No. 5,721,114 to Abrahamsen. In a more preferred embodiment, the apo A-I agonist is a peptide agonist. In a preferred mode of the embodiment, the apo A-I peptide agonist for administration in conjunction with the compounds of the invention is a peptide of U.S. Pat. No. 6,004,925 or 6,037,323 to Dasseux.

The present compositions can also be administered together with apolipoprotein E (apo E). In a preferred mode of the embodiment, the apoE for administration in conjunction with the compounds of the invention is produced by the method of U.S. Pat. No. 5,834,596 to Ageland.

In yet other embodiments, the present compositions can be administered together with an HDL-raising drug; an HDL enhancer; or a regulator of the apolipoprotein A-I, apolipoprotein A-IV and/or apolipoprotein genes.

5.8.1. Combination Therapy with Cardiovascular Drugs

The present compositions can be administered together with a known cardiovascular drug. Cardiovascular drugs for use in combination with the compounds of the invention to prevent or treat cardiovascular diseases include but are not limited to peripheral antiadrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., amrinone, milrinone, enoximone, fenoximone, imazodan, sulmazole), antidysrhythmic drugs, calcium entry blockers, ranitine, bosentan, and rezulin.

5.8.2. Combination Therapy for Cancer Treatment

The present compositions can be administered together with treatment with irradiation or one or more chemotherapeutic agents. For irridiation treatment, the irradiation can be gamma rays or X-rays. For a general overview of radiation therapy, see Hellman, Chapter 12: Principles of Radiation Therapy Cancer, in: Principles and Practice of Oncology, DeVita et al., eds., $2^{nd}$. Ed., J.B. Lippencott Company, Philadelphia. Useful chemotherapeutic agents include methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a specific embodiment, a composition of the invention further comprises one or more chemotherapeutic agents and/or is administered concurrently with radiation therapy. In another specific embodiment, chemotherapy or radiation therapy is administered prior or subsequent to administration of a present composition, preferably at least an hour, five hours, 12 hours, a day, a week, a month, more preferably several months (e.g., up to three months), subsequent to administration of a composition of the invention.

6. EXAMPLE

Synthesis of Compound A

6.1. Method A

In a three neck 2 liter round bottom flask fitted with a dropping funnel, thermometer, condenser with HCl trap and mechanical stirrer, 146.2 g (2 mol) of tetrahydrofuran (THF) and 102.4 g (0.66 mol) of phosphorus oxychloride were carefully added through the dropping funnel. To the well stirred mixture, 20 ml $H_2SO_4$ were added cautiously, and the temperature was brought to 85° C. with an oil bath, then the heating was stopped. After approximately 20 minutes, the temperature rose to 100° C. A strong exothermic reaction then occurred and the temperature rose to 140° C. The color of the reaction mixture turned brown and the evolution of HCl was violent. When the addition was complete (no more gas evolution), the reaction mixture was left to reach 70° C., and 200 ml tap water was added. The mixture was heated at reflux for 30 minutes, and the unreacted THF and the 1,4-dichlorobutane formed as byproduct were removed by azeotropic distillation at atmospheric pressure. The distillation residue was separated in a separatory funnel into an oily layer (the product) and an aqueous layer, which was treated with 200 ml water, then extracted with ether (3×150 ml). The combined organic fractions were washed with sodium bicarbonate 5% (2×150 ml), saturated aqueous ammonium chloride (1×150 ml), dried anhydrous $Na_2SO_4$, and the solvent was evaporated in the vacuum. The crude product was distilled under reduced pressure. The main fraction was 83.2 g at 83° to 87° C. (0.4-0.6 mm) at 90% purity. Yield of bis(4-chlorobutyl)ether was 56%.

4,4-Dichlorobutyl ether (40 g, 0.2 mol), sodium iodide (67 g, excess) and 500 ml acetone was added to a 3-neck 1-L round bottom flask fitted condenser with a calcium chloride trap and magnetic stirrer. The mixture was heated under reflux for seven days, while the color of the reaction mixture turned yellow. The reaction mixture was then filtered, and the acetone was removed in vacuo. The residue was washed with water (2×100 ml), dried (anhydrous $CaCl_2$), and the crude product was filtered from the drying agent, to give 77 g of bis(4-iodobutyl)ether of ca. 80% purity. Yield ca. 80%.

THF (150 ml) and ethyl isobutyrate (17.4 g, 22 ml, 0.15 mol) were added under argon to a 1-L 3 neck round bottom flask fitted with a condenser, a dropping funnel, pressure equalizer, and a magnetic stirrer. The mixture was then cooled to −78° C. A solution of LDA (75 ml, 2.0 Mn THF/heptane) was added dropwise with a syringe. After the addition was complete, the reaction mixture was stirred at −78° C. for one additional hour, then the solution of bis-(4-iodobutyl)ether (18 g, 0.05 mmol) and HMPA (10 ml) in 50 ml THF was added dropwise at −78° C. When the addition was complete, the reaction mixture was allowed to reach room temperature, then was left stirring overnight.

The reaction mixture was cautiously poured onto 50 grams ice cold 20 ml concentrated HCl, and was extracted with diethel ether (2×100 ml). The combined ethereal layers were dried over anhydrous sodium sulphate, the solvent was evaporated under vacuum, and the organic residue (27 g) was used without further purification.

Lithium aluminum hydride (4 g, 0.1 mol) and diethyl ether (250 ml) were added under argon to a one liter three neck round bottom argon-purged flask fitted with a condenser, a dropping funnel pressure equalizer, and a magnetic stirrer. Bis(5-carbethoxy-5-methylhexyl)ether (15 g, 40 mmol) in diethyl ether (50 ml) was added to the solution under vigorous stirring. After the addition was complete, the reaction mixture was stirred for one hour, then the excess lithium aluminum hydride was destroyed by cautious addition of water (50 ml), followed by hydrolysis with 25% $H_2SO_4$ (25 ml). The reaction mixture was separated in a separatory funnel, and the aqueous layer was extracted with diethyl ether (2×100 ml). The combined ethereal layers were washed with 5% aq. sodium bicarbonate (1×50 ml), saturated aq. ammonium chloride (50 ml) and finally dried over anhydrous ammonium sulfate. The solvent was evaporated under vacuum to afford crude Compound A. 6 g of the crude product was passed through silica gel and 2.8 g of Compound A (ca. 90% purity) was obtained. Yield 85%.

6.2. Method B

STEP A (Synthesis of 6-Bromo-2-ethoxycarbonyl-2-methylhexane): In a 1-L 3-neck round-bottomed flask fitted with condenser, dropping funnel pressure equalizer and magnetic stirrer, purged with argon and maintained under argon, were added ethyl isobutyrate (84 ml, 0.63 mol) and THF (120 ml). The mixture was cooled to −78° C., when a solution of LDA (300 ml, 2.0 M in THF/heptane) was added dropwise with a syringe. After the addition was complete, the reaction mixture was stirred at −78° C. for 1 hr. To this mixture, 1,4-dibromobutane (105 ml, 0.84 mol) was added at −78° C., followed by HMPA (90 ml). The reaction mixture was stirred for 30 min at −78° C., then the cooling was stopped. The reaction was left to warm to room temperature, and was quenched with a saturated $NH_4Cl$ solution (1.8 L). The aqueous layer was extracted with ethyl acetate (3×100 ml), the organic extracts combined were washed with brine (100 ml), 5% HCl (100 ml) and saturated $NaHCO_3$ (100 ml). The organic phase was dried ($MgSO_4$) and the solvent was evaporated under vacuum. The residue was distilled under reduced pressure to provide the above-titled compound (105.2 g, 70%) (bp 65° C./0.15 mmHg). $^1H$ NMR $CDCl_3$, δ (ppm): 4.15 (q, J=4 Hz, 2H), 3.41 (t, J=5.3 Hz, 2H), 1.85 (qv, J=4 Hz, 2H), 1.60-1.45 (m, 2H), 1.40-1.30 (m, 2H), 1.28 (t, J=4 Hz, 3H), 1.20 (s, 6H); $^3C$ NMR $CDCl_3$, δ (ppm): 177.3, 60.0, 41.8; 39.4, 33.2, 32.9, 24.9, 23.34, 14.02.

STEP B (Synthesis of 6-Bromo-2,2-dimethyl-1-hydroxyhexane): In a 1-L 3-neck round-bottomed flask fitted with condenser, dropping funnel pressure equalizer and magnetic stirrer were placed dry benzene (300 ml) and 6-bromo-2,2-dimethylhexanoate (40 g, 0.159 mol) under argon. To this solution, DIBAL (400 ml as a 1M solution in hexane) was added over 45 min at room temperature, via a syringe. During the addition, the temperature rose to ca. 50° C., and when the exothermic reaction ceased, the mixture was heated to 50-60° C. for an additional 4 hrs. The reaction mixture was allowed to reach room temperature and stir overnight. The resulting mixture was treated with water (ca. 50 ml) under vigorous stirring, while cooling in an ice-bath. Diethyl ether (200 ml) was added to facilitate the stirring. The ice bath was removed when no more evolution of gas occurred. The reaction product, as a white sludge, was filtered through a fritted glass funnel and the filtrate was evaporated under vacuum. $CHCl_3$ (ca. 300 ml) was added to the resulting residue and the resulting solution was washed with saturated aqueous $NHCl_4$ (200 ml) and brine (200 ml), then dried ($MgSO_4$). The solvent was evaporated under vacuum, to provide 27.30 g (82.2% yield) of the above-titled compound: $^1H$ NMR $CDCl_3$, δ (ppm): 3.38 (t, J=7.4 Hz, 2H), 3.50-3.40 (brs, 1H, OH), 3.22 (d, J=5.6 Hz, 2H), 1.85 (qv, J=7.4 Hz, 2H), 1.50-1.35 (m, 2H), 1.30-1.20 (m, 2H), 0.85 (s, 6H). $^{13}C$ NMR $CDCl_3$, δ (ppm): 71.4, 37.5, 34.9; 33.9, 33.4, 23.7, 22.4.

STEP C (Synthesis of 6-Bromo-2,2-dimethyl-1(tetrahydropyranyloxy)hexane): In a 500 ml three-neck flask fitted with a condenser and magnetic stirrer was placed under argon a mixture of 6-bromo-2,2-dimethyl-1-hydroxyhexane (25 g, 0.119 mol), dichloromethane (300 ml) and p-toluenesulfonic acid (0.15 g, 0.78 mmol). 3,4-Dihydro-2H-pyran (12.57 g, 0.1495 mol) was added slowly to the mixture at 0° C. The reaction mixture was stirred at room temperature for one hour, and then the mixture was filtered through aluminum oxide, which was further washed with dichloromethane (200 ml). The combined fractions were evaporated under vacuum to provide 33.73 g (97%) of the above-titled compound as a pale-yellow residue, ca. 90%: $^1H$ NMR $CDCl_3$, δ (ppm): 4.48-4.52 (m, 1H), 3.90-3.75 (m, 1H), 3.50-3.35 (m, 4H), 2.95 (d, J=12 Hz, 1H), 1.90-1.20 (m, 12H), 0.90 (s, 6H); $^{13}C$ NMR $CDCl_3$, δ (ppm): 99.0, 76.2, 61.8, 38.2, 34.0, 33.8, 33.6, 30.5, 25.5, 24.5, 24.4, 22.5, 19.3.

STEP D (Synthesis of 2,2-Dimethyl-5-hydroxy-1(tetrahydropyranyloxy)hexane): In a 250 ml flask equipped with a magnetical stirrer and reflux condenser were placed 6-bromo-1(tetrahydropyranyloxy)-2,2-dimethylhexane (10 g, 0.034 mol) and DMSO (50 ml), then the mixture was treated with $K_2CO_3$ (10 g 0.068 mol) in water (100 ml). The reaction mixture was heated under reflux for two days, then was allowed to cool to room temperature and quenched with water (150 ml). The solution was adjusted to pH 7 with 1M HCl and extracted with ether (3×100 ml). The organic layers combined were then washed with saturated $NH_4Cl$ (150 ml) and brine (150 ml), dried ($MgSO_4$), and the solvent was removed under reduced pressure, to provide 6.63 g of the above-titled compound as a colorless liquid (85% yield). $^1H$ NMR $CDCl_3$, δ (ppm): 4.40-4.50 (m, 1H), 3.90-3.75 (m, 1H), 3.38 (t, J=6.8 Hz, 1H), 2.97 (d, J=9.3 Hz, 1H), 2.50 (brs, 1H, OH), 1.90-1.20 (m, 12H), 0.84 (s, 3H), 0.86 (s, 3H); $^{13}C$ NMR $CDCl_3$, δ (ppm): 99.0, 76.2, 62.3, 61.8, 38.8, 34.0, 33.4, 30.5, 25.4, 24.4, 24.3, 19.9, 19.3.

STEPS E and F (Compound A): A suspension of NaH (1.05 g of 60% dispersion in mineral oil, washed with petroleum ether (3×25 ml) under $N_2$ and dried in a $N_2$ flow, 26.1 mmol) in 30 ml of freshly distilled THF was cooled to 0° C., then 2,2-dimethyl-5-hydroxy-1(tetrahydropyranyloxy)hexane (2 g, 8.69 mmol) in 50 ml of THF was added dropwise. The mixture was stirred at room temperature for 30 min, then heated at 60° C. for 1 hr, and finally stirred overnight at room temperature. The suspension was cooled to 0° C., when 6-bromo-2,2-dimethyl-1-(tetrahydropyranyloxy)hexane (2.54 g, 0.00869 mol) in 50 ml of THF was added dropwise. The resulting mixture was heated at reflux for ca. 36 h, then diluted with 200 ml of ice-water, and most of the solvent was removed under vacuum. The resulting residue was extracted with ether (3×150 ml), the combined ethereal extracts were washed with saturated NH$_4$Cl (200 ml), brine (200 ml), and dried (Na$_2$SO$_4$). The solvent was then removed in vacuo to give 2 g of crude product in the form of a yellow oil, containing ca. 60% of bis(5,5-dimethyl-6(tetrahydropyran-yloxy)hexyl)ether. The crude product was dissolved in acetone (50 ml), stirred with 1 M HCl (50 ml) at 5° C. for 3 h and then left under stirring at room temperature for 3 days. An aqueous saturated NaHCO$_3$ solution was added to adjust to pH 7 and then the mixture was extracted with ether (3×100 ml). The extract was washed with sat. NH$_4$Cl (150 ml) and brine (150 ml), then dried (Na$_2$SO$_4$). The solvent was removed under vacuum to give ca. 1.5 g of yellow oil, which was subsequently fractionated, to provide Compound A as a yellow residue (1 g) (42% yield over two steps). $^1$H NMR CDCl$_3$, δ (ppm): 3.42 (t, J=6.8 Hz, 4H), 3.20 (s, 4H), 2.80 (brs, 2H), 1.48 (qv, J=6.8 Hz, 4H), 1.10-1.30 (m, 8H), 0.76 (s, 12H); $^{13}$C NMR CDCl$_3$, δ (ppm): 71.1, 70.6, 38.1, 34.8, 30.2, 23.8, 20.3. HRMS (POS FAB NBA) 275.257. Calcd for C$_{16}$H$_{35}$O$_3$ 275.258 (M+1).

7. EXAMPLE

Synthesis of Compounds of Formula XL, XLI, and XLII

7.1. Bis(5-phosphoryl-5-methylhexyl)ether tetrasodium salt

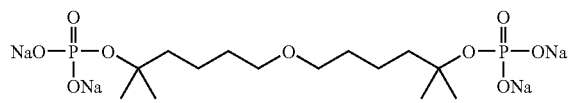

Bis(5-hydroxy-5-methylhexyl)ether: In a 250 ml 3-neck round-bottomed flask fitted with condenser, dropping funnel pressure equalizer and magnetic stirrer, purged with argon and maintained under argon, were added 30 ml solution of methylmagnesium iodide, 3M in diethyl ether (0.09 mole Grignard reagent), and 30 ml diethyl ether. bis((Carboxymethyl)butyl)ether (3.6 g, 0.015 mole) (prepared as an oil from 4,4'-dicarboxybutyl ether, K. Alexander et al., 1948, *J. Am. Chem. Soc.* 70:1839 and diazomethane) in 20 ml diethyl ether was added dropwise, with a slow rate, to allow a gentle reflux. After the addition was complete, the reaction was allowed to reach the room temperature, and then was left under stirring for four hours. The reaction mixture was cautiously poured onto 200 ml of a mixture of saturated aqueous ammonium chloride and 200 ml ice, and was stirred until no more solid was observed at the interface of the ethereal and aqueous layers. The organic layer was then separated in a separatory funnel, and the aqueous layer was extracted four times, each time with 75 ml diethyl ether. The ethereal layers combined were dried over sodium sulfate, the solvent evaporated in vacuum, and the organic residue was dried under vacuum for 2 hr. An amount of 3.3 g (85% yield) of bis(5-hydroxy-5-methylhexyl)ether was obtained, which was used without further purification. $^1$H NMR (300 MHz, CDCl$_3$) δ ppm, 3.40 (t, J=7.4 Hz, 4H), 1.60 (brs, OH, 2H), 1.58 (qv, J=6.2 Hz, 4H), 1.50-1.40 (m, 8H), 1.21 (s, 12H); $^{13}$C NMR (75 MHz, CDCl$_3$) δ ppm, 70.9, 70.7, 43.6, 30.2, 29.3, 21.1.

Bis-(5-Dibenzyloxyphosphoryl-5-methylhexyl)ether: A solution of bis(5-hydroxy-5-methylhexyl)ether (1.5 g, 5 mmol) in 200 mL of CH$_2$Cl$_2$ and 1H-tetrazole (2.38 g, 34 mmol) was stirred at room temperature, while a solution of dibenzyl N,N-diisopropylphosphoramidite (5.45 g, 16 mmol) in 50 mL of CH$_2$Cl$_2$ was added. The mixture was stirred at room temperature for 1 h and cooled to −40° C., m-CPBA (70%, 4.5 g) in 50 ml CH$_2$Cl$_2$ was added. The reaction was stirred for 30 min at 0° C. and then 30 min at room temperature. The mixture was washed (10% aqueous NaHCO$_3$), dried (Na$_2$SO$_4$), concentrated, and purified via chromatography (SiO$_2$ using 50% EtOAc-pentane) to give 2.1 g (55%) of bis-(5-Dibenzyloxyphosphoryl-5-methylhexyl)ether as a viscous colorless oil: $^1$H NMR (300 MHz, CDCl$_3$) δ ppm 7.40-7.20 (m, 20H, phenyl), 4.95-5.05 (m, 8H), 3.36 (t, J=7 Hz, 4H), 1.80-1.20 (m, 8H), 1.45 (s, 12H); $^{13}$C NMR (75 MHz, CDCl$_3$) δ ppm, 128.6-127.5 (m), 70.6, 68.7 (J=6.8 Hz), 67.3 (J=6.0 Hz), 42.7 (J=4.0 Hz), 29.9, 27.5 (J=3.7 Hz), 20.9; HRMS (POS FAB) 767.347. Calcd for C$_{42}$H$_{57}$O$_9$P$_2$ 767.347.

Bis-(5-Phosphoryl-5-methylhexyl)ether tetrasodium salt: A solution of bis(dibenzylphosphate) (3.4 g, 4.4 mmol), NaHCO$_3$ (1.4 g, 17.6 mmol), and Pd/C (10%, 1.8 g) in EtOH—H$_2$O (5:1 v/v, 300 mL) was shaken at 54 psi initial pressure for 2 h. The catalyst was filtered off and washed with 300 mL of water. The mixed solutions were filtered through a membrane filter, and then the solvent was removed under vacuum. The residue was recovered in 100 mL water, extracted with CHCl$_3$ and the aqueous layer filtered through a membrane filter. Removal of water by lyophilization gave 2 of solid Bis-(5-Phosphoryl-5-methylhexyl)ether tetrasodium salt, yield 70%: $^1$H NMR (300 MHz, D$_2$O) δ ppm, 3.28 (t, J=5.0 Hz, 4H), 1.28 (qv, J=5.0 Hz, 4H), 1.20-1.10 (m, 8H), 1.10 (s, 12H); $^{13}$C NMR (75 MHz, CDCl$_3$) δ ppm, 77.7 (J=7.1 Hz), 70.8, 42.9 (J=4.8 Hz), 27.2 (J=3.2 Hz), 23.8, 20.8; ESI/MS (m/z) 494 (M), 406 (M+4H−4Na).

7.2. Bis(5-Phosphoryl-5-methylpenyl)ether tetrasodium salt

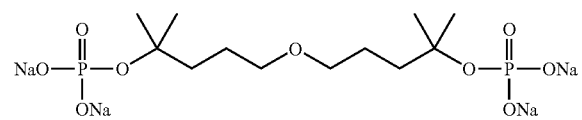

Bis-(4-Hydroxy-4-methylpentyl)ether: In a 250 ml 3-neck round-bottomed flask fitted with condenser, dropping funnel pressure equalizer and magnetic stirrer, purged with argon and maintained under argon, were added 90 ml solution of methylmagnesium iodide, 3M in diethyl ether (0.27 mole Grignard reagent), and 90 ml diethyl ether. bis((Carboxymethyl)propyl)ether (9.81 g, 0.045 mole) (prepared as an oil from 4,4'-dicarboxybutyl ether, W. Reppe et al., *Ann. Chem.* 1955, 596, 169 and diazomethane) in 20 ml diethyl ether was added dropwise, with a slow rate, to allow a gentle reflux. After the addition was complete, the reaction was allowed to reach the room temperature, and then was left under stirring for four hours. The reaction mixture was cautiously poured onto 500 ml of a mixture of aq. satd. ammonium chloride and 500 ml ice, and was stirred until no more solid was observed at the interface of the ethereal and aqueous layers. The organic layer was then separated in a separatory funnel, and the aqueous layer was extracted four times, each time with 75 ml diethyl ether. The ethereal layers combined were dried on anh. sodium sulfate, the solvent evaporated in vacuum, and the organic residue containing the bis-(4-hydroxy-4-methylpentyl)ether was dried under vacuum for 2 hr. An amount of 9.6 g of diol (98% yield) was obtained as a pale-yellow oil, and was used without further purification. $^1$H NMR (300 MHz, CDCl$_3$) δ ppm, 3.40 (t, J=6.2 Hz, 4H), 3.00 (brs, OH, 2H), 1.60-1.40 (m, 8H), 1.10 (s, 12H); $^{13}$C NMR (75 MHz, CDCl$_3$) δ ppm, 71.3, 70.0, 40.4, 29.0, 24.4.

Bis(4-Dibenzyloxyphosphoryl-4-methylpentyl)ether: A solution of diol (1.33 g, 6 mmol) in 200 mL of CH$_2$Cl$_2$ and 1H-tetrazole (2.38 g, 34 mmol) was stirred at room temperature, while a solution of dibenzyl N,N-diisopropylphosphoramidite (5.45 g, 16 mmol) in 50 mL of CH$_2$Cl$_2$ was added. The mixture was stirred at room temperature for 1 h and cooled to −40° C., m-CPBA (70%, 4.5 g) in 50 ml CH$_2$Cl$_2$ was added, and the reaction was stirred for 30 min at 0° C. and then 30 min at room temperature. The mixture was washed (10% aqueous NaHCO$_3$), dried (Na$_2$SO$_4$), concentrated, and purified via chromatography (SiO$_2$ using 50% EtOAc-pentane) to give 6 g (55%) of bis(4-Dibenzyloxyphosphoryl-4-methylpentyl)ether as a viscous colorless oil: $^1$H NMR ppm (300 MHz, CDCl$_3$) d 7.4-7.2 (m, 20H, phenyl), 5.2-4.8 (m, 8H), 3.4-3.6 (m, 2H), 1.8-1.6 (m, 8H), 1.5 (s, 6H), 1.1 (s, 6H); $^{13}$C NMR (75 MHz, CDCl$_3$) δ ppm, 135.9-135.2 (m), 127-129 (m), 85.3 (J=7.5 Hz), (71.3, 70.6 (C1, C1')), 68.9 (J=3.0 Hz), 67.3 (J=5.2 Hz), (45.1 (J=4.0 Hz), 39.3 (J=4.0 Hz) (C4, C4')), 40.7, 29.2, 27.4 (J=3.0 Hz), 24.6, 24.3 (C3, C3'), 18.1; HRMS (POS FAB) 739.317. Calcd for C$_{40}$H$_{53}$O$_9$P$_2$ 739.316.

Bis(4-Phosphoryl-4-methylpenyl)ether tetrasodium salt: A solution of bis(dibenzylphosphate) (3.1 g, 4.2 mmol), NaHCO$_3$ (1.4 g, 17.6 mmol), and Pd/C (10%, 1.8 g) in EtOH—H$_2$O (5:1 v/v, 300 mL) was shaken at 54 psi initial pressure for 2 h. The catalyst was filtered off and washed with 300 mL of water. The mixed solutions were filtered through a membrane filter, then the solvent was removed under vacuum. The residue was recovered in 100 mL water, extracted with CHCl$_3$ and the aqueous layer filtered through a membrane filter. Removal of water by lyophilization gave 3.7 of solid bis(4-Phosphoryl-4-methylpenyl)ether tetrasodium salt, yield 92%: $^1$H NMR (300 MHz, D$_2$O) δ ppm 3.30-3.20 (m, 4H); 1.80-1.60 (m, 8H), 1.70 (s, 12H); $^{13}$C NMR (75 MHz, D$_2$O) δ ppm 81.0 (m), 29.6, 29.0, 27.1, 23.9; ESI/MS (m/z) 467 (M+H), 378 (M+4H−4Na).

7.3. 2,12-Dimethyltridecyl 2,12-diphosphate tetrasodium salt

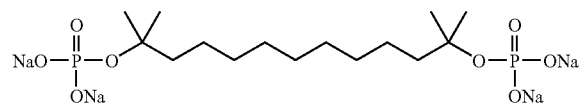

2,12-Dimethyltridecane-2,12-diol: In a 500 ml 3-neck round-bottomed flask fitted with condenser, dropping funnel pressure equalizer and magnetic stirrer, purged with argon and maintained under argon, were added 80 ml solution of methylmagnesium iodide, 3M in diethyl ether (0.09 mole Grignard reagent), and 100 ml diethyl ether. Dimethyl undecanedioate (14 g, 0.057 mole, Fluka) in 50 ml diethyl ether was added dropwise, with a slow rate, to allow a gentle reflux. After the addition was complete, the reaction was allowed to reach the room temperature, then was left under stirring for four hours. The reaction mixture was cautiously poured onto 500 ml of a mixture of aq. satd. ammonium chloride and 500 ml ice, and was stirred until no more solid was observed at the interface of the ethereal and aqueous layers. The organic layer was then separated in a separatory funnel, and the aqueous layer was extracted four times, each time with 100 ml diethyl ether. The ethereal layers combined were dried on anh. sodium sulfate, the solvent evaporated in vacuum, and the organic residue was dried under vacuum for 2 hr. An amount of 12 g of 2,12-Dimethyltridecane-2,12-diol (95% yield) was obtained, as white crystals m.p 58.5-59.5° C. and used without purification. $^1$H NMR (300 MHz, CDCl$_3$) δ ppm, 1.60 (brs, OH, 2H), 1.50-1.25 (m, 18H), 1.20 (s, 12H); $^{13}$C NMR (75 MHz, CDCl$_3$) δ ppm, 70.9, 43.9, 30.1, 29.5, 29.4, 29.1, 24.2.

2,12-Dibenzyloxyphosphoryl-2,12-dimethyltridecane: A solution of diol (3.4 g, 13.7 mmol) in 650 mL of CH$_2$Cl$_2$ and 1H-tetrazole (6.51 mg, 93 mmol) was stirred at room temperature, while a solution of dibenzyl N,N-diisopropylphosphoramidite (15.17 g, 44 mmol) in 50 mL of CH$_2$Cl$_2$ was added. The mixture was stirred at room temperature for 1 h and cooled to −40° C., m-CPBA (70%, 12.8 g, 0.055 mol) in 120 ml CH$_2$Cl$_2$ was added, and the reaction was stirred for 30 min at 0° C. and then 30 min at room-temperature. The mixture was washed (10% aqueous NaHCO$_3$), dried (Na$_2$SO$_4$), concentrated and chromatographed on SiO$_2$ using 50% EtOAc-pentane, to give 5.5 g (53%) of 2,12-Dibenzyloxyphosphoryl-2,12-dimethyltridecane colorless oil: $^1$H NMR (300 MHz, CDCl$_3$) δ ppm, 7.40-7.20 (m, 20H, phenyl), 5.05-4.95 (m, 4H), 1.70-1.20 (m, 10H), 1.22 (s, 12H), 1.20-1.10 (m, 8H); $^{13}$C NMR (75 MHz, CDCl$_3$) δ ppm, 136.1 (m), 128.4-127.5 (m), 85.9 (J=7.0 Hz), 68.6 (J=7.0 Hz), 67.1 (J=6.0 Hz), 42.7 (J=4.0 Hz), 29.8, 29.5, 27.5 (J=3.7 Hz), 24.1; LRMS (m/z) (M$^+$) 766.

2,12-Dimethyltridecyl 2,12-diphosphate tetrasodium salt: A solution of bis(dibenzylphosphate) (3.4 g, 4.4 mmol), NaHCO$_3$ (1.4 g, 17.6 mmol), and Pd/C (10%, 1.8 g) in EtOH—H$_2$O (5:1 v/v, 300 mL) was shaken at 54 psi initial pressure for 2 h. The catalyst was filtered off and washed with 300 mL of water. The mixed solutions were filtered through a membrane filter, then the solvent was removed under vacuum. The residue was recovered in 100 mL water, extracted with CHCl$_3$ and the aqueous layer filtered through a membrane filter. Removal of water by lyophilization gave 1.4 of 2,12-dimethyltridecyl 2,12-diphosphate tetrasodium salt, yield 98%: $^1$H NMR (300 MHz, D$_2$O) δ ppm, 1.30-1.20 (m, 2H); 1.10-1.00 (m, 8H), 1.10 (s, 12H); $^{31}$P NMR (258 MHz, D$_2$O) δ ppm, 4.20; ESI/MS (m/z) 403 (M−H−4Na), 471 (M−Na).

8. EXAMPLE

Effects of Illustrative Compounds of the Invention on LDL-Cholesterol, HDL-Cholesterol and Triglyceride Levels in Male Sprague-Dawley Rats Illustrative compounds of the invention were administered daily at a dose of 100 mg/kg to chow fed male Sprague-Dawley rats for seven days in the morning by oral gavage in 1.5% carboxymethylcellulose/0.2% Tween-20 (dosing vehicle). Animals were weighed daily. Animals were allowed free access to rodent chow and water throughout the study. After the seventh dose, animals were sacrificed in the evening and blood serum was assayed for lipoprotein cholesterol profiles, serum triglycerides, total cholesterol VLDL, LDL, and HDL cholesterol, and the ratio of HDL cholesterol to that of VLDL plus LDL cholesterol, apolipoproteins A-I, C-II, C-III, and E by immunoelectrophoresis, and percent weight gain.

Table 1 shows the effect of Compound A, Compound B, Compound C, Compound D and Compound E on serum LDL-cholesterol, HDL-cholesterol and triglycerides in chow-fed male Sprague-Dawley rats following seven days of treatment. The five compounds were tested in two separate experiments. In each experiment, the experimental data were normalized against a control group of rats which received the dosing vehicle alone.

| Compound | (N) | Treatment Duration (days) | Dose (mg/kg/day) | LDL-Cholesterol (% change) | HDL-Cholesterol (% change) | Triglyceride (% change) |
|---|---|---|---|---|---|---|
| Control | 5 | 7 | 0 | (0) | (0) | (0) |
| Compound A | 5 | 7 | 100 | −27.7 | +21.1 | +7.6 |
| Compound B | 5 | 7 | 100 | +23.2 | +40.7 | −31.1 |
| Compound C | 5 | 7 | 100 | −4.0 | +11.6 | +32.6 |
| Compound D | 5 | 7 | 100 | −17.0 | +13.3 | +28.0 |
| Compound E | 5 | 7 | 100 | −41.0 | +49.1 | −30.5 |

Figure 2:
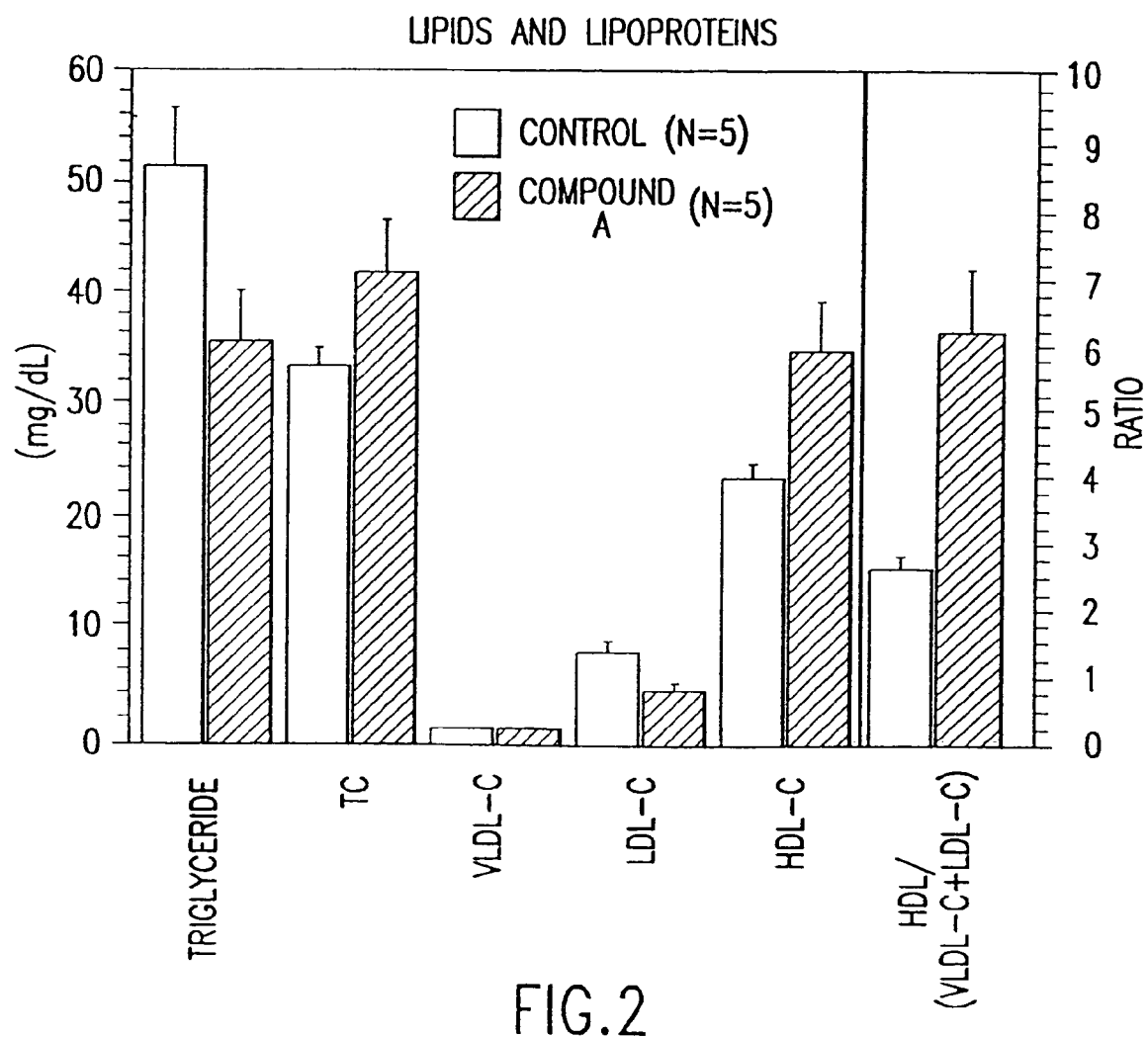
FIG. 2 shows the lipid and lipoprotein levels of Male Sprague-Dawley rats following one week of treatment with Compound A.
Figure 3:
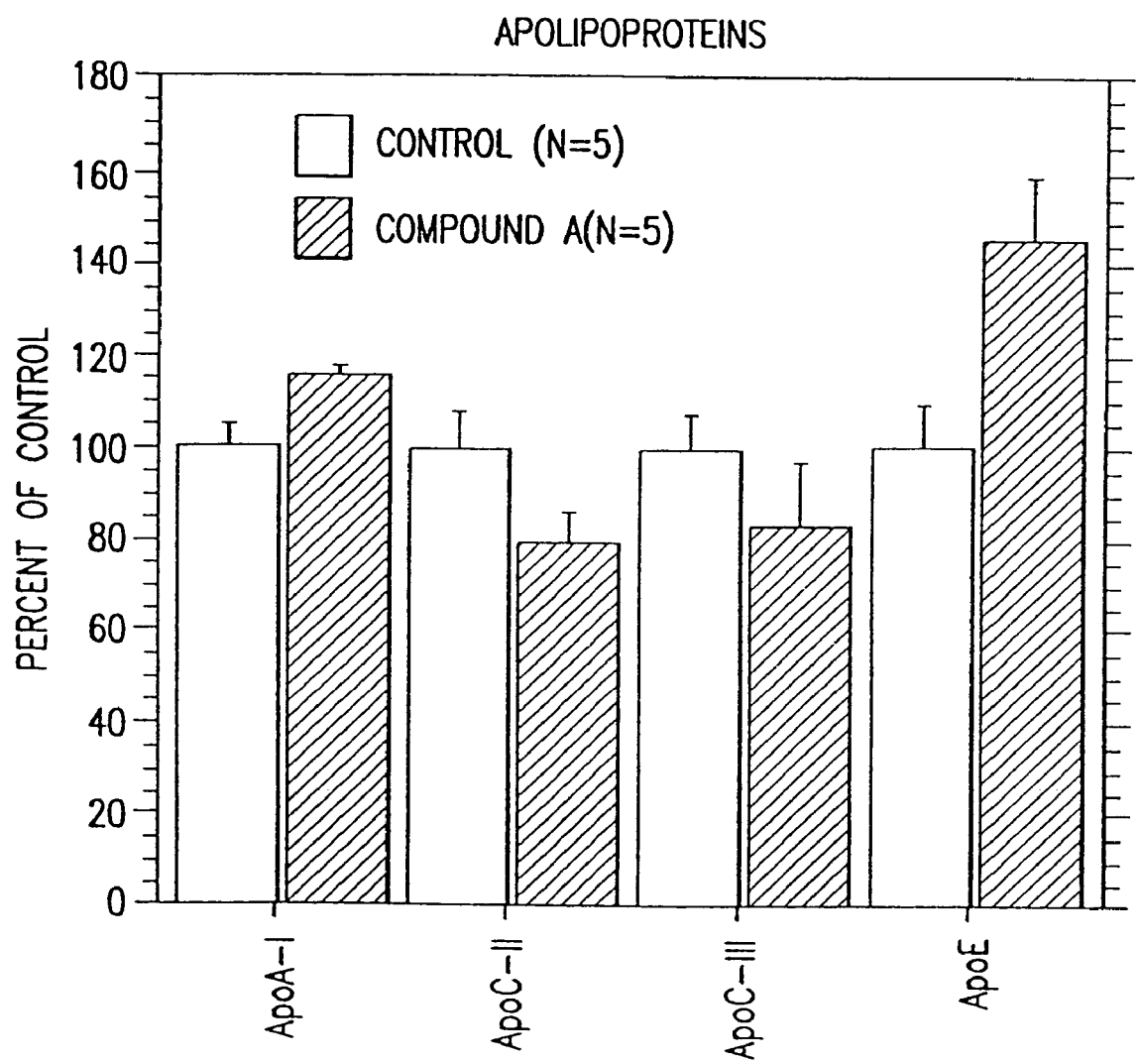
FIG. 3 shows the apolipoprotein levels of Male Sprague-Dawley rats following one week of treatment with Compound A.
Figure 4:
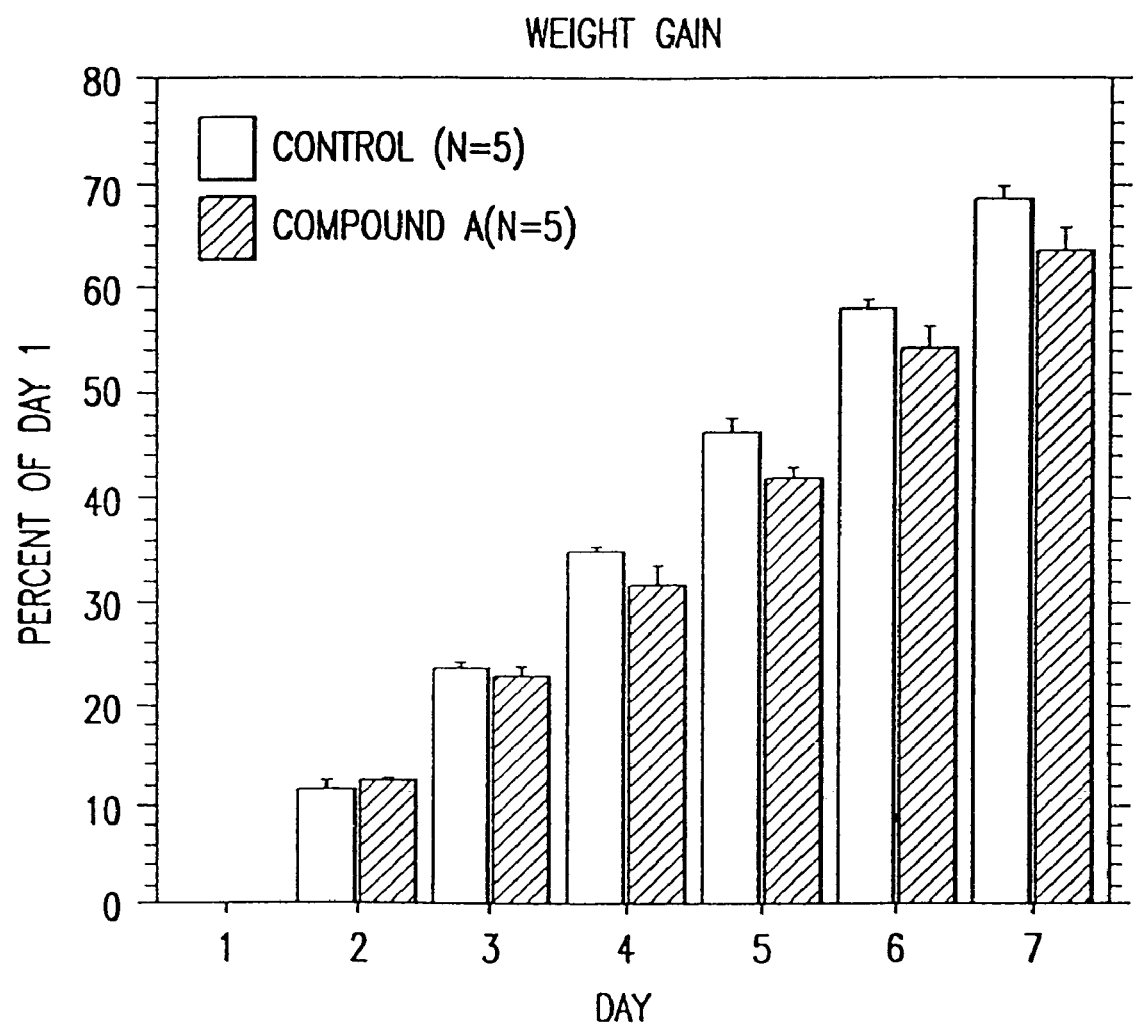
FIG. 4 shows the percentage weight gain of Male Sprague-Dawley rats following one week of treatment with Compound A.

The data tabulated above and other data collected from these experiments are graphically depicted for Compound A. FIG. 1 shows lipoprotein-cholesterol profiles, which indicate that treatment with Compound A results in reduction of LDL cholesterol and elevation of HDL cholesterol when compared to animals treated with the dosing vehicle alone. Compound A treatment also reduces serum triglycerides by 31% and elevates total serum cholesterol by 26% (FIG. 2). The change in total cholesterol was reflected by no change in VLDL cholesterol, a reduction in LDL cholesterol by 41% and an elevation in HDL cholesterol by 49%. The ratio of HDL to non-HDL cholesterol (VLDL plus LDL) improved from 2.6±0.2 to 6.2±1.0 following treatment with Compound A, a 2.44 fold improvement in the ratio (FIG. 2). Compared to control treatment, Compound A-treatment of the rats elevated apolipoprotein A-I and E by 16% and 46%, respectively, and reduced apolipoprotein C-II and C-III by 20% and 16%, respectively (FIG. 3). Compound A also reduced the percentage body weight gain resulting from growth compared to the control group after seven days of treatment (63.4±1.9% vs. 68.3±1.2% weight gain; FIG. 4). Accordingly, Compounds A, B, C, D, and E or pharmaceutically acceptable salts thereof are useful for promoting higher levels of circulating HDL, the "good" cholesterol, and raising the ratio of HDL:non-HDL cholesterol in the blood.

9. EXAMPLE

Effects of Illustrative Compounds of the Invention on LDL-Cholesterol, HDL-Cholesterol and Triglyceride Levels in Obese Female Zucker Rats

9.1. Experiment A

Dosing vehicle, Compound A (86 mg/kg of body weight) or troglitazone (120 mg/kg of body weight) was administered to eight week old female obese Zucker rats daily for seven days in the morning by oral gavage in 1.5% carboxymethyl-cellulose/0.2% Tween-20. Troglitazone was obtained commercially. Finely crushed tablets were suspended in vehicle for dosing. Orbital blood samples were obtained following a six-hour fast prior to the initial dose and also following the seventh dose.

Figure 5:
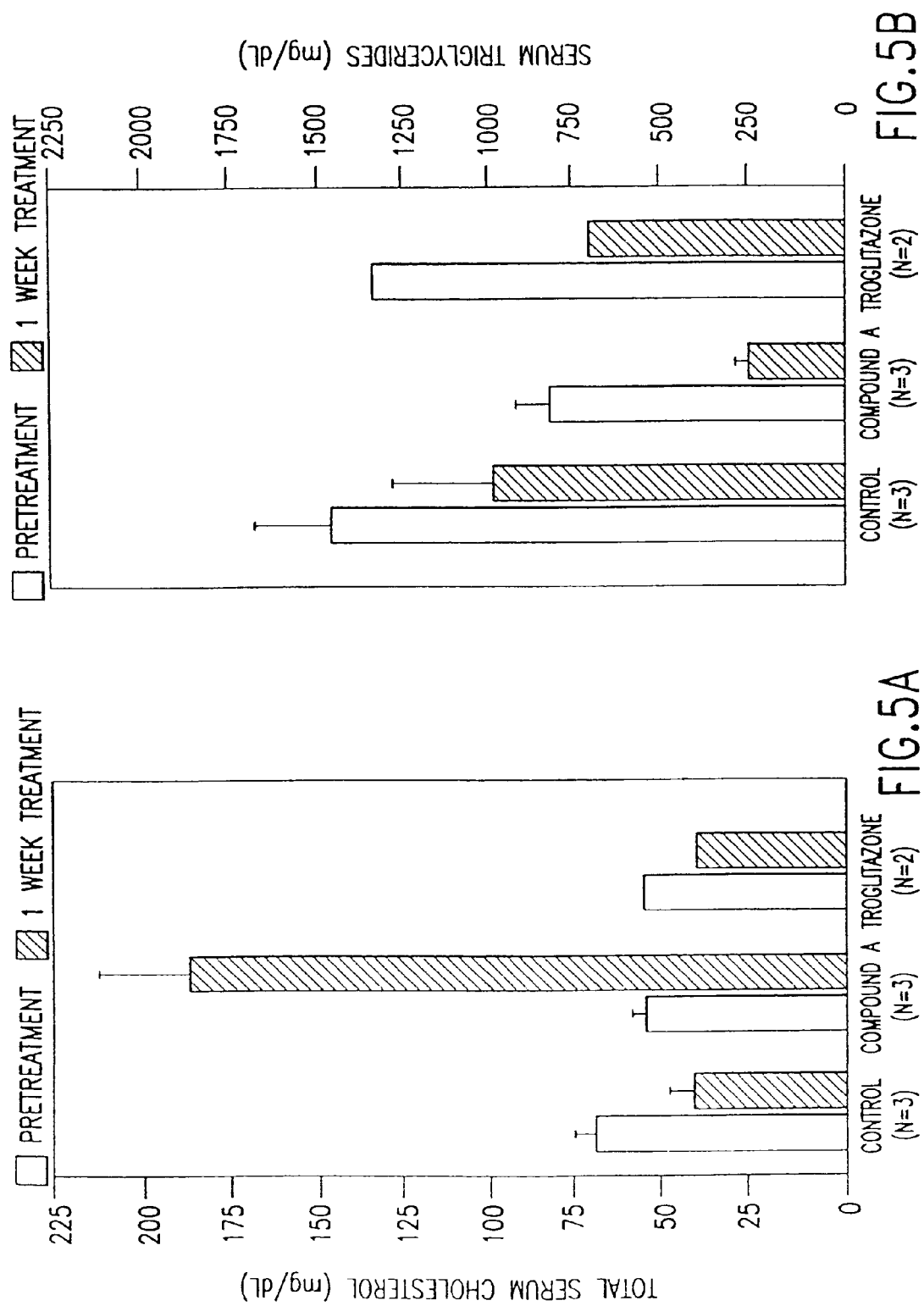
FIG. 5 shows the effect on serum cholesterol and triglyceride levels in obese female Zucker rats following one week of treatment with Compound A or troglitazone.
Figure 6:
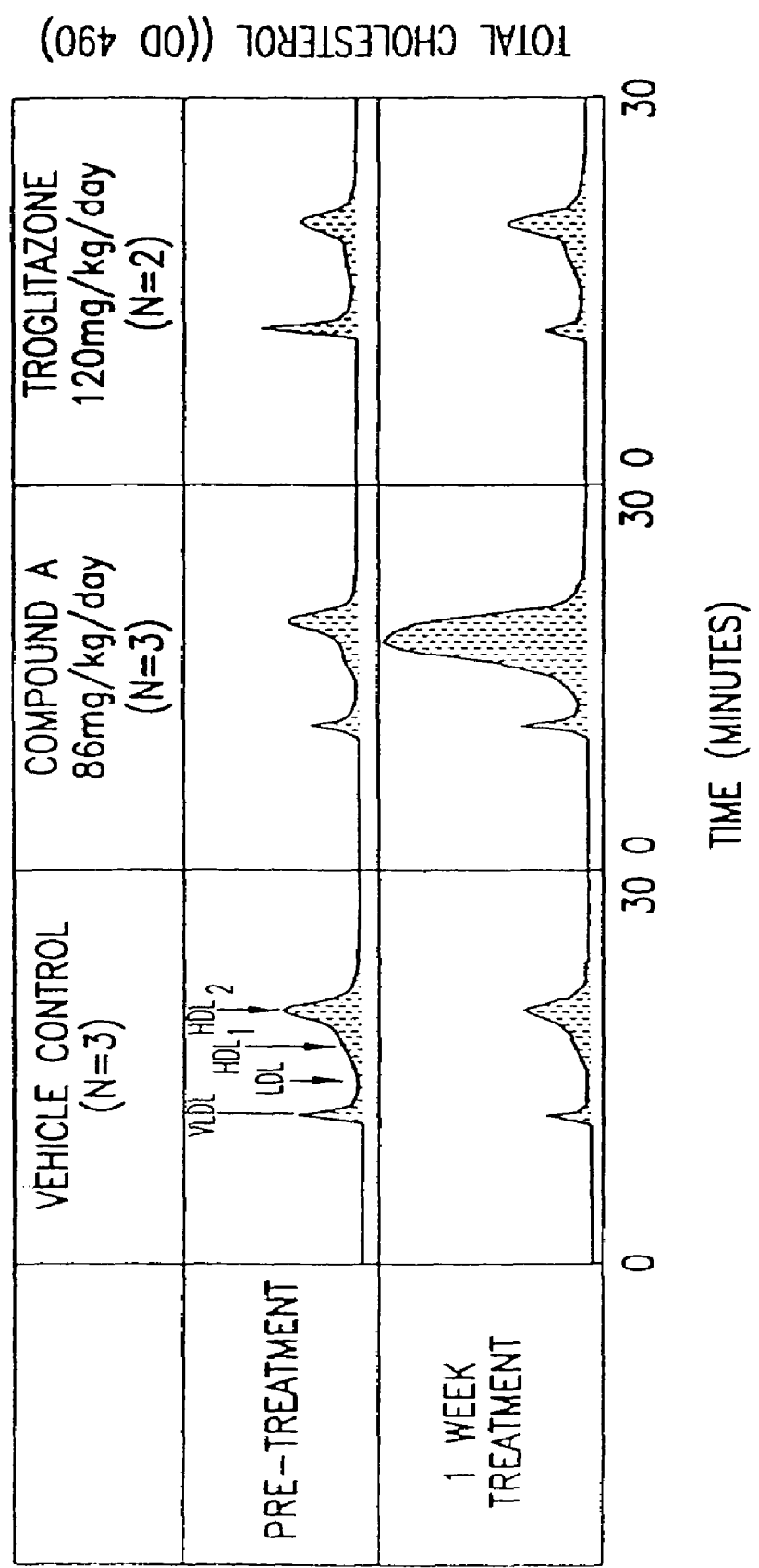
FIG. 6 shows the effect on serum lipoprotein cholesterol profile in obese female Zucker rats following one week of treatment with Compound A or troglitazone.
Figure 7:
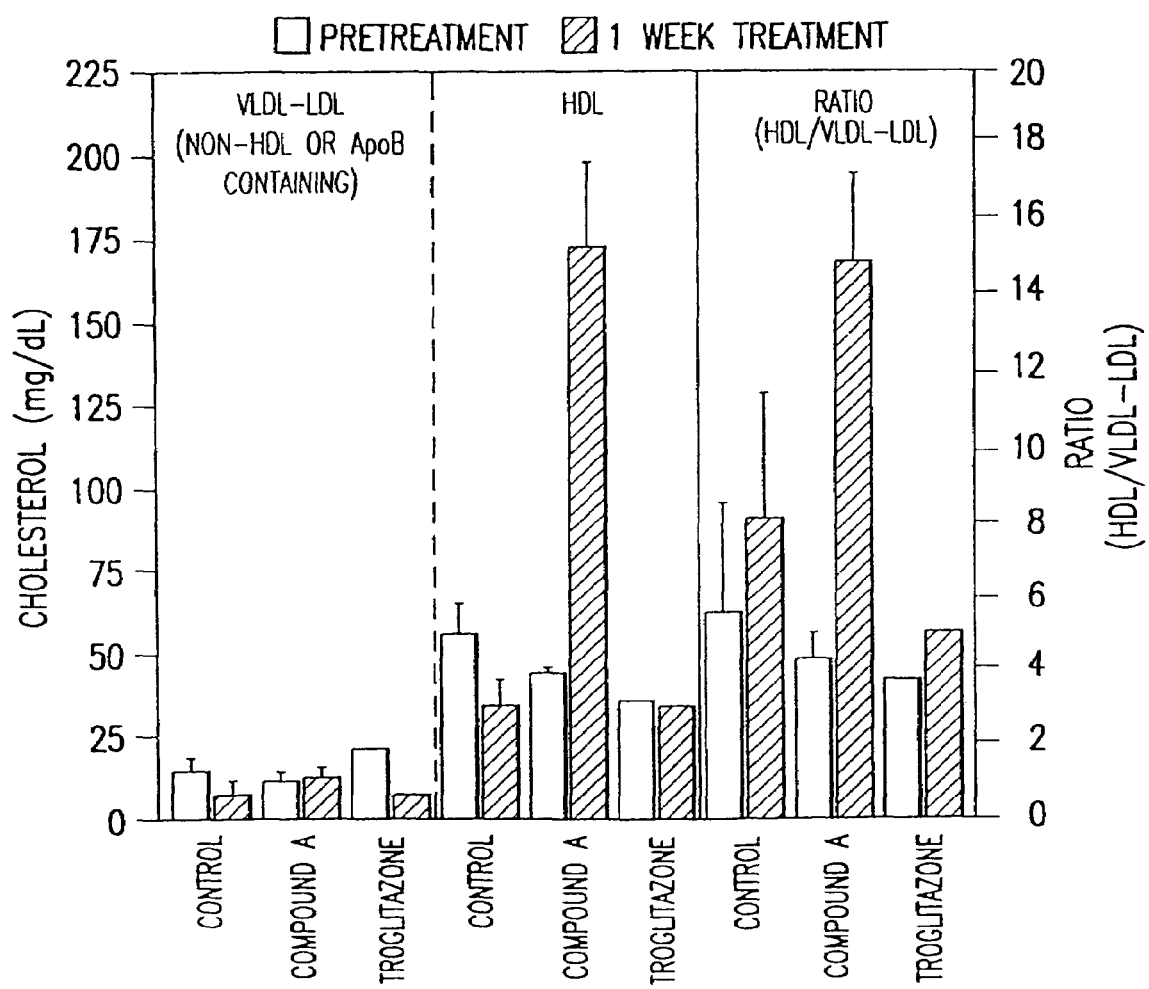
FIG. 7 shows the total VLDL and LDL, total HDL, and the HDL:(VLDL+LDL) ratio following one week of Compound A or troglitazone treatment of obese female Zucker rats.
Figure 8B:
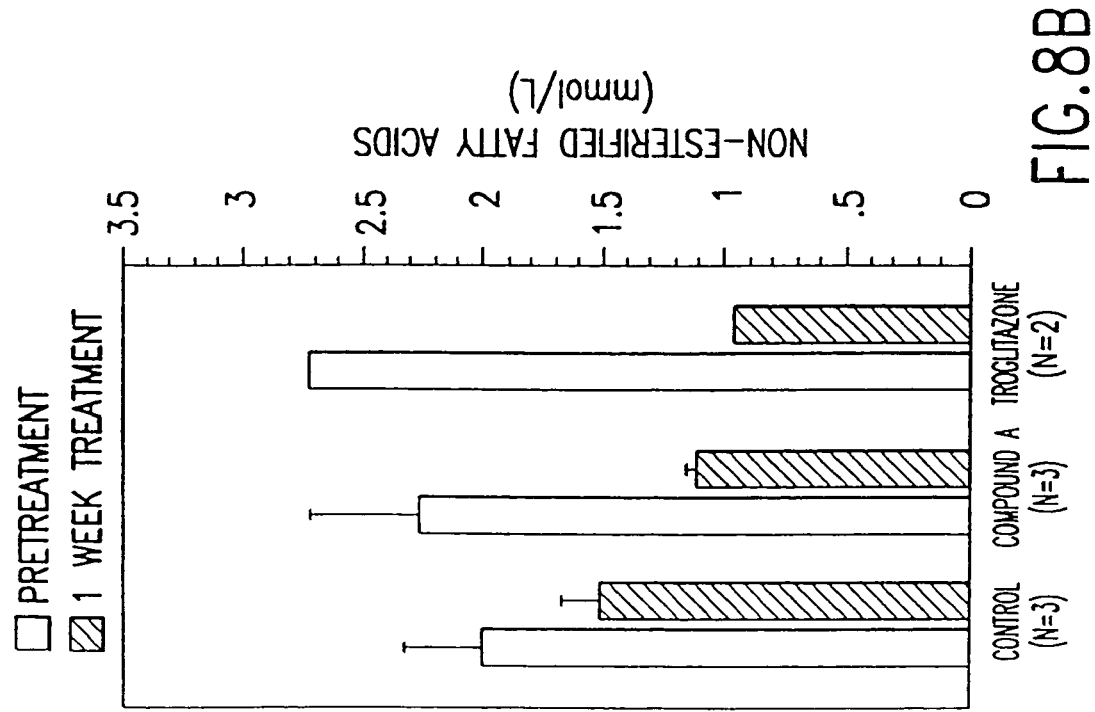
FIG. 8 shows serum glucose and non-esterified fatty acid levels of obese female Zucker rats following one week of Compound A or troglitazone treatment.
Figure 8A:
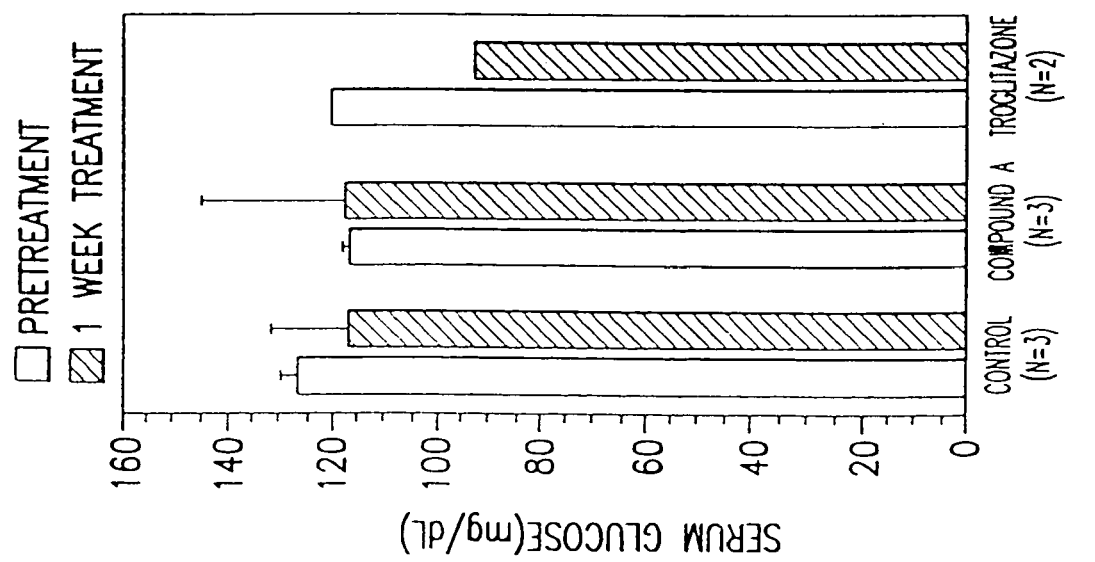
Figure 9:
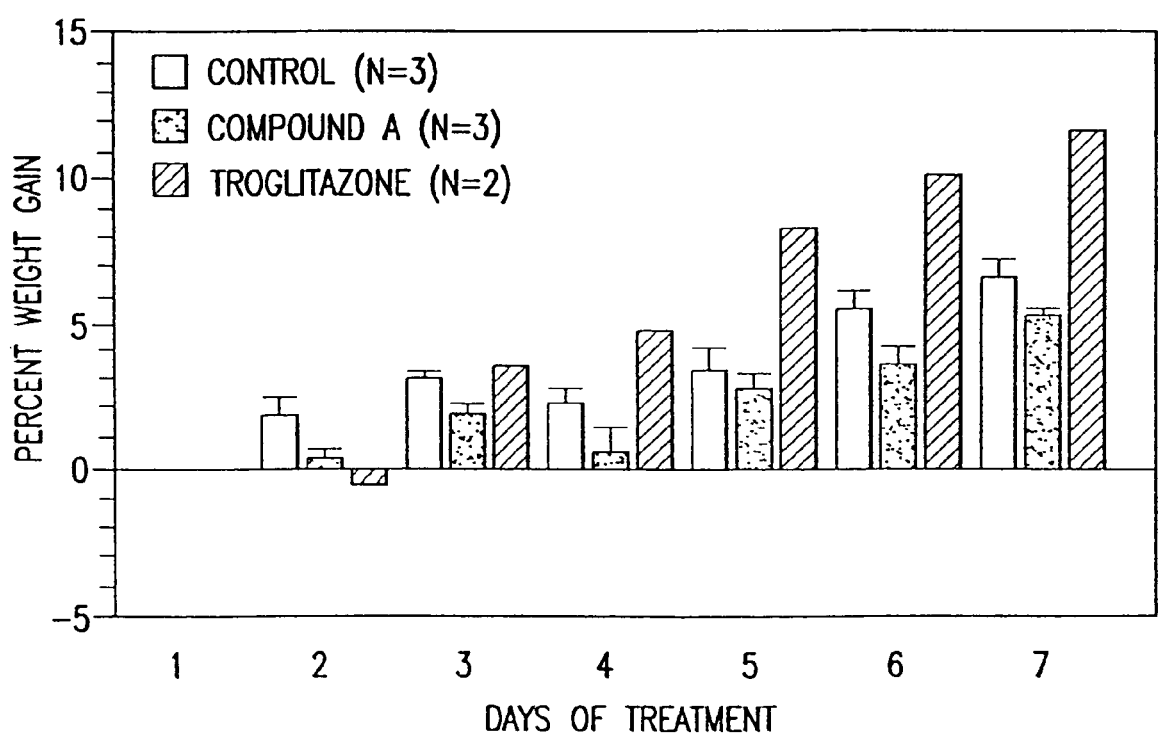
FIG. 9 shows the percentage weight gain of obese female Zucker rats following one week of Compound A or troglitazone treatment.

Blood serum was assayed for total cholesterol and triglycerides (FIG. 5), lipoprotein cholesterol profiles (FIG. 6), VLDL plus LDL cholesterol combined (also referred to as apo B containing lipoprotein cholesterol or non-HDL cholesterol), HDL cholesterol, and the ratio of HDL cholesterol to that of VLDL plus LDL cholesterol (FIG. 7), serum glucose, and non-esterified fatty acids (FIG. 8), and percent weight gain (FIG. 9). In the Zucker rats, Compound A increased total serum cholesterol by 3.3-fold after one week of treatment, while the vehicle and troglitazone treatment resulted in a reduction of this variable (FIG. 5A). Serum triglycerides were markedly reduced with Compound A treatment 68% (FIG. 5B). Lipoprotein cholesterol profiles show treatment with Compound A resulted in a marked alteration in the distribution of cholesterol among lipoproteins (FIG. 6). In particular, Compound A caused a marked elevation in HDL cholesterol after one week of treatment. Using the serum total cholesterol values (FIG. 5A) and the lipoprotein cholesterol distribution (FIG. 6), the amount of cholesterol associated with non-HDL (i.e., VLDL plus LDL) and HDL were determined (FIG. 7). Compound A increased non-HDL cholesterol slightly (+10.3%) but significantly increased HDL cholesterol 3.9-fold. In contrast, troglitazone reduced non-HDL and HDL cholesterol by 67% and 4%, respectively. When these data are expressed as a ratio of HDL/non-HDL cholesterol it can be clearly seen that Compound A markedly improves the ratio from 4.2 (pre-treatment) to 14.9 (one week treatment), a 3.6-fold increase.

Typically, impaired glucose tolerance is the metabolic symptom of eight to 12 week-old-obese female Zucker rats. The animals are able to maintain normal to slightly elevated glucose levels at the expense of elevated insulin levels. As shown in FIG. 8A, pre-treatment and post-treatment serum glucose levels were similar for all treatments within normal range. Compound A treatment did not induce a hypoglycemic state. Typically, these animals also have elevated non-esterified fatty acids in this pre-diabetic state. These levels were reduced with Compound A and troglitazone treatment by 52% and 65%, respectively (FIG. 8B).

One adverse effect of troglitazone treatment is weight gain, largely due to increased adipose mass. As shown in FIG. 9, troglitazone treatment in female Zucker rats caused the greatest increase in weight gain (+11.6%). Zucker rats treated with vehicle alone showed a 6.6% increased weight after seven days, while Zucker rats treated with Compound A showed a 5.4% increase in body weight.

Accordingly, Compound A, or a pharmaceutically acceptable salt thereof, is useful for reducing serum triglycerides, elevating circulating HDL, improving the ratio of HDL:LDL in the blood, without the adverse side effect of promoting weight gain in a patient to whom the compound is administered.

9.2. Experiments B, C, D, & E

Figure 10A:
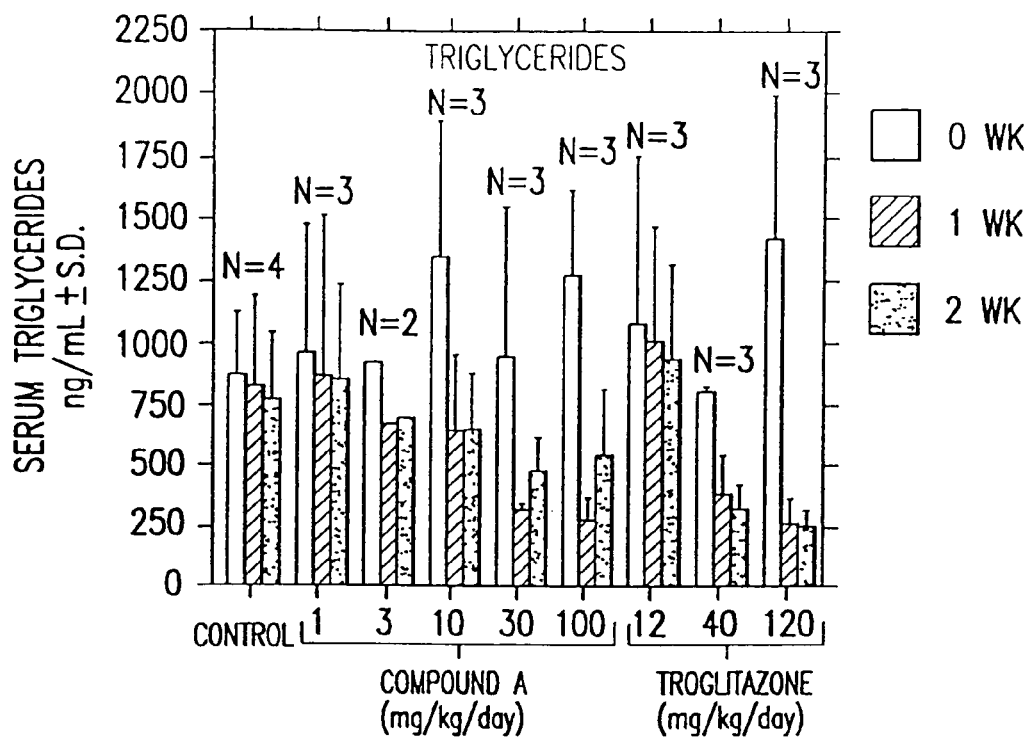
FIG. 10 shows the amount and percentage reduction of serum triglycerides in obese female Zucker rats following 1- and 2-week treatment with Compound A or troglitazone.
Figure 10B:
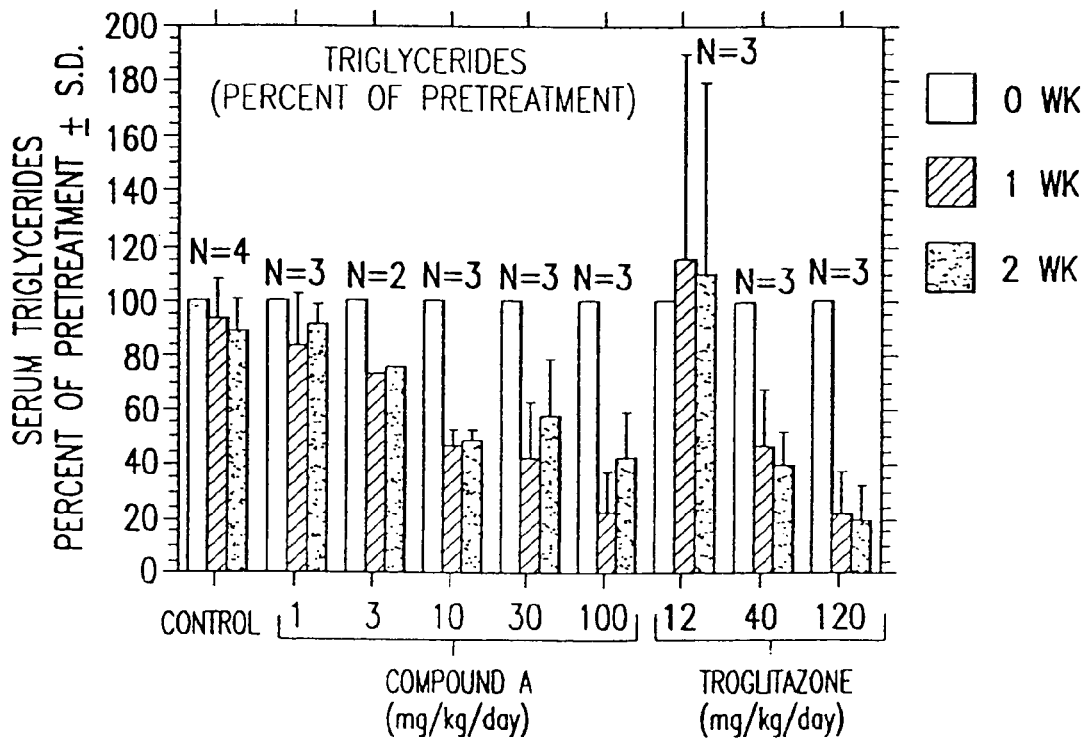

In a number of different experiments, illustrative compounds of the invention and troglitazone were administered daily at various doses to 10-week old chow fed obese female Zucker rats for 14 days in the morning by oral gavage in 1.5% carboxymethylcellulose/0.2% Tween-20 (dosing vehicle). Animals were weighed daily. Animals were allowed free access to rodent chow and water throughout the study. Blood glucose was determined after a 6-hour fast in the afternoon without anesthesia from a tail vein. Serum was also prepared from a blood sample subsequently obtained from the orbital venous plexus (with $O_2/CO_2$ anesthesia) prior to and after one week treatment and used lipid and insulin determinations. At two weeks, blood glucose was again determined after a 6-hour fast without anesthesia from a tail vein. Soon thereafter, animals were sacrificed by $CO_2$ inhalation in the evening and cardiac blood serum was collected and assessed for various lipids and insulin. Body weight was determined daily prior to dosing and at the time of euthanasia. Table 2 shows effects of the Compound A and Compound B compared to troglitazone on the percent change in serum non-HDL cholesterol, HDL-cholesterol, triglyceride and body weight (relative to pretreatment values) in fasted (6 hours) chow-fed obese female Zucker rats.

tive dose of approximately 3 mg/kg (FIG. 10). Reduction of triglycerides by troglitazone was observed only at doses of 40 and 120 mg/kg (FIG. 10).

Figure 11A:
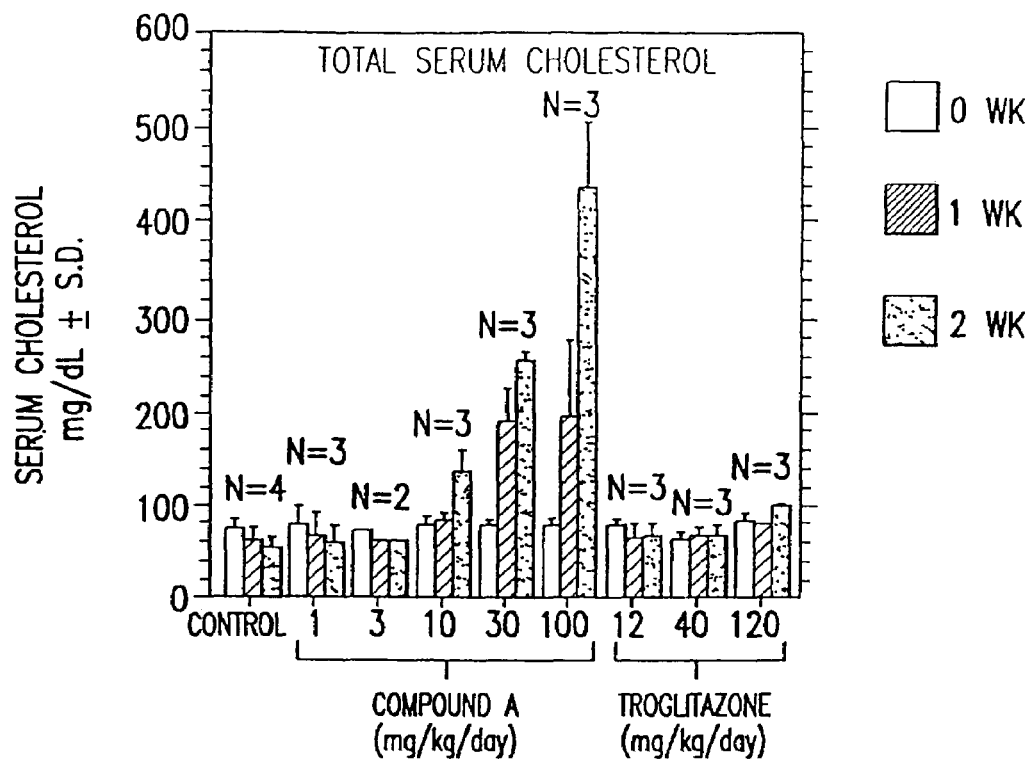
FIG. 11 shows the effect of Compound A or troglitazone treatment of obese female Zucker rats on HDL, LDL and total serum total cholesterol.
Figure 11B:
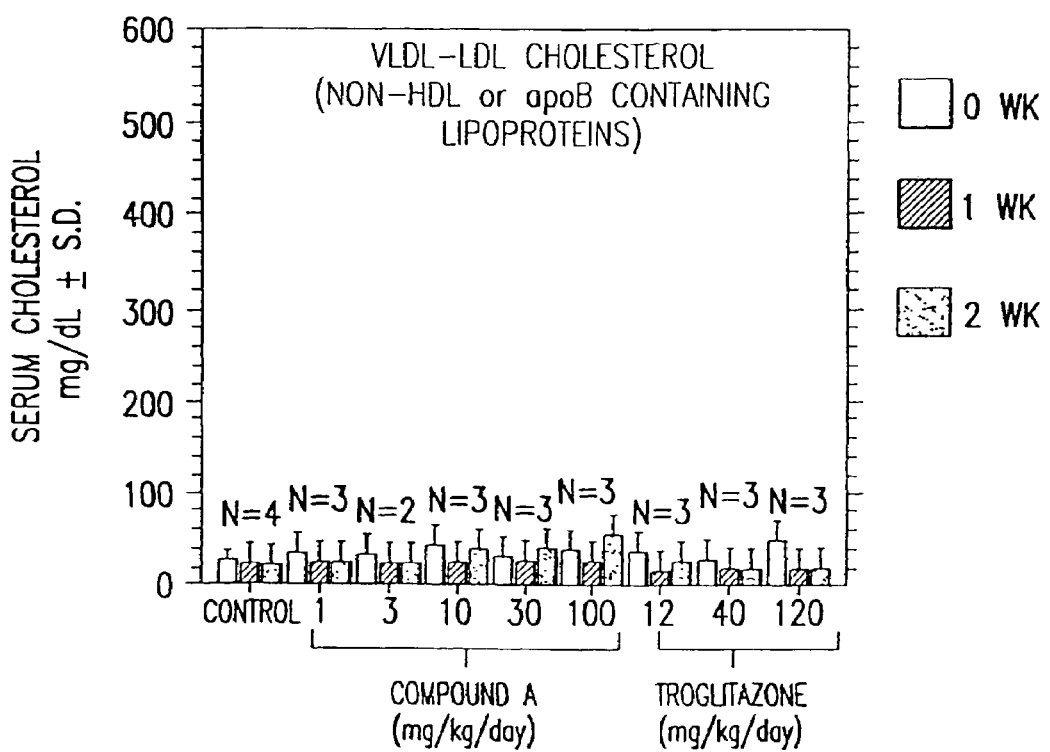
Figure 11C:
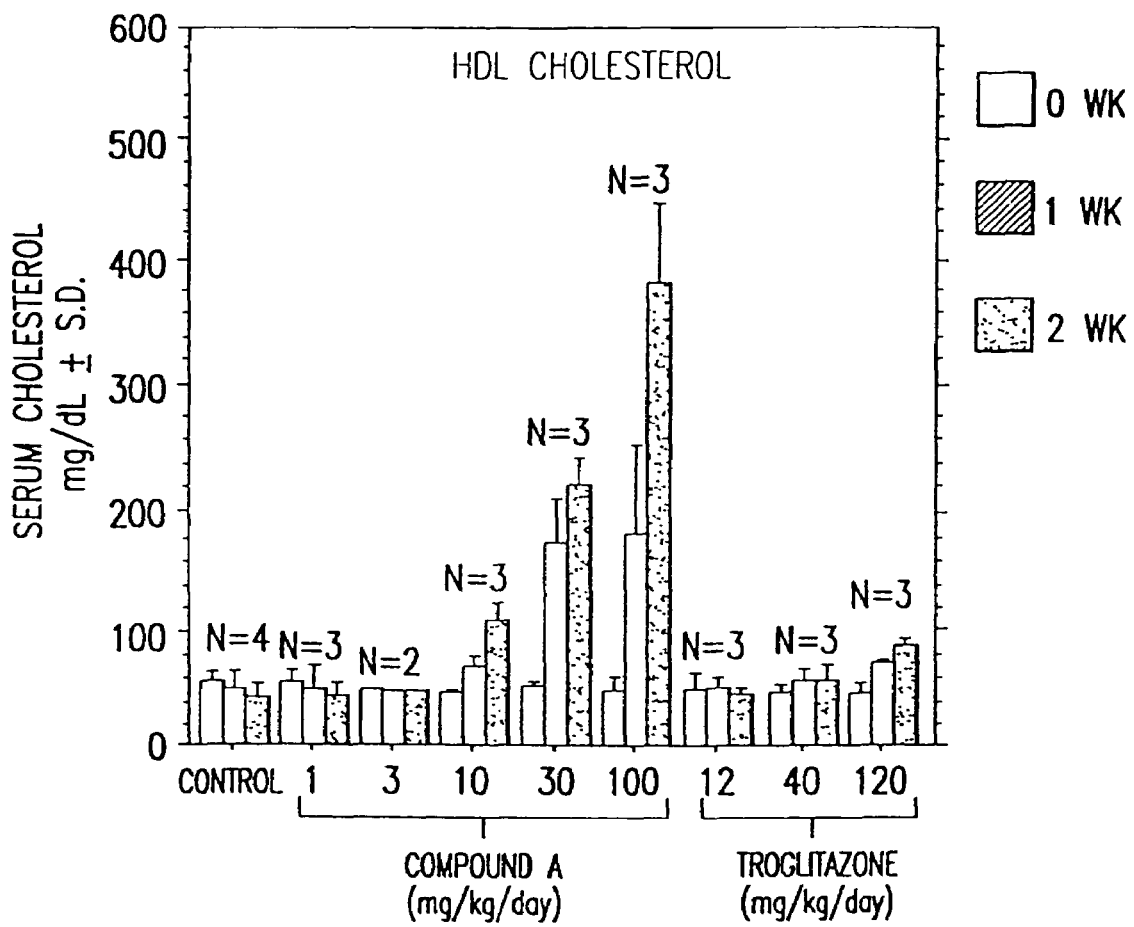

Compound A treatment elevated serum total cholesterol in a dose- and treatment duration-dependent manner beginning at a dose of approximately 10 mg/kg/day (FIG. 11). With longer treatment (i.e. two weeks verses one week) the elevation of serum total cholesterol was greater for all Compound A doses greater or equal to 10 mg/kg (FIG. 11). For troglitazone, total cholesterol was only modestly elevated at the highest dose (120 mg/kg) and only after two weeks of treatment (FIG. 11). Elevation in serum cholesterol observed with Compound A were largely reflected by a marked elevation in HDL-cholesterol. The rise in HDL-cholesterol caused by Compound A was dose- and treatment duration-dependent. At the highest Compound A dose used (i.e. 100 mg/kg), HDL-cholesterol was elevated 9-fold (802% increase) after two weeks of treatment (FIG. 11). Troglitazone caused a markedly lower elevation in HDL at the 120 mg/kg dose (122% increase).

Figure 12A:
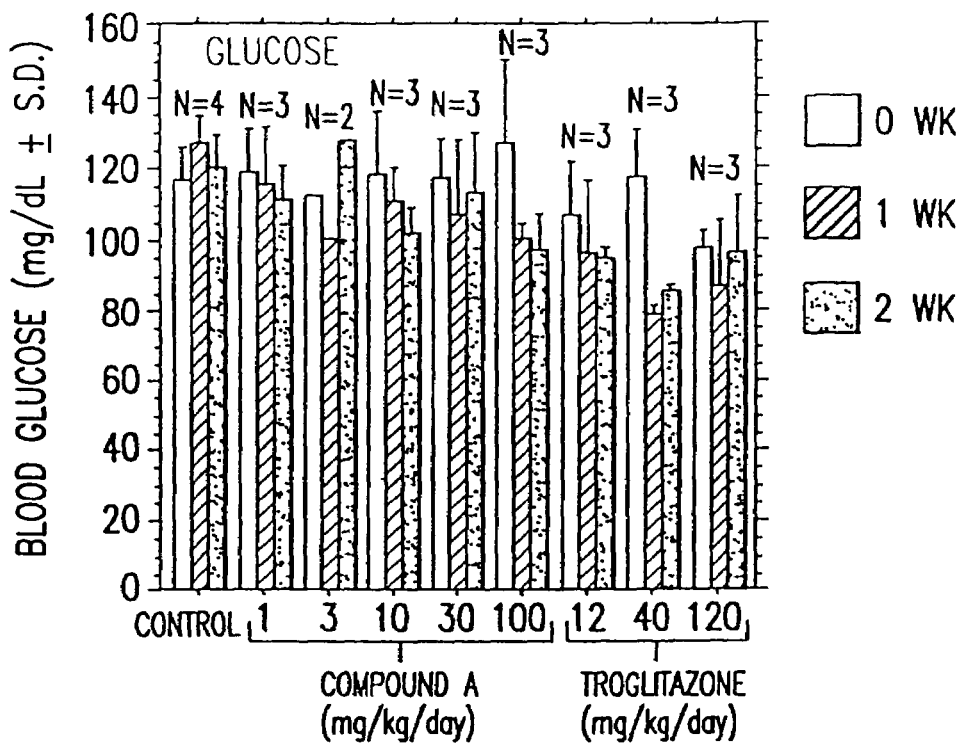
FIG. 12 shows the effect of Compound A or troglitazone on the blood glucose of obese female Zucker rats.
Figure 12B:
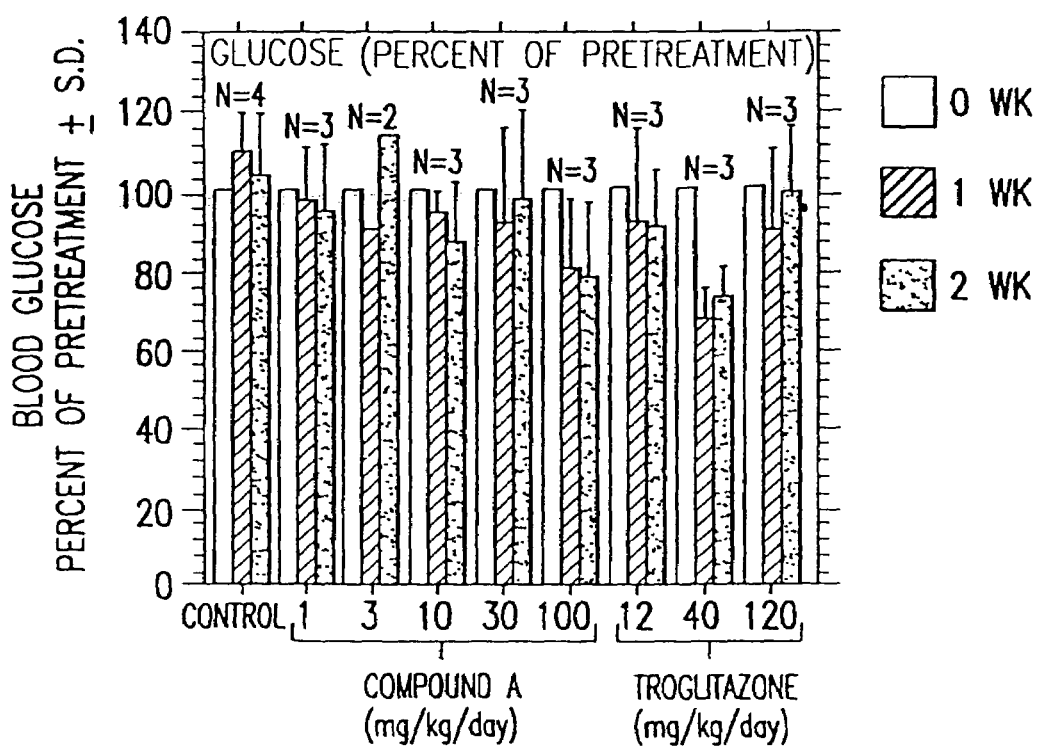

Blood glucose (FIG. 12) and serum insulin levels (FIG. 13) were determined from fasted rats just prior to and following one and two weeks of treatment. Blood glucose was maintained at slightly elevated levels for 10-12 week old obese Zucker rats during treatment with all doses of Compound A and troglitazone, with the exception of the 100 mg/kg and 40 mg/kg doses, respectively, whereby both compounds showed a tendency to lower blood glucose. For troglitazone, this glucose lowering effect was not dose dependent, since it did not occur at 120 mg/kg. Relative to pretreatment values, serum insulin (FIG. 13) in control animals sharply rose as the

TABLE 2

| Experiment | Compound | (N) | Treatment Duration (days) | Dose (mg/kg/day) | Non HDL-Cholesterol (% of Pretreatment) | HDL-Cholesterol (% of Pretreatment) | Triglycerides (% of Pretreatment) | Body Weight Gain (% of Pretreatment) |
|---|---|---|---|---|---|---|---|---|
| B | Control | 3 | 14 | 0 | +217.5 | −43.1 | −31.9 | +10.7 |
| B | Compound B | 3 | 14 | 100 | +257.1 | −23.3 | +24.6 | +12.0 |
| B | Troglitazone | 2 | 14 | 120 | −44.0 | +44.2 | −76.6 | +21.7 |
| C | Control | 4 | 14 | 0 | −25.6 | −29.8 | −11.2 | +16.7 |
| C | Compound A | 3 | 14 | 1 | −25.6 | −24.1 | −8.8 | +16.7 |
| C | Compound A | 2 | 14 | 3 | −29.6 | −3.7 | −24.6 | +17.5 |
| C | Compound A | 3 | 14 | 10 | −14.2 | +154.4 | −50.9 | +10.7 |
| C | Compound A | 3 | 14 | 30 | +38.4 | +369.7 | −42.0 | +11.3 |
| C | Compound A | 3 | 14 | 100 | +45.1 | +801.8 | −57.0 | +9.2 |
| C | Troglitazone | 3 | 14 | 12 | −10.6 | +1.9 | +10.7 | +20.2 |
| C | Troglitazone | 3 | 14 | 40 | −50.5 | +36.1 | −59.6 | +21.2 |
| C | Troglitazone | 3 | 14 | 120 | −67.5 | +122.4 | −79.2 | +25.5 |
| D | Control | 3 | 14 | 0 | +15.2 | −12.2 | +1.6 | +10.6 |
| D | Compound A | 3 | 14 | 10 | +49.3 | +133.9 | −11.1 | +2.2 |
| D | Compound A | 2 | 14 | 100 | +7.5 | +187.9 | −62.9 | +4.5 |
| D | Troglitazone | 3 | 14 | 120 | −51.0 | +41.3 | −65.9 | +13.8 |
| E | Control | 3 | 14 | 0 | −13.1 | +10.2 | +12.0 | +21.9 |
| E | Compound A | 1 | 14 | 100 | +7.2 | +232.1 | −43.2 | +19.1 |
| E | Troglitazone | 3 | 14 | 120 | −67.4 | +47.9 | −69.4 | +14.4 |

Generally, Compound A improved the ratio of non-HDL cholesterol to HDL cholesterol content relative to both control animals and troglitazone-treated animals. Additionally, Compound A generally reduced serum triglyceride content and did not cause the body weight increases seen in troglitazone-treated animals.

Figure 13A:
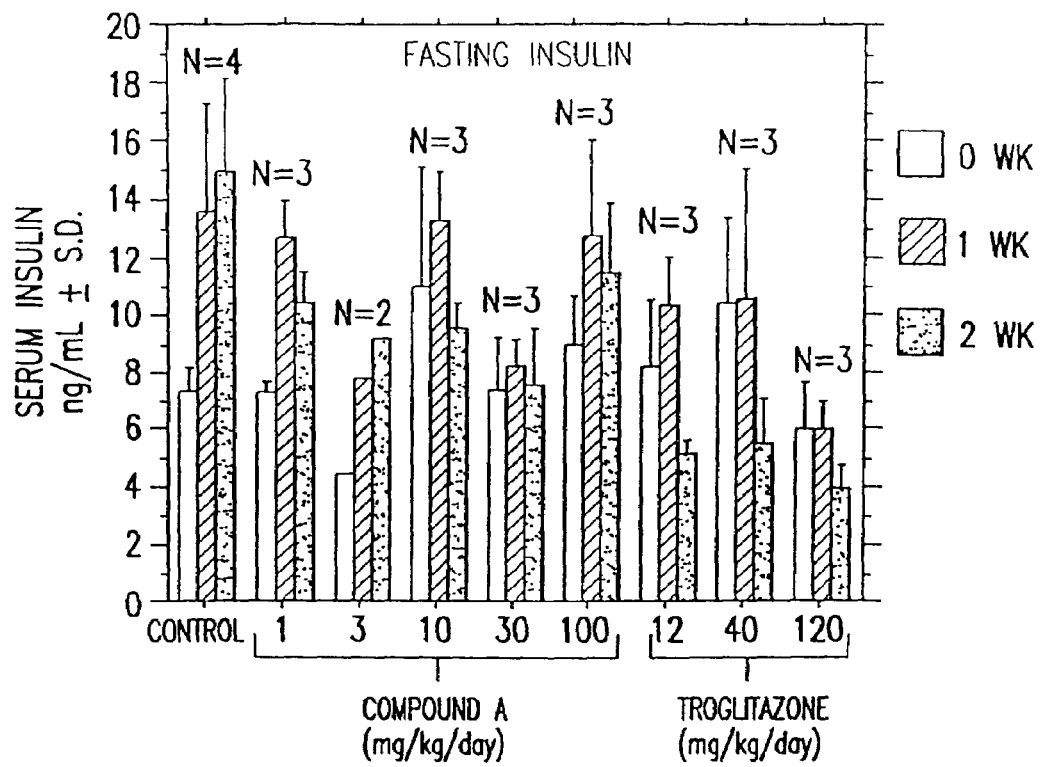
FIG. 13 shows the effect of Compound A or troglitazone on the serum insulin levels of obese female Zucker.
Figure 13B:
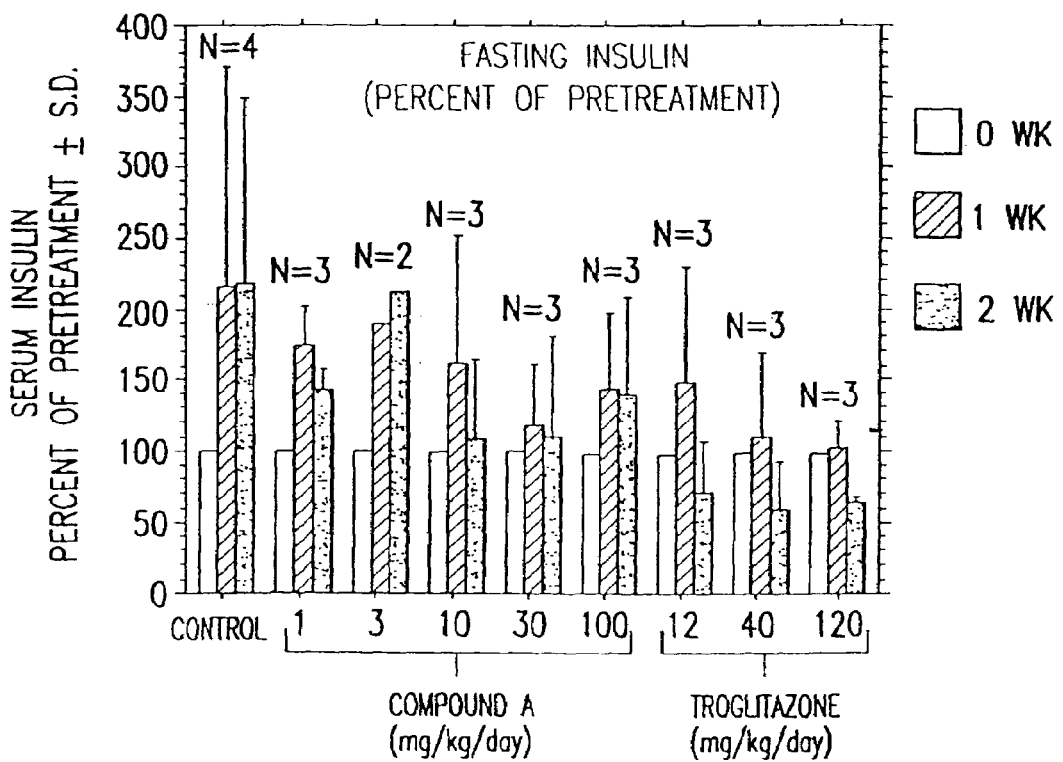
Figure 14A:
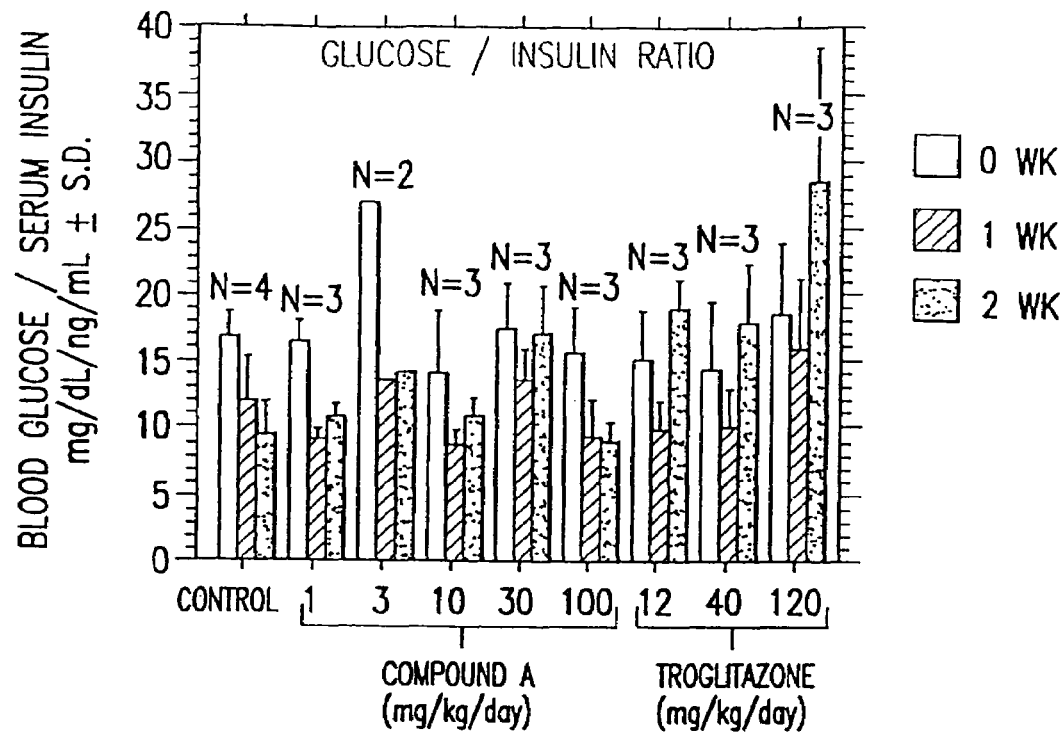
FIG. 14 shows the effect of Compound A or troglitazone on the glucose to insulin ratio in obese female Zucker rats.
Figure 14B:
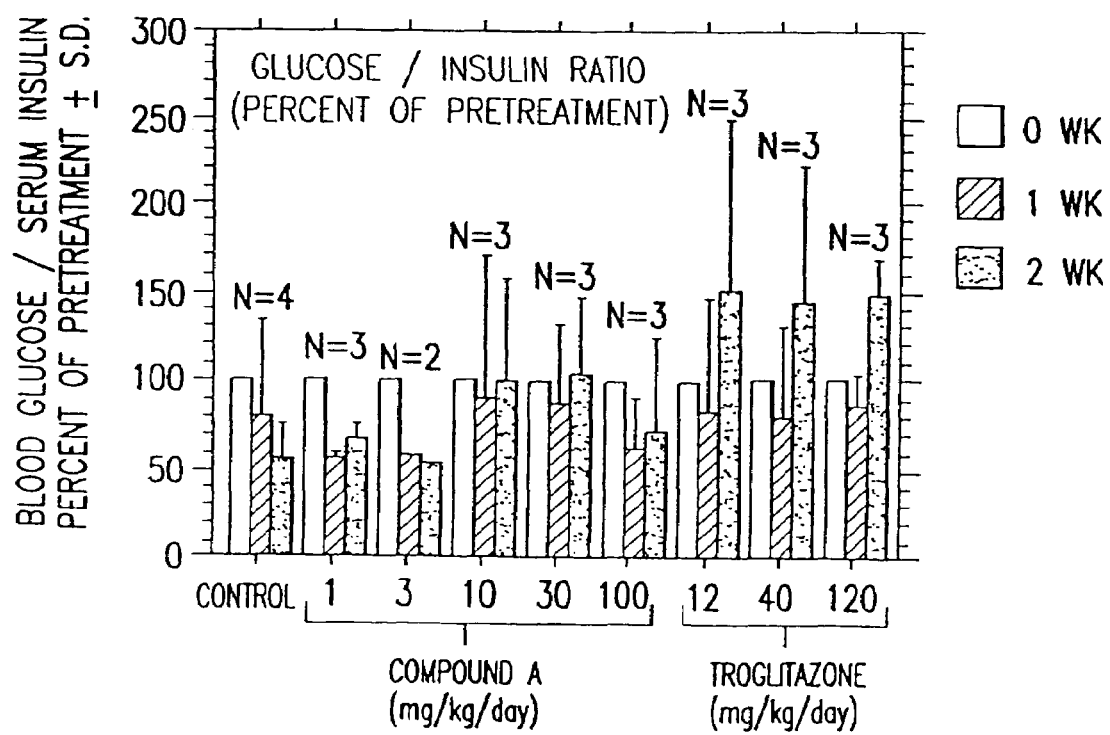

The data from Experiment C concerning Compound A are graphically depicted in FIGS. 10-16. Compound A treatment reduced serum triglyceride levels at all doses. Reduction in serum triglycerides was dose dependent with a minimal effecanimals became older. At dosages of 1 and 3 mg/kg of Compound A, a similar sharp rise in insulin levels was observed. However, at the higher Compound A doses, this sharp rise in serum insulin was largely curtailed or minimized. For troglitazone, serum insulin levels were reduced following two weeks of treatment at all doses tested (FIG. 13). One measure of improved insulin sensitivity (i.e. as impaired glucose tolerance progresses as the animals age), is a sustained or improved ratio of fasting serum glucose to insulin. The glucose to insulin ratio in these animals is shown in FIG. 14. In the control and the 1 and 3 mg/kg of Compound A groups, the glucose to insulin ratio declined by approximately ⅓ to ½ as the animals aged two weeks. In contrast, at 10 and 30 mg/kg Compound A, the glucose to insulin ratio was sustained at pretreatment levels. At 100 mg/kg of Compound A, the glucose to insulin ratio was reduced, suggesting this dose superseded the optimal dose for sustaining insulin sensitivity for the compound. Troglitazone at all doses sustained the glucose to insulin ratio after one week treatment and increased this ratio after two weeks of treatment (FIG. 14).

Figure 15:
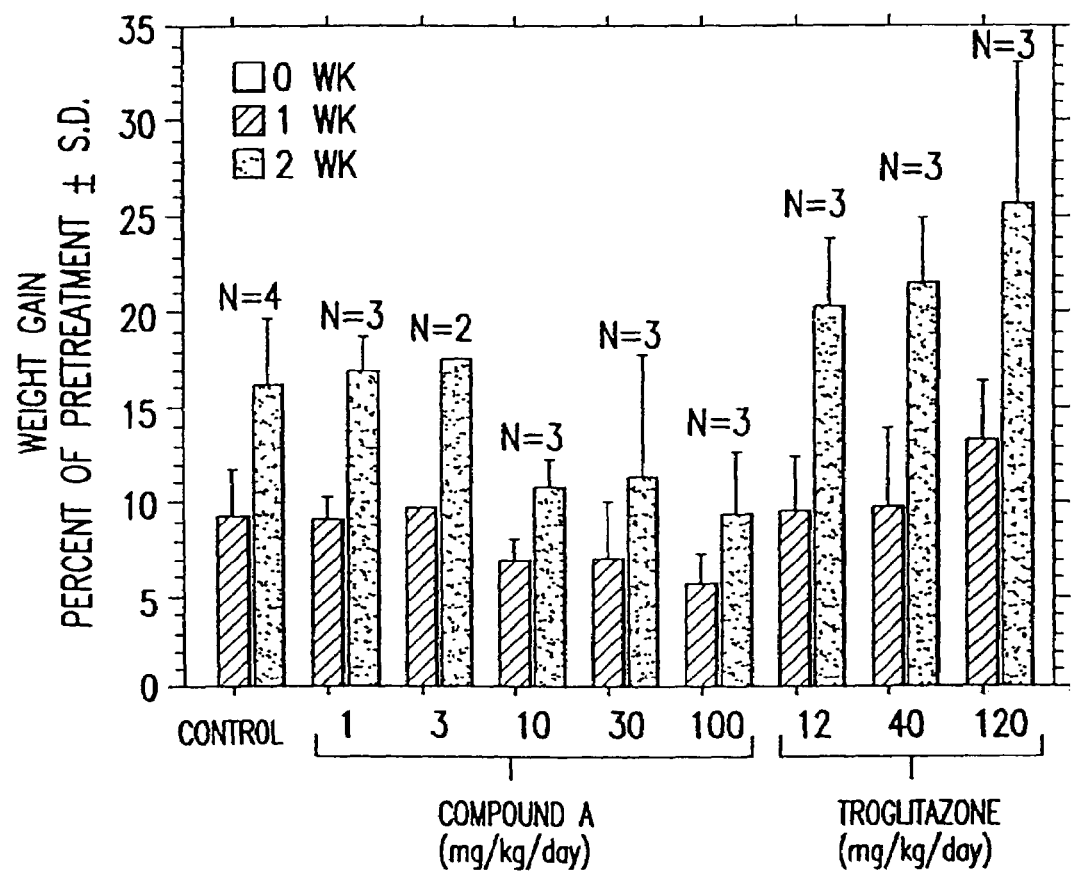
FIG. 15 shows the weekly percent weight gain in the Zucker rats during treatment with Compound A or troglitazone.

FIG. 15 shows the weekly percent weight gain in the Zucker rats during treatment. Control rats gained 9.1 and 16 percent of their initial weight after one and two weeks respectively. With Compound A treatment, all treatment groups gained weight. At the lower doses (1 and 3 mg/kg) weight gain was similar to controls. However, weight gain was markedly reduced at 10, 30 and 100 mg/kg of Compound A after both one and two weeks of treatment, suggesting Compound A may have thermogenic properties. In contrast, troglitazone treatment caused increased weight gain after one week at 120 mg/kg and increased weight gain after two weeks at all treatment doses (12, 40 and 120 mg/kg).

Figure 16:
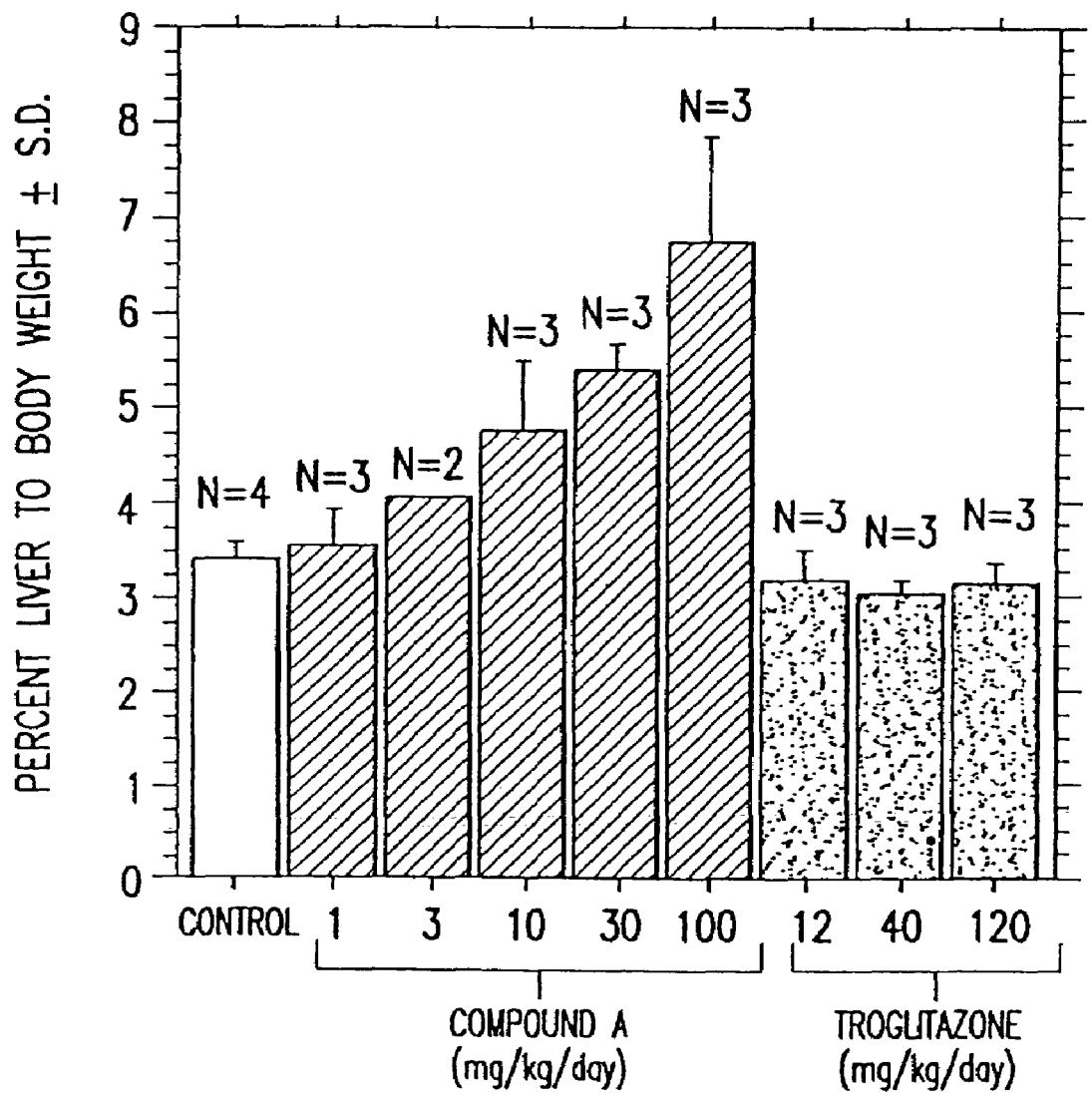
FIG. 16 shows the percent liver to body weight ratio in obese female Zucker rats after two weeks of treatment with Compound A or troglitazone.

Percent liver to body weight was determined after two weeks of treatment at the time of sacrifice (FIG. 16). Following Compound A treatment, liver to body weight increased in a dose dependent manner. For troglitazone, liver to body weight was reduced at all doses. The gain in liver to body weight in rats suggests to the inventors, without intending any limitation as to the mechanism by which the compounds of the invention act, that Compound A may be a peroxisomal proliferator activator receptor ligand.

Accordingly, Compound A, or a pharmaceutically acceptable salt thereof, is useful for improving the ratio HDL:non-HDL cholesterol in the blood, reducing serum triglycerides, elevating HDL-cholesterol, lowering blood glucose, and/or improving insulin sensitivity, without the adverse side effect of promoting weight gain in a patient to whom the compound is administered.

10. EXAMPLE

Effect of Compound A on Lipoprotein Cholesterol Profile in LDL Receptor-Deficient Mice Homozygous familial hypercholesterolemia is a rare human disease (~1/1,000,000) characterized by absent or defective LDL receptors, markedly elevated serum LDL cholesterol levels and very early and severe onset of atherosclerosis. The more common form of this disease in humans, heterozygous familial hypercholesterolemia, occurs in about one in every 500 humans. Patients with the heterozygous form of this disease also present with elevated LDL levels and early onset of atherosclerosis.

The effect of Compound A on LDL levels in a murine model of homozygous familial hypercholesterolemia (Ishibashi et al., 1993, *J. Clin. Invest.* 92:883-893; Ishibashi et al., 1994, *J. Clin. Invest.* 93:1885-1893) was studied. LDL receptor-deficient mice have elevated LDL cholesterol relative to wild type mice when fed a chow diet. When fed cholesterol-enriched diets, these mice develop atherosclerosis.

Figure 17:
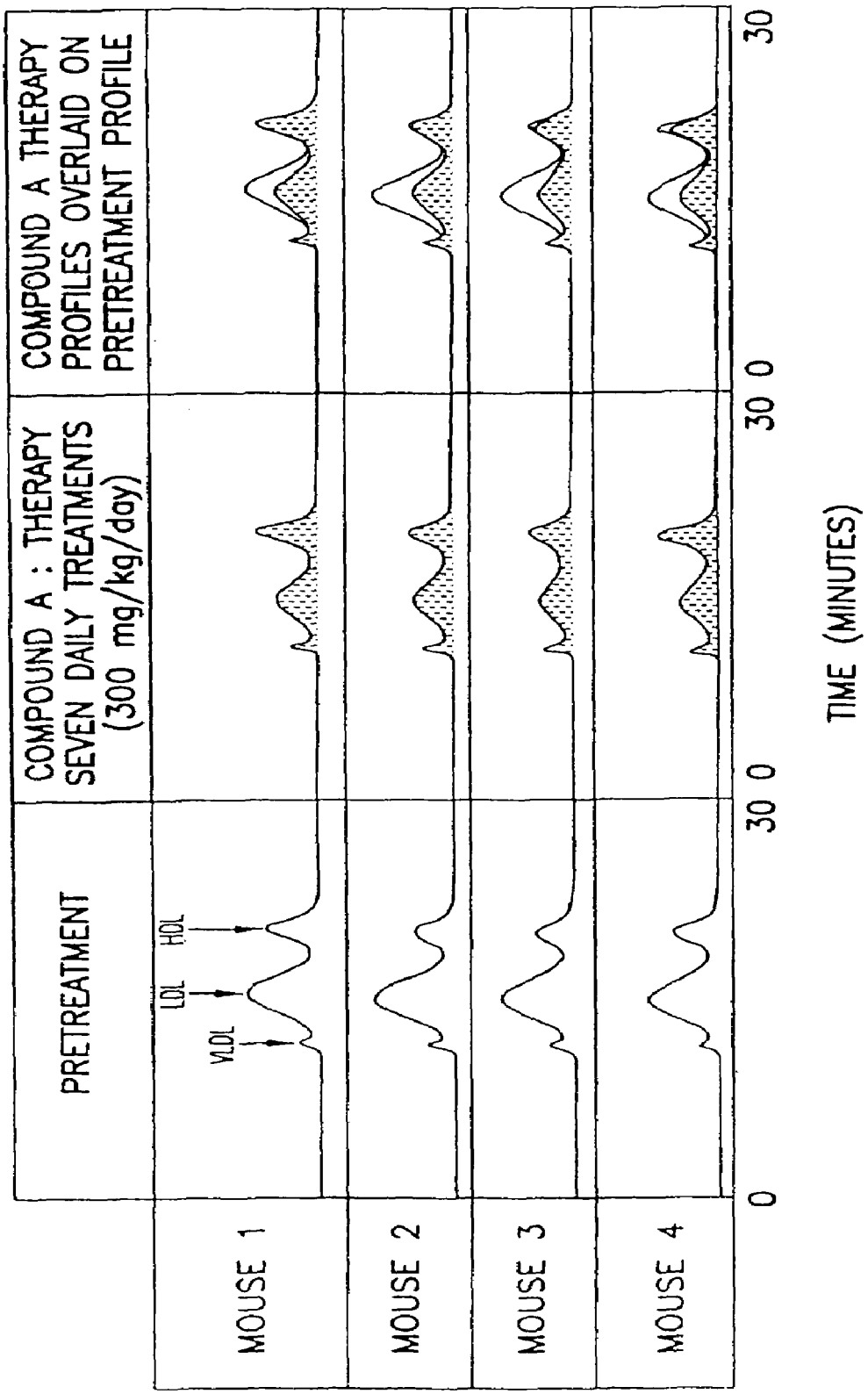
FIG. 17 shows the effect on the serum lipoprotein cholesterol profile of LDL receptor deficient mice following seven daily treatments with Compound A.

FIG. 17 shows the lipoprotein cholesterol profiles (Bisgaier et al., *J. Lipid Res.* 38:2502-2515) of 4 chow-fed female LDL receptor deficient mice prior to and following therapy with 300 mg/kg/day of Compound A. All mice showed a rapid and significant reduction in LDL cholesterol after one week of treatment. In addition, FIG. 17 shows that Compound A caused HDL elevation in all treated mice.

Accordingly, Compound A, or a pharmaceutically acceptable salt thereof, is useful for reducing circulating LDL levels and/or increasing circulating HDL in a patient with a dyslipidemia, including homozygous familial hypercholesterolemia.

11. EXAMPLE

Effect of Illustrative Compounds of the Invention on the Synthesis of Non-Saponified and Saponified Lipids in Hepatocytes Isolated from a Male Sprague-Dawley Rat A male Sprague-Dawley rat was anesthetized by administration of sodium pentobarbitol by intraparitoneal injection at 50 mg/kg. In situ perfusion of the liver was performed as follows. The abdomen of the animal was opened, the portal vein canulated, and the liver perfused with WOSH solution (149 mM NaCl, 9.2 mM Na HEPES, 1.7 mM Fructose, 0.5 mM EGTA, 0.029 mM Phenol red, 10 U/ml heparin, pH 7.5) at a flow rate of 30 ml/min for 6 minutes. To digest the liver, DSC solution (6.7 mM KCl, 143 mM NaCl, 9.2 mM Na HEPES, 5 mM $CaCl_2$-$2H_2O$, 1.7 mM Fructose, 0.029 mM Phenol red, 0.2% BSA, 100 U/ml collagenase Type I, 93 U/ml Hyaluronidase, 160 BAEE/ml trypsin inhibitor, pH 7.5) was perfused through the liver at a flow rate of 30 ml/min for 6 minutes at a temperature of 37° C. After digestion, cells were dispersed in a solution of DMEM– (DMEM containing 2 mM GlutMax-1, 0.2% BSA, 5% FBS, 12 nM insulin, 1.2 µM hydrocortisone) to stop the digestion process. The crude cell suspension was filtered through three layers of stainless steel mesh with pore sizes of 250, 106, and 75 µm respectively. Filtered cells were centrifuged at 50×g for two minutes and the supernatant discarded. The resulting cell pellet was resuspended in DMEM and centrifuged again. This final cell pellet was resuspended in DMEM+HS solution (DMEM containing 2 mM GlutMax-1, 20 nM delta-aminolevulinic acid, 17.4 mM MEM non-essential amino acids, 20% FBS, 12 nM insulin, 1.2 µM hydrocortisone) and plated to form monolayer cultures at a density of $100×10^3$ cells/$cm^2$ on collagen coated culture dishes. Four hours after initial plating, media was changed to DMEM+ (DMEM containing 2 mM GlutMax-1, 20 nM delta-aminolevulinic acid, 17.4 mM MEM non-essential amino acids, 10% FBS, 12 nM insulin, 1.2 µM hydrocortisone) and remained on cells overnight.

To test the effect of illustrative compounds of the invention on synthesis rates of non-saponified and saponified lipids, the monolayer cultures were exposed to 1 µM of lovastatin or 100 µM Compound A, B, D, E or F in DMEM+ containing 1 µCi/ml $^{14}$C-acetate. Control cells were exposed to the same media lacking lovastatin or the test compounds. All cells were exposed to 0.1% DMSO. Metabolic labeling with $^{14}$C-acetate continued for 2 hr at 37° C. After labeling, cells were washed twice with 1 ml of PBS followed by lysing in 1 ml of deionized water. Cells were scraped from the dishes, transferred to glass tubes and sonicated. 2.5 ml of 2:1 chloroform/methanol mixture was added followed by 1.5 ml of Phosphate Buffered Saline (PBS). To correct for extraction efficiency in the upcoming extractions, 3000 dpm of $^3$H-cholesterol was added to each tube. Tubes were shaken for 30 min. to extract lipids into the organic phase followed by centrifugation for 10 minutes at 1000×g to separate the organic and aqueous phases. The lower organic phase containing total lipids was removed and placed in a new tube. The organic solution was evaporated under $N_2$. The dry lipid extract was resuspended in 1 ml of 93% ethanol containing 1 M KOH and placed at 70° C. for 2.5 hours. After the reaction and cooling, 2 ml of hexane and 2.5 ml of water was added to each tube followed by rigorous shaking for 10 min. Tubes were centrifuged for 10 min. at 1000×g and the organic (top) layer containing the non-saponified lipids was transferred to a new tube followed by evaporation of the organic solvent under $N_2$. The aqueous phase containing the saponified lipids was also transferred to a new tube. The non-saponified lipid extract, after drying, was resuspended in toluene and an aliquot of the suspension was added to a scintillation cocktail for radioactive counting. The number of $^{14}C$ counts representing the incorporation of $^{14}C$-acetate into non-saponified lipids was corrected for extraction efficiency, based on the recovery of $^3H$ counts extracted. To isolate saponified lipids, 1.5 ml of aqueous phase solution was mixed with 400 μl of 1 M HCl, and then lipids were extracted by the addition of 2.5 ml of 2:1 chloroform:methanol, 1.5 ml of PBS, and 1 ml of water followed by rigorous shaking and isolation of the organic phase. The organic phase from this extraction was evaporated under $N_2$ and resuspended in toluene. Its radioactivity was counted using scintillant to provide the rate of $^{14}C$-acetate incorporation into saponified lipid.

Figure 18:
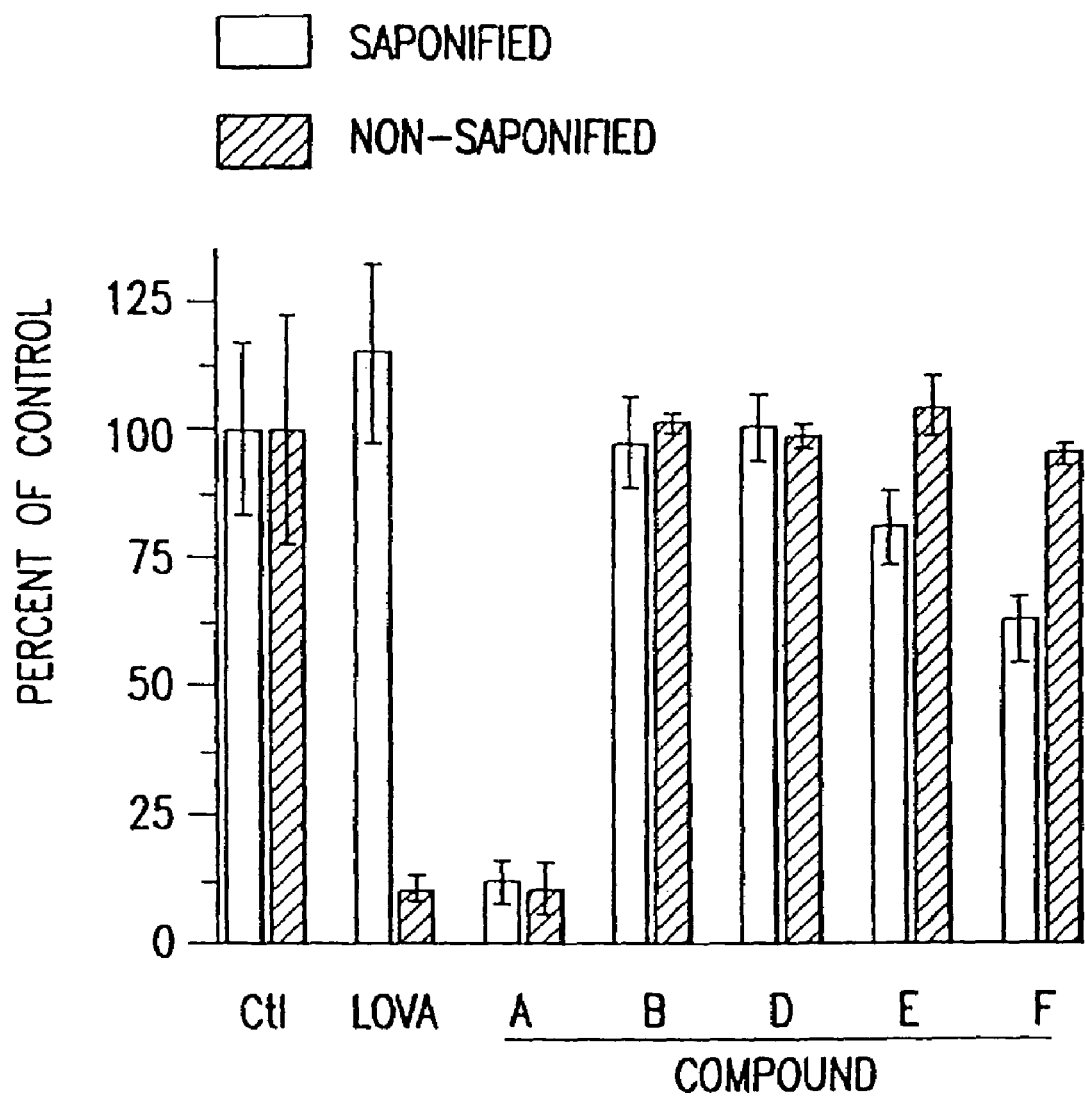
FIG. 18 shows the rates of synthesis of non-saponified and saponified lipid in primary rat hepatocytes upon treatment with Compound A, Compound B, Compound D, Compound E, Compound F, or lovastatin.

FIG. 18 shows the rates of saponified and non-saponified lipid synthesis following treatment with lovastatin and illustrative compounds of the invention. Data are represented as a percent of no compound treatment (control). Data are represented as the mean of three measurements +/−one standard deviation. The data indicate that illustrative compounds of the invention are useful for inhibiting saponified and/or non-saponified lipid synthesis. In particular, Compound A reduced the rate of both saponified and non-saponified lipid synthesis by at least 85% in the rat hepatocytes. Compounds E and F also reduced the rates of saponified fatty acid synthesis. Accordingly, Compound A, or a pharmaceutically acceptable salt thereof, is useful for inhibiting the synthesis of saponified and/or non-saponified fatty acids. Compounds E and E, or pharmaceutically acceptable salts thereof, are also useful for inhibiting the synthesis of saponified fatty acids.

12. EXAMPLE

Measurement of the Cytotoxicity of Illustrative Compounds of the Invention

To evaluate the effects of illustrative compounds of the invention on cytotoxicity, monolayer hepatocyte cultures were exposed to increasing concentrations of up to 250 μM Compound A, B, C, or D in DMEM+ for 24 hours. Control cells were exposed to the same media lacking a test compound. All cells were exposed to 0.1% DMSO. The measure of cytotoxicity, release of lactate dehydrogenase (LDH) from the cytosolic compartment of hepatocyte monolayer cultures, reflects damage to the plasma membrane. The assay, based on the method of Wroblewski and LaDue, 1955, *Proc. Soc. Exp. Biol. Med.* 90:210-213; see also Ulrich et al., 1995, *Toxicol. Lett.* 82/83:107-115, describing the use of hepatocytes as models for hepatic toxicity), measures the LDH activity in tissue culture medium and a cell homogenate. Briefly, all the media were removed from plates and transferred to a separate plate. Following removal of media, attached cells were lysed with a hypotonic Tris/Glycerol/EDTA buffer (0.1 M Tris, 20% glycerol, 1 mM EDTA pH 7.3). Activity of LDH in medium and cells was measured spectrophotometrically by monitoring the rate of pyruvate reduction to lactate, coupled with oxidation of NADH; the rate of absorbance change was measured at 340 nm. Cytotoxicity was expressed as ratio using the following equation: (LDH in medium/(LDH in medium+LDH in solubilized hepatocytes))=R.

Figure 19:
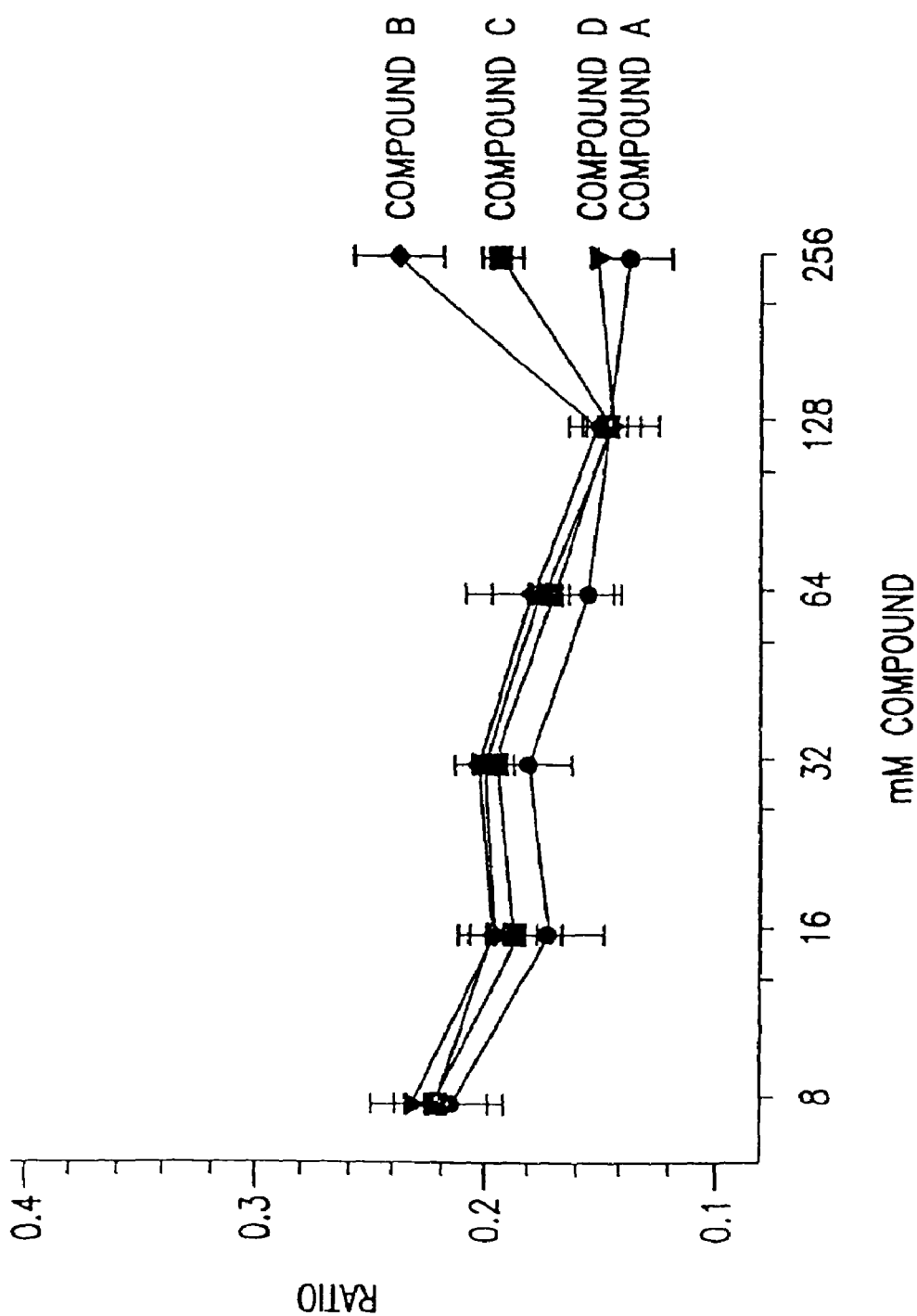
FIG. 19 shows the ratio of LDH leakage in primary rat hepatocytes contacted in vitro with increasing concentrations of Compounds A, B, C, or D during a 24 hr period.

FIG. 19 shows the results of these experiments. At all concentrations tested, none of Compounds A, B, C, or D resulted in the secretion of more than approximately 25-30% of total LDH in the medium. For Compound A, toxicity was assayed at 2.5-fold the compound's therapeutically effective concentration. These experiments indicate that the toxicity of the compounds of the invention is low. Accordingly, Compounds A, B, C and D, and pharmaceutically acceptable thereof, are potentially suitable for human use without toxic side effects.

13. EXAMPLE

Insulin Sensitization Effects of Compound A

The effects of Compound A on rate of differentiation of 3T3-L1 cells from a "committed pre-adipocyte" to an "adipocyte" phenotype in the absence or presence of insulin is tested. The differentiation of 3T3-L1 cells to an adipocyte-like phenotype is highly dependent upon insulin. This insulin-dependent changes in cellular morphology and metabolism, including: expression of adipocyte-specific genes, greatly increased levels of glucose uptake and metabolism, induction of GLUT4 (and increased expression of GLUT1) glucose transporters, greatly increased lipid synthesis and deposition of intracellular lipid droplets. In this assay the degree of differentiation was a reflection of the rate of lipid synthesis, as measured through incorporation of $^{14}C$-acetate over 2 hours. Thus the ability of a compound to stimulate a submaximal insulin response would suggest an insulin-sensitizing activity (Kletzein et al., 1991, *Molecular Pharm.* 41:393-398).

3T3-L1 stem cells were induced to differentiate with dexamethasone, isobutylmethylxanthine and insulin (Green and Kehinde, 1975, *Cell* 5:19-27). Cells were plated in Dulbecco's modified Eagle medium containing 10% calf serum and grown to confluence. Cells were then refreshed with 10% fetal calf serum, and treated with 0.5 mM isobutylmethylxanthine and 250 nM dexamethasone, but no additional insulin, for 48 hours. This treatment induced the differentiation of 3T3-L1 cells into pre-adipocytes. Conversion of preadipocytes to adipocyte phenotype requires the removal of dexamethasone and the presence of insulin, which stimulates differentiation of preadipocytes into adipocytes in a concentration- and time-dependent manner. A maximal insulin effect occurs at about 100 nM insulin, and leads to nearly complete (95-100%) conversion to adipocytes within 4 days.

The preadipocytes were then treated for 4 days with various concentrations of Compound A in 5% fetal calf serum in Dulbecco's modified Eagles medium, with or without a submaximal concentration of insulin (30 nM). Following this four-day treatment, the preadipocytes were pulsed with 0.1 μCi $^{14}C$-acetate per well for 2 hours. Cell were then washed with phosphate buffered saline, lysed with 0.1 N NaOH, and $^{14}C$-acetate incorporation into lipids was determined using phase separation and liquid scintillation counting.

Figure 20:
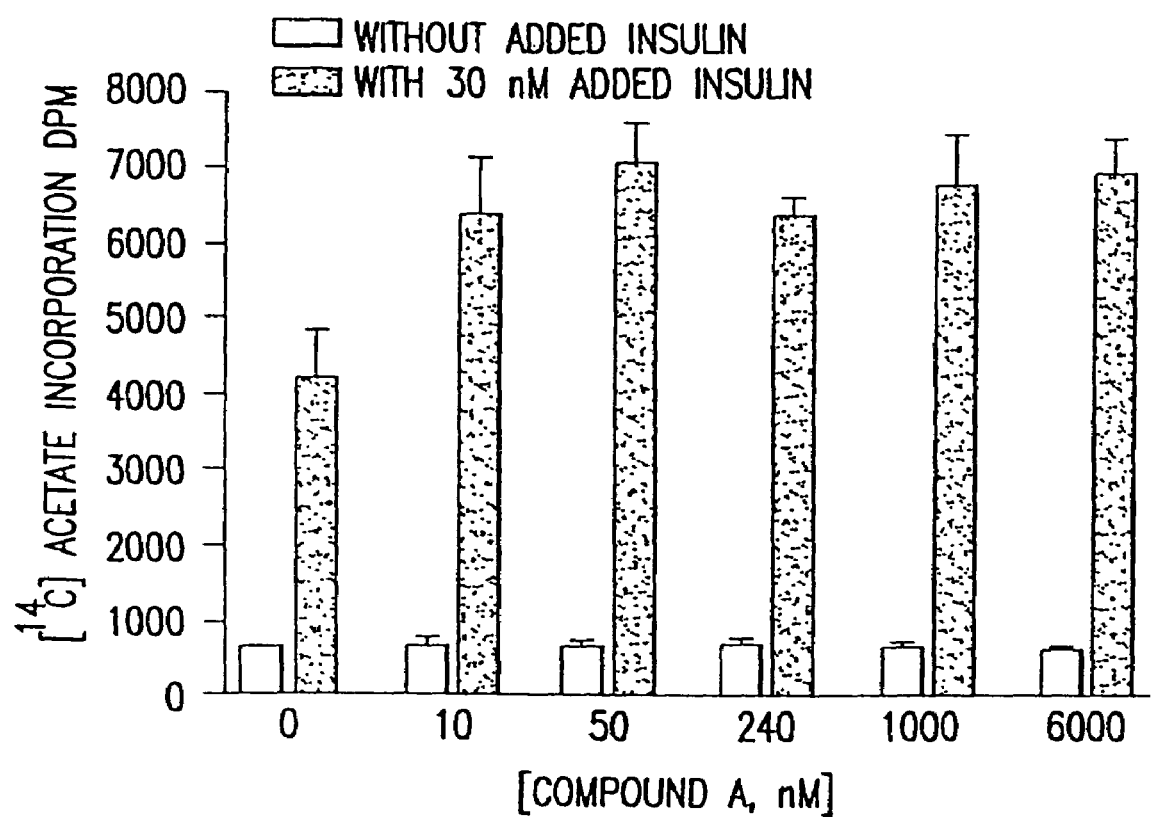
FIG. 20 shows the insulin sensitizing effects of Compound A on cultured preadipocytes.

FIG. 20 shows the results of these experiments. Data are represented as the mean +/−one standard deviation for three measurements. Without Compound A, $^{14}C$-acetate incorporation into lipids was 4201 DPM in the presence of insulin and 545 DPM in the absence of insulin. In the presence of Compound A, $^{14}C$-acetate incorporation increased by approximately 40%, indicating that Compound A potentiates the insulin-dependent increase in acetate incorporation. Accordingly, Compound A or a pharmaceutically acceptable salt thereof is suitable for use as an insulin sensitizer.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference.

What is claimed is:

1. A method for treating a disorder of glucose metabolism comprising administering to a patient in need of such treatment a therapeutically effective amount of a compound of formula I:

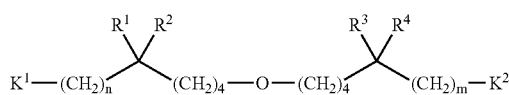

or a pharmaceutically acceptable salt thereof wherein:

$R^1$, $R^2$, $R^3$, and $R^4$ are independently selected from the group consisting of ($C_1$-$C_6$)alkyl, ($C_2$-$C_6$)alkenyl, ($C_2$-$C_6$)alkynyl, phenyl, and benzyl; or $R^1$, $R^2$, and the carbon to which they are attached are taken together to form a ($C_3$-$C_7$)cycloalkyl group; or $R^3$, $R^4$ and the carbon to which they are attached are taken together to form a ($C_3$-$C_7$)cycloalkyl group; or $R^1$, $R^2$, and the carbon to which they are attached and $R^3$, $R^4$, and the carbon to which they are attached are taken together to form a ($C_3$-$C_7$)cycloalkyl group, with the proviso that none of $R^1$, $R^2$, $R^3$, or $R^4$ is —$(CH_2)_{0-4}C{\equiv}CH$;

n and m are independent integers ranging from 0 to 4;

$K^1$ and $K^2$ are independently selected from the group consisting of —$CH_2OH$, —$C(O)OH$, —$CHO$, —$C(O)OR^5$, —$OC(O)R^5$, —$SO_3H$,

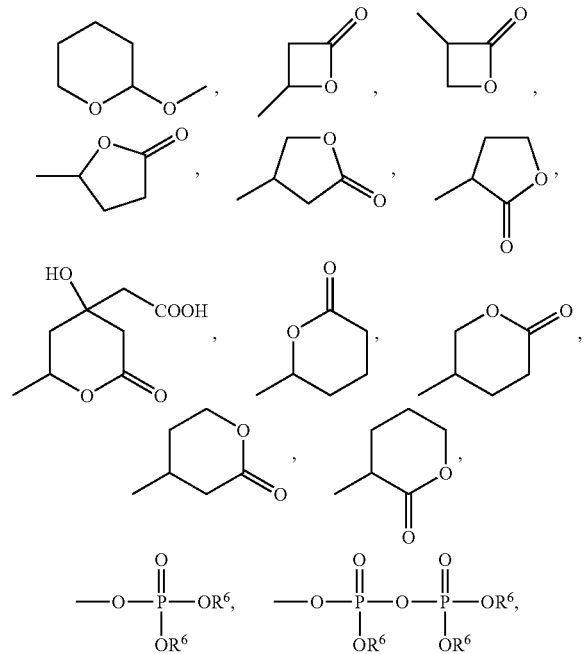

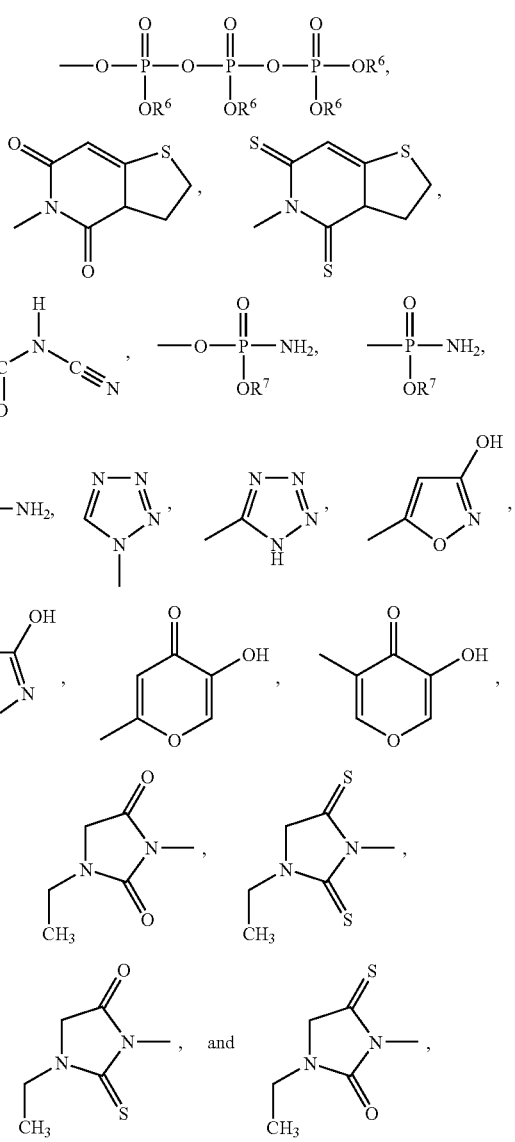

$R^5$ is selected from the group consisting of ($C_1$-$C_6$)alkyl, ($C_2$-$C_6$)alkenyl, ($C_2$-$C_6$)alkynyl, phenyl, and benzyl;

each $R^6$ is independently selected from the group consisting of H, ($C_1$-$C_6$)alkyl, ($C_2$-$C_6$)alkenyl, and ($C_2$-$C_6$)alkynyl;

$R^7$ is selected from the group consisting of H, ($C_1$-$C_6$)alkyl, ($C_2$-$C_6$)alkenyl, and ($C_2$-$C_6$)alkynyl; and with the proviso that when n and m are both 1 or both 0, then $K^1$ and $K^2$ are not both X, wherein X is selected from the group consisting of —COOH, —CHO, —$C(O)OR^5$,

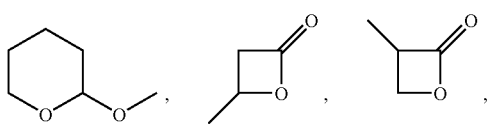

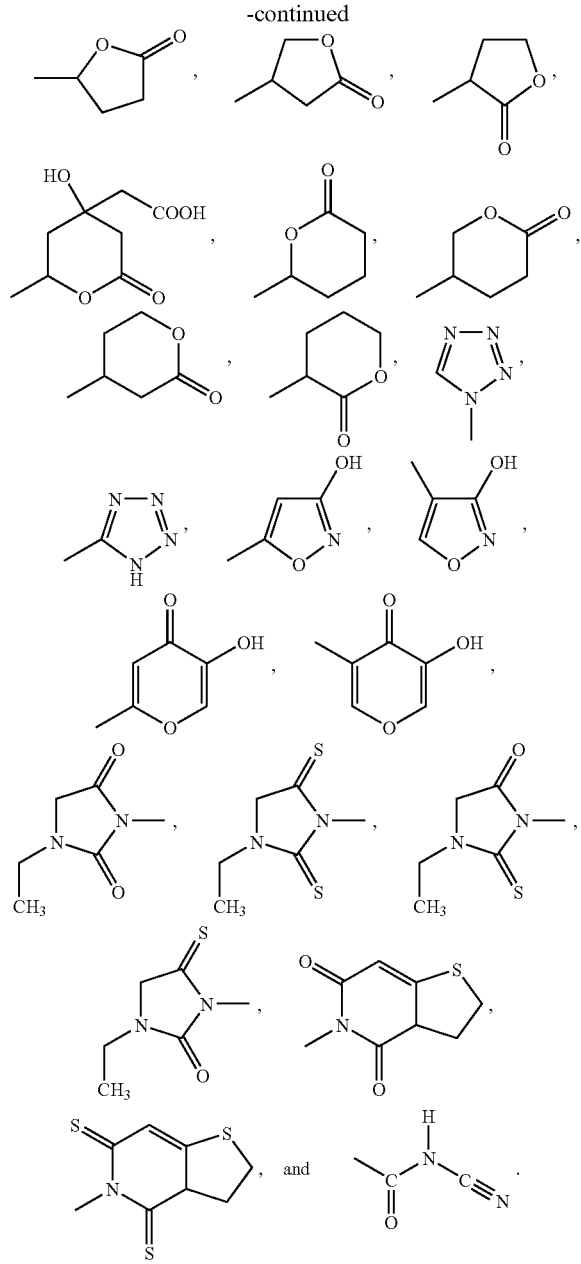

2. method for treating a disorder of glucose metabolism comprising administering to a patient in need of such treatment a therapeutically effective amount of a compound selected from:
6-(6-hydroxy-5,5-dimethyl-hexyloxy)-2,2-dimethyl-hexan-1-ol;
7-(7-hydroxy-5,5-dimethyl-heptyloxy)-3,3-dimethyl-heptan-1-ol;
6-(6-hydroxy-5,5-dimethyl-hexyloxy)-2,2-dimethyl-hexanoic acid;
7-(6-hydroxy-5,5-dimethyl-hexyloxy)-3,3-dimethyl-heptanoic acid;
6-(7-hydroxy-5,5-dimethyl-heptyloxy)-2,2-dimethyl-hexanoic acid;
7-(7-hydroxy-5,5-dimethyl-heptyloxy)-3,3-dimethyl-heptanoic acid;
6-(8-hydroxy-5,5-dimethyl-octyloxy)-2,2-dimethyl-hexanoic acid;
7-(8-hydroxy-5,5-dimethyl-octyloxy)-3,3-dimethyl-heptanoic acid;
8-(8-hydroxy-5,5-dimethyl-octyloxy)-4,4-dimethyl-octanoic acid;
6-(9-hydroxy-5,5-dimethyl-nonyloxy)-2,2-dimethyl-hexanoic acid;
7-(9-hydroxy-5,5-dimethyl-nonyloxy)-3,3-dimethyl-heptanoic acid;
8-(9-hydroxy-5,5-dimethyl-nonyloxy)-4,4-dimethyl-octanoic acid;
9-(9-hydroxy-5,5-dimethyl-nonyloxy)-5,5-dimethyl-nonanoic acid;
6-(10-hydroxy-5,5-dimethyl-decyloxy)-2,2-dimethyl-hexanoic acid;
7-(10-hydroxy-5,5-dimethyl-decyloxy)-3,3-dimethyl-heptanoic acid;
8-(10-hydroxy-5,5-dimethyl-decyloxy)-4,4-dimethyl-octanoic acid;
9-(10-hydroxy-5,5-dimethyl-decyloxy)-5,5-dimethyl-nonanoic acid;
10-(10-hydroxy-5,5-dimethyl-decyloxy)-6,6-dimethyl-decanoic acid;
phosphoric acid mono-(5-(6-hydroxy-5,5-dimethyl-hexyloxy)-1,1-dimethyl-pentyl) ester;
phosphoric acid mono-(6-(6-hydroxy-5,5-dimethyl-hexyloxy)-2,2-dimethyl-hexyl) ester;
phosphoric acid mono-(5-(7-hydroxy-5,5-dimethyl-heptyloxy)-1,1-dimethyl-pentyl) ester;
phosphoric acid mono-(6-(7-hydroxy-5,5-dimethyl-heptyloxy)-2,2-dimethyl-hexyl) ester;
phosphoric acid mono-(5-(8-hydroxy-5,5-dimethyl-octyloxy)-1,1-dimethyl-pentyl) ester;
phosphoric acid mono-(6-(8-hydroxy-5,5-dimethyl-octyloxy)-2,2-dimethyl-hexyl) ester;
phosphoric acid mono-(7-(8-hydroxy-5,5-dimethyl-octyloxy)-3,3-dimethyl-heptyl) ester;
phosphoric acid mono-(5-(9-hydroxy-5,5-dimethyl-nonyloxy)-1,1-dimethyl-pentyl) ester;
phosphoric acid mono-(6-(9-hydroxy-5,5-dimethyl-nonyloxy)-2,2-dimethyl-hexyl) ester;
phosphoric acid mono-(7-(9-hydroxy-5,5-dimethyl-nonyloxy)-3,3-dimethyl-heptyl) ester;
phosphoric acid mono-(8-(9-hydroxy-5,5-dimethyl-nonyloxy)-4,4-dimethyl-octyl) ester;
phosphoric acid mono-(5-(10-hydroxy-5,5-dimethyl-decyloxy)-1,1-dimethyl-pentyl) ester;
phosphoric acid mono-(6-(10-hydroxy-5,5-dimethyl-decyloxy)-2,2-dimethyl-hexyl) ester;
phosphoric acid mono-(7-(10-hydroxy-5,5-dimethyl-decyloxy)-3,3-dimethyl-heptyl) ester;
phosphoric acid mono-(8-(10-hydroxy-5,5-dimethyl-decyloxy)-4,4-dimethyl-octyl) ester;
phosphoric acid mono-(9-(10-hydroxy-5,5-dimethyl-decyloxy)-5,5-dimethyl-nonyl) ester;
2,2-dimethyl-6-(5-methyl-5-phosphonooxy-hexyloxy)-hexanoic acid;
3,3-dimethyl-7-(5-methyl-5-phosphonooxy-hexyloxy)-heptanoic acid;
6-(5,5-dimethyl-6-phosphonooxy-hexyloxy)-2,2-dimethyl-hexanoic acid;
7-(5,5-dimethyl-6-phosphonooxy-hexyloxy)-3,3-dimethyl-heptanoic acid;
6-(5,5-dimethyl-7-phosphonooxy-heptyloxy)-2,2-dimethyl-hexanoic acid;

7-(5,5-dimethyl-7-phosphonooxy-heptyloxy)-3,3-dimethyl-heptanoic acid;
8-(5,5-dimethyl-7-phosphonooxy-heptyloxy)-4,4-dimethyl-octanoic acid;
6-(5,5-dimethyl-8-phosphonooxy-octyloxy)-2,2-dimethyl-hexanoic acid;
7-(5,5-dimethyl-8-phosphonooxy-octyloxy)-3,3-dimethyl-heptanoic acid;
8-(5,5-dimethyl-8-phosphonooxy-octyloxy)-4,4-dimethyl-octanoic acid;
9-(5,5-dimethyl-8-phosphonooxy-octyloxy)-5,5-dimethyl-nonanoic acid;
6-(5,5-dimethyl-9-phosphonooxy-nonyloxy)-2,2-dimethyl-hexanoic acid;
7-(5,5-dimethyl-9-phosphonooxy-nonyloxy)-3,3-dimethyl-heptanoic acid;
8-(5,5-dimethyl-9-phosphonooxy-nonyloxy)-4,4-dimethyl-octanoic acid;
9-(5,5-dimethyl-9-phosphonooxy-nonyloxy)-5,5-dimethyl-nonanoic acid;
10-(5,5-dimethyl-9-phosphonooxy-nonyloxy)-6,6-dimethyl-decanoic acid;
phosphoric acid mono-(1,1-dimethyl-5-(5-methyl-5-phosphonooxy-hexyloxy)-pentyl) ester;
phosphoric acid mono-(2,2-dimethyl-6-(5-methyl-5-phosphonooxy-hexyloxy)-hexyl) ester;
phosphoric acid mono-(6-(5,5-dimethyl-6-phosphonooxy-hexyloxy)-2,2-dimethyl-hexyl) ester;
phosphoric acid mono-(3,3-dimethyl-7-(5-methyl-5-phosphonooxy-hexyloxy)-heptyl) ester;
phosphoric acid mono-(7-(5,5-dimethyl-6-phosphonooxy-hexyloxy)-3,3-dimethyl-heptyl) ester;
phosphoric acid mono-(7-(5,5-dimethyl-7-phosphonooxy-heptyloxy)-3,3-dimethyl-heptyl) ester;
phosphoric acid mono-(4,4-dimethyl-8-(5-methyl-5-phosphonooxy-hexyloxy)-octyl) ester;
phosphoric acid mono-(8-(5,5-dimethyl-6-phosphonooxy-hexyloxy)-4,4-dimethyl-octyl) ester;
phosphoric acid mono-(8-(5,5-dimethyl-7-phosphonooxy-heptyloxy)-4,4-dimethyl-octyl) ester;
phosphoric acid mono-(8-(5,5-dimethyl-8-phosphonooxy-octyloxy)-4,4-dimethyl-octyl) ester;
phosphoric acid mono-(5,5-dimethyl-9-(5-methyl-5-phosphonooxy-hexyloxy-nonyl) ester;
phosphoric acid mono-(9-(5,5-dimethyl-6-phosphonooxy-hexyloxy)-5,5-dimethyl-nonyl) ester;
phosphoric acid mono-(9-(5,5-dimethyl-7-phosphonooxy-heptyloxy)-5,5-dimethyl-nonyl) ester;
phosphoric acid mono-(9-(5,5-dimethyl-8-phosphonooxy-octyloxy)-5,5-dimethyl-nonyl) ester;
phosphoric acid mono-(9-(5,5-dimethyl-9-phosphonooxy-nonyloxy)-5,5-dimethyl-nonyl) ester;
6-(6-hydroxy-5,5-dimethyl-hexyloxy)-2-methyl-hexane-2-sulfonic acid amide;
6-(6-hydroxy-5,5-dimethyl-hexyloxy)-2,2-dimethyl-hexane-1-sulfonic acid amide;
6-(7-hydroxy-5,5-dimethyl-heptyloxy)-2-methyl-hexane-2-sulfonic acid amide;
6-(7-hydroxy-5,5-dimethyl-heptyloxy)-2,2-dimethyl-hexane-1-sulfonic acid amide;
6-(8-hydroxy-5,5-dimethyl-octyloxy)-2-methyl-hexane-2-sulfonic acid amide;
6-(8-hydroxy-5,5-dimethyl-octyloxy)-2,2-dimethyl-hexane-1-sulfonic acid amide;
7-(8-hydroxy-5,5-dimethyl-octyloxy)-3,3-dimethyl-heptane-1-sulfonic acid amide;
6-(9-hydroxy-5,5-dimethyl-nonyloxy)-2-methyl-hexane-2-sulfonic acid amide;
6-(9-hydroxy-5,5-dimethyl-nonyloxy)-2,2-dimethyl-hexane-1-sulfonic acid amide;
7-(9-hydroxy-5,5-dimethyl-nonyloxy)-3,3-dimethyl-heptane-1-sulfonic acid amide;
8-(9-hydroxy-5,5-dimethyl-nonyloxy)-4,4-dimethyl-octane-1-sulfonic acid amide;
6-(10-hydroxy-5,5-dimethyl-decyloxy)-2-methyl-hexane-2-sulfonic acid amide;
6-(10-hydroxy-5,5-dimethyl-decyloxy)-2,2-dimethyl-hexane-1-sulfonic acid amide;
7-(10-hydroxy-5,5-dimethyl-decyloxy)-3,3-dimethyl-heptane-1-sulfonic acid amide;
8-(10-hydroxy-5,5-dimethyl-decyloxy)-4,4-dimethyl-octane-1-sulfonic acid amide;
9-(10-hydroxy-5,5-dimethyl-decyloxy)-5,5-dimethyl-nonane-1-sulfonic acid amide;
2,2-dimethyl-6-(5-methyl-5-sulfamoyl-hexyloxy)-hexanoic acid;
3,3-dimethyl-7-(5-methyl-5-sulfamoyl-hexyloxy)-heptanoic acid;
6-(5,5-dimethyl-6-sulfamoyl-hexyloxy)-2,2-dimethyl-hexanoic acid;
7-(5,5-dimethyl-6-sulfamoyl-hexyloxy)-3,3-dimethyl-heptanoic acid;
6-(5,5-dimethyl-7-sulfamoyl-heptyloxy)-2,2-dimethyl-hexanoic acid;
7-(5,5-dimethyl-7-sulfamoyl-heptyloxy)-3,3-dimethyl-heptanoic acid;
8-(5,5-dimethyl-7-sulfamoyl-heptyloxy)-4,4-dimethyl-octanoic acid;
6-(5,5-dimethyl-8-sulfamoyl-octyloxy)-2,2-dimethyl-hexanoic acid;
7-(5,5-dimethyl-8-sulfamoyl-octyloxy)-3,3-dimethyl-heptanoic acid;
8-(5,5-dimethyl-8-sulfamoyl-octyloxy)-4,4-dimethyl-octanoic acid;
9-(5,5-dimethyl-8-sulfamoyl-octyloxy)-5,5-dimethyl-nonanoic acid;
6-(5,5-dimethyl-9-sulfamoyl-nonyloxy)-2,2-dimethyl-hexanoic acid;
7-(5,5-dimethyl-9-sulfamoyl-nonyloxy)-3,3-dimethyl-heptanoic acid;
8-(5,5-dimethyl-9-sulfamoyl-nonyloxy)-4,4-dimethyl-octanoic acid;
9-(5,5-dimethyl-9-sulfamoyl-nonyloxy)-5,5-dimethyl-nonanoic acid;
10-(5,5-dimethyl-9-sulfamoyl-nonyloxy)-6,6-dimethyl-decanoic acid;
2-methyl-6-(5-methyl-5-sulfamoyl-hexyloxy)-hexane-2-sulfonic acid amide;
2,2-dimethyl-6-(5-methyl-5-sulfamoyl-hexyloxy)-hexane-1-sulfonic acid amide;
6-(5,5-dimethyl-6-sulfamoyl-hexyloxy)-2,2-dimethyl-hexane-1-sulfonic acid amide;
3,3-dimethyl-7-(5-methyl-5-sulfamoyl-hexyloxy)-heptane-1-sulfonic acid amide;
7-(5,5-dimethyl-6-sulfamoyl-hexyloxy)-3,3-dimethyl-heptane-1-sulfonic acid amide;
7-(5,5-dimethyl-7-sulfamoyl-heptyloxy)-3,3-dimethyl-heptane-1-sulfonic acid amide;
4,4-dimethyl-8-(5-methyl-5-sulfamoyl-hexyloxy)-octace-1-sulfonic acid amide;
8-(5,5-dimethyl-6-sulfamoyl-hexyloxy)-4,4-dimethyl-octane-1-sulfonic acid amide;

8-(5,5-dimethyl-7-sulfamoyl-heptyloxy)-4,4-dimethyl-octane-1-sulfonic acid amide;
8-(5,5-dimethyl-8-sulfamoyl-octyloxy)-4,4-dimethyl-octane-1-sulfonic acid amide;
5,5-dimethyl-9-(5-methyl-5-sulfamoyl-hexyloxy)-nonane-1-sulfonic acid amide;
9-(5,5-dimethyl-6-sulfamoyl-hexyloxy)-5,5-dimethyl-nonane-1-sulfonic acid amide;
9-(5,5-dimethyl-7-sulfamoyl-heptyloxy)-5,5-dimethyl-nonane-1-sulfonic acid amide;
9-(5,5-dimethyl-8-sulfamoyl-octyloxy)-5,5-dimethyl-nonane-1-sulfonic acid amide;
9-(5,5-dimethyl-9-sulfamoyl-octyloxy)-5,5-dimethyl-nonane-1-sulfonic acid amide;
1-ethyl-3-(5-(6-hydroxy-5,5-dimethyl-hexyloxy)-1,1-dimethyl-pentyl)-imidazolidine-2,4-dione;
1-ethyl-3-(6-(6-hydroxy-5,5-dimethyl-hexyloxy)-2,2-dimethyl-hexyl)-imidazolidine-2,4-dione;
1-ethyl-3-(5-(7-hydroxy-5,5-dimethyl-heptyloxy)-1,1-dimethyl-pentyl)-imidazolidine-2,4-dione;
1-ethyl-3-(6-(7-hydroxy-5,5-dimethyl-heptyloxy)-2,2-dimethyl-hexyl)-imidazolidine-2,4-dione;
1-ethyl-3-(5-(8-hydroxy-5,5-dimethyl-octyloxy)-1,1-dimethyl-pentyl)-imidazolidine-2,4-dione;
1-ethyl-3-(6-(8-hydroxy-5,5-dimethyl-octyloxy)-2,2-dimethyl-hexyl)-imidazolidine-2,4-dione;
1-ethyl-3-(7-(8-hydroxy-5,5-dimethyl-octyloxy)-3,3-dimethyl-heptyl)-imidazolidine-2,4-dione;
1-ethyl-3-(5-(9-hydroxy-5,5-dimethyl-nonyloxy)-1,1-dimethyl-pentyl)-imidazolidine-2,4-dione;
1-ethyl-3-(6-(9-hydroxy-5,5-dimethyl-nonyloxy)-2,2-dimethyl-hexyl)-imidazolidine-2,4-dione;
1-ethyl-3-(7-(9-hydroxy-5,5-dimethyl-nonyloxy)-3,3-dimethyl-heptyl)-imidazolidine-2,4-dione;
1-ethyl-3-(8-(9-hydroxy-5,5-dimethyl-nonyloxy)-4,4-dimethyl-octyl)-imidazolidine-2,4-dione;
1-ethyl-3-(5-(10-hydroxy-5,5-dimethyl-decyloxy)-1,1-dimethyl-pentyl)-imidazolidine-2,4-dione;
1-ethyl-3-(6-(10-hydroxy-5,5-dimethyl-decyloxy)-2,2-dimethyl-hexyl)-imidazolidine-2,4-dione;
1-ethyl-3-(7-(10-hydroxy-5,5-dimethyl-decyloxy)-3,3-dimethyl-heptyl)-imidazolidine-2,4-dione;
1-ethyl-3-(8-(10-hydroxy-5,5-dimethyl-decyloxy)-4,4-dimethyl-octyl)-imidazolidine-2,4-dione;
1-ethyl-3-(9-(10-hydroxy-5,5-dimethyl-decyloxy)-5,5-dimethyl-nonyl)-imidazolidine-2,4-dione;
6-(5-(3-ethyl-2,5-dioxo-imidazolidin-1-yl)-5-methyl-hexyloxy)-2,2-dimethyl-hexanoic acid;
7-(5-(3-ethyl-2,5-dioxo-imidazolidin-1-yl)-5-methyl-hexyloxy)-3,3-dimethyl-heptanoic acid;
6-(6-(3-ethyl-2,5-dioxo-imidazolidin-1-yl)-5,5-dimethyl-hexyloxy)-2,2-dimethyl-hexanoic acid;
7-(6-(3-ethyl-2,5-dioxo-imidazolidin-1-yl)-5,5-dimethyl-hexyloxy)-3,3-dimethyl-heptanoic acid;
6-(7-(3-ethyl-2,5-dioxo-imidazolidin-1-yl)-5,5-dimethyl-heptyloxy)-2,2-dimethyl-hexanoic acid;
7-(7-(3-ethyl-2,5-dioxo-imidazolidin-1-yl)-5,5-dimethyl-heptyloxy)-3,3-dimethyl-heptanoic acid;
8-(7-(3-ethyl-2,5-dioxo-imidazolidin-1-yl)-5,5-dimethyl-heptyloxy)-4,4-dimethyl-octanoic acid;
6-(8-(3-ethyl-2,5-dioxo-imidazolidin-1-yl)-5,5-dimethyl-octyloxy)-2,2-dimethyl-hexanoic acid;
7-(8-(3-ethyl-2,5-dioxo-imidazolidin-1-yl)-5,5-dimethyl-octyloxy)-3,3-dimethyl-heptanoic acid;
8-(8-(3-ethyl-2,5-dioxo-imidazolidin-1-yl)-5,5-dimethyl-octyloxy)-4,4-dimethyl-octanoic acid;
9-(8-(3-ethyl-2,5-dioxo-imidazolidin-1-yl)-5,5-dimethyl-octyloxy)-5,5-dimethyl-nonanoic acid;
6-(9-(3-ethyl-2,5-dioxo-imidazolidin-1-yl)-5,5-dimethyl-nonyloxy)-2,2-dimethyl-hexanoic acid;
7-(9-(3-ethyl-2,5-dioxo-imidazolidin-1-yl)-5,5-dimethyl-nonyloxy)-3,3-dimethyl-heptanoic acid;
8-(9-(3-ethyl-2,5-dioxo-imidazolidin-1-yl)-5,5-dimethyl-nonyloxy)-4,4-dimethyl-octanoic acid;
9-(9-(3-ethyl-2,5-dioxo-imidazolidin-1-yl)-5,5-dimethyl-nonyloxy)-5,5-dimethyl-nonanoic acid;
10-(9-(3-ethyl-2,5-dioxo-imidazolidin-1-yl)-5,5-dimethyl-nonyloxy)-6,6-dimethyl-decanoic acid;
3-(5-(5-(3-ethyl-2,5-dioxo-imidazolidin-1-yl)-5-methyl-hexyloxy)-1,1-dimethyl-pentyl)-1-ethyl-imidazolidine-2,4-dione;
3-(5-(6-(3-ethyl-2,5-dioxo-imidazolidin-1-yl)-5,5-dimethyl-hexyloxy)-1,1-dimethyl-pentyl)-1-ethyl-imidazolidine-2,4-dione;
3-(6-(6-(3-ethyl-2,5-dioxo-imidazolidin-1-yl)-5,5-dimethyl-hexyloxy)-2,2-dimethyl-hexyl)-1-ethyl-imidazolidine-2,4-dione;
3-(5-(7-cyclopentyl-5,5-dimethyl-heptyloxy)-1,1-dimethyl-pentyl)-1-ethyl-imadazolidine-2,4-dione;
3-(6-(7-(3-ethyl-2,5-dioxo-imidazolidin-1-yl)-5,5-dimethyl-heptyloxy)-2,2-dimethyl-hexyl)-1-ethyl-imidazolidine-2,4-dione;
3-(7-(7-(3-ethyl-2,5-dioxo-imidazolidin-1-yl)-5,5-dimethyl-heptyloxy)-3,3-dimethyl-heptyl)-1-ethyl-imidazolidine-2,4-dione;
3-(5-(8-(3-ethyl-2,5-dioxo-imidazolidin-1-yl)-5,5-dimethyl-octyloxy)-1,1-dimethyl-pentyl)-1-ethyl-imidazolidine-2,4-dione;
3-(6-(8-(3-ethyl-2,5-dioxo-imidazolidin-1-yl)-5,5-dimethyl-octyloxy)-2,2-dimethyl-hexyl)-1-ethyl-imidazolidine-2,4-dione;
3-(7-(8-(3-ethyl-2,5-dioxo-imidazolidin-1-yl)-5,5-dimethyl-octyloxy)-3,3-dimethyl-heptyl)-1-ethyl-imidazolidine-2,4-dione;
3-(8-(8-(3-ethyl-2,5-dioxo-imidazolidin-1-yl)-5,5-dimethyl-octyloxy)-4,4-dimethyl-octyl)-1-ethyl-imidazolidine-2,4-dione;
3-(5-(9-cyclopentyl-5,5-dimethyl-nonyloxy)-1,1-dimethyl-pentyl)-1-ethyl-imidazolidine-2,4-dione;
3-(6-(9-(3-ethyl-2,5-dioxo-imidazolidin-1-yl)-5,5-dimethyl-nonyloxy)-2,2-dimethyl-hexyl)-1-ethyl-imidazolidine-2,4-dione;
3-(7-(9-(3-ethyl-2,5-dioxo-imidazolidin-1-yl)-5,5-dimethyl-nonyloxy)-3,3-dimethyl-heptyl)-1-ethyl-imidazolidine-2,4-dione;
3-(8-(9-(3-ethyl-2,5-dioxo-imidazolidin-1-yl)-5,5-dimethyl-nonyloxy)-4,4-dimethyl-octyl)-1-ethyl-imidazolidine-2,4-dione;
3-(9-(9-(3-ethyl-2,5-dioxo-imidazolidin-1-yl)-5,5-dimethyl-nonyloxy)-5,5-dimethyl-nonyl)-1-ethyl-imidazolidine-2,4-dione;
2,2-diethyl-6-(5-ethyl-5-hydroxymethyl-heptyloxy)-hexan-1-ol;
7-(5,5-diethyl-7-hydroxy-heptyloxy)-3,3-diethyl-heptan-1-ol;
2,2-diethyl-6-(5-ethyl-5-hydroxymethyl-heptyloxy)-hexanoic acid;
3,3-diethyl-7-(5-ethyl-5-hydroxymethyl-heptyloxy)-heptanoic acid;
6-(5,5-diethyl-7-hydroxy-heptyloxy)-2,2-diethyl-hexanoic acid;
7-(5,5-diethyl-7-hydroxy-heptyloxy)-3,3-diethyl-heptanoic acid;

6-(5,5-diethyl-8-hydroxy-octyloxy)-2,2-diethyl-hexanoic acid;
7-(5,5-diethyl-8-hydroxy-octyloxy)-3,3-diethyl-heptanoic acid;
8-(5,5-diethyl-8-hydroxy-octyloxy)-4,4-diethyl-octanoic acid;
6-(5,5-diethyl-9-hydroxy-nonyloxy)-2,2-diethyl-hexanoic acid;
7-(5,5-diethyl-9-hydroxy-nonyloxy)-3,3-diethyl-heptanoic acid;
8-(5,5-diethyl-9-hydroxy-nonyloxy)-4,4-diethyl-octanoic acid;
9-(5,5-diethyl-9-hydroxy-nonyloxy)-5,5-diethyl-nonanoic acid;
6-(5,5-diethyl-10-hydroxy-decyloxy)-2,2-diethyl-hexanoic acid;
7-(5,5-diethyl-10-hydroxy-decyloxy)-3,3-diethyl-heptanoic acid;
8-(5,5-diethyl-10-hydroxy-decyloxy)-4,4-diethyl-octanoic acid;
9-(5,5-diethyl-10-hydroxy-decyloxy)-5,5-diethyl-nonanoic acid;
10-(5,5-diethyl-10-hydroxy-decyloxy)-6,6-diethyl-decanoic acid;
phosphoric acid mono-(1,1-diethyl-5-(5-ethyl-5-hydroxymethyl-heptyloxy)-pentyl) ester;
phosphoric acid mono-(2,2-diethyl-6-(5-ethyl-5-hydroxymethyl-heptyloxy)-hexyl) ester;
phosphoric acid mono-(5-(5,5-diethyl-7-hydroxy-heptyloxy)-1,1-diethyl-pentyl) ester;
phosphoric acid mono-(6-(5,5-diethyl-7-hydroxy-heptyloxy)-2,2-diethyl-hexyl) ester;
phosphoric acid mono-(5-(5,5-diethyl-8-hydroxy-octyloxy)-1,1-diethyl-pentyl)ester;
phosphoric acid mono-(6-(5,5-diethyl-8-hydroxy-octyloxy)-2,2-diethyl-hexyl)ester;
phosphoric acid mono-(7-(5,5-diethyl-8-hydroxy-octyloxy)-3,3-diethyl-heptyl)ester;
phosphoric acid mono-(5-(5,5-diethyl-9-hydroxy-nonyloxy)-1,1-diethyl-pentyl) ester;
phosphoric acid mono-(6-(5,5-diethyl-9-hydroxy-nonyloxy)-2,2-diethyl-hexyl)ester;
phosphoric acid mono-(7-(5,5-diethyl-9-hydroxy-nonyloxy)-3,3-diethyl-heptyl) ester;
phosphoric acid mono-(8-(5,5-diethyl-9-hydroxy-nonyloxy)-4,4-diethyl-octyl)ester;
phosphoric acid mono-(5-(5,5-diethyl-10-hydroxy-decyloxy)-1,1-diethyl-pentyl) ester;
phosphoric acid mono-(6-(5,5-diethyl-10-hydroxy-decyloxy)-2,2-diethyl-hexyl) ester;
phosphoric acid mono-(7-(5,5-diethyl-10-hydroxy-decyloxy)-3,3-diethyl-heptyl) ester;
phosphoric acid mono-(8-(5,5-diethyl-10-hydroxy-decyloxy)-4,4-diethyl-octyl) ester;
phosphoric acid mono-(9-(5,5-diethyl-10-hydroxy-decyloxy)-5,5-diethyl-nonyl) ester;
2,2-diethyl-6-(5-ethyl-5-phosphonooxy-heptyloxy)-hexanoic acid;
3,3-diethyl-7-(5-ethyl-5-phosphonooxy-heptyloxy)-heptanoic acid;
2,2-diethyl-6-(5-ethyl-5-phosphonooxymethyl-heptyloxy)-hexanoic acid;
3,3-diethyl-7-(5-ethyl-5-phosphonooxymethyl-heptyloxy)-heptanoic acid;
6-(5,5-diethyl-7-phosphonooxy-heptyloxy)-2,2-diethyl-hexanoic acid;
7-(5,5-diethyl-7-phosphonooxy-heptyloxy)-3,3-diethyl-heptanoic acid;
8-(5,5-diethyl-7-phosphonooxy-heptyloxy)-4,4-diethyl-octanoic acid;
6-(5,5-diethyl-8-phosphonooxy-octyloxy)-2,2-diethyl-hexanoic acid;
7-(5,5-diethyl-8-phosphonooxy-octyloxy)-3,3-diethyl-heptanoic acid;
8-(5,5-diethyl-8-phosphonooxy-octyloxy)-4,4-diethyl-octanoic acid;
9-(5,5-diethyl-8-phosphonooxy-octyloxy)-5,5-diethyl-nonanoic acid;
6-(5,5-diethyl-9-phosphonooxy-nonyloxy)-2,2-diethyl-hexanoic acid;
7-(5,5-diethyl-9-phosphonooxy-nonyloxy)-3,3-diethyl-heptanoic acid;
8-(5,5-diethyl-9-phosphonooxy-nonyloxy)-4,4-diethyl-octanoic acid;
9-(5,5-diethyl-9-phosphonooxy-nonyloxy)-5,5-diethyl-nonanoic acid;
10-(5,5-diethyl-9-phosphonooxy-nonyloxy)-6,6-diethyl-decanoic acid;
phosphoric acid mono-(1,1-diethyl-5-(5-ethyl-5-phosphonooxy-heptyloxy)-pentyl) ester;
phosphoric acid mono-(1,1-diethyl-5-(5-ethyl-5-phosphonooxymethyl-heptyloxy)-pentyl) ester;
phosphoric acid mono-(2,2-diethyl-6-(5-ethyl-5-phosphonooxymethyl-heptyloxy)-hexyl) ester;
phosphoric acid mono-(3,3-diethyl-7-(5-ethyl-5-phosphonooxy-heptyloxy)-heptyl) ester;
phosphoric acid mono-(3,3-diethyl-7-(5-ethyl-5-phosphonooxymethyl-heptyloxy)-heptyl) ester;
phosphoric acid mono-(7-(5,5-diethyl-7-phosphonooxy-heptyloxy)-3,3-diethyl-heptyl) ester;
phosphoric acid mono-(4,4-diethyl-8-(5-ethyl-5-phosphonooxy-heptyloxy)-octyl) ester;
phosphoric acid mono-(4,4-diethyl-8-(5-ethyl-5-phosphonooxymethyl-heptyloxy)-octyl) ester;
phosphoric acid mono-(8-(5,5-diethyl-7-phosphonooxy-heptyloxy)-4,4-diethyl-octyl) ester;
phosphoric acid mono-(8-(5,5-diethyl-8-phosphonooxy-octyloxy)-4,4-diethyl-octyl) ester;
phosphoric acid mono-(5,5-diethyl-9-(5-ethyl-5-phosphonooxy-heptyloxy)-nonyl) ester;
phosphoric acid mono-(5,5-diethyl-9-(5-ethyl-5-phosphonooxymethyl-heptyloxy)-nonyl) ester;
phosphoric acid mono-(9-(5,5-diethyl-7-phosphonooxy-heptyloxy)-5,5-diethyl-nonyl) ester;
phosphoric acid mono-(9-(5,5-diethyl-8-phosphonooxy-octyloxy)-5,5-diethyl-nonyl) ester;
phosphoric acid mono-(9-(5,5-diethyl-9-phosphonooxy-nonyloxy)-5,5-diethyl-nonyl) ester;
6-(6-hydroxy-5,5-diethyl-hexyloxy)-3-ethyl-heptane-2-sulfonic acid amide;
6-(6-hydroxy-5,5-diethyl-hexyloxy)-2,2-diethyl-hexane-1-sulfonic acid amide;
6-(7-hydroxy-5,5-diethyl-heptyloxy)-3-ethyl-heptane-2-sulfonic acid amide;
6-(7-hydroxy-5,5-diethyl-heptyloxy)-2,2-diethyl-hexane-1sulfonic acid amide;
7-(5,5-diethyl-8-hydroxy-octyloxy)-3-ethyl-heptane-3-sulfonic acid amide;
6-(5,5-diethyl-8-hydroxy-octyloxy)-2,2-diethyl-hexane-1-sulfonic acid amide;
7-(5,5-diethyl-8-hydroxy-octyloxy)-3,3-diethyl-heptane-1-sulfonic acid amide;

7-(5,5-diethyl-9-hydroxy-nonyloxy)-3-ethyl-heptane-3-sulfonic acid amide;
6-(5,5-diethyl-9-hydroxy-nonyloxy)-2,2-diethyl-hexane-1-sulfonic acid amide;
7-(5,5-diethyl-9-hydroxy-nonyloxy)-3,3-diethyl-heptane-1-sulfonic acid amide;
8-(5,5-diethyl-9-hydroxy-nonyloxy)-4,4-diethyl-octane-1-sulfonic acid amide;
7-(5,5-diethyl-10-hydroxy-decyloxy)-3-ethyl-heptane-3-sulfonic acid amide;
6-(5,5-diethyl-10-hydroxy-decyloxy)-2,2-diethyl-hexane-1-sulfonic acid amide;
7-(5,5-diethyl-10-hydroxy-decyloxy)-3,3-diethyl-heptane-1-sulfonic acid amide;
8-(5,5-diethyl-10-hydroxy-decyloxy)-4,4-diethyl-octane-1-sulfonic acid amide;
9-(5,5-diethyl-10-hydroxy-decyloxy)-5,5-diethyl-nonane-1-sulfonic acid amide;
2,2-diethyl-6-(5-ethyl-5-sulfamoyl-heptyloxy)-hexanoic acid;
3,3-diethyl-7-(5-ethyl-5-sulfamoyl-heptyloxy)-heptanoic acid;
2,2-diethyl-6-(5-ethyl-5-sulfamoylmethyl-heptyloxy)-hexanoic acid;
3,3-diethyl-7-(5-ethyl-5-sulfamoylmethyl-heptyloxy)-heptanoic acid;
6-(5,5-diethyl-7-sulfamoyl-heptyloxy)-2,2-diethyl-hexanoic acid;
7-(5,5-diethyl-7-sulfamoyl-heptyloxy)-3,3-diethyl-heptanoic acid;
8-(5,5-diethyl-7-sulfamoyl-heptyloxy)-4,4-diethyl-octanoic acid;
6-(5,5-diethyl-8-sulfamoyl-octyloxy)-2,2-diethyl-hexanoic acid;
7-(5,5-diethyl-8-sulfamoyl-octyloxy)-3,3-diethyl-heptanoic acid;
8-(5,5-diethyl-8-sulfamoyl-octyloxy)-4,4-diethyl-octanoic acid;
9-(5,5-diethyl-8-sulfamoyl-octyloxy)-5,5-diethyl-nonanoic acid;
6-(5,5-diethyl-9-sulfamoyl-nonyloxy)-2,2-diethyl-hexanoic acid;
7-(5,5-diethyl-9-sulfamoyl-nonyloxy)-3,3-diethyl-heptanoic acid;
8-(5,5-diethyl-9-sulfamoyl-nonyloxy)-4,4-diethyl-octanoic acid;
9-(5,5-diethyl-9-sulfamoyl-nonyloxy)-5,5-diethyl-nonanoic acid;
10-(5,5-diethyl-9-sulfamoyl-nonyloxy)-6,6-diethyl-decanoic acid;
3-ethyl-7-(5-ethyl-5-sulfamoyl-heptyloxy)-heptane-3-sulfonic acid amide;
3-ethyl-7-(5-ethyl-5-sulfamoylmethyl-heptyloxy)-heptane-3-sulfonic acid amide;
2,2-diethyl-6-(5-ethyl-5-sulfamoylmethyl-heptyloxy)-hexane-1-sulfonic acid amide;
3,3-diethyl-7-(5-ethyl-5-sulfamoyl-heptyloxy)-heptane-1-sulfonic acid amide;
3,3-diethyl-7-(5-ethyl-5-sulfamoylmethyl-heptyloxy)-heptane-1-sulfonic acid amide;
7-(5,5-diethyl-7-sulfamoyl-heptyloxy)-3,3-diethyl-heptane-1-sulfonic acid amide;
4,4-diethyl-8-(5-ethyl-5-sulfamoyl-heptyloxy)-octane-1-sulfonic acid amide;
4,4-diethyl-8-(5-ethyl-5-sulfamoylmethyl-heptyloxy)-octane-1-sulfonic acid amide;
8-(5,5-diethyl-7-sulfamoyl-heptyloxy)-4,4-diethyl-octane-1-sulfonic acid amide;
8-(5,5-diethyl-8-sulfamoyl-octyloxy)-4,4-diethyl-octane-1-sulfonic acid amide;
5,5-diethyl-9-(5-ethyl-5-sulfamoyl-heptyloxy)-nonane-1-sulfonic acid amide;
5,5-diethyl-9-(5-ethyl-5-sulfamoylmethyl-heptyloxy)-nonane-1-sulfonic acid amide;
9-(5,5-diethyl-7-sulfamoyl-heptyloxy)-5,5-diethyl-nonane-1-sulfonic acid amide;
9-(5,5-diethyl-8-sulfamoyl-octyloxy)-5,5-diethyl-nonane-1-sulfonic acid amide;
9-(5,5-diethyl-9-sulfamoyl-nonyloxy)-5,5-diethyl-nonane-1-sulfonic acid amide;
3-(1,1-diethyl-5-(5-ethyl-5-hydroxymethyl-heptyloxy)-pentyl)-1-ethyl-imidazolidine-2,4-dione;
3-(2,2-diethyl-6-(5-ethyl-5-hydroxymethyl-heptyloxy)-hexyl)-1-ethyl-imidazolidine-2,4-dione;
3-(5-(5,5-diethyl-7-hydroxy-heptyloxy)-1,1-diethyl-pentyl)-1-ethyl-imidazolidine-2,4-dione;
3-(6-(5,5-diethyl-7-hydroxy-heptyloxy)-2,2-diethyl-hexyl)-1-ethyl-imidazolidine-2,4-dione;
3-(5-(5,5-diethyl-8-hydroxy-octyloxy)-1,1-diethyl-pentyl)-1-ethyl-imidazolidine-2,4-dione;
3-(6-(5,5-diethyl-8-hydroxy-octyloxy)-2,2-diethyl-hexyl)-1-ethyl-imidazolidine-2,4-dione;
3-(7-(5,5-diethyl-8-hydroxy-octyloxy)-3,3-diethyl-heptyl)-1-ethyl-imidazolidine-2,4-dione;
3-(5-(5,5-diethyl-9-hydroxy-nonyloxy)-1,1-diethyl-pentyl)-1-ethyl-imidazolidine-2,4-dione;
3-(6-(5,5-diethyl-9-hydroxy-nonyloxy)-2,2-diethyl-hexyl)-1-ethyl-imidazolidine-2,4-dione;
3-(7-(5,5-diethyl-9-hydroxy-nonyloxy)-3,3-diethyl-heptyl)-1-ethyl-imidazolidine-2,4-dione;
3-(8-(5,5-diethyl-9-hydroxy-nonyloxy)-4,4-diethyl-octyl)-1-ethyl-imidazolidine-2,4-dione;
3-(5-(5,5-diethyl-10-hydroxy-decyloxy)-1,1-diethyl-pentyl)-1-ethyl-imidazolidine-2,4-dione;
3-(6-(5,5-diethyl-10-hydroxy-decyloxy)-2,2-diethyl-hexyl)-1-ethyl-imidazolidine-2,4-dione;
3-(7-(5,5-diethyl-10-hydroxy-decyloxy)-3,3-diethyl-heptyl)-1-ethyl-imidazolidine-2,4-dione;
3-(8-(5,5-diethyl-10-hydroxy-decyloxy)-4,4-diethyl-octyl)-1-ethyl-imidazolidine-2,4-dione;
3-(9-(5,5-diethyl-10-hydroxy-decyloxy)-5,5-diethyl-nonyl)-1-ethyl-imidazolidine-2,4-dione;
2,2-diethyl-6-(5-ethyl-5-(3-ethyl-2,5-dioxo-imidazolidin-1-yl)-heptyloxy)-hexanoic acid;
3,3-diethyl-7-(5-ethyl-5-(3-ethyl-2,5-dioxo-imidazolidin-1-yl)-heptyloxy)-heptanoic acid;
2,2-diethyl-6-(5-ethyl-5-(3-ethyl-2,5-dioxo-imidazolidin-1-ylmethyl)-heptyloxy)-hexanoic acid;
3,3-diethyl-7-(5-ethyl-5-(3-ethyl-2,5-dioxo-imidazolidin-1-ylmethyl)-heptyloxy)-heptanoic acid;
6-(5,5-diethyl-7-(3-ethyl-2,5-dioxo-imidazolidin-1-yl)-heptyloxy)-2,2-diethyl-hexanoic acid;
7-(5,5-diethyl-7-(3-ethyl-2,5-dioxo-imidazolidin-1-yl)-heptyloxy)-3,3-diethyl-heptanoic acid;
8-(5,5-diethyl-7-(3-ethyl-2,5-dioxo-imidazolidin-1-yl)-heptyloxy)-4,4-diethyl-octanoic acid;
6-(5,5-diethyl-8-(3-ethyl-2,5-dioxo-imidazolidin-1-yl)-octyloxy)-2,2-diethyl-hexanoic acid;
7-(5,5-diethyl-8-(3-ethyl-2,5-dioxo-imidazolidin-1-yl)-octyloxy)-3,3-diethyl-heptanoic acid;
8-(5,5-diethyl-8-(3-ethyl-2,5-dioxo-imidazolidin-1-yl)-octyloxy)-4,4-diethyl-octanoic acid;

9-(5,5-diethyl-8-(3-ethyl-2,5-dioxo-imidazolidin-1-yl)-octyloxy)-5,5-diethyl-nonanoic acid;
6-(5,5-diethyl-9-(3-ethyl-2,5-dioxo-imidazolidin-1-yl)-nonyloxy)-2,2-diethyl-hexanoic acid;
7-(5,5-diethyl-9-(3-ethyl-2,5-dioxo-imidazolidin-1-yl)-nonyloxy)-3,3-diethyl-heptanoic acid;
8-(5,5-diethyl-9-(3-ethyl-2,5-dioxo-imidazolidin-1-yl)-nonyloxy)-4,4-diethyl-octanoic acid;
9-(5,5-diethyl-9-(3-ethyl-2,5-dioxo-imidazolidin-1-yl)-nonyloxy)-5,5-diethyl-nonanoic acid;
10-(5,5-diethyl-9-(3-ethyl-2,5-dioxo-imidazolidin-1-yl)-nonyloxy)-6,6-diethyl-decanoic acid;
3-(5-(5-(3-ethyl-2,5-dioxo-imidazolidin-1-yl)-5-ethyl-heptyloxy)-1,1-diethyl-pentyl)-1-ethyl-imidazolidine-2,4-dione;
3-(5-(5-(3-ethyl-2,5-dioxo-imidazolidin-1-yl)-methyl-5-ethyl-heptyloxy)-1,1-diethyl-pentyl)-1-ethyl-imidazolidine-2,4-dione;
3-(6-(5-(3-ethyl-2,5-dioxo-imidazolidin-1-yl)-methyl-5-ethyl-heptyloxy)-2,2-diethyl-hexyl)-1-ethyl-imidazolidine-2,4-dione;
3-(5-(7-(3-ethyl-2,5-dioxo-imidazolidin-1-yl)-5,5-diethyl-heptyloxy)-1,1-diethyl-pentyl)-1-ethyl-imidazolidine-2,4-dione;
3-(6-(7-(3-ethyl-2,5-dioxo-imidazolidin-1-yl)-5,5-diethyl-heptyloxy)-2,2-diethyl-hexyl)-1-ethyl-imidazolidine-2,4-dione;
3-(7-(7-(3-ethyl-2,5-dioxo-imidazolidin-1-yl)-5,5-diethyl-heptyloxy)-3,3-diethyl-heptyl)-1-ethyl-imidazolidine-2,4-dione;
3-(5-(8-(3-ethyl-2,5-dioxo-imidazolidin-1-yl)-5,5-diethyl-octyloxy)-1,1-diethyl-pentyl)-1-ethyl-imidazolidine-2,4-dione;
3-(6-(8-(3-ethyl-2,5-dioxo-imidazolidin-1-yl)-5,5-diethyl-octyloxy)-2,2-diethyl-hexyl)-1-ethyl-imidazolidine-2,4-dione;
3-(7-(8-(3-ethyl-2,5-dioxo-imidazolidin-1-yl)-5,5-diethyl-octyloxy)-3,3-diethyl-heptyl)-1-ethyl-imidazolidine-2,4-dione;
3-(8-(8-(3-ethyl-2,5-dioxo-imidazolidin-1-yl)-5,5-diethyl-octyloxy)-4,4-diethyl-octyl)-1-ethyl-imidazolidine-2,4-dione;
3-(5-(9-(3-ethyl-2,5-dioxo-imidazolidin-1-yl)-5,5-diethyl-nonyloxy)-1,1-diethyl-pentyl)-1-ethyl-imidazolidine-2,4-dione;
3-(6-(9-(3-ethyl-2,5-dioxo-imidazolidin-1-yl)-5,5-diethyl-nonyloxy)-2,2-diethyl-hexyl)-1-ethyl-imidazolidine-2,4-dione;
3-(7-(9-(3-ethyl-2,5-dioxo-imidazolidin-1-yl)-5,5-diethyl-nonyloxy)-3,3-diethyl-heptyl)-1-ethyl-imidazolidine-2,4-dione;
3-(8-(9-(3-ethyl-2,5-dioxo-imidazolidin-1-yl)-5,5-diethyl-nonyloxy)-4,4-diethyl-octyl)-1-ethyl-imidazolidine-2,4-dione; or
3-(9-(9-(3-ethyl-2,5-dioxo-imidazolidin-1-yl)-5,5-diethyl-nonyloxy)-5,5-diethyl-nonyl)-1-ethyl-imidazolidine-2,4-dione; or a pharmaceutically acceptable salt thereof.

3. The method of claim 2, wherein the compound is 6-(6-hydroxy-5,5-dimethylhexyloxy)-2,2-dimethyl-hexan-1-ol; or a pharmaceutically acceptable salt thereof.

4. The method of claim 2, wherein the patient is human.

5. The method of claim 2, wherein the route of administration is intranasal.

6. The method of claim 5, wherein the dosage is 0.01 picograms to 1 milligram per kilogram of the patient's body weight.

7. The method of claim 2 wherein the route of administration is oral, intravenous, intradermal, intramuscular, intraperitoneal, subcutanous, epidural, sublingual, intracerebral, intravaginal, transdermal or inhalation.

8. The method of claim 7, wherein the dosage is 0.001 milligram to 200 milligrams per kilogram of the patient's body weight.

9. The method of claim 7, wherein the dosage is 0.01 milligram to 70 milligrams per kilogram of the patient's body weight.

10. The method of claim 7, wherein the dosage is 0.1 milligram to 50 milligrams per kilogram of the patient's body weight.

11. The method of claim 7, wherein the dosage is 0.5 milligram to 20 milligrams per kilogram of the patient's body weight.

12. The method of claim 2, further comprising the administration of a statin.

13. The method of claim 3 wherein the patient is a human.

14. The method of claim 3, wherein the route of administration is oral, intravenous, intradermal, intramuscular, intraperitoneal, subcutanous, epidural, sublingual, intracerebral, intravaginal, transdermal or inhalation.

15. The method of claim 14, wherein the dosage is 0.001 milligram to 200 milligrams per kilogram of the patient's body weight.

16. The method of claim 14, wherein the dosage is 0.01 milligrams to 70 milligrams per kilogram of the patient's body weight.

17. The method of claim 14, wherein the dosage is 0.1 milligrams to 50 milligrams per kilogram of the patient's body weight.

18. The method of claim 14, wherein the dosage is 0.5 milligrmas to 20 milligrams per kilogram of the patient's body weight.

19. The method of claim 3, further comprising the administration of a statin.

* * * * *

UNITED STATES PATENT AND TRADEMARK OFFICE
CERTIFICATE OF CORRECTION

| | |
|---|---|
| PATENT NO. | : 7,709,515 B2 |
| APPLICATION NO. | : 10/990304 |
| DATED | : May 4, 2010 |
| INVENTOR(S) | : Jean-Louis Henri Dasseux |

It is certified that error appears in the above-identified patent and that said Letters Patent is hereby corrected as shown below:

In column 144, claim 1, line 48, after "group consisting" replace "Of" with --of--.

In column 145, claim 2, line 52, before "method for treating" insert --A--.

Signed and Sealed this

Second Day of November, 2010

David J. Kappos
*Director of the United States Patent and Trademark Office*